US010125116B2

(12) United States Patent
Hedstrom et al.

(10) Patent No.: US 10,125,116 B2
(45) Date of Patent: Nov. 13, 2018

(54) COMPOUNDS AND METHODS FOR TREATING MAMMALIAN GASTROINTESTINAL MICROBIAL INFECTIONS

(71) Applicants: Brandeis University, Waltham, MA (US); University of Georgia Research Foundation, Inc., Athens, GA (US); The Brigham and Women's Hospital, Inc., Boston, MA (US)

(72) Inventors: Lizbeth K. Hedstrom, Newton, MA (US); Gregory D. Cuny, Houston, TX (US); Deviprasad R. Gollapalli, Waltham, MA (US); Sivapriya Kirubakaran, Chennai (IN); Sushil K. Maurya, Leeds (GB); Boris Striepen, Athens, GA (US); Suresh K. Gorla, Gurgaon (IN); Corey R. Johnson, Waltham, MA (US); Mandapati Kavitha, Gurgaon (IN); Jihan Khan, Somerville, MA (US)

(73) Assignees: Brandeis University, Waltham, MA (US); University of Georgia Research Foundation, Inc., Athens, GA (US); The Brigham and Women's Hospital, Inc., Boston, MA (US)

( * ) Notice: Subject to any disclaimer, the term of this patent is extended or adjusted under 35 U.S.C. 154(b) by 176 days.

(21) Appl. No.: 14/571,673

(22) Filed: Dec. 16, 2014

(65) Prior Publication Data

US 2015/0099781 A1 Apr. 9, 2015

Related U.S. Application Data

(62) Division of application No. 13/257,418, filed as application No. PCT/US2010/028178 on Mar. 22, 2010, now Pat. No. 8,969,342.

(Continued)

(51) Int. Cl.

| | | |
|---|---|---|
| *C07D 401/12* | (2006.01) | |
| *C07C 233/15* | (2006.01) | |
| *C07C 235/24* | (2006.01) | |
| *C07C 235/38* | (2006.01) | |
| *C07C 237/20* | (2006.01) | |
| *C07C 255/60* | (2006.01) | |
| *C07C 275/28* | (2006.01) | |
| *C07C 275/30* | (2006.01) | |
| *C07C 275/42* | (2006.01) | |
| *C07C 309/15* | (2006.01) | |
| *C07D 209/08* | (2006.01) | |
| *C07D 209/12* | (2006.01) | |
| *C07D 209/30* | (2006.01) | |
| *C07D 215/38* | (2006.01) | |

(Continued)

(52) U.S. Cl.
CPC .......... *C07D 401/12* (2013.01); *C07C 233/15* (2013.01); *C07C 235/24* (2013.01); *C07C 235/38* (2013.01); *C07C 237/20* (2013.01); *C07C 255/60* (2013.01); *C07C 275/28* (2013.01); *C07C 275/30* (2013.01); *C07C 275/42* (2013.01); *C07C 309/15* (2013.01); *C07D 209/08* (2013.01); *C07D 209/12* (2013.01); *C07D 209/30* (2013.01); *C07D 215/38* (2013.01); *C07D 235/26* (2013.01); *C07D 237/32* (2013.01); *C07D 249/06* (2013.01); *C07D 263/56* (2013.01); *C07D 263/57* (2013.01); *C07D 295/192* (2013.01); *C07D 401/04* (2013.01); *C07D 401/14* (2013.01); *C07D 409/04* (2013.01); *C07D 413/04* (2013.01); *C07D 417/04* (2013.01); *C07D 417/14* (2013.01); *C07D 471/08* (2013.01); *C07D 491/052* (2013.01)

(58) Field of Classification Search
CPC .................................................... C07D 400/12
See application file for complete search history.

(56) References Cited

U.S. PATENT DOCUMENTS

| | | |
|---|---|---|
| 3,931,203 A | 1/1976 | Kilbourn et al. |
| 4,143,061 A | 3/1979 | Kubo et al. |

(Continued)

FOREIGN PATENT DOCUMENTS

| | | |
|---|---|---|
| DE | 2 200 325 | 7/1973 |
| DE | 26 59 404 | 7/1977 |

(Continued)

OTHER PUBLICATIONS

Katritzky et al., Bioorganic & Medicinal Chemistry (2008), 16(14), 7055-7069.*

(Continued)

*Primary Examiner* — Paul V Ward
(74) *Attorney, Agent, or Firm* — Foley Hoag LLP

(57) ABSTRACT

Described herein are compounds, and pharmaceutically acceptable salts and prodrugs thereof, which are useful as inhibitors of IMPDH. In certain embodiments, a compound of the invention selectively inhibits a parasitic IMPDH versus a host IMPDH. Further, the invention provides pharmaceutical compositions comprising one or more compounds of the invention. The invention also relates to methods of treating various parasitic and bacterial infections in mammals. Moreover, the compounds may be used alone or in combination with other therapeutic or prophylactic agents, such as anti-virals, anti-inflammatory agents, antimicrobials and immunosuppressants.

21 Claims, 66 Drawing Sheets

Related U.S. Application Data

(60) Provisional application No. 61/162,013, filed on Mar. 20, 2009.

(51) Int. Cl.

| | |
|---|---|
| C07D 235/26 | (2006.01) |
| C07D 237/32 | (2006.01) |
| C07D 263/56 | (2006.01) |
| C07D 263/57 | (2006.01) |
| C07D 295/192 | (2006.01) |
| C07D 401/04 | (2006.01) |
| C07D 401/14 | (2006.01) |
| C07D 409/04 | (2006.01) |
| C07D 413/04 | (2006.01) |
| C07D 417/04 | (2006.01) |
| C07D 417/14 | (2006.01) |
| C07D 471/08 | (2006.01) |
| C07D 491/052 | (2006.01) |
| C07D 249/06 | (2006.01) |

(56) References Cited

U.S. PATENT DOCUMENTS

| | | | |
|---|---|---|---|
| 5,807,876 | A | 9/1998 | Armistead et al. |
| 6,867,299 | B2 | 3/2005 | Broadhurst et al. |
| 7,763,700 | B2* | 7/2010 | Mori .................. C07D 235/18 528/96 |
| 8,501,713 | B2* | 8/2013 | Wynne .................. A61K 45/06 514/80 |
| 8,518,980 | B2* | 8/2013 | Wynne .................. A61K 31/343 514/375 |
| 8,969,342 | B2 | 3/2015 | Hedstrom et al. |
| 9,447,134 | B2 | 9/2016 | Hedstrom et al. |
| 2003/0195202 | A1 | 10/2003 | Armistead et al. |
| 2005/0197368 | A1 | 9/2005 | Leban et al. |
| 2008/0167340 | A1 | 7/2008 | deLong et al. |
| 2010/0022547 | A1 | 1/2010 | Hedstrom et al. |
| 2011/0177999 | A1* | 7/2011 | Singh .................. A61K 31/137 514/1.8 |
| 2012/0264760 | A1 | 10/2012 | Hedstrom et al. |
| 2015/0099781 | A1 | 4/2015 | Hedstrom et al. |

FOREIGN PATENT DOCUMENTS

| | | |
|---|---|---|
| GB | 1 332 102 | 10/1973 |
| JP | 0929260 | * 11/1997 |
| WO | WO-99/07672 | 2/1999 |
| WO | WO-00/25768 | 5/2000 |
| WO | WO-2007/008529 | 1/2007 |
| WO | WO-2009/018344 | 2/2009 |
| WO | WO-2009/137404 | 11/2009 |

OTHER PUBLICATIONS

Alper-Hayta et al., European Journal of Medicinal Chemistry (2008), 43(11), 2568-2578.*
Gundla et al., (J'nal of Med. Chem 2008). Varga et al., In Vivo (2005), 19(6), 1087-1091.*
Nicola et al. (Biochem/Biophy Research Comm., 2007).*
Temiz-Arpaci et al., QSARs of some antibacterial active benzoxazoles against B. subtilis Ankara Universitesi Eczacilik Fakultesi Dergisi (2002), 31 (2), 73-81.*
Temiz Arpaci et al., Synthesis and antimicrobial activity of some novel 2-(p-substituted-phenyl)-5-substituted-carbonylaminobenzoxazoles Farmaco (2002), 57(3), 175-181.*
STN Registry (included in the Office Action), 2017.*
Gollapalli et al., "Structural determinants of inhibitor selectivity in prokaryotic IMP dehydrogenases," Chem Biol, 17:1084-91 (2010).
Gorla et al., "Optimization of benzoxazole-based inhibitors of *Cryptosporidium parvum* inosine 5'-monophosphate dehydrogenase," J Med Chem, 56:4028-43 (2013).
Gorla et al., "Selective and potent urea inhibitors of *Cryptosporidium parvum* inosine 5'-monophosphate dehydrogenase," J Med Chem, 55:7759-71 (2012).
Hackam et al., "Translation of Research Evidence From Animals to Humans," JAMA, 296(14):1731-1732 (2006).
International Search Report from corresponding international application No. PCT/US2013/055585, dated Aug. 12, 2014.
Johnson et al., "Phthalazinone inhibitors of inosine-5'-monophosphate dehydrogenase from *Cryptosporidium parvum*," Bioorg Med Chem Lett, 23:1004-7 (2013).
Jordan, V. Craig, "Tamoxifen: A Most Unlikely Pioneering Medicine," Nature Reviews: Drug Discovery, 2:205-213 (2003).
Makowska-Grzyska et al., "*Bacillus anthracis* inosine 5'-monophosphate dehydrogenase in action: The first bacterial series of structures of phosphate ion-, substrate-, and product-bound complexes," Biochem, 51:6148-63.
Striepen, B. et al., "Building the Perfect Parasite: Cell Division in Apicomplexa", *PLoS Pathog.*, 3(6):0691-0698 (2007).
Striepen, B. et al., "Gene transfer in the evolution of parasite nucleotide biosynthesis", *PNAS*, 101(9):3154-3159 (National Academy of Sciences, USA, Mar. 2, 2004).
Sullivan, W. J. et al., "IMP Dehydrogenase from the Protozoan Parasite *Toxoplasma gondii*", *Antimicrobial Agents and Chemotherapy*, 49(6):2172-2179 (American Society for Microbiology, USA, 2005).
Umejiego, N. N. et al., "*Cryptosporidium parvum* IMP Dehydrogenase: Identification of Functional, Structural, and Dynamic Properties That Can Be Exploited for Drug Design", *Journal of Biological Chemistry*, 279(39):40320-40327 (The American Society for Biochemistry and Molecular Biology, Inc., USA, 2004).
Umejiego, N. N. et al., "Targeting a prokaryotic protein in eukaryotic pathogen: identification of lead compounds against Cryptosporidiosis", Chem Biol., 15(1):70-77 (2007).
Whitby, F.G. et al., "Crystal Structure of *Tritrichomonas feotus* Inosine-5'-monophosphate Dehydrogenase and the Enzyme-Product Complex", Biochemistry 36, 10666-10674 (1997).
Bosanac et al., "A Photoactivated Precipiton for Reagant Sequestration in Solution-Phase Synthesis," J. Am. Chem. Soc., 124(16):4194-4195 (2002).
Chen et al., "Identification of Novel and Potent Isoquinoline Aminooxazole-Based IMPDH Inhibitors," Biorganic & Medicinal Chemistry Letters, 13(7):1345-1348 (2003).
Corbin et al., "Complexation-Induced Unfolding of Heterocyclic Ureas. Simple Foldamers Equilibrate with Multiply Hyrdogen-Bonded Sheetlike Structures," J. Am. Chem. Soc., 123(43):10475-10488 (2001).
Hall et al., "Ure Host Monomers for Stoichiometric Molecular Imprinting of Oxyanions," J. Org. Chem., 70:1732-1736 (2005).
Hosseinzadeh et al., "Copper-catalyzed arylation of phenylurea using $KF/Al_2O_3$," Tetrahedron Letters, 49(5):840-843 (2008).
Lambert et al., "Aliphatic Nitro-compounds. Part XIX. Friedel-Crafts Reactions with α- and β-Nitro-olefins," J. Chem. Soc., 42-46 (1949).
Supplementary European Search Report dated Oct. 9, 2012 from EP 10754239.1.

* cited by examiner

Figure 1

| Number | Compound | IC$_{50}$ |
|---|---|---|
| 1 | naphthalen-1-yloxy-CH(CH₃)-triazole-N-(4-chlorophenyl) | 108 nM |
| 2 | naphthalen-1-yloxy-CH(CH₃)-triazole-N-(4-bromophenyl) | 143 nM |
| 3 | naphthalen-1-yloxy-CH(iPr)-triazole-N-(4-chlorophenyl) | > 5 µM |
| 4 | naphthalen-1-yloxy-CH(CH₃)-(5-Ph)triazole-N-(4-chlorophenyl) | > 5 µM |
| 5 | naphthalen-1-yloxy-CH(CH₃)-triazole-N-(2,4-dichlorophenyl) | 750 nM |
| 6 | naphthalen-1-yloxy-CH(CH₃)-triazole-N-(2,6-dichlorophenyl) | > 5 µM |
| 7 | (4-chloronaphthalen-1-yl)oxy-CH(CH₃)-triazole-N-(4-chlorophenyl) | 60 nM |

Figure 2

| Number | Compound | IC$_{50}$ |
|---|---|---|
| 8 | | 637 nM |
| 9 | | >20 µM |
| 10 | | 330 nM |
| 11 | | 250 nM |
| 12 | | 141 nM |
| 13 | | 68 nM |
| 14 | | 63 nM |

Figure 3
| Number | Compound | IC$_{50}$ |
|---|---|---|
| 15 | 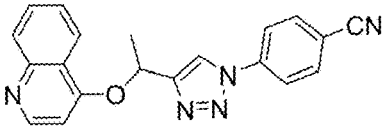 | 98 nM |
| 16 | 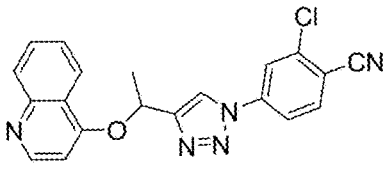 | 39 nM |
| 17 | 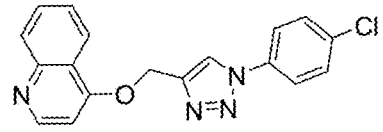 | 660 nM |
| 18 | 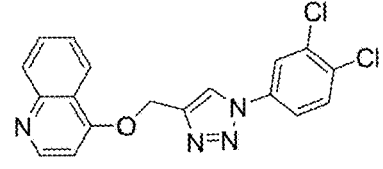 | 210 nM |
| 19 | 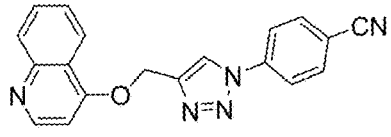 | >5 μM |
| 20 | 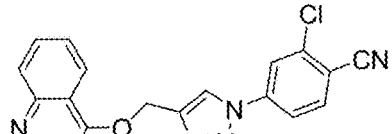 | >5 μM |
| 21 | 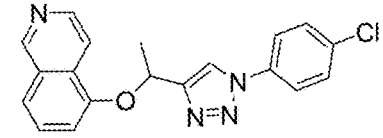 | 8 nM |

Figure 4
| Number | Compound | IC$_{50}$ |
|---|---|---|
| 22 | 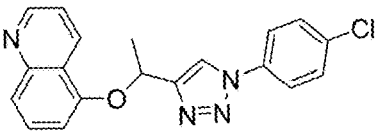 | 30 nM |
| 23 | 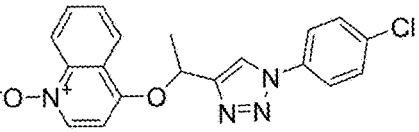 | 43 nM |
| 24 | 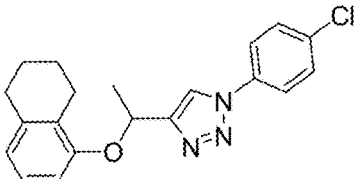 | >5 µM |
| 25 | 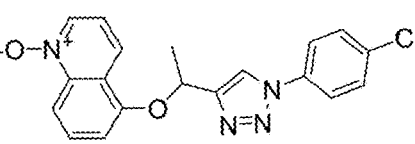 | 43 nM |
| 26 | 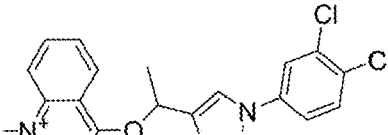 | 20 nM |
| 27 | 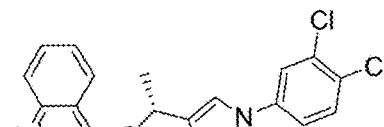 | |
| 28 |  | 15 nM |

Figure 5

| Number | Compound | IC$_{50}$ |
|---|---|---|
| 29 | (quinoline-O-C(R)(CH₃)-triazole-N-phenyl(Cl)(CN)) | 35 nM |
| 30 | (quinoline-O-C(S)(CH₃)-triazole-N-phenyl(Cl)(Cl)) | 565 nM |
| 31 | (quinoline-O-C(S)(CH₃)-triazole-N-phenyl(Cl)(CN)) | 660 nM |
| 32 | (quinoline N-oxide-O-C(CH₃)-triazole-N-phenyl(Cl)) | 30 nM |
| 33 | (quinoline N-oxide-O-C(R)(CH₃)-triazole-N-phenyl(Cl)) | 18 nM |
| 34 | (benzimidazole-thiazole, CH₂-triazole-N-phenyl(Cl)) | 680 nM |

Figure 6
| Number | Compound | IC$_{50}$ |
|---|---|---|
| 35 | 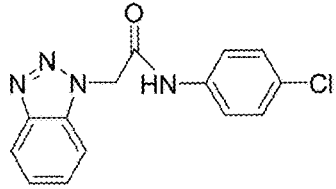 | >5 µM |
| 36 | 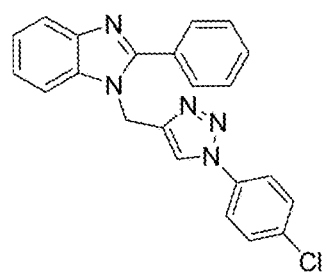 | 32 nM |
| 37 | 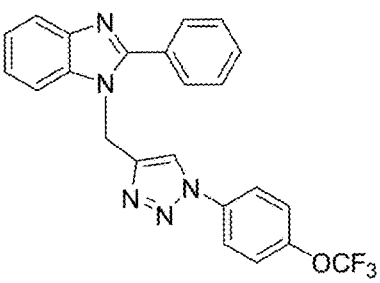 | |
| 38 | 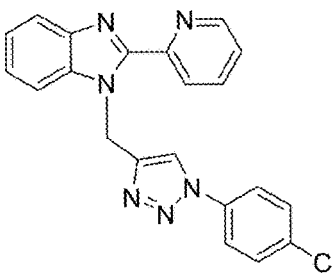 | |
| 39 | 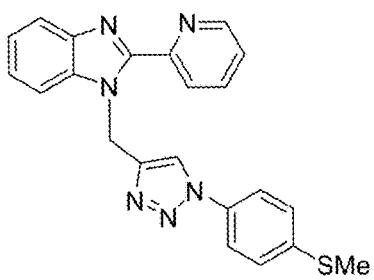 | |

| Compound | R¹ | R² | X | Y | IC$_{50}$ (μM) | |
|---|---|---|---|---|---|---|
| | | | | | (−) BSA[a] | (+) BSA |
| 1 | Me | 4-Cl | CH | CH | 0.13 ± 0.03 | 0.78 ± 0.2 |
| 3 | $i$-Pr | 4-Cl | CH | CH | > 5 | ND[b] |
| 6 | Me | 2-Cl | CH | CH | > 5 | ND |
| 7 | Me | 4-Cl | CCl | CH | 0.087 ± 0.03 | 3.9 ± 0.08 |
| 13 | Me | 4-Cl | N | CH | 0.024 ± 0.008 | 0.23 ± 0.06 |
| 17 | H | 4-Cl | N | CH | 0.44 ± 0.2 | 0.48 ± 0.2 |
| 14 | Me | 3,4-di-Cl | N | CH | 0.020 ± 0.01 | 0.70 ± 0.2 |
| 15 | Me | 4-CN | N | CH | 0.14 ± 0.03 | 0.34 ± 0.1 |
| 15 | Me | 3-Cl, 4-CN | N | CH | 0.040 ± 0.002 | 1.4 ± 0.4 |
| 28 | ($R$)-Me | 3,4-di-Cl | N | CH | 0.009 ± 0.006 | 0.65 ± 0.1 |
| 30 | ($S$)-Me | 3,4-di-Cl | N | CH | 0.13 ± 0.03 | 0.88 ± 0.03 |
| 29 | ($R$)-Me | 3-Cl, 4-CN | N | CH | 0.031 ± 0.009 | 1.1 ± 0.2 |
| 31 | ($S$)-Me | 3-Cl, 4-CN | N | CH | 0.60 ± 0.05 | 2.3 ± 0.04 |
| 21 | ($R$)-Me | 4-Cl | CH | N | 0.009 ± 0.001 | 0.030 ± 0.001 |
| 23 | Me | 4-Cl | N$^+$-O$^-$ | CH | 0.029 ± 0.01 | 0.050 ± 0.002 |
| 26 | Me | 3,4-di-Cl | N$^+$-O$^-$ | CH | 0.018 ± 0.003 | 0.042 ± 0.003 |
| 25 | Me | 4-Cl | CH | N$^+$-O$^-$ | 0.044 ± 0.002 | 0.059 ± 0.02 |
| 33 | ($R$)-Me | 4-Cl | N$^+$-O$^-$ | CH | 0.013 ± 0.005 | 0.050 ± 0.02 |
| 32 | ($R$)-Me | 4-Cl | CH | N$^+$-O$^-$ | 0.024 ± 0.005 | 0.052 ± 0.01 |

Figure 11

| Code | Compounds | IC$_{50}$ |
|---|---|---|
| 52 | quinoline-O-CH(CH$_3$)-oxadiazole-(4-chlorophenyl) | >5 µM |

Figure 12

| Code | Compounds | IC$_{50}$ |
|---|---|---|
| 53 | phenyl-O-CH(CH$_3$)-C(=O)-NH-(4-chlorophenyl) | 3.33 µM |
| 54 | phenyl-O-CH(CH$_3$)-C(=O)-NH-(4-OCH$_3$-phenyl) | 3.7 µM |
| 55 | benzyl-CH(NH$_2$)-C(=O)-NH-(4-chlorophenyl) | >10 µM |
| 56 | phenyl-O-CH(CH$_3$)-C(=O)-NH-(2-fluorophenyl) | >10 µM |
| 57 | phenyl-O-CH(CH$_3$)-C(=O)-NH-(4-pyridyl) | >10 µM |

Figure 13

| Code | Compounds | IC$_{50}$ |
|---|---|---|
| 58 | 2-phenoxy-N-(4-fluorophenyl)propanamide | > 10 μM |
| 59 | 2-(4-chlorophenoxy)-N-(4-chlorophenyl)propanamide | 1.3 μM |
| 60 | 2-(4-chlorophenoxy)-N-phenylpropanamide | > 20 μM |
| 61 | 2-(3-chlorophenoxy)-N-(4-chlorophenyl)propanamide | 1.16 μM |
| 62 | 2-(2-chlorophenoxy)-N-(4-chlorophenyl)propanamide | 1.16 μM |
| 63 | 2-(4-methylphenoxy)-N-(4-chlorophenyl)propanamide | 3.44 μM |
| 64 | 2-(4-methoxyphenoxy)-N-(4-chlorophenyl)propanamide | 2.11 μM |
| 65 | 2-(4-aminophenoxy)-N-(4-chlorophenyl)propanamide | 10.39 μM |
| 66 | 2-(4-hydroxyphenoxy)-N-(4-chlorophenyl)propanamide | 1.89 μM |
| 67 | N-(4-chlorophenyl)-1H-indole-2-carboxamide | > 20 μM |

Figure 14

| Code | Compounds | IC$_{50}$ |
|---|---|---|
| 68 | benzofuran-2-carboxamide-N-(4-chlorophenyl) | > 20 μM |
| 69 | 2-(4-fluorophenoxy)-N-(4-chlorophenyl)propanamide | 2.58 μM |
| 70 | 2-(4-(trifluoromethyl)phenoxy)-N-(4-chlorophenyl)propanamide | 4.4 μM |
| 71 | 3-(4-chlorophenoxy)-N-(4-chlorophenyl)butanamide | > 20 μM |
| 72 | 2-(4-chlorophenoxy)-N-(4-chlorophenyl)acetamide | > 20 μM |
| 73 | (S)-2-phenoxy-N-(4-chlorophenyl)propanamide | 1.75 μM |
| 74 | (R)-2-phenoxy-N-(4-chlorophenyl)propanamide | >15 μM |
| 75 | 2-hydroxy-3-phenyl-N-(4-chlorophenyl)propanamide | > 20 μM |
| 76 | 2-(4-chlorophenoxy)-2-methyl-N-(4-chlorophenyl)propanamide | > 20 μM |

Figure 15
| Code | Compounds | IC$_{50}$ |
|---|---|---|
| 77 | 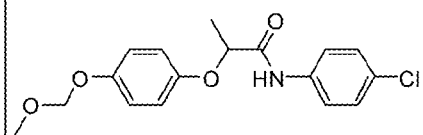 | 0.91 µM |
| 78 | 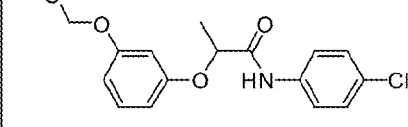 | 1.77 µM |
| 79 | 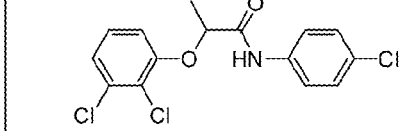 | 0.81 µM |
| 80 | 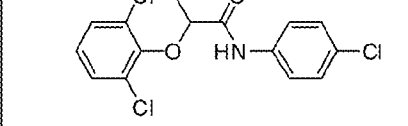 | > 20 µM |
| 81 | 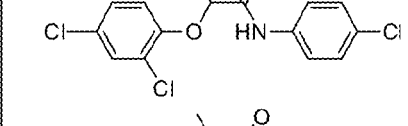 | 2.6 µM |
| 82 | 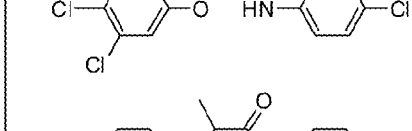 | 3.2 µM |
| 83 | 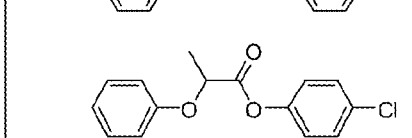 | 1.7 µM |
| 84 | 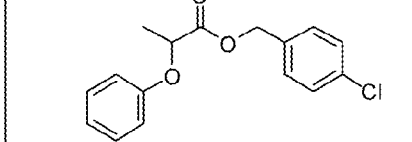 | > 20 µM |
| 85 |  | > 20 µM |

Figure 16

| S.No | Compounds | IC$_{50}$ |
|---|---|---|
| 86 | | > 20 µM |
| 87 | | > 20 µM |
| 88 | | > 20 µM |
| 89 | | 1.4 µM |
| 90 | | 1.5 µM |
| 91 | | 0.4 µM |
| 92 | | 0.4 µM |
| 93 | | 0.6 µM |
| 94 | | 0.25 µM |
| 95 | | 2 µM |

Figure 17
| Code | Compounds | IC$_{50}$ |
|---|---|---|
| 96 | 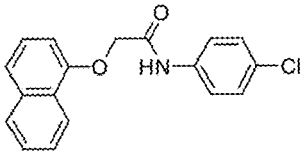 | 2 µM |
| 97 | 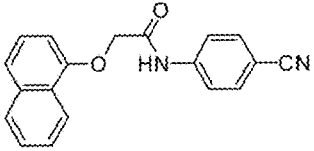 | >5 µM |
| 98 | 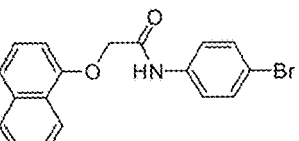 | 1.5 µM |
| 99 | 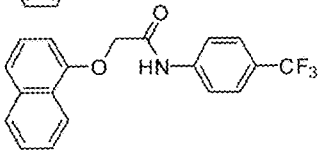 | >5 µM |
| 100 | 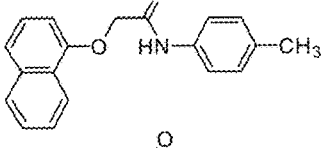 | >5 µM |
| 101 | 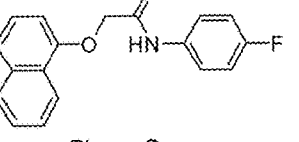 | >5 µM |
| 102 | 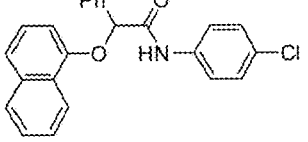 | >5 µM |
| 103 | 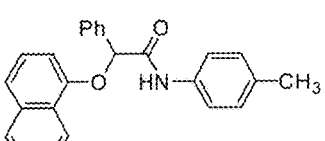 | >5 µM |
| 104 | 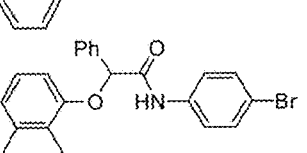 | >5 µM |

Figure 18
| Code | Compounds | IC$_{50}$ |
|---|---|---|
| 105 | 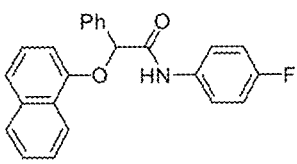 | >5 μM |
| 106 | 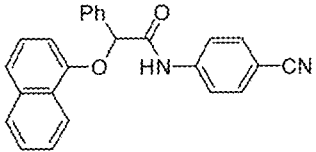 | >5 μM |
| 107 | 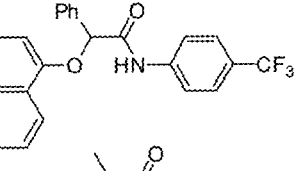 | >5 μM |
| 108 | 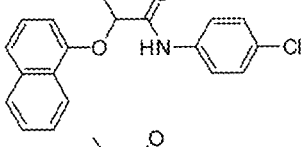 | 250 nM |
| 109 | 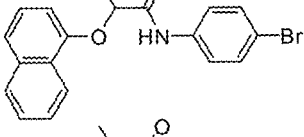 | 195 nM |
| 110 | 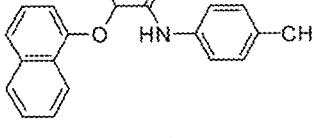 | >5 μM |
| 111 | 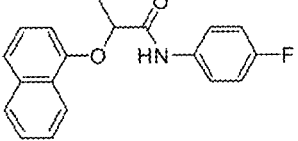 | >5 μM |
| 112 | 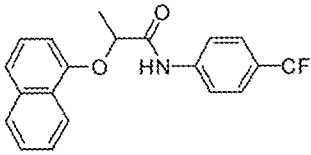 | 438 nM |
| 113 | 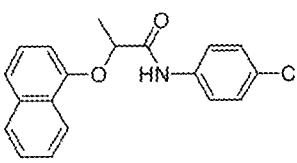 | 800 nM |

Figure 19

| Code | Compounds | IC$_{50}$ |
|---|---|---|
| 114 | *quinoline-O-CH(CH₃)-C(=O)-NH-(4-chlorophenyl)* | 824 nM |
| 115 | *naphthalene-O-CH(iPr)-C(=O)-NH-(4-bromophenyl)* | 124 nM |
| 116 | *naphthalene-O-CH(iPr)-C(=O)-NH-(4-chlorophenyl)* | 223 nM |
| 117 | *naphthalene-O-CH(CH₃)-C(=O)-CH₂-(4-bromophenyl)* | > 5 µM |
| 118 | *naphthalene-O-CH(CH₃)-CH₂-NH-C(=O)-(4-chlorophenyl)* | > 5 µM |
| 119 | *naphthalene-O-CH(cyclopropyl)-C(=O)-NH-(4-chlorophenyl)* | > 5 µM |
| 120 | *naphthalene-O-CH(cyclopropyl)-C(=O)-NH-(4-bromophenyl)* | > 5 µM |

Figure 20

| Code | Compounds | IC$_{50}$ |
|---|---|---|
| 121 | (naphthyloxy-cyclohexyl-acetamide with 4-Cl phenyl) | > 5 µM |
| 122 | (naphthyloxy-cyclohexyl-acetamide with 4-Br phenyl) | > 5 µM |

Figure 21

| Code | Compounds | IC$_{50}$ |
|---|---|---|
| 123 | (benzimidazole-thiazole acetamide with 4-OMe phenyl) | 1.2 µM |
| 124 | (benzimidazole-thiazole propanamide with 4-OMe phenyl) | 1.0 µM |

Figure 22
| Code | Compounds | IC$_{50}$ |
|---|---|---|
| 125 | 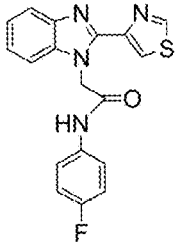 | 880 nM |
| 126 | 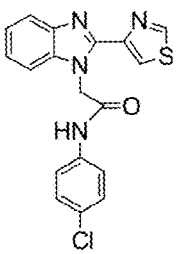 | 156 nM |
| 127 | 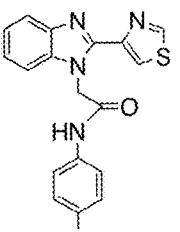 | 711 nM |
| 128 | 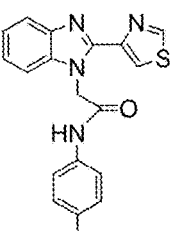 | 1.6 µM |
| 129 | 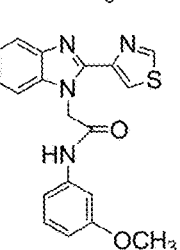 | ~5 µM |

Figure 23
| S.No | Compounds | IC$_{50}$ |
|---|---|---|
| 130 | 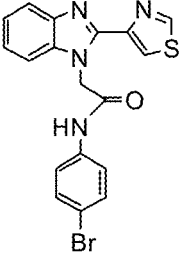 | 96 nM |
| 131 | 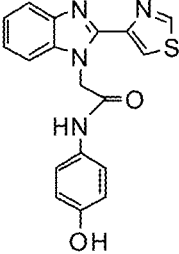 | ~5 µM |
| 132 | 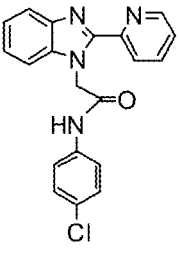 | 158 nM |
| 133 | 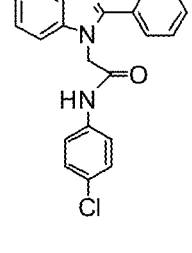 | 206 nM |
| 134 | 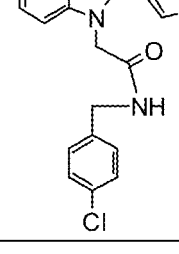 | ~5 µM |

Figure 24

| S.No | Compounds | IC$_{50}$ |
|------|-----------|-----------|
| 135 | 4-chlorophenyl-NH-CH$_2$-C(=O)-imidazole | ~5 µM |
| 136 | benzimidazole-thiazole with CH$_2$-C(=O)-NH-(2-chlorophenyl) | ~5 µM |
| 137 | benzimidazole-thiazole with CH$_2$-C(=O)-NH-NH-(4-chlorophenyl) | 600 nM |
| 138 | benzimidazole-thiazole with CH$_2$-C(=O)-NH-S(=O)$_2$-(4-chlorophenyl) | ~5 µM |
| 139 | benzimidazole-thiazole with CH$_2$-C(=O)-morpholine | ~5 µM |
| 140 | benzimidazole-thiazole with CH(iPr)-C(=O)-NH-(4-chlorophenyl) | ~5 µM |

Figure 25
| Code | Compounds | IC$_{50}$ |
|---|---|---|
| 141 | 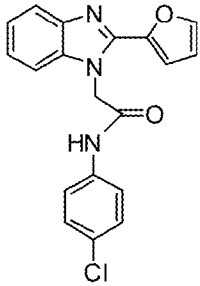 | ~5 μM |
| 142 | 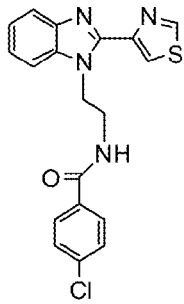 | ~5 μM |
| 143 | 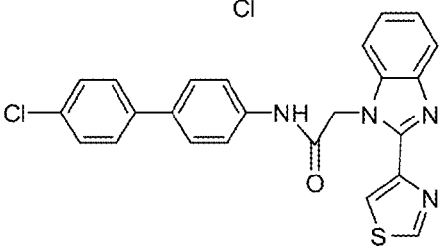 | ~5 μM |
| 144 | 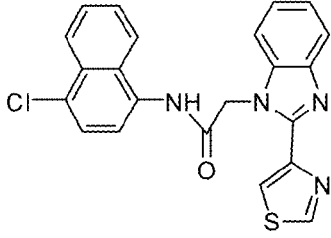 | > 5 μM |
| 145 | 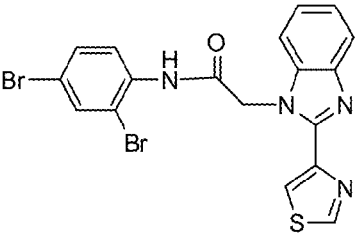 | > 5 μM |

Figure 26
| Code | Compounds | IC$_{50}$ |
|------|-----------|-----------|
| 146 | 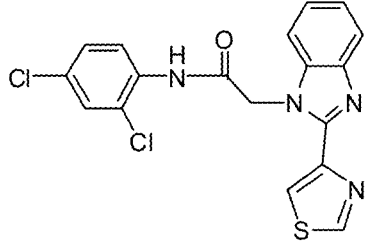 | > 5 µM |
| 147 | 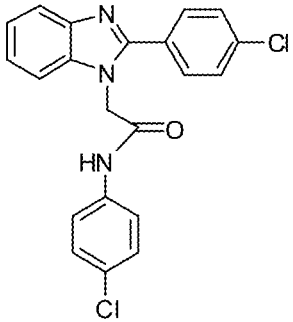 | 450 nM |
| 148 | 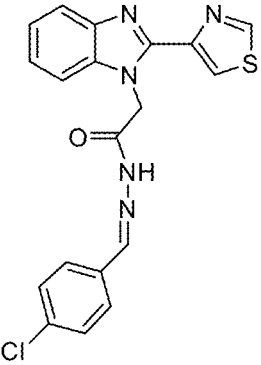 | > 5 µM |

Figure 27

| Code | Compounds | IC$_{50}$ |
|------|-----------|-----------|
| 149 | 2-phenyl-benzimidazole-N-CH$_2$-C(=O)-NH-(4-bromophenyl) | >5 µM |
| 150 | 2-(2-pyridyl)-benzimidazole-N-CH$_2$-C(=O)-NH-(4-bromophenyl) | 50 nM |
| 151 | 2-(3-pyridyl)-benzimidazole-N-CH$_2$-C(=O)-NH-(4-chlorophenyl) | >5 µM |
| 152 | 2-(2-chlorophenyl)-benzimidazole-N-CH$_2$-C(=O)-NH-(4-chlorophenyl) | 610 nM |

Figure 28
| Code | Compounds | IC$_{50}$ |
|---|---|---|
| 153 | 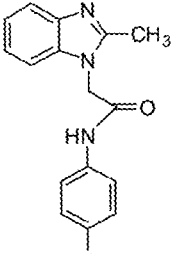 | >5 μM |
| 154 | 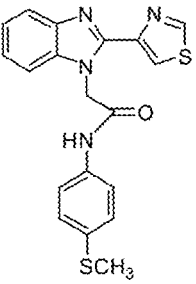 | 120 nM |
| 155 | 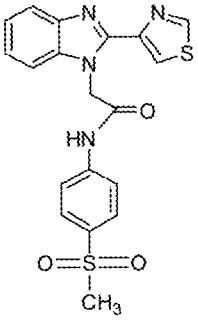 | >5 μM |
| 156 | 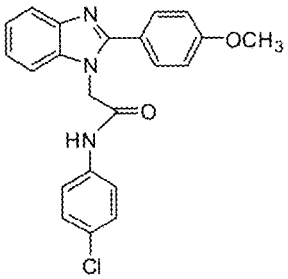 | >5 μM |

Figure 29
| Code | Compounds | IC$_{50}$ |
|---|---|---|
| 157 | 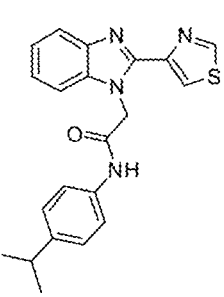 | >5 µM |
| 158 | 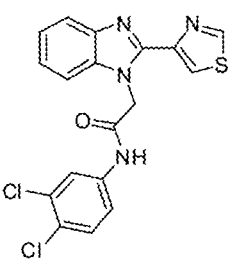 | >5 µM |
| 159 | 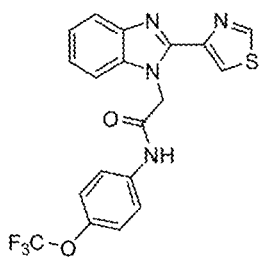 | 135 nM |
| 160 | 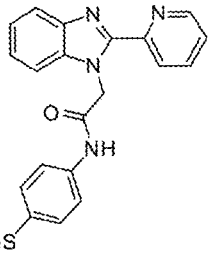 | 50 nM |

Figure 30
| Code | Compounds | IC$_{50}$ |
|---|---|---|
| 161 | 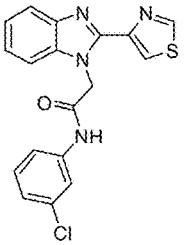 | |
| 162 | 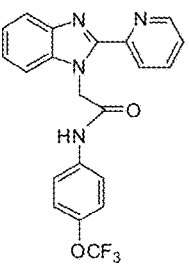 | 1.7 µM |

Figure 31
| Code | Compounds | IC$_{50}$ |
|---|---|---|
| 163 | 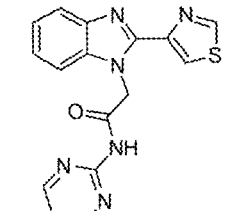 | >5 µM |
| 164 | 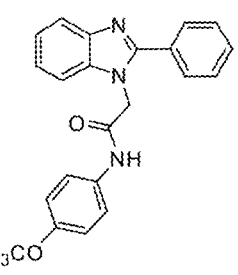 | >5 µM |
| 165 | 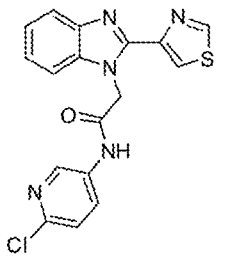 | >5 µM |
| 166 | 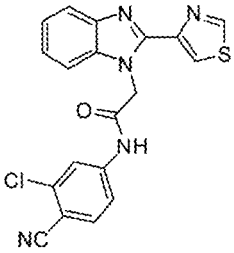 | 160 nM |
| 167 | 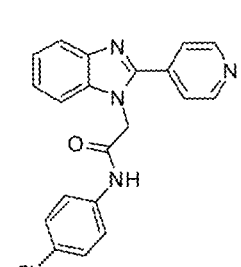 | >5 µM |

Figure 32

| Code | Compounds | IC$_{50}$ |
|---|---|---|
| 168 | benzimidazole-thiazole with N-(4-cyanophenyl)acetamide | 370 nM |
| 169 | 2-(4-fluorophenyl)benzimidazole with N-(4-chlorophenyl)acetamide | 870 nM |
| 170 | 2-(4-hydroxyphenyl)benzimidazole with N-(4-chlorophenyl)acetamide | >5 μM |
| 171 | benzimidazole-thiazole with N-(4-chlorophenyl)acetamide | 42 nM |
| 172 | benzimidazole-thiophene with N-(4-chlorophenyl)acetamide | 20 nM |

Figure 33

| Code | Compounds | IC$_{50}$ |
|---|---|---|
| 173 | | >5 µM |
| 174 | | 20 nM |
| 175 | | 75 nM |
| 176 | | 60 nM |
| 177 | | 35 nM |

Figure 34

| Code | Compounds | IC$_{50}$ |
|---|---|---|
| 178 | | 130 nM |
| 179 | | 950 nM |
| 180 | | 198 nM |
| 181 | | 200 nM |
| 182 | | 5500 nM |
| 183 | | >20000 nM |
| 184 | | >20000 nM |
| 185 | | >20000 nM |

| Compound | R | X | IC$_{50}$ (μM) | |
|---|---|---|---|---|
| | | | (-) BSA[a] | (+) BSA |
| 93 | Me | CH | 1.06 ± 0.1 | 1.64 ± 0.2 |
| 102 | Ph | CH | > 5 | ND[b] |
| 116 | i-Pr | CH | 0.71 ± 0.1 | 0.83 ± 0.2 |
| 119 | c-Pr | CH | > 5 | ND |
| 114 | Me | N | 0.66 ± 0.2 | 0.86 ± 0.2 |

Figure 37

| Code | Compounds | IC$_{50}$ |
|---|---|---|
| A111 | quinoline-O-CH$_2$-triazole-naphthyl | 102 |
| A112 | Cl-naphthyl-O-CH(CH$_3$)-triazole-naphthyl | 567 |
| A113 | quinoline N-oxide-O-CH(CH$_3$)-triazole-naphthyl | 2.2 |

Figure 38
| Code | Compounds | IC$_{50}$ |
|---|---|---|
| A114 | 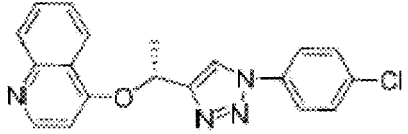 | 3.6 nM |
| A115 | 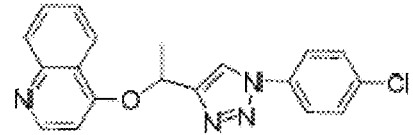 | 1.8 nM |
| A116 | 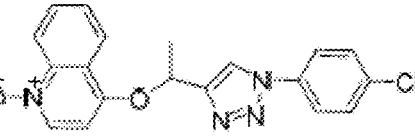 | — |
| A117 | 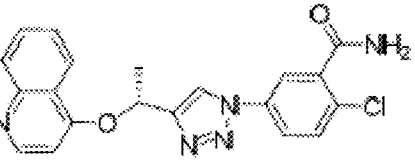 | 19 nM |
| A118 | 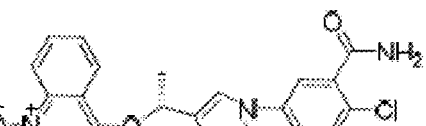 | 47 nM |
| A119 | 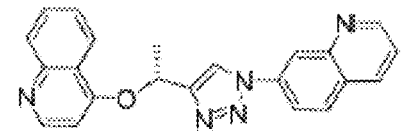 | 1.2 nM |

Figure 39
| Code | Compounds | IC$_{50}$ |
|---|---|---|
| C-68 | 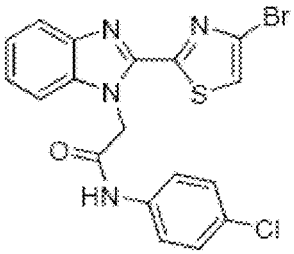 | >5 µM |
| C-69 | 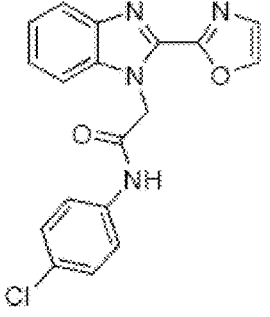 | 170 nM |
| C-70 | 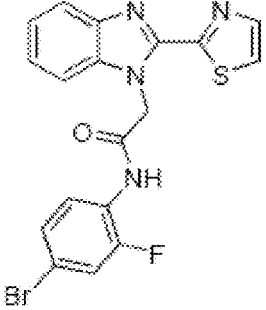 | 260 nM |

| Cmpd | R₁ | R₂ | IC$_{50}$ (nM) | |
|---|---|---|---|---|
| | | | *Cp*IMPDH | hIMPDH2 |
| C (123) | thiazol-4-yl | 4-OMePh | 1200 ± 200 [a] | ≥200,000 [a,b] |
| C10 (126) | thiazol-4-yl | 4-ClPh | 120 ± 40 | ≥20,000 [c] |
| C14 (130) | thiazol-4-yl | 4-BrPh | 60 ± 30 | ≥20,000 [c] |
| C86 | thiazol-4-yl | 3,4-di-ClPh | 30 ± 10 | ≥40,000 [d] |
| C90 | thiazol-4-yl | 2-Naph | 7 ± 4 | ≥40,000 [d] |
| C61 (171) | thiazol-2-yl | 4-ClPh | 30 ± 10 | ≥40,000 [d] |
| C64 (174) | thiazol-2-yl | 4-BrPh | 28 ± 9 | ≥40,000 [d] |
| C84 | thiazol-2-yl | 3,4-di-ClPh | 18 ± 5 | ≥8,000 [e] |
| C97 | thiazol-2-yl | 2-Naph | 8 ± 3 | ≥40,000 [d] |

Figure 56

| Compound | Mouse plasma stability $t_{1/2}$ (min) | Mouse Microsomes $t_{1/2}$ (min) | Human plasma stability $t_{1/2}$ (min) | Human Microsomes $t_{1/2}$ (min) |
|---|---|---|---|---|
| A105 | >120 | 112 | n.d. | n.d. |
| A109 | >120 | 105 | n.d. | n.d. |
| A110 | n.d. | 340 | n.d. | n.d. |
| C10 (126) | >120 | 11.5 | >120 | 54.1 |
| C14 (130) | n.d. | n.d. | >120 | 29.6 |
| C16 (132) | >120 | 8.84 | n.d. | n.d. |
| C17 (133) | >120 | 30.6 | >120 | 39.3 |
| C61 (171) | ~30 | 11.7 | n.d. | n.d. |
| C67 (177) | >120 | 5.94 | n.d. | n.d. |
| C79 | >120 | 13.1 | n.d. | n.d. |
| C85 | >120 | 5.89 | n.d. | n.d. |
| P16 | >120 | 24.9 | n.d. | n.d. |
| P19 | >120 | 5.93 | n.d. | n.d. |
| P24 | >120 | 77.0 | n.d. | n.d. |
| P25 | >120 | 14000 | n.d. | n.d. |
| P27 | >120 | 44.9 | n.d. | n.d. |
| P32 | >120 | 193 | n.d. | n.d. |
| P64 | n.d. | 37.8 | n.d. | n.d. |
| P69 | n.d. | 41.2 | n.d. | n.d. |
| P70 | n.d. | 19.7 | n.d. | n.d. |

Figure 62A
| ID | Structure | CpIMPDH Enzyme IC$_{50}$ (µM) | CpIMPDH Enzyme IC$_{50}$ (µM) + BSA | T. gondii wild-type EC$_{50}$ (µM) | T. gondii ΔHXGPRT EC$_{50}$ (µM) | T. gondii CpIMPDH EC$_{50}$ (µM) | T. gondii model selectivity$^a$ | % HCT-8 growth inhibition, compound at 25 µM | C. parvum EC$_{50}$ (µM) |
|---|---|---|---|---|---|---|---|---|---|
| A (53) | 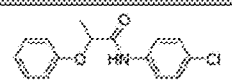 | 3.0 ± 0.5$^c$ | 3.9 ± 0.5$^c$ | 9.1 | 11 | 5.0 | 1.8 | 100 ± 10 | 25-50$^{e,f}$ |
| A23 (79) | 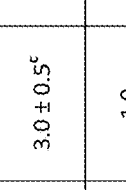 | 1.9 | N.D. | >40$^b$ | >40$^b$ | 26 | 1.5 | 98 ± 8 | N.D. |
| A26 (69) | 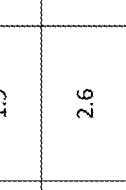 | 2.6 | N.D. | 7.4 | 5.9 | 4.2 | 1.8 | 67 ± 2 | >50$^f$ |
| A31 (61) | 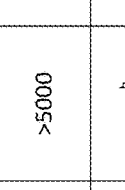 | >5000 | N.D. | 22 | 21 | 18 | 1.2 | 100 ± 20 | N.D. |
| A30 (60) | 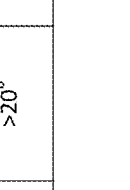 | >20$^b$ | N.A. | >20$^b$ | >20$^b$ | >20$^b$ | 1.0 | 90 ± 10 | N.D. |

Figure 62B

| | Structure | | | | | | | |
|---|---|---|---|---|---|---|---|---|
| A34 (64) | (structure) | 910 | N.D. | 16 | 15 | 4.5 | 3.6 | 100 ± 2 | >50[f] |
| A36 (66) | (structure) | 680 ± 90 | N.D. | 2.1 | 0.9 | 1.0 | 2.1 | 50 ± 10 | >50[f] |
| A57 104 | (structure) | >5[b] | 870 | 2.3 | 2.0 | 2.6 | 0.9 | 90 ± 20 | N.D. |
| A61 109 | (structure) | 0.20 | N.A. | 4.7 | 4.5 | 8.6 | 0.6 | 68 ± 3 | N.D. |
| A64 112 | (structure) | 0.44 | N.D. | 1.6 | 1.8 | 2.0 | 0.8 | 65 ± 3 | N.D. |
| A66 102 | Cl for Br in A57 | >5[b,c] | N.A. | 1.7 | 1.5 | 2.2 | 0.8 | 67 ± 3 | N.D. |
| A67 114 | (structure) | 0.7 ± 0.2[c] | 0.9 ± 0.2[c] | 3.7 | ND | 1.7 | 2.2 | 51 ± 3 | 25-50[f] |
| A68 115 | (structure) | 0.82 | N.D. | 3.2 | 2.6 | 4.6 | 0.7 | 81 ± 2 | N.D. |

Figure 62C

| | | | | | | | | |
|---|---|---|---|---|---|---|---|---|
| A82 (7) | structure | 0.09 ± 0.03$^c$ | 3.9 ± 0.1$^c$ | 5 ± 2 | 4 ± 1 | 5 ± 2 | 0.9 | -8 ± 2 | 6-13 |
| A89 (13) | structure | 0.02 ± 0.08$^c$ | 0.23 ± 0.06$^c$ | 4.9 ± 0.9 | 6 ± 2 | 0.4 ± 0.2 | 14 | 35 ± 1 | <13 |
| A90 (14) | structure | 0.02 ± 0.01$^c$ | 0.7 ± 0.2$^c$ | 5 ± 3 | 4.5 ± 0.2 | 3 ± 2 | 1.5 | 6 ± 4 | 6-13 |
| A92 (16) | structure | 0.04 ± 0.01$^c$ | 1.4 ± 0.4$^c$ | 9 ± 2 | 8 ± 4 | 5 ± 1 | 1.6 | 30 ± 10 | 3-6 |
| A98 (21) | structure | 0.009 ± 0.001$^c$ | 0.03 ± 0.01$^c$ | 2.8 ± 0.1 | 2.3 ± 0.6 | <0.20$^d$ | >12 | 35 ± 7 | 3-6 |
| A99 (22) | structure | 0.031 ± 0.001 | 0.076 ± 0.009 | 4.7 | 3.4 | <0.20$^b$ | >17 | 42 ± 8 | 12-25 |
| A100 (23) | structure | 0.03 ± 0.01$^c$ | 0.050 ± 0.002$^c$ | >25$^b$ | 25$^b$ | 0.5 | 54 | 60 ± 10 | 12-25 |
| A102 (25) | structure | 0.044 ± 0.01$^c$ | 0.06 ± 0.02$^c$ | 23 ± 3 | 20 ± 5 | 0.3 ± 0.1 | 76 | 38 ± 1 | 12-25 |

Figure 62D

| | | | | | | | |
|---|---|---|---|---|---|---|---|
| A103 (26) | [structure] | 0.018 ± 0.003[c] | 0.042 ± 0.003[c] | 19 ± 4 | 17 ± 4 | 0.5 ± 0.4 | 36 | 67 ± 7 | <0.8 |
| A105 (28) | [structure] | 0.009 ± 0.006[c] | 0.009 ± 0.006[c] | 4 ± 2 | 3.3 ± 0.2 | 1.1 ± 0.5 | 2.9 | 20 ± 10 | 6-13 |
| A107 (30) | [structure] | 0.13 ± 0.03[c] | 0.88 ± 0.03[c] | 6 | 7 | 2.4 | 3.1 | 30 ± 20 | <13 |
| A108 (31) | [structure] | 0.60 ± 0.05[c] | 2.3 ± 0.04[c] | 5 | 5 | 3.9 | 1.3 | 50 ± 10 | 12-25 |
| A109 (32) | [structure] | 0.02 ± 0.01[c] | 0.05 ± 0.01[c] | >25[b] | >25[b] | 0.3 ± 0.1 | >86 | 16 | 12-25 |
| A110 (33) | [structure] | 0.013 ± 0.005[c] | 0.05 ± 0.02[c] | 23 ± 2 | >25[b] | <0.20[d] | >120 | 20 ± 10 | 0.8-1.6 |

|  | C | C10 | C14 | C16 | C17 |
|---|---|---|---|---|---|
| Enzyme IC50 (μM) | 1.2 | 0.16 | 0.096 | 0.16 | 0.21 |
| Toxo model IC50 (μM) (selectivity) | 12 (4) | 2.0 (5) | 1.5 (>20) | 2.4 (>20) | 1.0 (3) |
| Crypto model | + | +++ | +++ | - | +++ |
| Host Toxicity (10 μM) | - | - | - | - | - |

Figure 67
| Cmpd | IC$_{50}$ (μM) | | | | |
|---|---|---|---|---|---|
| | CpIMPDH[a] | HpIMPDH | BbIMPDH | SpIMPDH | EcIMPDH-S250A/L444Y |
|  A (53) | 3.3 (0.66) | 2.2 (1.1) | 1.4 (0.84) | 96 (12) | 1.8 (0.54) |
|  B | 1.6 (0.32) | 1.3 (0.65) | 1.8 (1.1) | 85 (11) | 0.70 (0.21) |
| 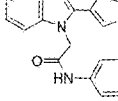 C (123) | 1.2 (0.24) | 0.60 (0.3) | 0.60 (0.36) | 70 (9.1) | 0.60 (0.18) |
| 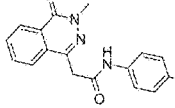 D | 5.4 (1.1) | 3.0 (1.5) | 1.7 (1.0) | 49 (6.4) | 2.3 (0.69) |
|  E | 1.6 (0.32) | 1.5 (0.75) | 0.90 (0.54) | 15 (2.0) | 1.8 (0.54) |
| 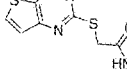 F | 1.4 (0.28) | 1.1 (0.55) | 0.80 (0.48) | 13 (1.7) | 1.1 (0.33) |
| 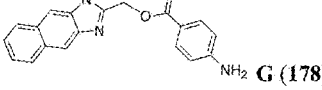 G (178) | 0.1 (0.02) | 0.30 (0.15) | 0.22 (0.13) | 0.55 (0.07) | 0.40 (0.12) |
| 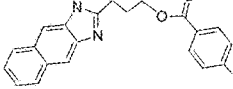 H | 0.9 (0.18) | 1.2 (0.6) | 0.90 (0.54) | 0.86 (0.11) | 1.0 (0.3) |

COMPOUNDS AND METHODS FOR TREATING MAMMALIAN GASTROINTESTINAL MICROBIAL INFECTIONS

RELATED APPLICATIONS

This application is a divisional of U.S. patent application Ser. No. 13/257,418, which is the United States National Stage of International Patent Application serial number PCT/US10/028,178, filed Mar. 22, 2010, which claims the benefit of priority to U.S. Provisional Patent Application Ser. No. 61/162,013, filed Mar. 20, 2009.

GOVERNMENT SUPPORT

This invention was made with government support under Grant No. U01 AI-75466 awarded by the National Institutes of Health. The government has certain rights in the invention.

BACKGROUND OF THE INVENTION

Organisms must synthesize nucleotides in order for their cells to divide and replicate. Nucleotide synthesis in mammals may be achieved through one of two pathways: the de novo synthesis pathway; or the salvage pathway. Different cell types use these pathways to differing extents.

Inosine-5'-monophosphate dehydrogenase (IMPDH; EC 1.1.1.205) is an enzyme involved in the biosynthesis of guanine nucleotides. IMPDH catalyzes the NAD-dependent oxidation of inosine-5'-monophosphate (IMP) to xanthosine-5'-monophosphate (XMP) [Jackson R. C. et al., Nature, 256, pp. 331-333, (1975)]. Regardless of species, the reaction involves the random addition of substrates. A conserved active site Cys residue attacks the C2 position of IMP and hydride is transferred to NAD, producing NADH and the E-XMP* intermediate. NADH is released and a mobile flap folds into the vacant NADH site, E-XMP* hydrolyzes and XMP is released [W. Wang and L. Hedstrom, Biochemistry 36, pp. 8479-8483 (1997); J. Digits and L. Hedstrom, Biochemistry 38, pp. 2295-2306 (1999); Gan et al., Biochemistry 42, pp 847-863 (2003)]. The hydrolysis step is at least partially rate-limiting in all of the IMPDHs examined to date. The enzyme is unusual in that a large conformational change occurs in the middle of a catalytic cycle.

IMPDH is ubiquitous in eukaryotes, bacteria and protozoa [Y. Natsumeda & S. F. Carr, Ann. N.Y. Acad., 696, pp. 88-93 (1993)]. The prokaryotic forms share 30-40% sequence identity with the human enzyme. Two isoforms of human IMPDH, designated type I and type II, have been identified and sequenced [F. R. Collart and E. Huberman, J. Biol. Chem., 263, pp. 15769-15772, (1988); Y. Natsumeda et al., J. Biol. Chem., 265, pp. 5292-5295, (1990)]. Each is 514 amino acids, and they share 84% sequence identity. Both IMPDH type I and type II form active tetramers in solution, with subunit molecular weights of 56 kDa [Y. Yamada et al., Biochemistry, 27, pp. 2737-2745 (1988)].

The de novo synthesis of guanine nucleotides, and thus the activity of IMPDH, is particularly important in B- and T-lymphocytes. These cells depend on the de novo, rather than salvage pathway to generate sufficient levels of nucleotides necessary to initiate a proliferative response to mitogen or antigen [A. C. Allison et al., Lancet II, 1179, (1975) and A. C. Allison et al., Ciba Found. Symp., 48, 207, (1977)].

Thus, IMPDH is an attractive target for selectively inhibiting the immune system without also inhibiting the proliferation of other cells.

Immunosuppression has been achieved by inhibiting a variety of enzymes including, for example, the phosphatase calcineurin (inhibited by cyclosporin and FK-506); dihydroorotate dehydrogenase, an enzyme involved in the biosynthesis of pyrimidines (inhibited by leflunomide and brequinar); the kinase FRAP (inhibited by rapamycin); and the heat shock protein hsp70 (inhibited by deoxyspergualin). [See B. D. Kahan, Immunological Reviews, 136, pp. 29-49 (1993); R. E. Morris, The Journal of Heart and Lung Transplantation, 12(6), pp. S275-S286 (1993)].

Inhibitors of IMPDH are also known. U.S. Pat. No. 5,380,879 (incorporated by reference) and U.S. Pat. No. 5,444,072 (incorporated by reference) and PCT publications WO 94/01105 and WO 94/12184 describe mycophenolic acid (MPA) and some of its derivatives as potent, uncompetitive, reversible inhibitors of human IMPDH type I ($K_i$=33 nM) and type II ($K_i$=9 nM). MPA has been demonstrated to block the response of B- and T-cells to mitogen or antigen [A. C. Allison et al., Ann. N.Y. Acad. Sci., 696, 63, (1993)].

Immunosuppressants, such as MPA, are useful drugs in the treatment of transplant rejection and autoimmune diseases. [R. E. Morris, Kidney Intl., 49, Suppl. 53, S-26, (1996)]. However, MPA is characterized by undesirable pharmacological properties, such as gastrointestinal toxicity and poor bioavailability. [L. M. Shaw, et al., Therapeutic Drug Monitoring, 17, pp. 690-699, (1995)].

A novel noncompetitive inhibitor of IMPDH, merimepodib, has immunosuppressive activity, is orally bioavailable, and inhibits the proliferation of primary human, mouse, rat, and dog lymphocytes at concentrations of ~100 nM. Studies have demonstrated that merimepodib a potent, specific, and reversible IMPDH inhibitor that selectively inhibits lymphocyte proliferation. It is currently in clinical trials to treat hepatitis C virus.

Nucleoside analogs such as tiazofurin, ribavirin and mizoribine also inhibit IMPDH [L. Hedstrom, et al. Biochemistry, 29, pp. 849-854 (1990); L. Hedstrom, et al. Curr. Med. Chem. 1999, 6, 545-561]. These compounds require activation to either the adenine dinucleotide (tiazofurin) or monophosphate derivatives (ribavirin and mizoribine) that inhibit IMPDH. These activation pathways are often absent in the cell of interest. In addition, nucleoside analogs suffer from lack of selectivity and can be further metabolized to produce inhibitors of other enzymes. Therefore, nucleoside analogs are prone to toxic side effects.

Mycophenolate mofetil, a prodrug which quickly liberates free MPA in vivo, was recently approved to prevent acute renal allograft rejection following kidney transplantation. [L. M. Shaw, et al., Therapeutic Drug Monitoring, 17, pp. 690-699, (1995); H. W. Sollinger, Transplantation, 60, pp. 225-232 (1995)]. Several clinical observations, however, limit the therapeutic potential of this drug. [L. M. Shaw, et al., Therapeutic Drug Monitoring, 17, pp. 690-699, (1995)]. MPA is rapidly metabolized to the inactive glucuronide in vivo. [A. C. Allison and E. M. Eugui, Immunological Reviews, 136, pp. 5-28 (1993)]. The glucuronide then undergoes enterohepatic recycling causing accumulation of MPA in the gastrointestinal tract where it cannot exert its IMPDH inhibitory activity on the immune system. This fact effectively lowers the drug's in vivo potency, while increasing its undesirable gastrointestinal side effects.

IMPDH also plays a role in other physiological events. Increased IMPDH activity has been observed in rapidly proliferating human leukemic cell lines and other tumor cell lines, indicating IMPDH as a target for anti-cancer as well as immunosuppressive chemotherapy [M. Nagai et al., Cancer Res., 51, pp. 3886-3890, (1991)]. IMPDH has also been shown to play a role in the proliferation of smooth muscle cells, indicating that inhibitors of IMPDH, such as MPA, may be useful in preventing restenosis or other hyperproliferative vascular diseases [C. R. Gregory et al., Transplantation, 59, pp. 655-61 (1995); PCT publication WO 94/12184; and PCT publication WO 94/01105].

Additionally, IMPDH has been shown to play a role in viral replication in some viral cell lines. [S. F. Carr, J. Biol. Chem., 268, pp. 27286-27290 (1993)]. Analogous to lymphocyte and tumor cell lines, the implication is that the de novo, rather than the salvage, pathway is critical in the process of viral replication.

Cryptosporidiosis is a severe gastrointestinal disease caused by protozoan parasites of the genus *Cryptosporidium*. The most common causes of human disease are *C. parvum* and *C. hominis*, though disease can also result from *C. felis, C. meleagridis, C. canis,* and *C. muris* infection. Small children, pregnant women, the elderly, and immunocompromised people (e.g., AIDS patients) are at risk of severe, chronic and often fatal infection. [Carey, C. M., Lee, H., and Trevors, J. T., Water Res., 38, 818-62 (2004); and Fayer, R., Veterinary Parasitology, 126, 37-56 (2004)]. The *Cryptosporidium* parasites produce spore-like oocysts that are highly resistant to water chlorination. Several large outbreaks in the U.S. have been linked to drinking and recreational water. Infection rates are extremely high, with disease manifest in 30% of exposed individuals and a 50-70% mortality rate among immuno-compromised individuals. Furthermore, there is a growing and credible concern that these organisms could be deliberately introduced into the water supply in an act of bioterrorism. Effective drugs are urgently needed for the management of cryptosporidiosis in AIDS patients and/or epidemic outbreaks.

All parasitic protozoa lack purine biosynthetic enzymes and must salvage purines from their hosts, making this pathway an extremely attractive target for developing anti-protozoal drugs. IMPDH is a key enzyme in the purine salvage pathway of *C. parvum*. As discussed above, IMPDH is a validated drug target in immunosuppressive, cancer and viral therapy, so the human enzymes are extremely well studied. It has recently been shown that *C. parvum* IMPDH has very different properties than the human enzymes and that IMPDH inhibitors block parasite proliferation in vivo [N. N. Umejiego et al., J Biol Chem, 279 pp. 40320-40327 (2004); and B. Striepen et al., Proc Natl Acad Sci USA, 101 pp. 3154-9 (2004)].

Thus, there exists a need for potent IMPDH inhibitors with improved pharmacological properties and selectivities. Such inhibitors should have therapeutic potential as immunosuppressants, anti-cancer agents, anti-vascular hyperproliferative agents, antiinflammatory agents, antifungal agents, antipsoriatic and anti-viral agents. Specifically, there is a need for selective IMPDH inhibitors that can slow or block parasite and bacterial proliferation. The present invention fulfills this need and has other related advantages.

SUMMARY OF THE INVENTION

One aspect of the present invention relates to compounds, and pharmaceutically acceptable salts and prodrugs thereof, which are useful as inhibitors of IMPDH. In certain embodiments, a compound of the invention selectively inhibits a parasitic IMPDH versus a host (e.g., mammalian) IMPDH.

Further, the invention provides pharmaceutical compositions comprising one or more compounds of the invention. The invention also relates to methods of treating various parasitic and bacterial infections in mammals. Moreover, the compounds may be used alone or in combination with other therapeutic or prophylactic agents, such as anti-virals, anti-inflammatory agents, antimicrobials and immunosuppressants.

BRIEF DESCRIPTION OF THE FIGURES

FIG. 1 depicts triazole compounds 1-7 and their respective $IC_{50}$ values against recombinant *C. parvum* IMPDH.

FIG. 2 depicts triazole compounds 8-14 and their respective $IC_{50}$ values against recombinant *C. parvum* IMPDH.

FIG. 3 depicts triazole compounds 15-21 and their respective $IC_{50}$ values against recombinant *C. parvum* IMPDH.

FIG. 4 depicts triazole compounds 22-28 and their respective $IC_{50}$ values against recombinant *C. parvum* IMPDH.

FIG. 5 depicts triazole compounds 29-34 and their respective $IC_{50}$ values against recombinant *C. parvum* IMPDH.

FIG. 6 depicts triazole compounds 35-39 and their respective $IC_{50}$ values against recombinant *C. parvum* IMPDH.

FIG. 11 depicts oxadiazole compound 52 and its $IC_{50}$ value against recombinant *C. parvum* IMPDH.

FIG. 12 depicts amide compounds 53-57 and their respective $IC_{50}$ values against recombinant *C. parvum* IMPDH.

FIG. 13 depicts amide compounds 58-67 and their respective $IC_{50}$ values against recombinant *C. parvum* IMPDH.

FIG. 14 depicts amide compounds 68-76 and their respective $IC_{50}$ values against recombinant *C. parvum* IMPDH.

FIG. 15 depicts amide and ester compounds 77-85 and their respective $IC_{50}$ values against recombinant *C. parvum* IMPDH.

FIG. 16 depicts amide compounds 86-95 and their respective $IC_{50}$ values against recombinant *C. parvum* IMPDH.

FIG. 17 depicts amide compounds 96-104 and their respective $IC_{50}$ values against recombinant *C. parvum* IMPDH.

FIG. 18 depicts amide compounds 105-113 and their respective $IC_{50}$ values against recombinant *C. parvum* IMPDH.

FIG. 19 depicts amide and ketone compounds 114-120 and their respective $IC_{50}$ values against recombinant *C. parvum* IMPDH.

FIG. 20 depicts amide compounds 121-122 and their respective $IC_{50}$ values against recombinant *C. parvum* IMPDH.

FIG. 21 depicts amide compounds 123-124 and their respective IC$_{50}$ values against recombinant *C. parvum* IMPDH.

FIG. 22 depicts amide compounds 125-129 and their respective IC$_{50}$ values against recombinant *C. parvum* IMPDH.

FIG. 23 depicts amide compounds 130-134 and their respective IC$_{50}$ values against recombinant *C. parvum* IMPDH.

FIG. 24 depicts compounds 135-140 and their respective IC$_{50}$ values against recombinant *C. parvum* IMPDH.

FIG. 25 depicts amide compounds 141-145 and their respective IC$_{50}$ values against recombinant *C. parvum* IMPDH.

FIG. 26 depicts compounds 146-148 and their respective IC$_{50}$ values against recombinant *C. parvum* IMPDH.

FIG. 27 depicts amide compounds 149-152 and their respective IC$_{50}$ values against recombinant *C. parvum* IMPDH.

FIG. 28 depicts amide compounds 153-156 and their respective IC$_{50}$ values against recombinant *C. parvum* IMPDH.

FIG. 29 depicts amide compounds 157-160 and their respective IC$_{50}$ values against recombinant *C. parvum* IMPDH.

FIG. 30 depicts amide compounds 161-162 and their respective IC$_{50}$ values against recombinant *C. parvum* IMPDH.

FIG. 31 depicts amide compounds 163-167 and their respective IC$_{50}$ values against recombinant *C. parvum* IMPDH.

FIG. 32 depicts amide compounds 168-172 and their respective IC$_{50}$ values against recombinant *C. parvum* IMPDH.

FIG. 33 depicts amide compounds 173-177 and their respective IC$_{50}$ values against recombinant *C. parvum* IMPDH.

FIG. 34 depicts amide, ester, and ketone compounds 178-185 and their respective IC$_{50}$ values against recombinant *C. parvum* IMPDH.

FIG. 37 depicts triazole compounds A111-A113 and their respective IC$_{50}$ values against recombinant *C. parvum* IMPDH.

FIG. 38 depicts triazole compounds A114-A119 and their respective IC$_{50}$ values against recombinant *C. parvum* IMPDH.

FIG. 39 depicts amide compounds C68-C70 and their respective IC$_{50}$ values against recombinant *C. parvum* IMPDH.

Figure 40:
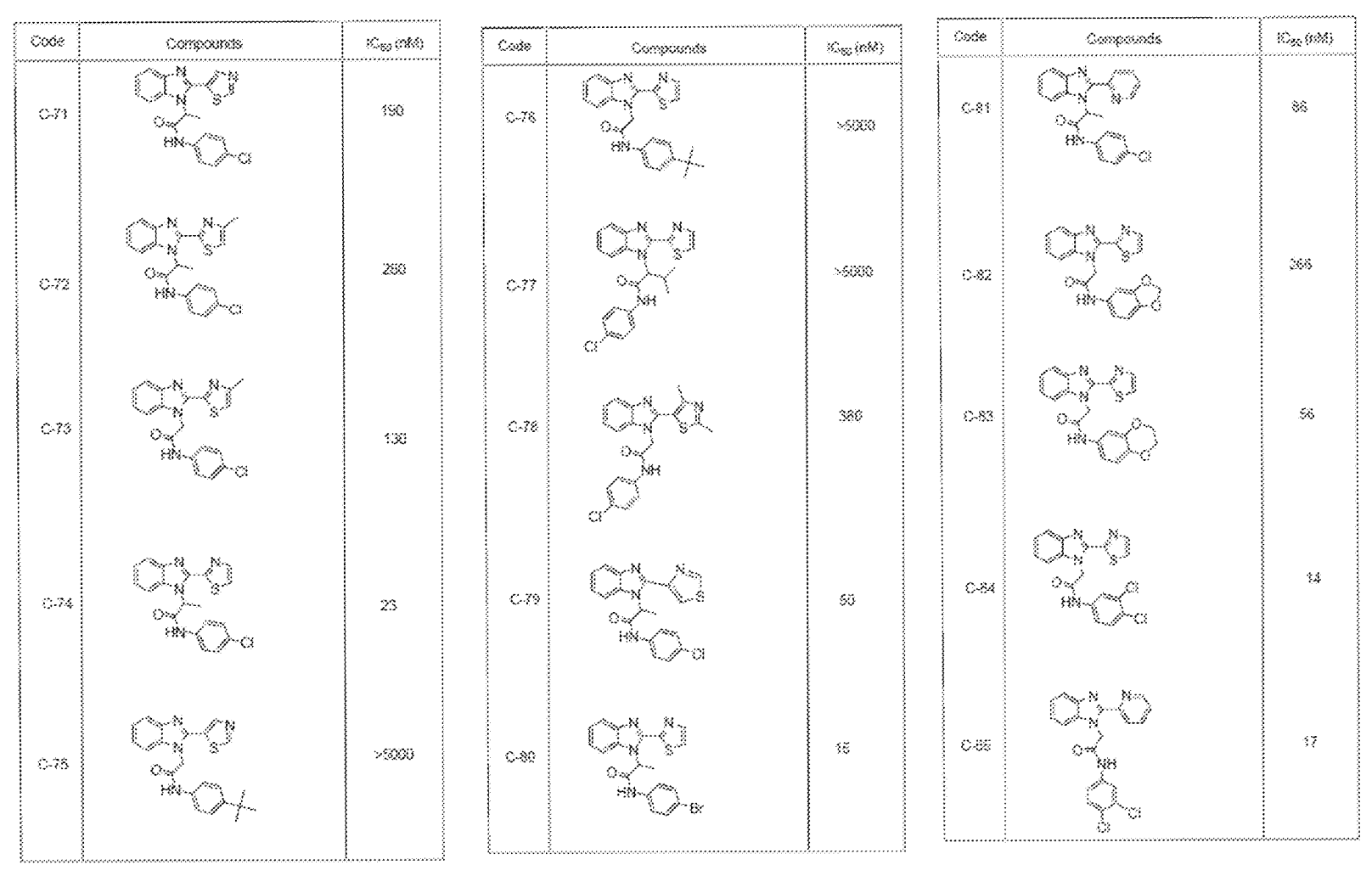

FIG. 40 depicts amide compounds C71-C85 and their respective IC$_{50}$ values against recombinant *C. parvum* IMPDH.

FIG. 41 depicts amide compounds C86-C100 and their respective IC$_{50}$ values against recombinant *C. parvum* IMPDH.

Figure 42:
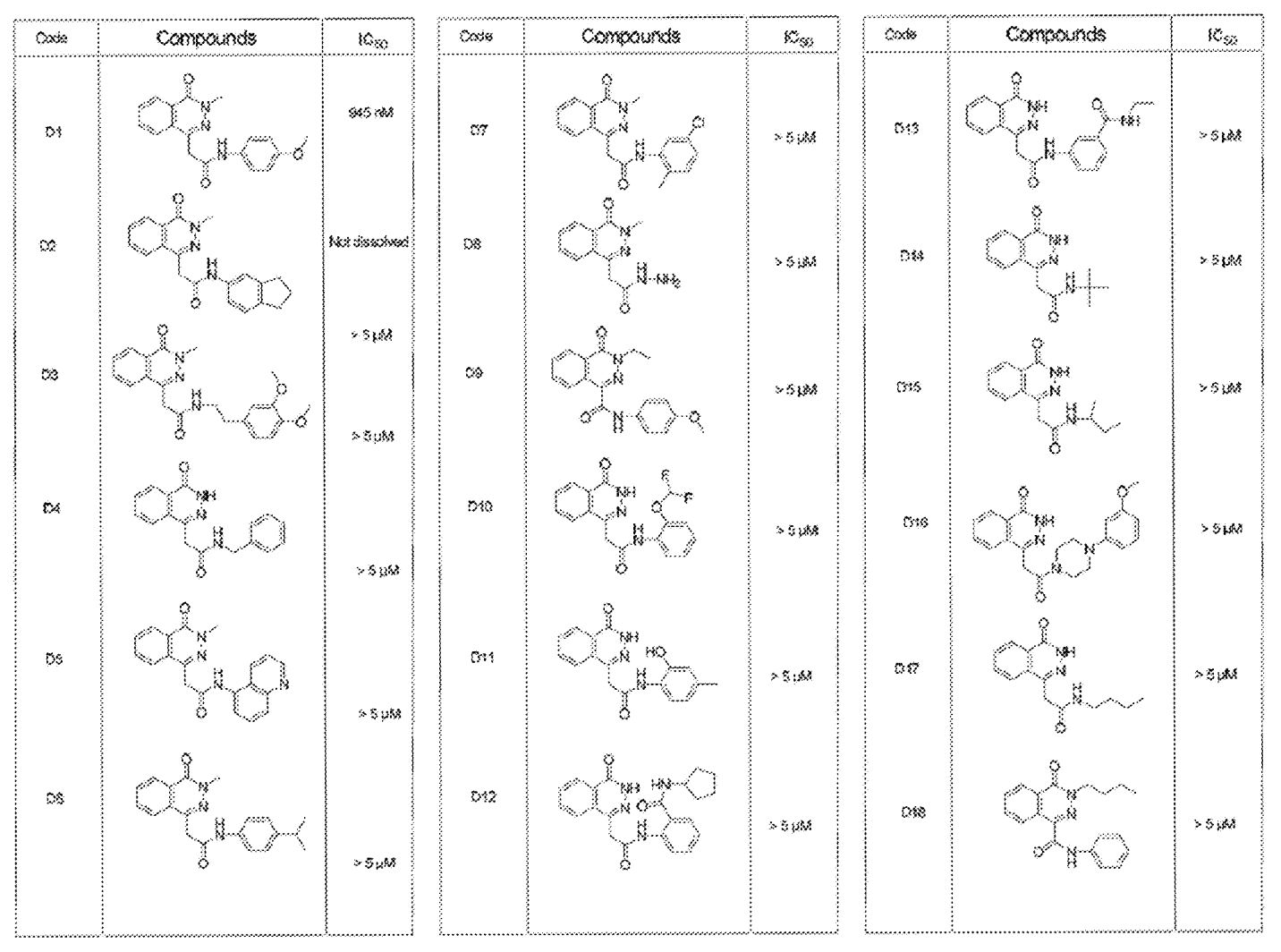

FIG. 42 depicts phthalazinone compounds D1-D18 and their respective IC$_{50}$ values against recombinant *C. parvum* IMPDH.

Figure 44:
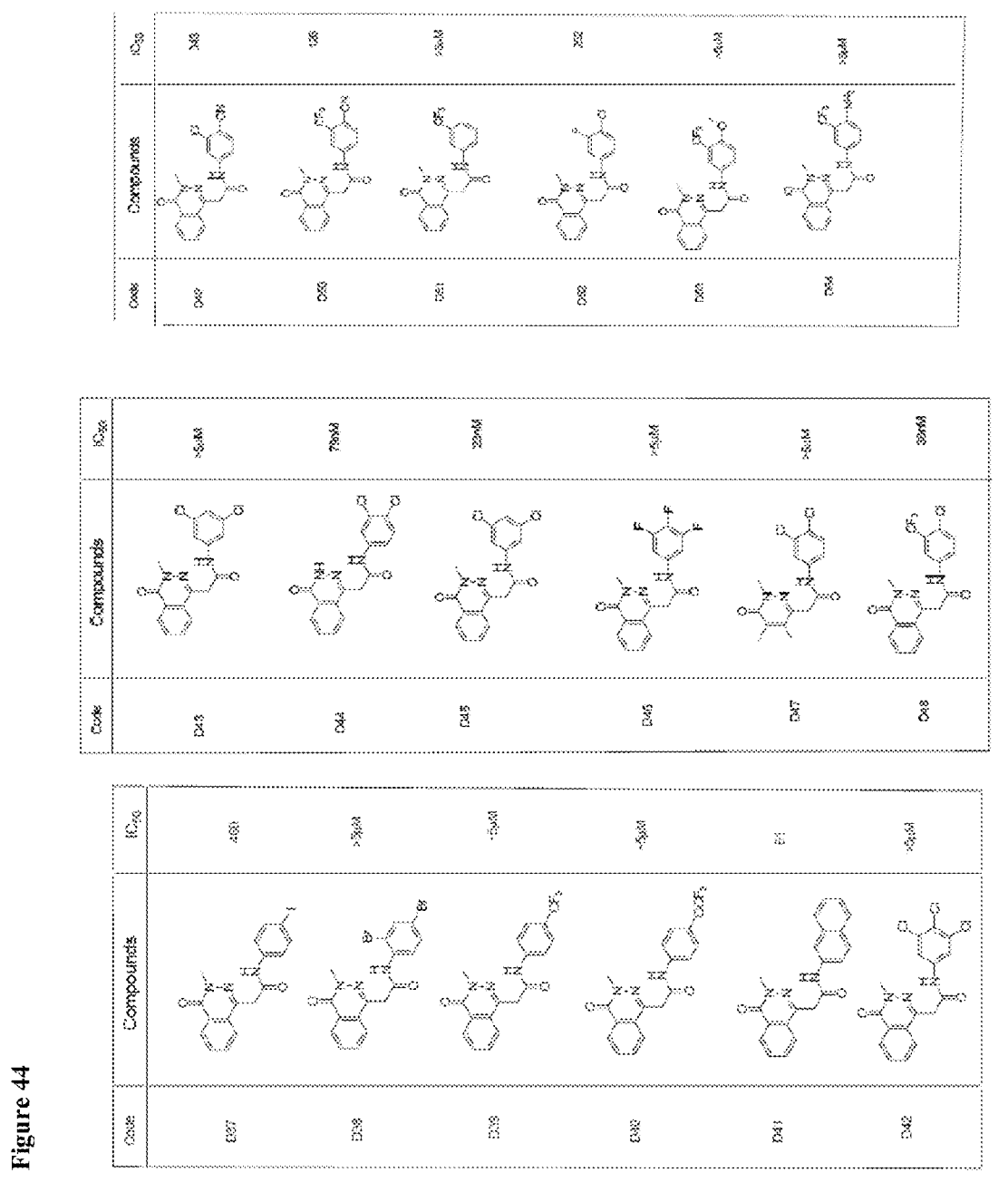

FIG. 44 depicts phthalazinone compounds D37-D54 and their respective IC$_{50}$ values against recombinant *C. parvum* IMPDH.

Figure 46:
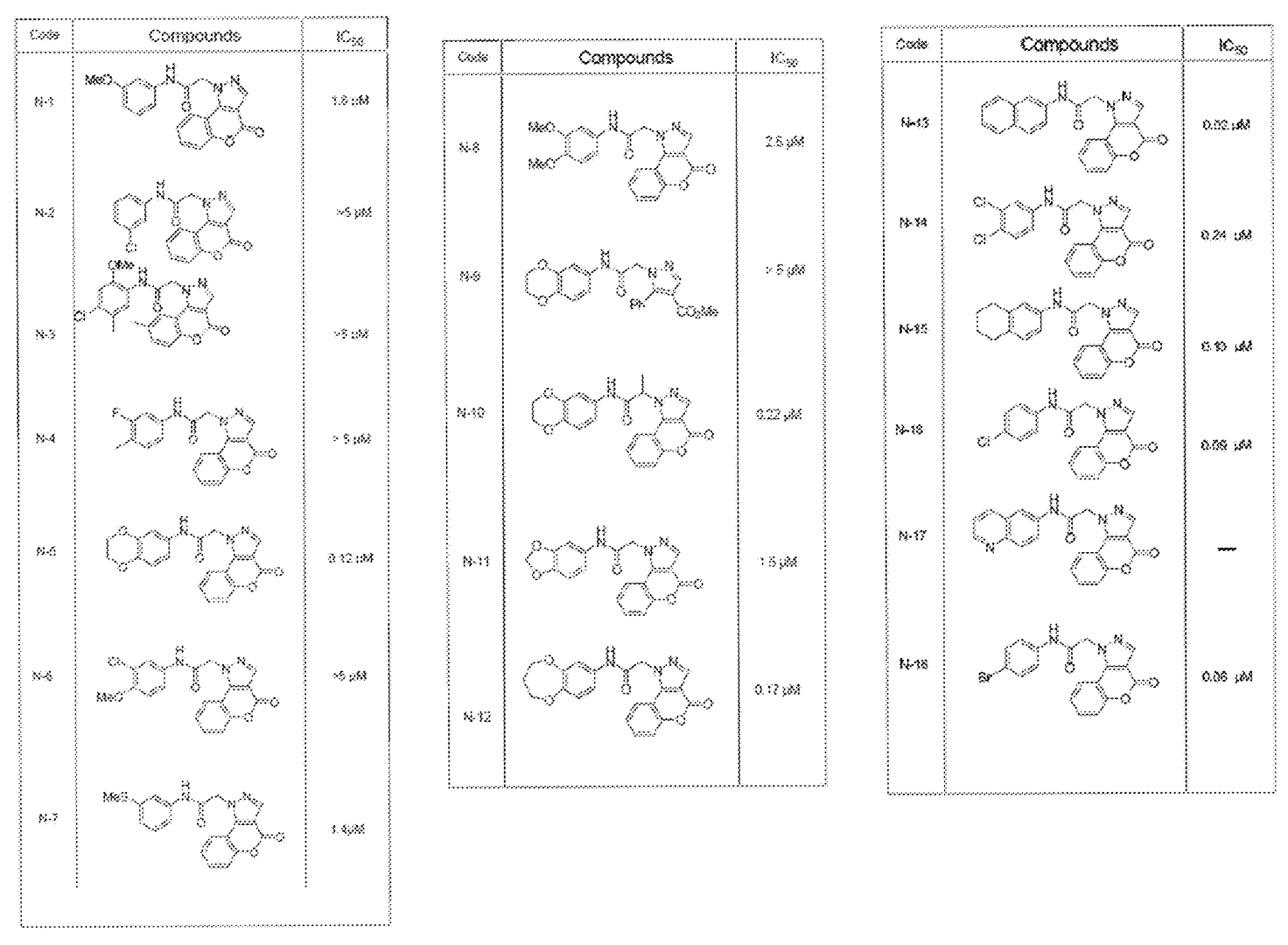

FIG. 46 depicts pyrazole compounds N1-N18 and their respective IC$_{50}$ values against recombinant *C. parvum* IMPDH.

Figure 47:
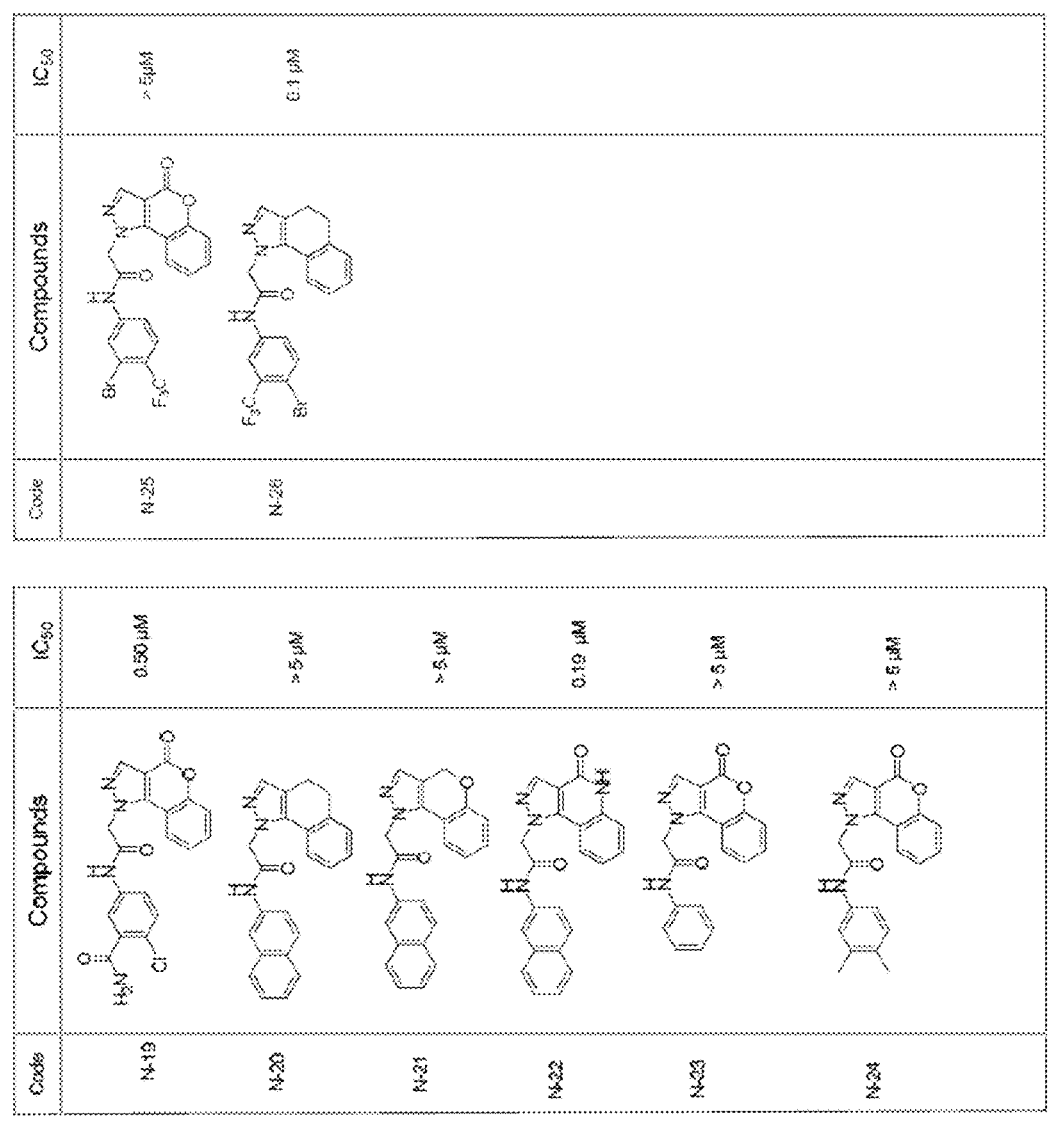

FIG. 47 depicts pyrazole compounds N19-N26 and their respective IC$_{50}$ values against recombinant *C. parvum* IMPDH.

Figure 48:
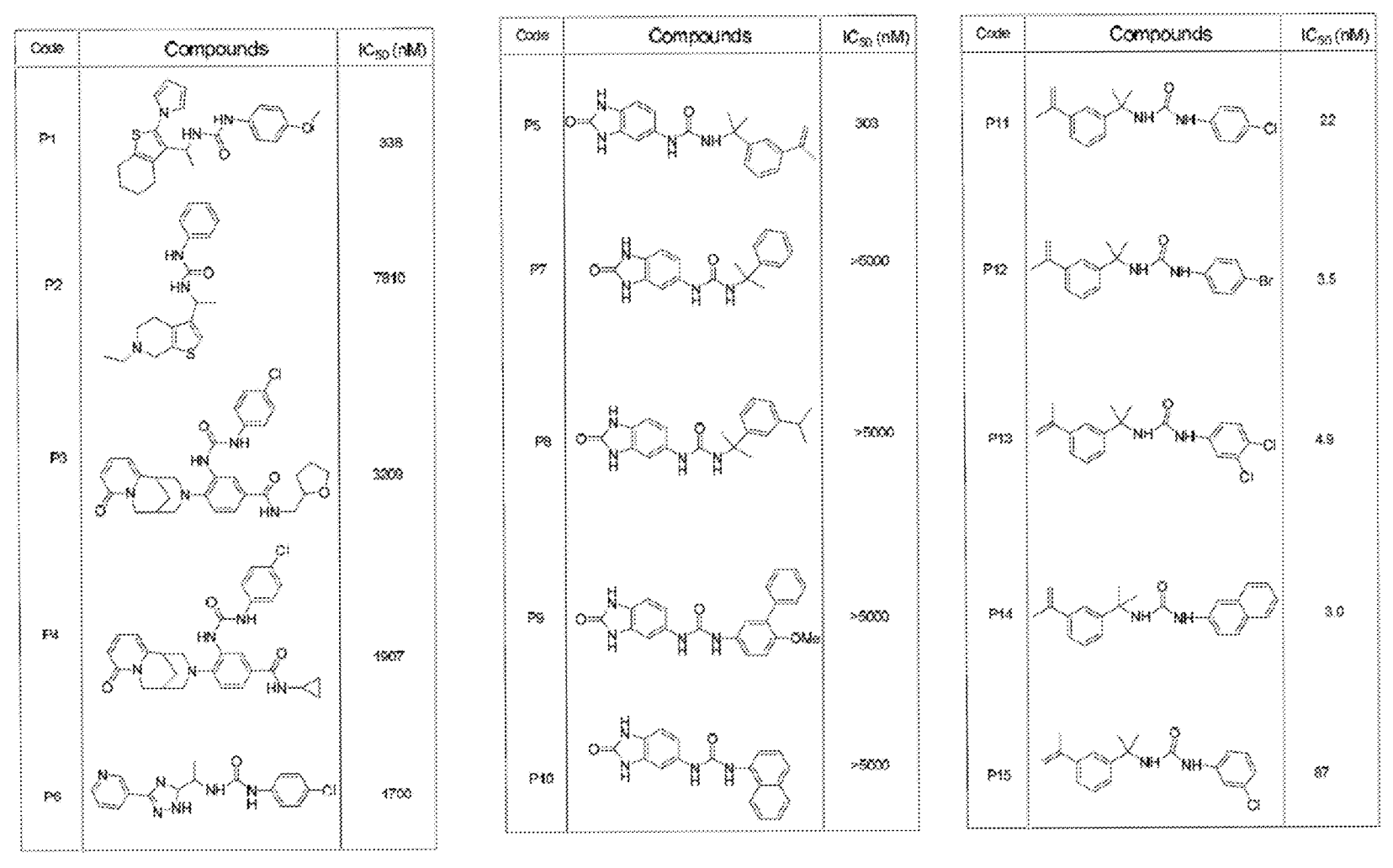

FIG. 48 depicts urea compounds P1-P15 and their respective IC$_{50}$ values against recombinant *C. parvum* IMPDH.

Figure 49:
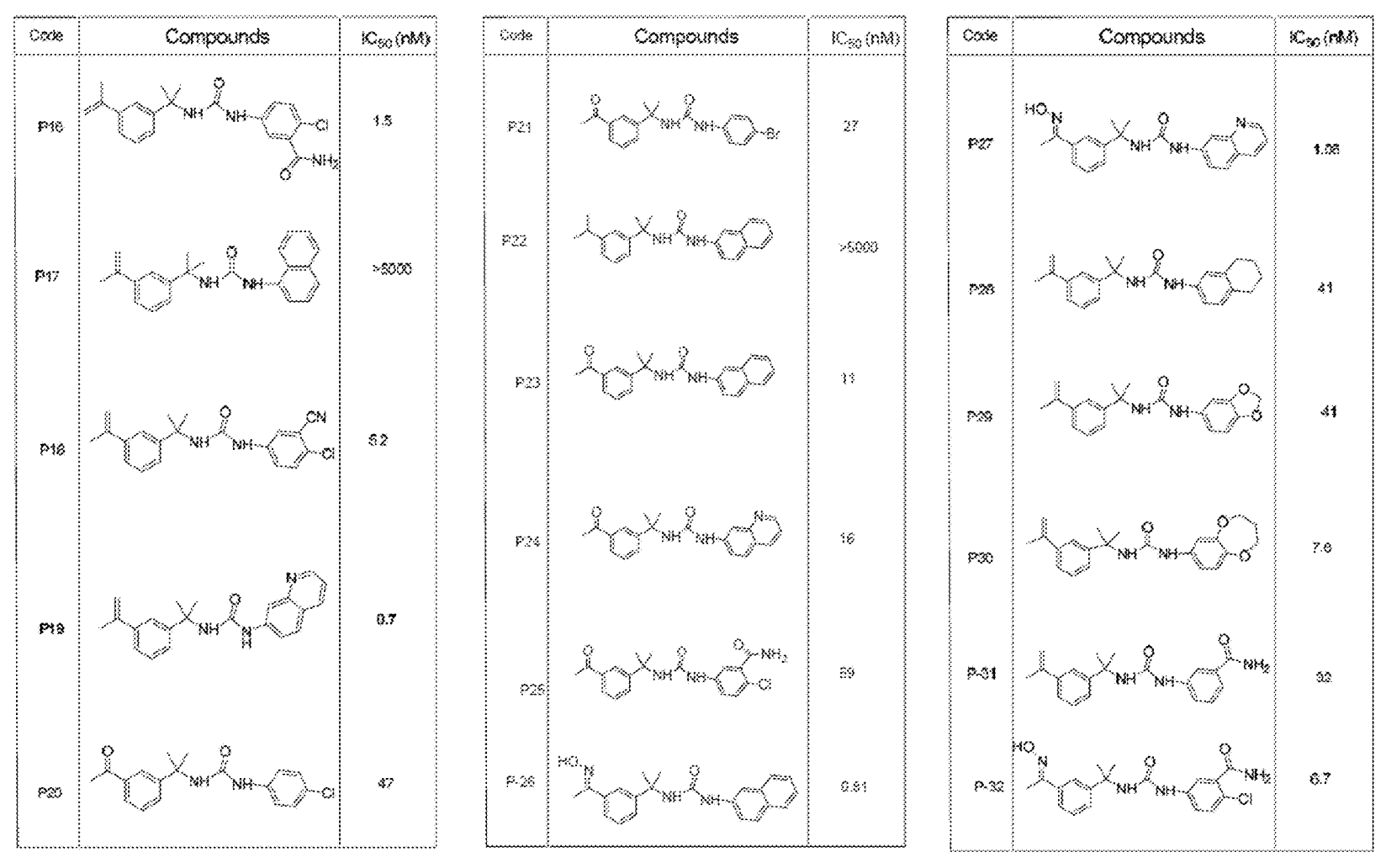

FIG. 49 depicts urea compounds P16-P32 and their respective IC$_{50}$ values against recombinant *C. parvum* IMPDH.

Figure 50:
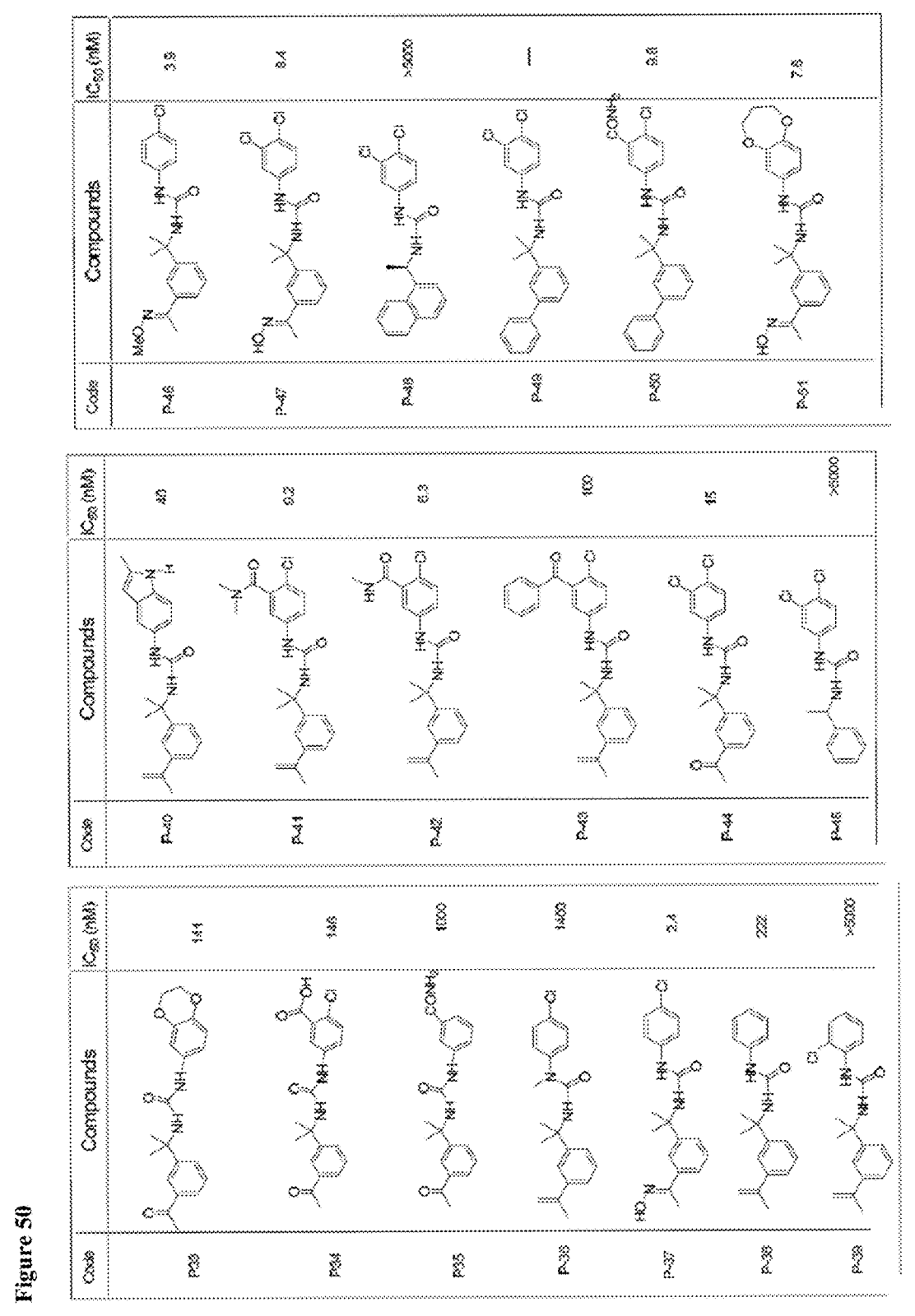

FIG. 50 depicts urea compounds P33-P51 and their respective IC$_{50}$ values against recombinant *C. parvum* IMPDH.

Figure 51:
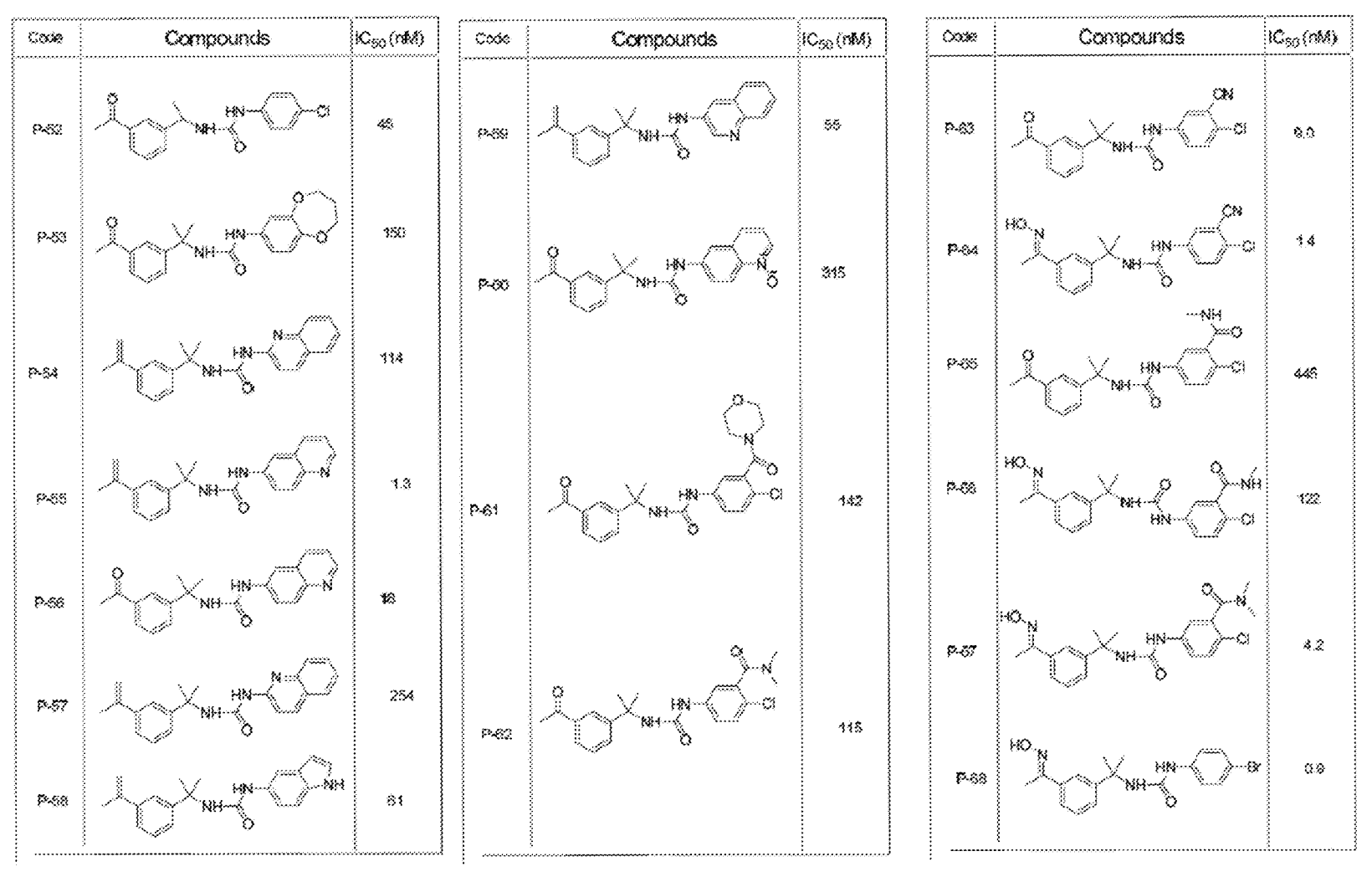

FIG. 51 depicts urea compounds P52-P68 and their respective IC$_{50}$ values against recombinant *C. parvum* IMPDH.

Figure 52:
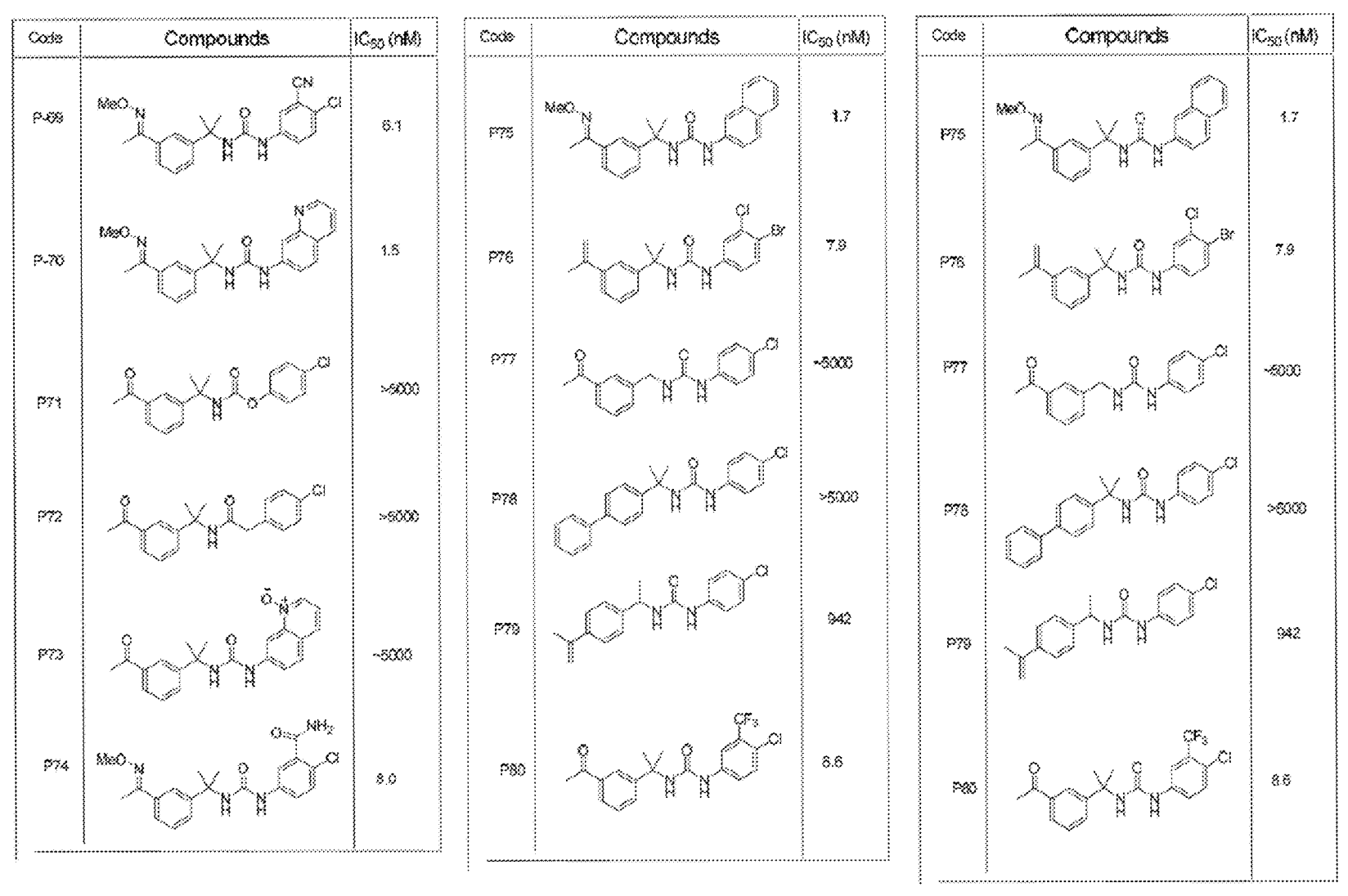

FIG. 52 depicts urea compounds P69-P80 and their respective IC$_{50}$ values against recombinant *C. parvum* IMPDH.

Figure 53:
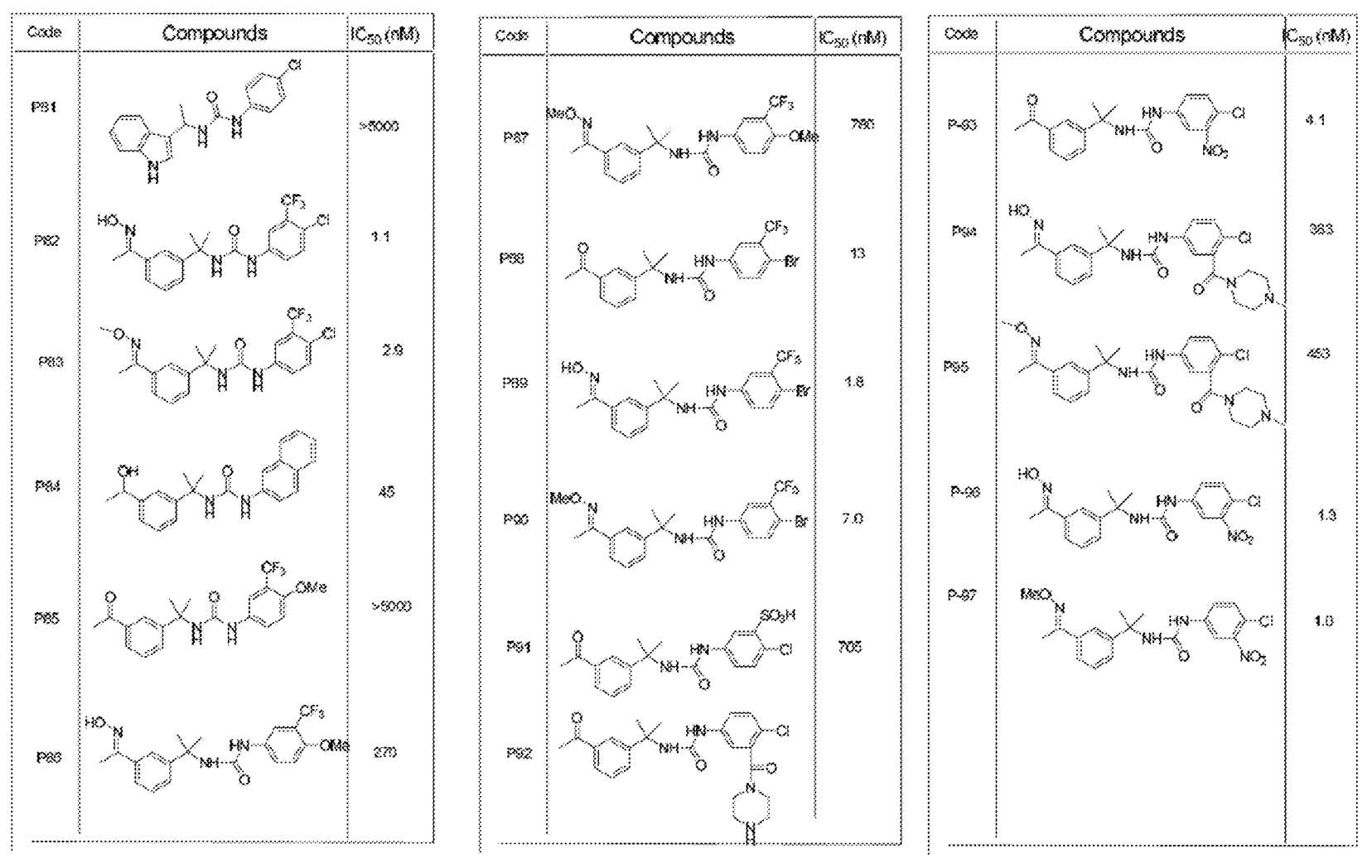

FIG. 53 depicts urea compounds P81-P97 and their respective IC$_{50}$ values against recombinant *C. parvum* IMPDH.

Figure 54:
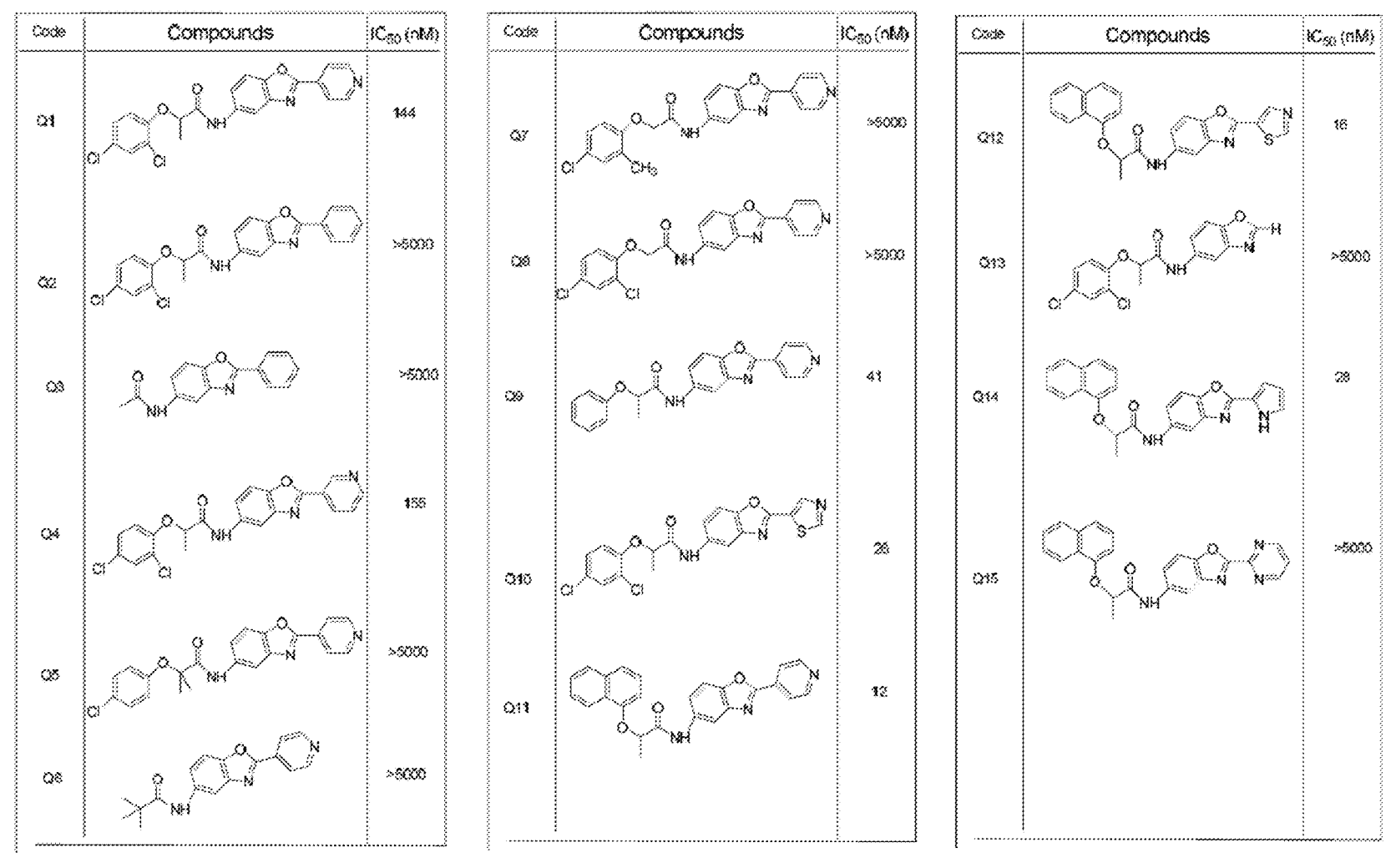

FIG. 54 depicts benzoxazole compounds Q1-Q15 and their respective IC$_{50}$ values against recombinant *C. parvum* IMPDH.

FIG. 55 tabulates inhibition of recombinant *C. parvum* IMPDH (CpIMPDH) and human IMPDH type 2 (hIMPDH2). b. ≤20% inhibition at 50 μM; c. ≤20% inhibition at 5 μM; d. ≤10% inhibition at 5 μM; e. ≤20% inhibition observed at 2 μM.

FIG. 56 tabulates the results of metabolic and plasma stability studies on various compounds of the invention.

FIG. 62A-D tabulates data for various compounds in enzyme assays (in the absence and presence of BSA), surrogate T. gondii model assay, host cell growth and tissue culture model of C. parvum infection. N.A., not applicable; N.D., not determined. a. Selectivity=T. gondii-CpIMPDH $EC_{50}$ versus wild-type T. gondii $EC_{50}$; b. highest concentration tested; c. Maurya et al.; d. lowest concentration tested; e. Umejiego et al.; f. qPCR assay.

FIG. 67 tabulates the inhibition of various IMPDHs by compounds A-H. Cp, *C. parvum*; Hp, *Helicobacter pylori*; Bb, *Borrelia burgdorferi*; Sp, *Streptococcus pylori*; ECIMPDH S250A/L444Y, *Escherichia coli* IMPDH containing an alanine residue at serine-240 and a leucine residue at tyrosine-444. These compounds (100 µM) do not inhibit IMPDHs from *E. coli, Leishmania donovanii* and *Tritrichomonas foetus*. "Intrinsic" values (adjusted for the competition with the mobile flap) are shown in parentheses.

DETAILED DESCRIPTION

Overview

Figure 7:
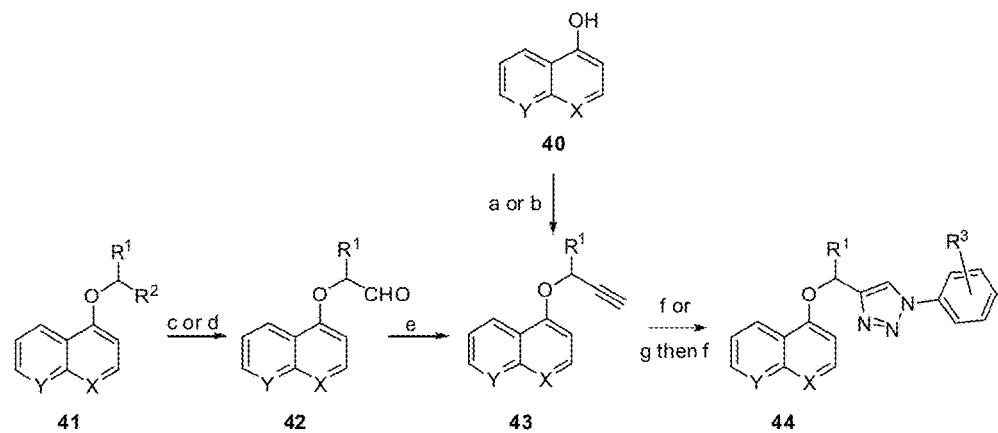
FIG. 7 depicts a general scheme for the preparation of various 1,2,3-triazoles. Reagents and conditions: X and Y=N, CH, or CCl. (a) [$R^1$=Me]MeCH(OH)CCH, 0° C., $Ph_3P$, 10 min, DEAD, rt, 12 h; (b) [$R^1$=H]BrCHCCH, $K_2CO_3$, DMF, rt, 12 h; (c) [$R^1$=i-Pr, $R^2$=$CO_2H$](i) $LiAlH_4$, THF, 0° C., 4 h, (ii) $(COCl)_2$, DMSO, DCM, $Et_3N$, −78° C., 3 h; (d) [$R^1$=Et, $R^2$=$CO_2Et$] DIBAL, THF, −78° C., 6 h; (e) (i) $CBr_4$, $Ph_3P$, DCM, 0° C., 2 h, (ii) n-BuLi, THF, −78° C., 2 h; (f) $R^3PhN_3$, $CH_3CN$, DIPA, CuI, rt, 30 min; (g) m-CPBA, DCM, 0° C., 12 h.

One aspect of the present invention relates to compounds, and pharmaceutically acceptable salts and prodrugs thereof, which are useful as inhibitors of IMPDH. In certain embodiments, a compound of the invention selectively inhibits a parasitic or bacterial IMPDH versus a host (e.g., mammalian) IMPDH. In certain embodiments, the present invention relates to selective inhibition of *Cryptosporidium* IMPDH in the presence of human inosine-5'-monophosphate-dehydrogenase (IMPDH type I and type II). Further, the invention provides pharmaceutical compositions comprising one or more compounds of the invention. The invention also relates to methods of treating various parasitic and bacterial infections in mammals. Moreover, the compounds may be used alone or in combination with other therapeutic or prophylactic agents, such as anti-virals, anti-inflammatory agents, antimicrobials and immunosuppressants.

IMPDH-Mediated Diseases.

IMPDH-mediated disease refers to any disease state in which the IMPDH enzyme plays a regulatory role in the metabolic pathway of that disease. Examples of IMPDH-mediated disease include transplant rejection and autoimmune diseases, such as rheumatoid arthritis, multiple sclerosis, juvenile diabetes, asthma, and inflammatory bowel disease, as well as other inflammatory diseases, cancer, viral replication diseases and vascular diseases.

For example, the compounds, compositions and methods of using them of the invention may be used in the treatment of transplant rejection (e.g., kidney, liver, heart, lung, pancreas (islet cells), bone marrow, cornea, small bowel and skin allografts and heart valve xenografts) and autoimmune diseases, such as rheumatoid arthritis, multiple sclerosis, juvenile diabetes, asthma, inflammatory bowel disease (Crohn's disease, ulcerative colitus), lupus, diabetes, mellitus myasthenia gravis, psoriasis, dermatitis, eczema, seborrhea, pulmonary inflammation, eye uveitis, hepatitis, Grave's disease, Hashimoto's thyroiditis, Behcet's or Sjorgen's syndrome (dry eyes/mouth), pernicious or immuno-haemolytic anaemia, idiopathic adrenal insufficiency, polyglandular autoimmune syndrome, and glomerulonephritis, scleroderma, lichen planus, viteligo (depigmentation of the skin), autoimmune thyroiditis, and alveolitis, inflammatory diseases such as osteoarthritis, acute pancreatitis, chronic pancreatitis, asthma and adult respiratory distress syndrome, as well as in the treatment of cancer and tumors, such as solid tumors, lymphomas and leukemia, vascular diseases, such as restenosis, stenosis and artherosclerosis, and DNA and RNA viral replication diseases, such as retroviral diseases, and herpes.

Selective Inhibition of Microbial IMPDH.

IMPDH enzymes are also known to be present in bacteria, fungi, and protozoans and thus may regulate microbial growth. As such, the IMPDH-inhibitor compounds, compositions and methods described herein may be useful as antibacterials, antifungals, and/or antiprotozoans, either alone or in combination with other antimicrobial agents.

Microbial inhibition can be measured by various methods, including, for example, IMPDH HPLC assays (measuring enzymatic production of XMP and NADH from IMP and NAD), IMPDH spectrophotometric assays (measuring enzymatic production of NADH from NAD or XMP from IMP), IMPDH fluorometric assays (measuring enzymatic production of NADH from NAD), IMPDH radioassays (measuring enzymatic production of radiolabeled XMP from radiolabeled IMP or tritium release into water from 2-$^3$H-IMP). [See C. Montero et al., Clinica Chimica Acta, 238, pp. 169-178 (1995)]. Additional assays known in the art can be used in ascertaining the degree of activity of an inventive compound as an IMPDH inhibitor. For example, activity of IMPDH I and IMPDH II can be measured following an adaptation of the method described in WO 97/40028. [See, additionally, U.S. Patent Application 2004/0102497 (incorporated by reference)].

Accordingly, in certain embodiments, the inventive compounds are capable of targeting and selectively inhibiting the IMPDH enzyme in bacteria. It is known that knocking out the IMPDH gene makes some bacteria avirulent, while has no effect on others. The effectiveness probably depends on which salvage pathways are operational in a given bacteria, and the environmental niche of the infection. It has been shown that IMPDHs from *H. pylori, S. pyogenes* and *B. burgdorferi* are sensitive to the inhibitors of the invention, and that the growth of *H. pylori* is blocked by inhibitors of the invention. It is also expected that various *Campylobacter, Arcobacter, Bacteroides, Fusobacterium, Burkholderia, Clostridia, Neisseria, Mycobacterium,* or *Acinetobacter* organisms will be inhibited by the compounds described herein. Organisms belonging to these genera are responsible for illnesses such as ulcers and acid reflux (*H. pylori*), Lyme disease (*B. burgdorferi*), infection (*S. pyogenes*), food poisoning (*C. jejuni* and *A. butzleri*), abscesses (*B. capillosis*), periodontitis (*F. nucleatum*), skin ulcers (*F. nucleatum*), Lemierre's syndrome (*F. nucleatum*), infection in cystic fibrosis (*B. cenocepacia*), pneumonia (*S. pneumoniae*), botulism (*C. botulinum*), gonorrhea (*N. gonorrhoeae*), tuberculosis (*M. tuberculosis*), leprosy (*M. leprae*), and drug resistant infection (*A. baumannii*). In addition, *Staphylococcus* and *Bacillus anthracis* are sensitive to mycophenolic acid, suggesting that IMPDH inhibitors of the invention may also be effective against these bacteria.

In addition, in certain embodiments, these compounds are capable of targeting and selectively inhibiting the IMPDH enzyme in fungi, as evidenced by the mycophenolic acid sensitivity of *Saccharomyces cerevisiae, Candida albicans, Cryptococcus neoformans, Aspergillus flavus* and *Trichophyton*.

Further, in certain embodiments, the inventive compounds are capable of targeting and selectively inhibiting the IMPDH enzyme in protozoans, such as *Toxoplasma, Eimeria, Cryptosporidium, Plasmodium, Babesia, Theileria, Neospora, Sarcocystis, Giardia, Entamoeba, Trichomonas, Leishmania* and *Trypanosoma*. In certain embodiments, these compounds are capable of targeting and selectively inhibiting the IMPDH enzyme in *Cryptosporidium parvum* and other *Cryptosporidium* species.

Selected Compounds of the Invention.

Triazole Series

In certain embodiments, the invention relates to a compound, or a pharmaceutically acceptable salt thereof, represented by Formula I:

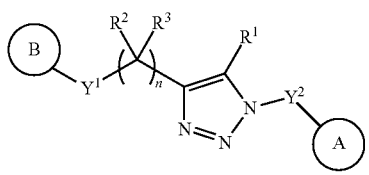

Formula I wherein, independently for each occurrence, $R^1$ is hydrogen, alkyl, aryl, heteroaryl, aralkyl, or heteroaralkyl;

$R^2$ is hydrogen or alkyl;

or $R^1$ and an instance of $R^2$ taken together with the carbon atoms to which they are attached form a 5-, 6-, or 7-membered aryl or heteroaryl ring;

$R^3$ is hydrogen or alkyl;

$Y^1$ is absent, O, or $NR^4$;

$Y^2$ is absent, O, $NR^4$, alkylene, $-(CH_2)_m-O-(CH_2)_p-$, $-(CH_2)_m-NR^4-(CH_2)_p-$, $-(CH_2)_m-C(=O)-(CH_2)_p-$, $-(CH_2)_m-C(=O)NR^4-(CH_2)_p-$, or $-(CH_2)_m-C(=O)O-(CH_2)_p-$;

n is 0, 1, 2, 3, or 4;

is aryl or heteroaryl;

is hydrogen, aryl, or heteroaryl;

$R^4$ is hydrogen or alkyl;

m is 0, 1, 2, 3, or 4; and p is 0, 1, or 2;

wherein, any of the aforementioned alkyl, aryl, heteroaryl, or aralkyl may be substituted with one or more groups independently selected from the group consisting of halo, azido, alkyl, haloalkyl, aralkyl, alkenyl, alkynyl, cycloalkyl, heterocyclyl, aryl, heteroaryl, heteroaralkyl, hydroxy, alkoxy, aryloxy, heteroaryloxy, amino, nitro, sulfhydryl, imino, amido, phosphonate, phosphinate, acyl, carboxyl, alkoxycarbonyl, acyloxy, silyl, alkylthio, sulfonate, sulfonyl, sulfonamido, formyl, cyano, and isocyano.

In certain embodiments, the invention relates to any one of the aforementioned compounds, wherein $Y^1$ is O or absent.

In certain embodiments, the invention relates to any one of the aforementioned compounds, wherein $Y^1$ is O.

In certain embodiments, the invention relates to any one of the aforementioned compounds, wherein $Y^1$ is absent.

In certain embodiments, the invention relates to any one of the aforementioned compounds, wherein $R^1$ is aryl or hydrogen.

In certain embodiments, the invention relates to any one of the aforementioned compounds, wherein $R^1$ is aryl.

In certain embodiments, the invention relates to any one of the aforementioned compounds, wherein $R^1$ is phenyl.

In certain embodiments, the invention relates to any one of the aforementioned compounds, wherein $R^1$ is hydrogen.

In certain embodiments, the invention relates to any one of the aforementioned compounds, wherein n is 1, 2, 3, or 4.

In certain embodiments, the invention relates to any one of the aforementioned compounds, wherein n is 0 or 1.

In certain embodiments, the invention relates to any one of the aforementioned compounds, wherein n is 1.

In certain embodiments, the invention relates to any one of the aforementioned compounds, wherein n is 0.

In certain embodiments, the invention relates to any one of the aforementioned compounds, wherein $R^2$ is hydrogen or alkyl.

In certain embodiments, the invention relates to any one of the aforementioned compounds, wherein $R^2$ is hydrogen.

In certain embodiments, the invention relates to any one of the aforementioned compounds, wherein $R^2$ is alkyl.

In certain embodiments, the invention relates to any one of the aforementioned compounds, wherein $R^2$ is methyl, ethyl, n-propyl, i-propyl, n-butyl, i-butyl, s-butyl, or t-butyl.

In certain embodiments, the invention relates to any one of the aforementioned compounds, wherein $R^2$ is methyl.

In certain embodiments, the invention relates to any one of the aforementioned compounds, wherein $R^2$ is ethyl.

In certain embodiments, the invention relates to any one of the aforementioned compounds, wherein $R^2$ is i-propyl.

In certain embodiments, the invention relates to any one of the aforementioned compounds, wherein $R^1$ and an instance of $R^2$ taken together with the carbon atoms to which they are attached form a 5- or 6-membered aryl ring.

In certain embodiments, the invention relates to any one of the aforementioned compounds, wherein $R^1$ and an instance of $R^2$ taken together with the carbon atoms to which they are attached form a 6-membered aryl ring.

In certain embodiments, the invention relates to any one of the aforementioned compounds, wherein $R^3$ is hydrogen or alkyl.

In certain embodiments, the invention relates to any one of the aforementioned compounds, wherein $R^3$ is hydrogen.

In certain embodiments, the invention relates to any one of the aforementioned compounds, wherein Y² is absent, —(CH₂)ₘ—C(=O)NR⁴—(CH₂)ₚ—, or —(CH₂)ₘ—C(=O)O—(CH₂)ₚ—.

In certain embodiments, the invention relates to any one of the aforementioned compounds, wherein Y² is absent.

In certain embodiments, the invention relates to any one of the aforementioned compounds, wherein Y² is —(CH₂)ₘ—C(=O)NR⁴—(CH₂)ₚ—.

In certain embodiments, the invention relates to any one of the aforementioned compounds, wherein Y² is —(CH₂)ₘ—C(=O)NR⁴—(CH₂)ₚ—; R⁴ is hydrogen; m is 1; and p is 0.

In certain embodiments, the invention relates to any one of the aforementioned compounds, wherein

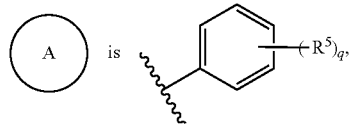
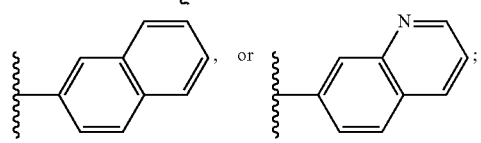

R⁵ is halo, azido, alkyl, haloalkyl, aralkyl, alkenyl, alkynyl, cycloalkyl, heterocyclyl, aryl, heteroaryl, heteroaralkyl, hydroxy, alkoxy, haloalkyloxy, aryloxy, heteroaryloxy, amino, nitro, sulfhydryl, imino, amido, phosphonate, phosphinate, acyl, carboxyl, alkoxycarbonyl, acyloxy, alkylthio, sulfonate, sulfonyl, sulfonamido, formyl, cyano, or isocyano; and q is 0 to 5 inclusive.

In certain embodiments, the invention relates to any one of the aforementioned compounds, wherein

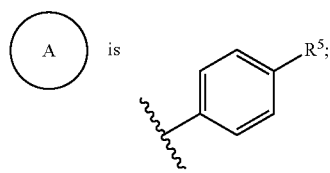

and R⁵ is selected from the group consisting of halo, alkoxy, haloalkyloxy, alkylthio, amido, and cyano.

In certain embodiments, the invention relates to any one of the aforementioned compounds, wherein

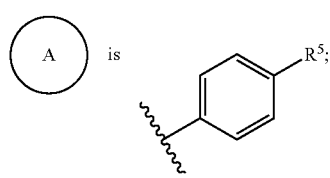

and R⁵ is halo.

In certain embodiments, the invention relates to any one of the aforementioned compounds, wherein

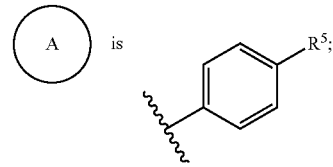

and R⁵ is chloro.

In certain embodiments, the invention relates to any one of the aforementioned compounds, wherein

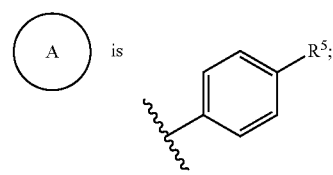

and R⁵ is bromo.

In certain embodiments, the invention relates to any one of the aforementioned compounds, wherein

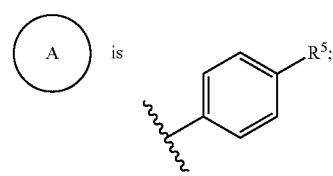

and R⁵ is alkoxy.

In certain embodiments, the invention relates to any one of the aforementioned compounds, wherein

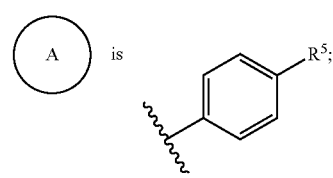

and R⁵ is methoxy.

In certain embodiments, the invention relates to any one of the aforementioned compounds, wherein

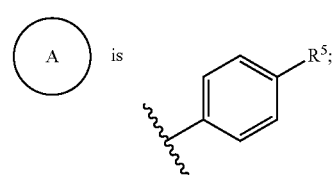

and R⁵ is haloalkyloxy.

In certain embodiments, the invention relates to any one of the aforementioned compounds, wherein

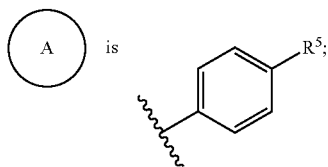

and $R^5$ is trifluoromethoxy.

In certain embodiments, the invention relates to any one of the aforementioned compounds, wherein

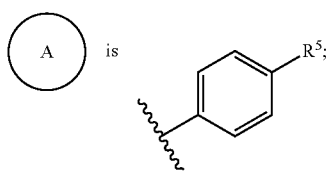

and $R^5$ is alkylthio.

In certain embodiments, the invention relates to any one of the aforementioned compounds, wherein

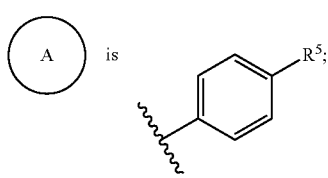

and $R^5$ is methylthio.

In certain embodiments, the invention relates to any one of the aforementioned compounds, wherein

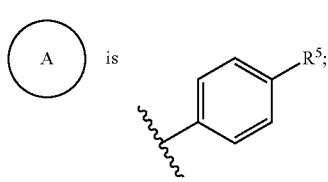

and $R^5$ is cyano.

In certain embodiments, the invention relates to any one of the aforementioned compounds, wherein

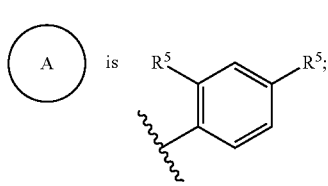

and $R^5$ is halo.

In certain embodiments, the invention relates to any one of the aforementioned compounds, wherein

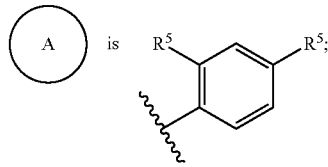

and $R^5$ is chloro.

In certain embodiments, the invention relates to any one of the aforementioned compounds, wherein

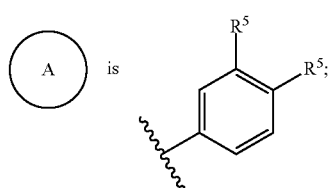

and $R^5$ is halo or cyano.

In certain embodiments, the invention relates to any one of the aforementioned compounds, wherein

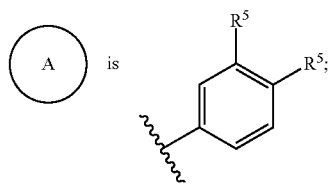

and $R^5$ is halo.

In certain embodiments, the invention relates to any one of the aforementioned compounds, wherein

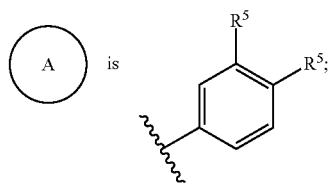

and $R^5$ is chloro.

In certain embodiments, the invention relates to any one of the aforementioned compounds, wherein

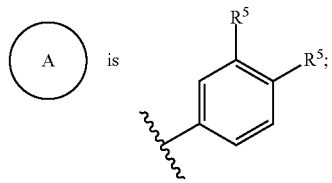

one instance of $R^5$ is halo; and one instance of $R^5$ is cyano.

In certain embodiments, the invention relates to any one of the aforementioned compounds, wherein A is 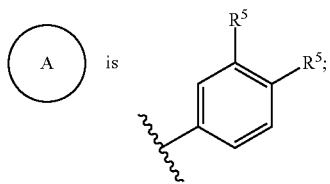

one instance of $R^5$ is halo; and one instance of $R^5$ is amido.

In certain embodiments, the invention relates to any one of the aforementioned compounds, wherein A is 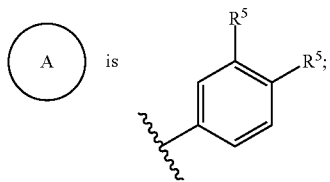

one instance of $R^5$ is chloro; and one instance of $R^5$ is cyano.

In certain embodiments, the invention relates to any one of the aforementioned compounds, wherein A is 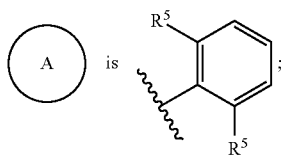

and $R^5$ is halo.

In certain embodiments, the invention relates to any one of the aforementioned compounds, wherein A is 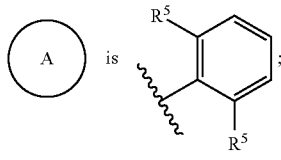

and $R^5$ is chloro.

In certain embodiments, the invention relates to any one of the aforementioned compounds, wherein A is 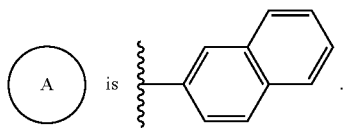

In certain embodiments, the invention relates to any one of the aforementioned compounds, wherein A is 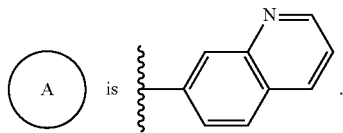

In certain embodiments, the invention relates to any one of the aforementioned compounds, wherein

is hydrogen or selected from the group consisting of

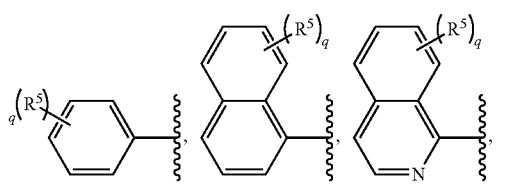

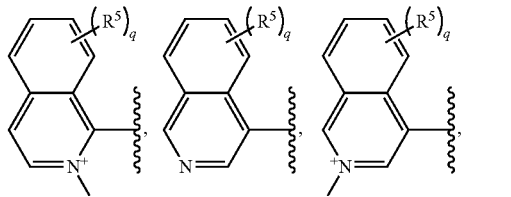

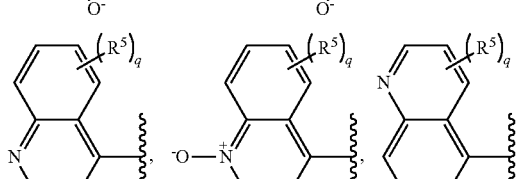

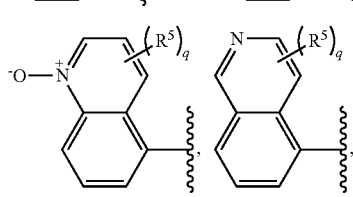

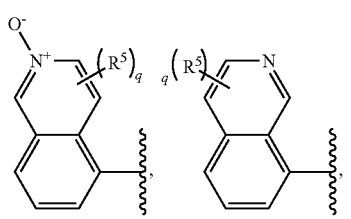

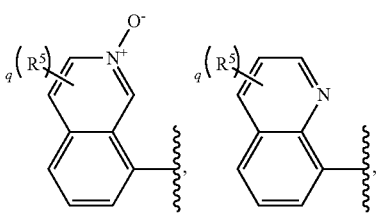

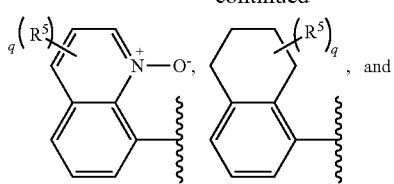

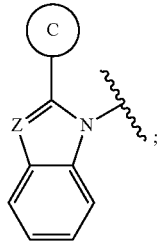

q is 0 to 5, inclusive; Z is —N— or —CH—;

is selected from the group consisting of hydrogen, alkyl, aryl, and heteroaryl; and $R^5$ is halo, azido, alkyl, haloalkyl, aralkyl, alkenyl, alkynyl, cycloalkyl, heterocyclyl, aryl, heteroaryl, heteroaralkyl, hydroxy, alkoxy, haloalkyloxy, aryloxy, heteroaryloxy, amino, nitro, sulfhydryl, imino, amido, phosphonate, phosphinate, acyl, carboxyl, alkoxycarbonyl, acyloxy, alkylthio, sulfonate, sulfonyl, sulfonamido, formyl, cyano, or isocyano; and $R^6$ is hydrogen or alkyl.

In certain embodiments, the invention relates to any one of the aforementioned compounds, wherein

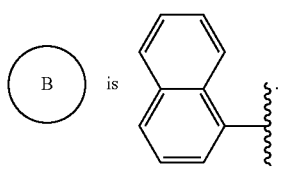

In certain embodiments, the invention relates to any one of the aforementioned compounds, wherein

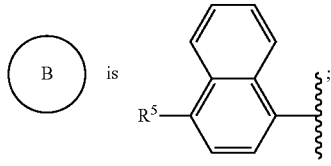

and $R^5$ is halo.

In certain embodiments, the invention relates to any one of the aforementioned compounds, wherein

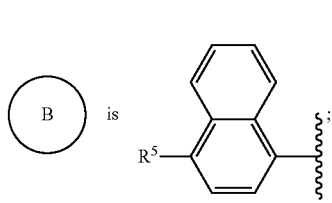

and $R^5$ is chloro.

In certain embodiments, the invention relates to any one of the aforementioned compounds, wherein

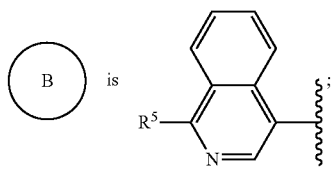

and $R^5$ is halo.

In certain embodiments, the invention relates to any one of the aforementioned compounds, wherein

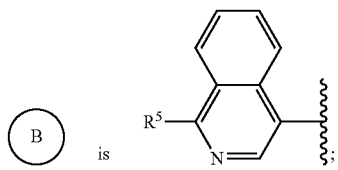

and $R^5$ is chloro.

In certain embodiments, the invention relates to any one of the aforementioned compounds, wherein

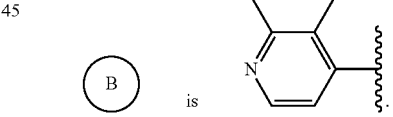

In certain embodiments, the invention relates to any one of the aforementioned compounds, wherein

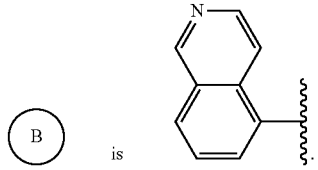

In certain embodiments, the invention relates to any one of the aforementioned compounds, wherein In certain embodiments, the invention relates to any one of the aforementioned compounds, wherein

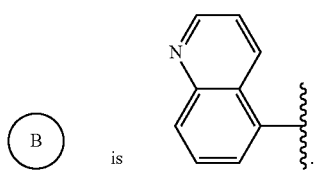

In certain embodiments, the invention relates to any one of the aforementioned compounds, wherein

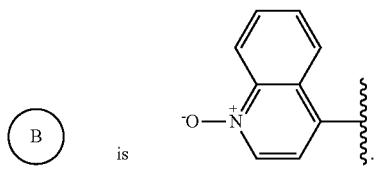

In certain embodiments, the invention relates to any one of the aforementioned compounds, wherein

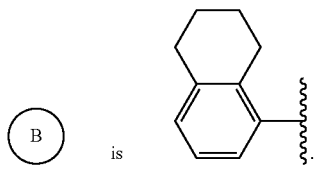

In certain embodiments, the invention relates to any one of the aforementioned compounds, wherein

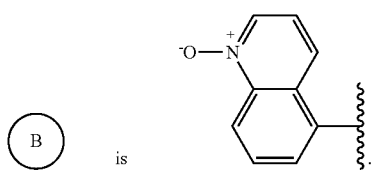

In certain embodiments, the invention relates to any one of the aforementioned compounds, wherein

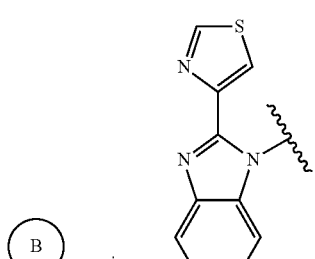

In certain embodiments, the invention relates to any one of the aforementioned compounds, wherein

is hydrogen.

In certain embodiments, the invention relates to any one of the aforementioned compounds, wherein

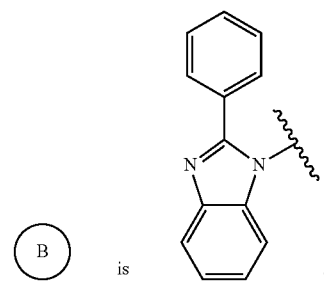

In certain embodiments, the invention relates to any one of the aforementioned compounds, wherein

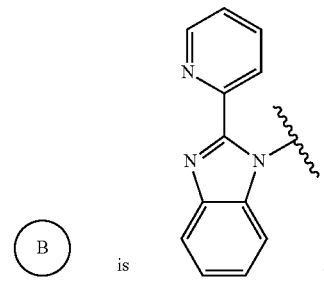

In certain embodiments, the invention relates to a compound, or a pharmaceutically acceptable salt thereof, selected from the group consisting of

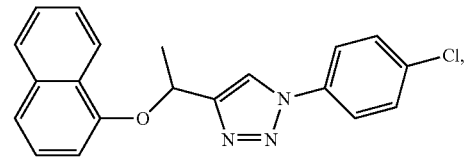

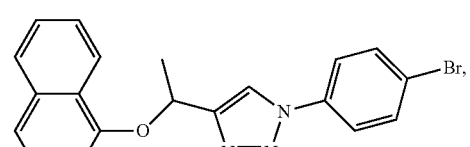

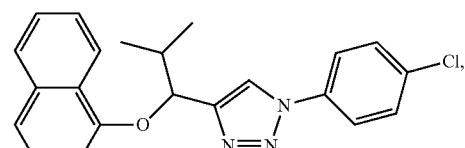

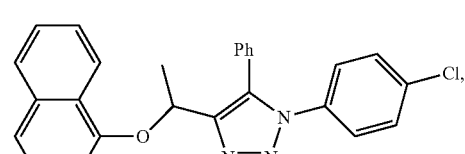

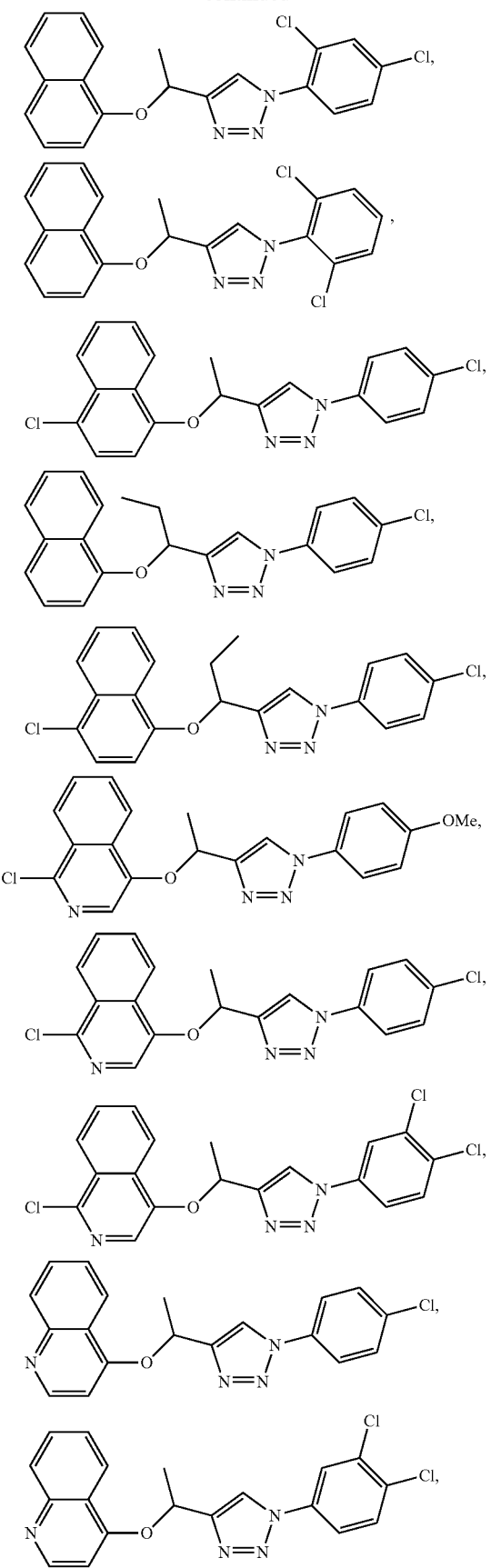
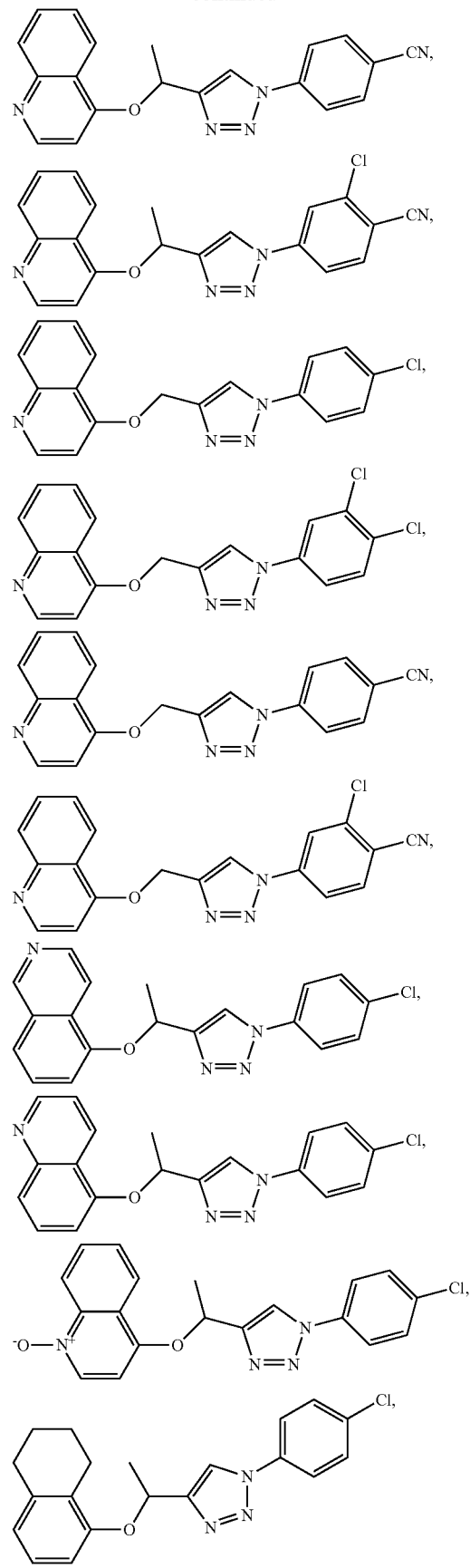

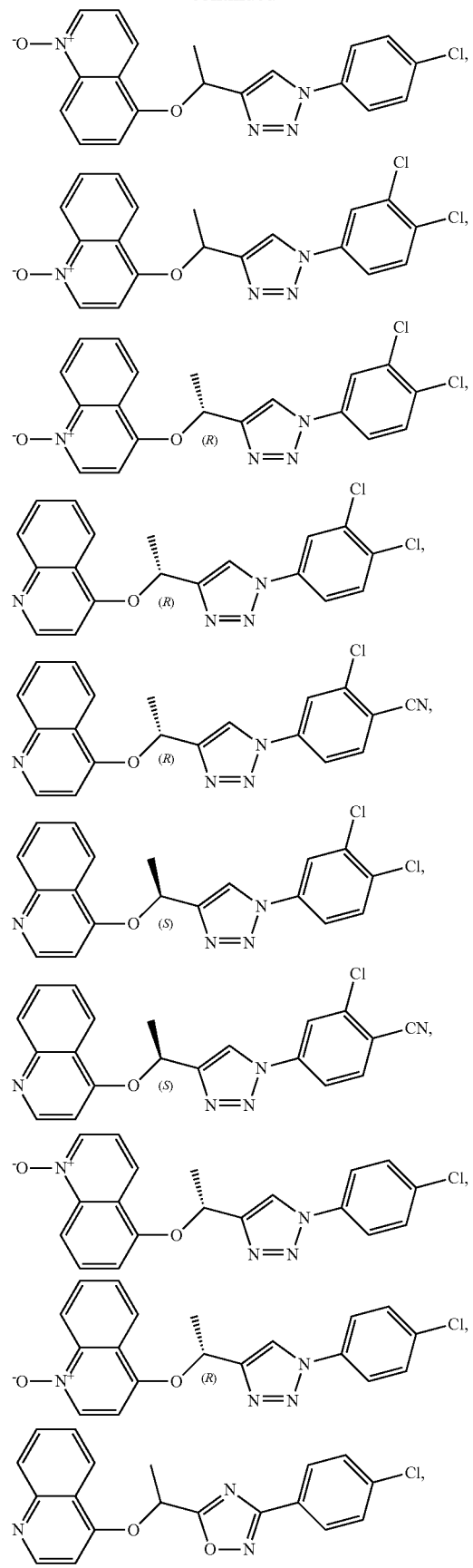
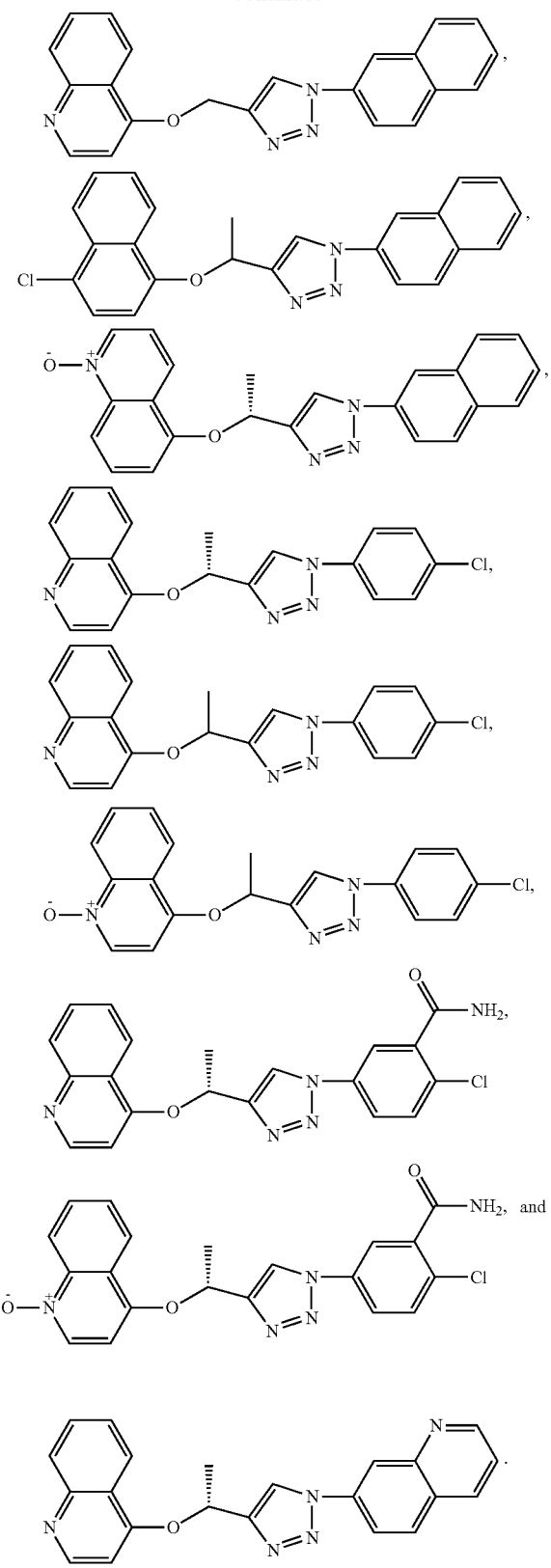
In certain embodiments, the invention relates to a compound, or a pharmaceutically acceptable salt thereof, selected from the group consisting of

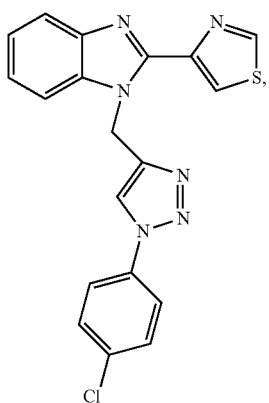

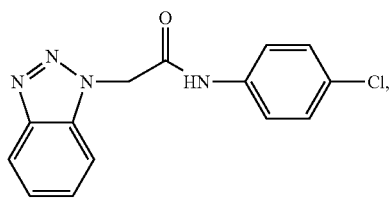

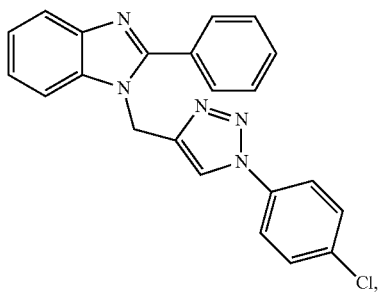

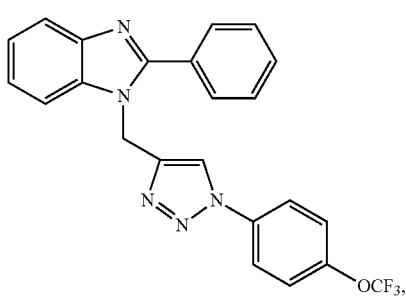

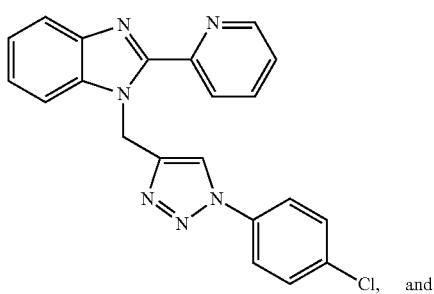

and

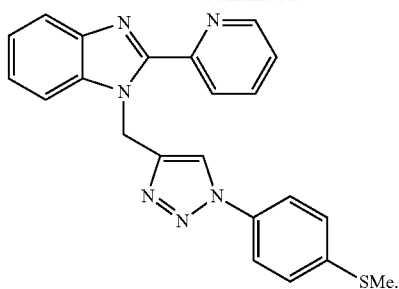

In certain embodiments, the invention relates to a compound, or a pharmaceutically acceptable salt thereof, represented by Formula II:

Formula II

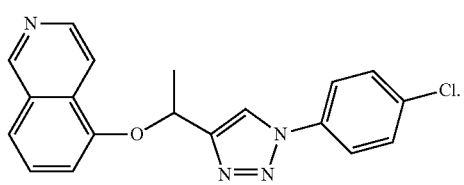

In certain embodiments, the invention relates to a compound, or a pharmaceutically acceptable salt thereof, represented by Formula III:

Formula III

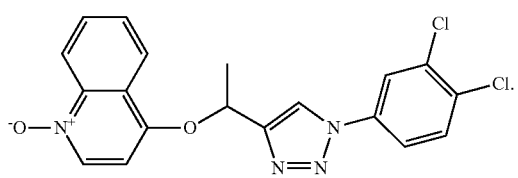

In certain embodiments, the invention relates to a compound, or a pharmaceutically acceptable salt thereof, represented by Formula IV:

Formula IV

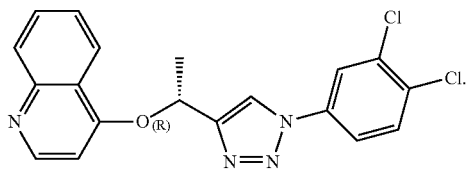

In certain embodiments, the invention relates to a compound, or a pharmaceutically acceptable salt thereof, represented by Formula V:

Formula V

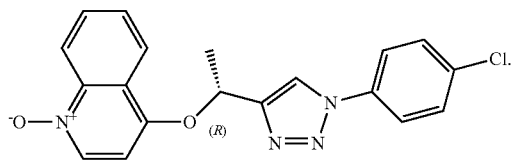

Amide Series

In certain embodiments, the invention relates to a compound, or a pharmaceutically acceptable salt thereof, represented by Formula VI:

Formula VI

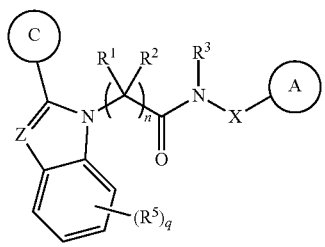

wherein, independently for each occurrence,
$R^1$ is hydrogen, alkyl, cycloalkyl, aryl, heteroaryl, aralkyl, or heteroaralkyl;
$R^2$ is hydrogen or alkyl;
$R^3$ is hydrogen or alkyl;
n is 0, 1, 2, 3, or 4;
X is absent, alkylene, —$NR^3$—, —$SO_2$—, or —$CR^3$=N—;
Z is —N= or —$CR^5$=;

is aryl or heteroaryl;

is selected from the group consisting of hydrogen, alkyl, aryl, and heteroaryl;
q is 0, 1, 2, 3, or 4; and
$R^5$ is halo, azido, alkyl, haloalkyl, aralkyl, alkenyl, alkynyl, cycloalkyl, heterocyclyl, aryl, heteroaryl, heteroaralkyl, hydroxy, alkoxy, haloalkyloxy, aryloxy, heteroaryloxy, amino, nitro, sulfhydryl, imino, amido, phosphonate, phosphinate, acyl, carboxyl, alkoxycarbonyl, acyloxy, alkylthio, sulfonate, sulfonyl, sulfonamido, formyl, cyano, or isocyano;
wherein, any of the aforementioned alkyl, aryl, heteroaryl, or aralkyl may be substituted with one or more groups independently selected from the group consisting of halo, azido, alkyl, haloalkyl, aralkyl, alkenyl, alkynyl, cycloalkyl, heterocyclyl, aryl, heteroaryl, heteroaralkyl, hydroxy, alkoxy, haloalkyloxy, aryloxy, heteroaryloxy, amino, nitro, sulfhydryl, imino, amido, phosphonate, phosphinate, acyl, carboxyl, alkoxycarbonyl, acyloxy, silyl, alkylthio, sulfonate, sulfonyl, sulfonamido, formyl, cyano, and isocyano.

In certain embodiments, the invention relates to any one of the aforementioned compounds, wherein X is absent, methylene, —NH—, —$SO_2$—, or —CH=N—.

In certain embodiments, the invention relates to any one of the aforementioned compounds, wherein X is absent.

In certain embodiments, the invention relates to any one of the aforementioned compounds, wherein X is methylene.

In certain embodiments, the invention relates to any one of the aforementioned compounds, wherein X is —NH—.

In certain embodiments, the invention relates to any one of the aforementioned compounds, wherein X is —$SO_2$—.

In certain embodiments, the invention relates to any one of the aforementioned compounds, wherein X is —CH=N—.

In certain embodiments, the invention relates to any one of the aforementioned compounds, wherein q is 0.

In certain embodiments, the invention relates to any one of the aforementioned compounds, wherein q is 1.

In certain embodiments, the invention relates to any one of the aforementioned compounds, wherein q is 1; and $R^5$ is halo.

In certain embodiments, the invention relates to any one of the aforementioned compounds, wherein q is 1; and $R^5$ is bromo.

In certain embodiments, the invention relates to any one of the aforementioned compounds, wherein Z is —N=.

In certain embodiments, the invention relates to any one of the aforementioned compounds, wherein n is 1, 2, 3, or 4.

In certain embodiments, the invention relates to any one of the aforementioned compounds, wherein n is 1 or 2.

In certain embodiments, the invention relates to any one of the aforementioned compounds, wherein n is 1.

In certain embodiments, the invention relates to any one of the aforementioned compounds, wherein n is 2.

In certain embodiments, the invention relates to any one of the aforementioned compounds, wherein $R^1$ is hydrogen or alkyl.

In certain embodiments, the invention relates to any one of the aforementioned compounds, wherein $R^1$ is hydrogen.

In certain embodiments, the invention relates to any one of the aforementioned compounds, wherein $R^1$ is alkyl.

In certain embodiments, the invention relates to any one of the aforementioned compounds, wherein $R^1$ is methyl, ethyl, n-propyl, or i-propyl.

In certain embodiments, the invention relates to any one of the aforementioned compounds, wherein $R^2$ is hydrogen.

In certain embodiments, the invention relates to any one of the aforementioned compounds, wherein $R^3$ is hydrogen.

In certain embodiments, the invention relates to any one of the aforementioned compounds, wherein

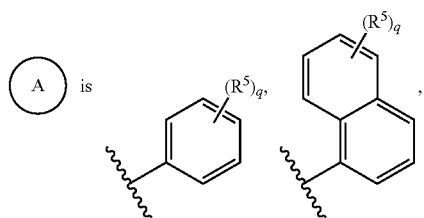

-continued

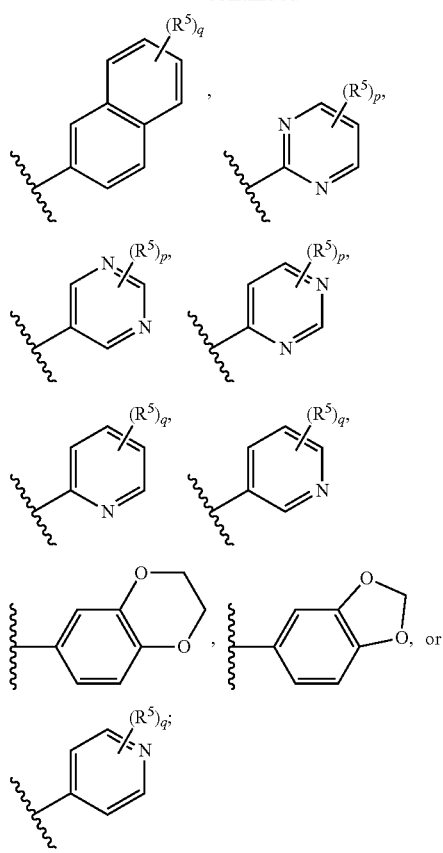

and p is 0, 1, 2, or 3.

In certain embodiments, the invention relates to any one of the aforementioned compounds, wherein

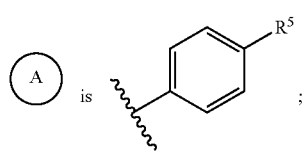

and $R^5$ is amido, alkoxy, halo, haloalkyl, aryl, haloaryl, alkyl, hydroxy, alkylthio, sulfonyl, haloalkoxy, or cyano.

In certain embodiments, the invention relates to any one of the aforementioned compounds, wherein

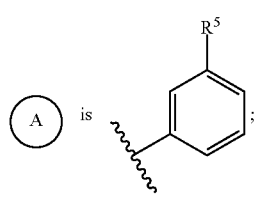

and $R^5$ is alkoxy or halo.

In certain embodiments, the invention relates to any one of the aforementioned compounds, wherein

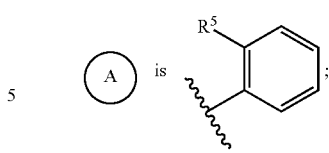

and $R^5$ is halo.

In certain embodiments, the invention relates to any one of the aforementioned compounds, wherein

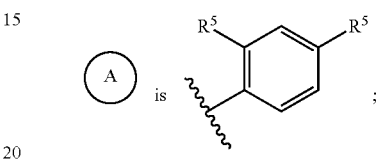

and $R^5$ is halo or cyano.

In certain embodiments, the invention relates to any one of the aforementioned compounds, wherein

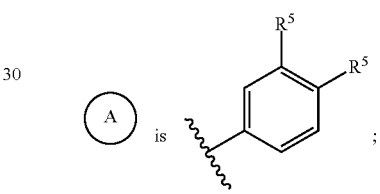

and $R^5$ is amido, halo, or cyano.

In certain embodiments, the invention relates to any one of the aforementioned compounds, wherein

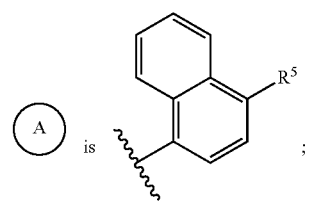

and $R^5$ is halo.

In certain embodiments, the invention relates to any one of the aforementioned compounds, wherein

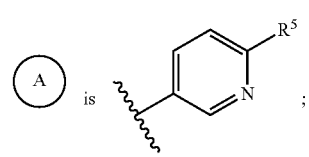

and $R^5$ is halo.

In certain embodiments, the invention relates to any one of the aforementioned compounds, wherein

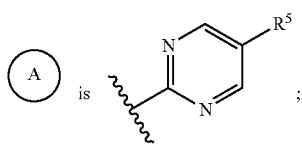

and R⁵ is halo.

In certain embodiments, the invention relates to any one of the aforementioned compounds, wherein

Ⓒ is hydrogen, alkyl,

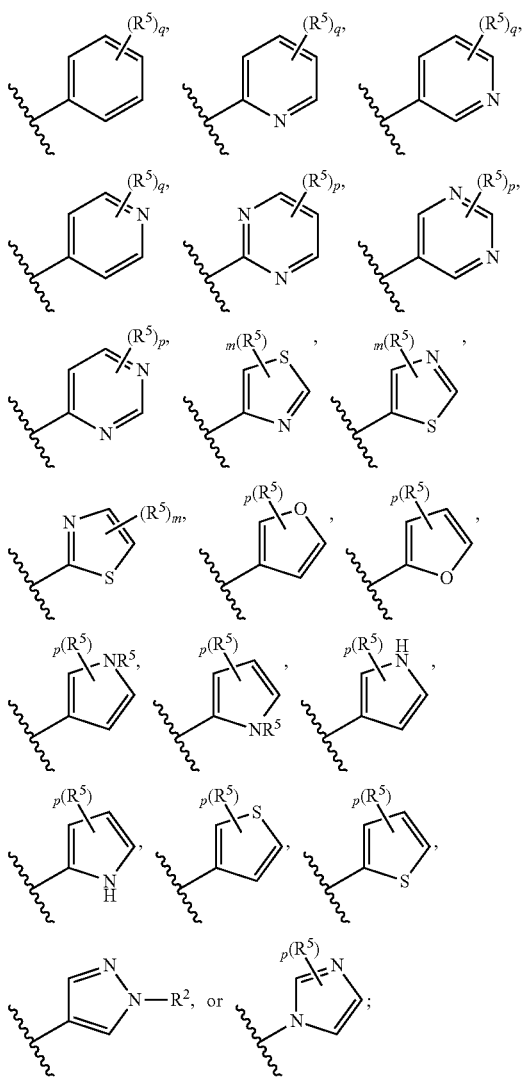

m is 0, 1, or 2; and p is 0, 1, 2, or 3.

In certain embodiments, the invention relates to any one of the aforementioned compounds, wherein

Ⓒ is hydrogen.

In certain embodiments, the invention relates to any one of the aforementioned compounds, wherein

Ⓒ is alkyl.

In certain embodiments, the invention relates to any one of the aforementioned compounds, wherein

Ⓒ is methyl, ethyl, or propyl.

In certain embodiments, the invention relates to any one of the aforementioned compounds, wherein

In certain embodiments, the invention relates to any one of the aforementioned compounds, wherein

In certain embodiments, the invention relates to any one of the aforementioned compounds, wherein Ⓒ is In certain embodiments, the invention relates to any one of the aforementioned compounds, wherein Ⓒ is In certain embodiments, the invention relates to any one of the aforementioned compounds, wherein

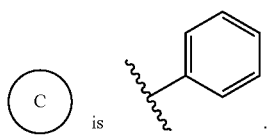

In certain embodiments, the invention relates to any one of the aforementioned compounds, wherein

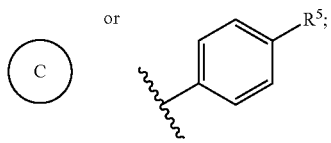

and R⁵ is halo, hydroxy, or alkoxy.

In certain embodiments, the invention relates to any one of the aforementioned compounds, wherein

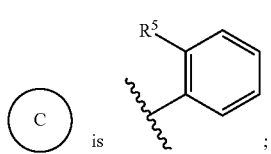

and R⁵ is halo.

In certain embodiments, the invention relates to any one of the aforementioned compounds, wherein

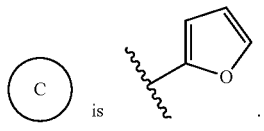

In certain embodiments, the invention relates to any one of the aforementioned compounds, wherein

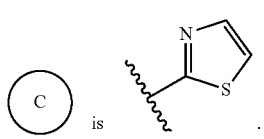

In certain embodiments, the invention relates to any one of the aforementioned compounds, wherein

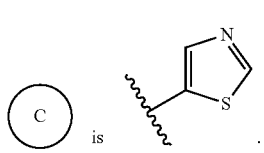

In certain embodiments, the invention relates to any one of the aforementioned compounds, wherein

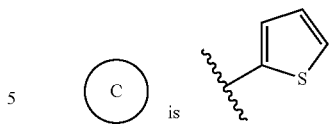

In certain embodiments, the invention relates to any one of the aforementioned compounds, wherein

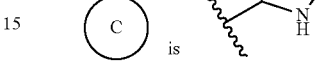

In certain embodiments, the invention relates to any one of the aforementioned compounds, wherein

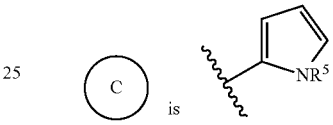

and R⁵ is alkoxycarbonyl.

In certain embodiments, the invention relates to any one of the aforementioned compounds, wherein

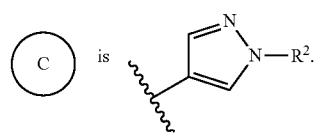

In certain embodiments, the invention relates to any one of the aforementioned compounds, wherein

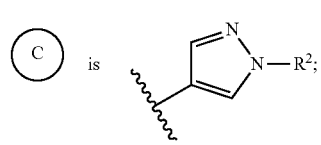

and R² is alkyl.

In certain embodiments, the invention relates to any one of the aforementioned compounds, wherein

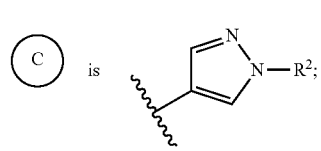

and R² is methyl.

In certain embodiments, the invention relates to a compound, or a pharmaceutically acceptable salt thereof, selected from the group consisting of

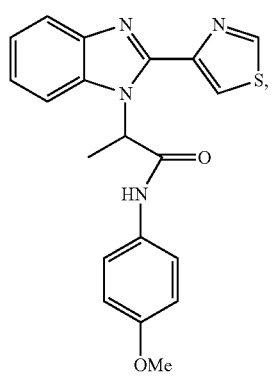
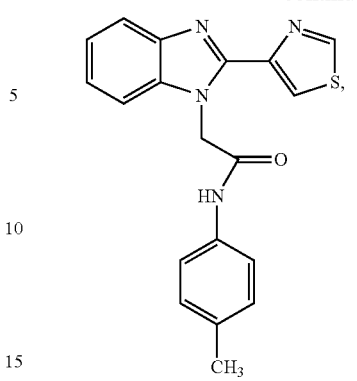
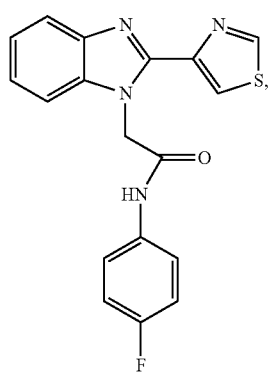
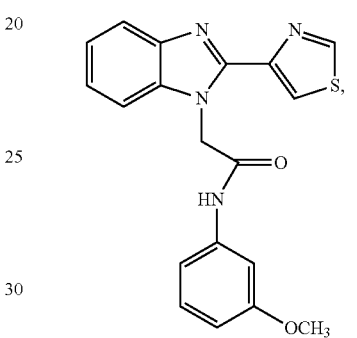
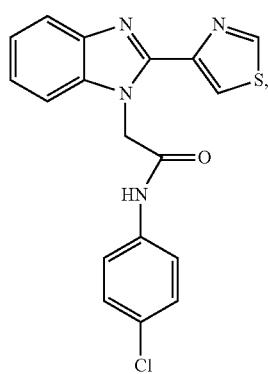
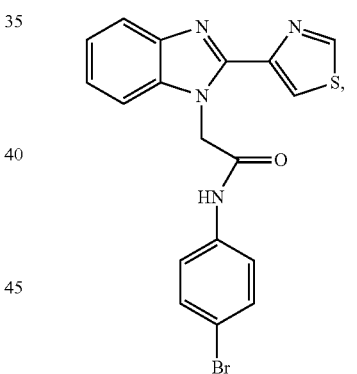
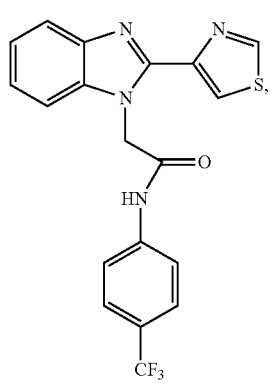
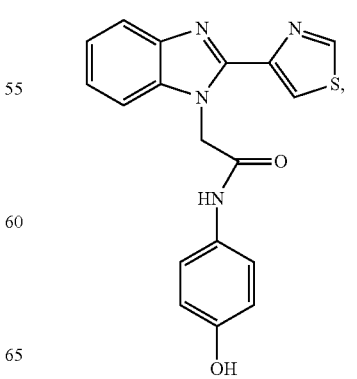

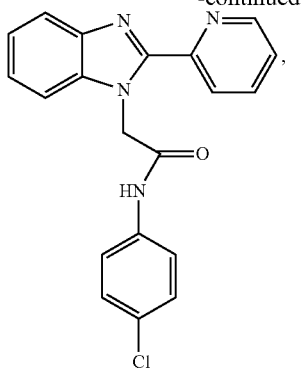
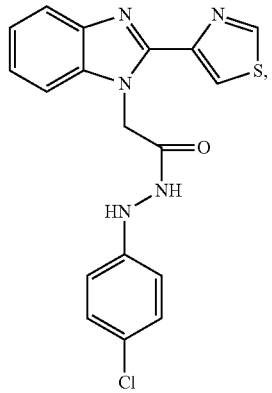
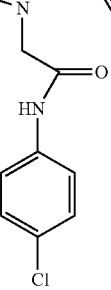
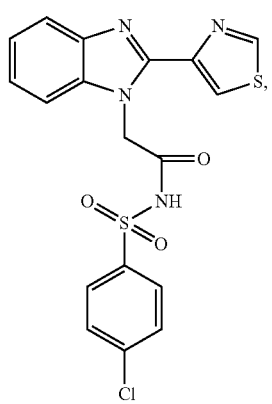
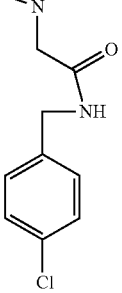
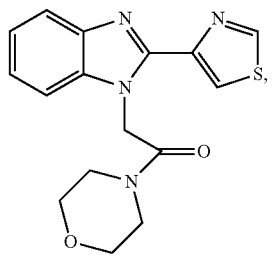
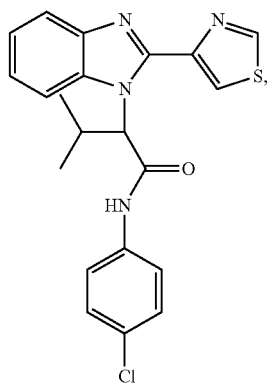
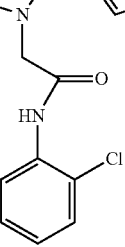

41
-continued
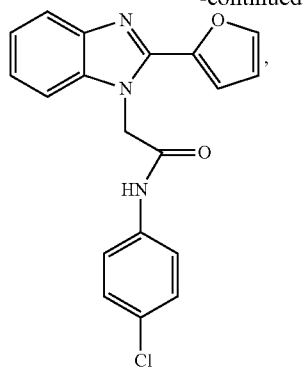
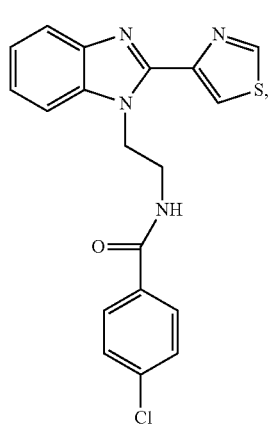
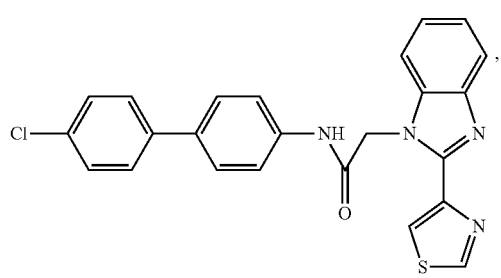
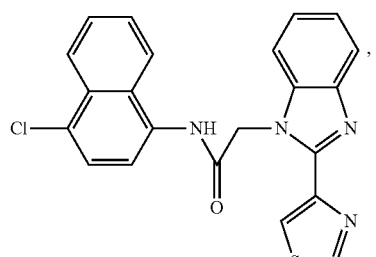
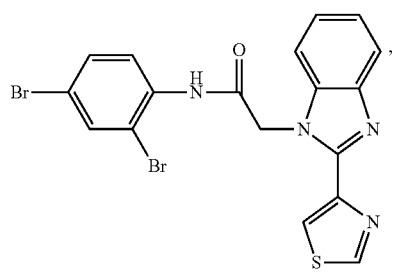
42
-continued
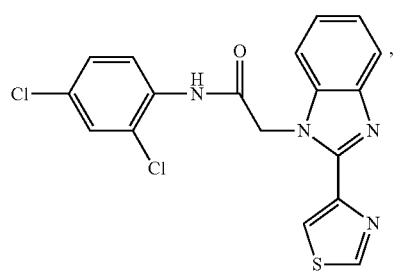
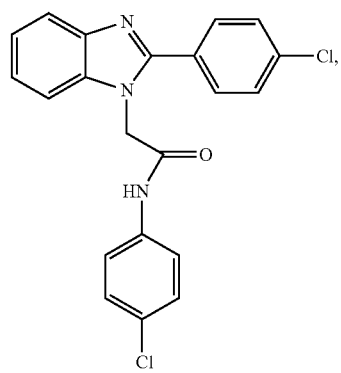
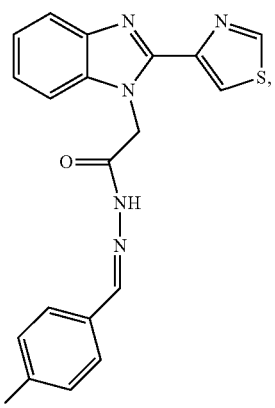
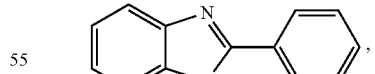
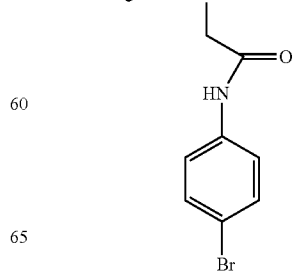

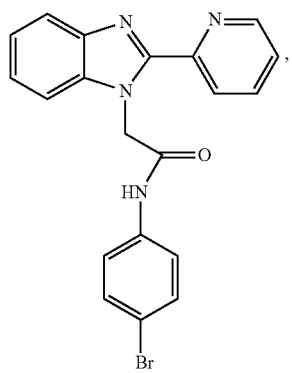
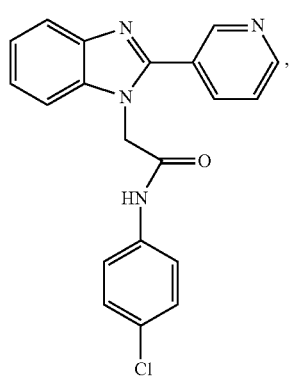
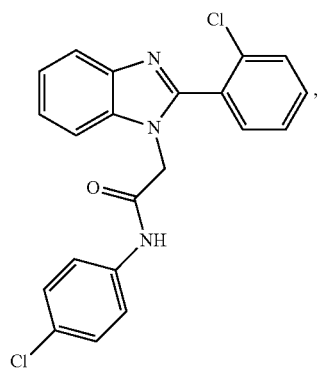
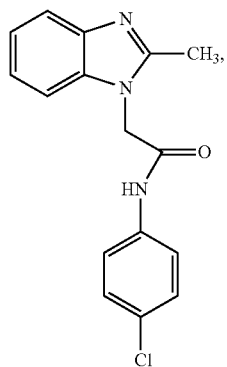
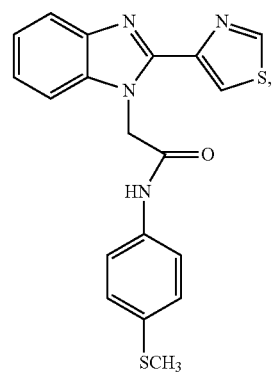
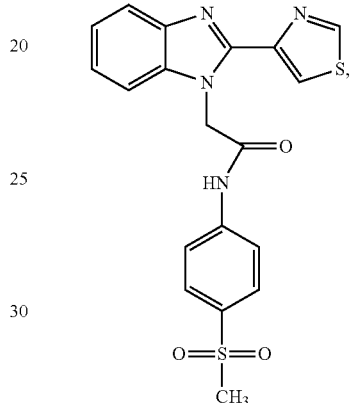
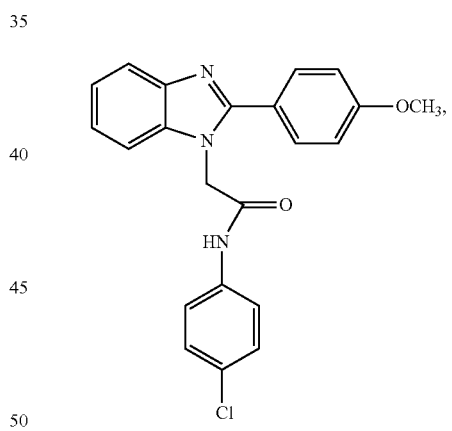
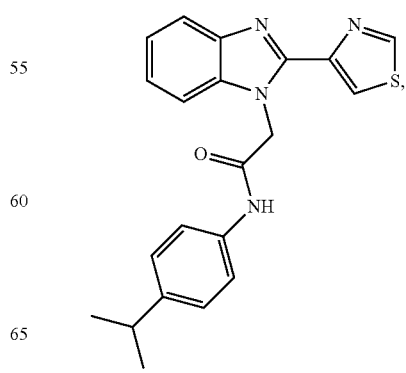

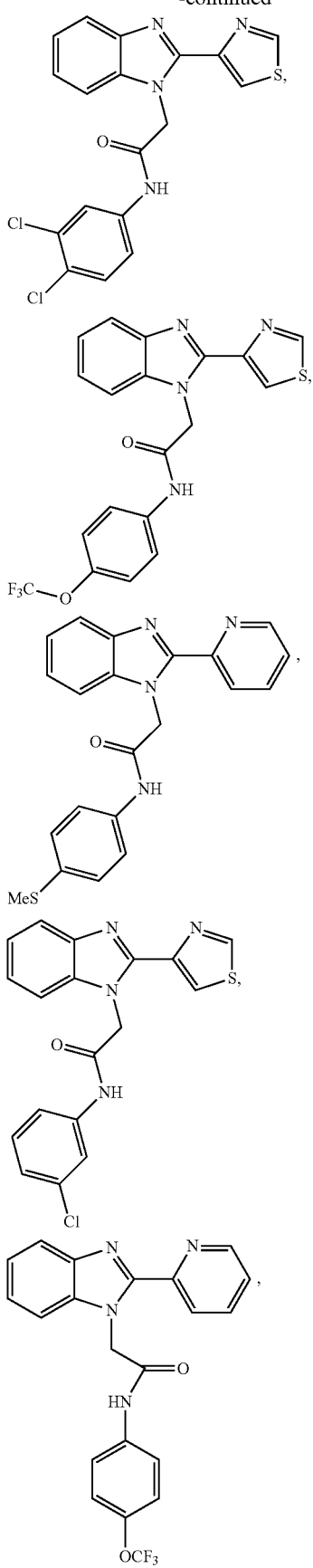
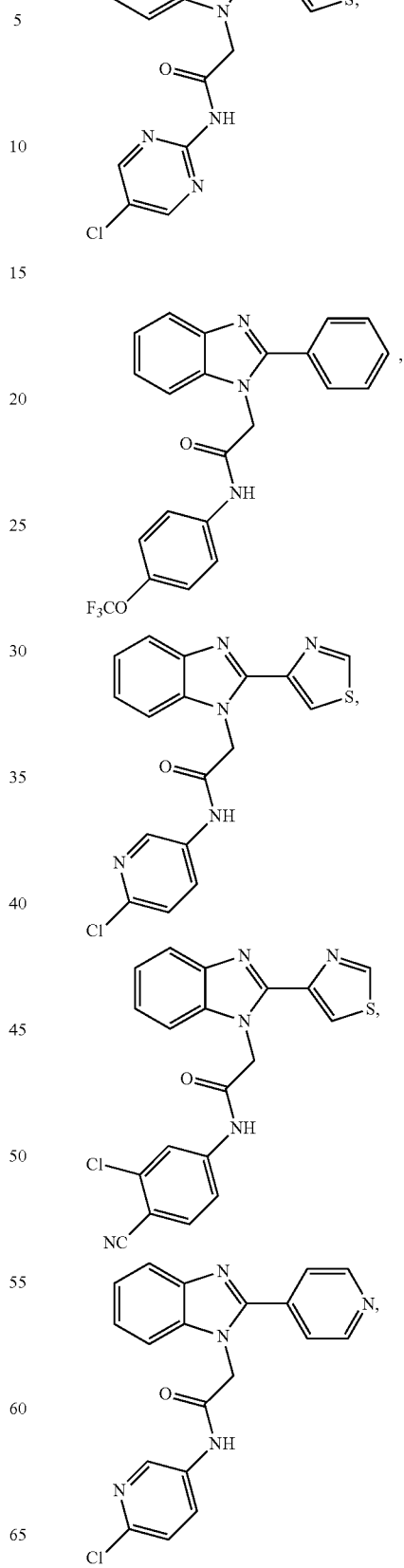

47

48

49
-continued
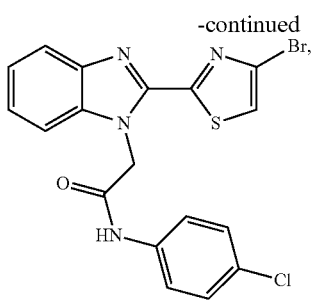
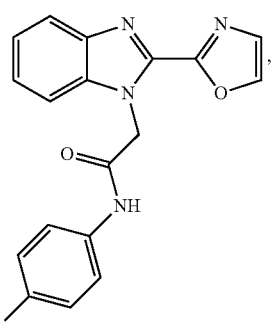
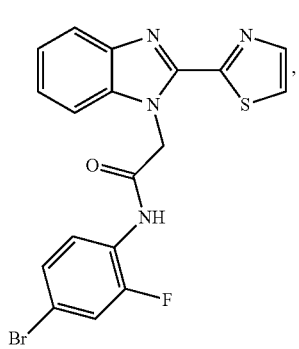
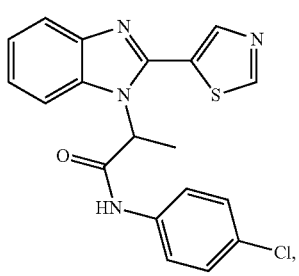
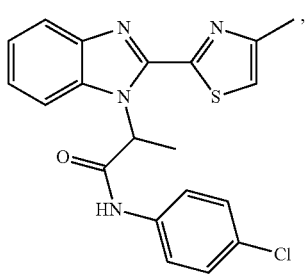
50
-continued
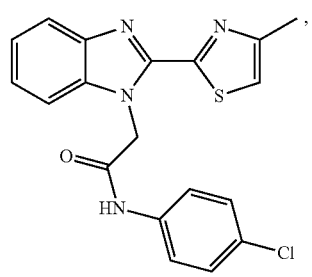
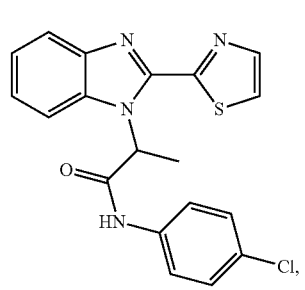
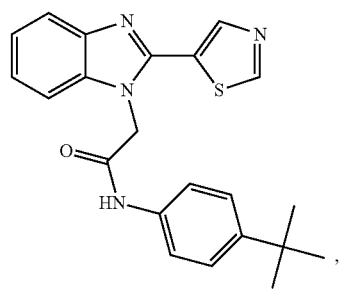
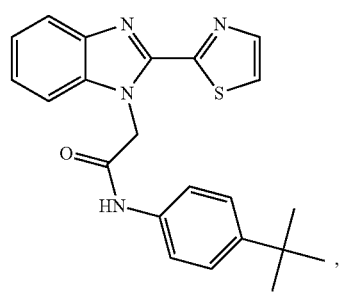
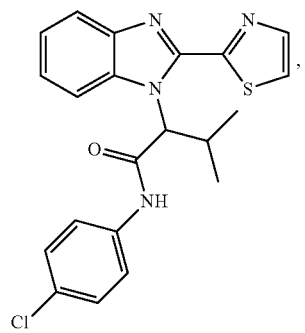

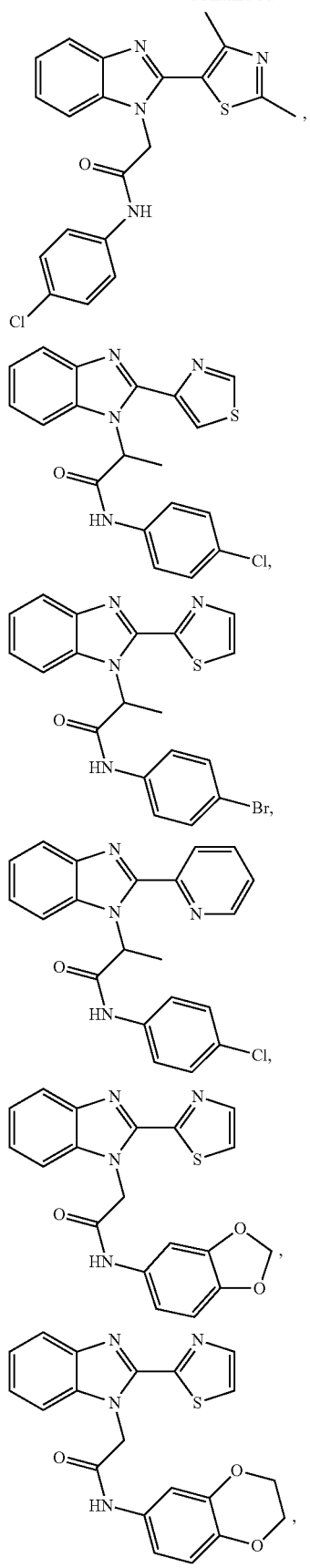
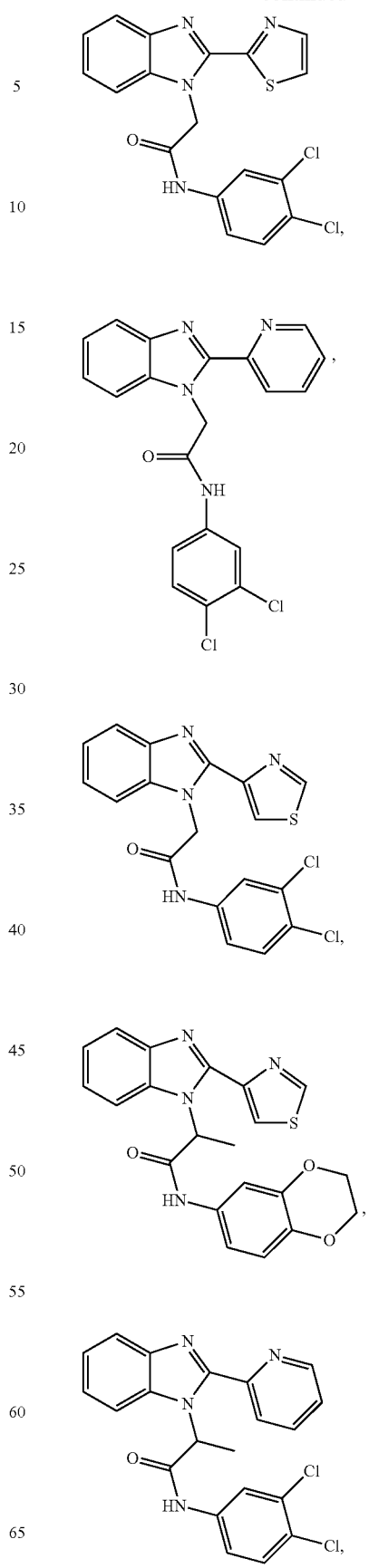

53
-continued
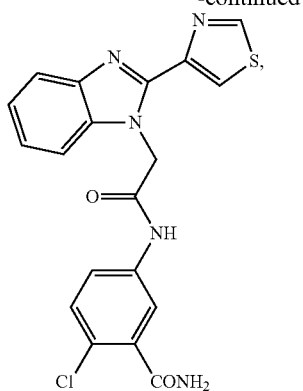
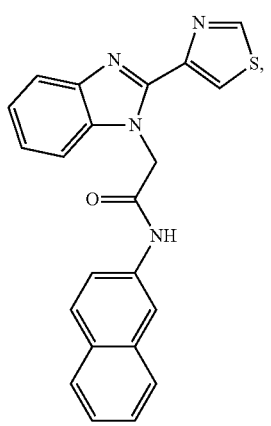
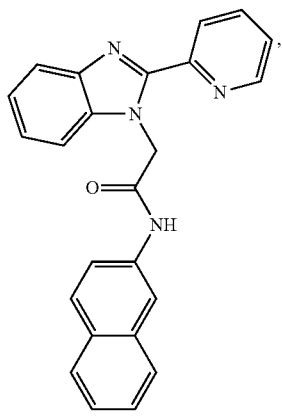
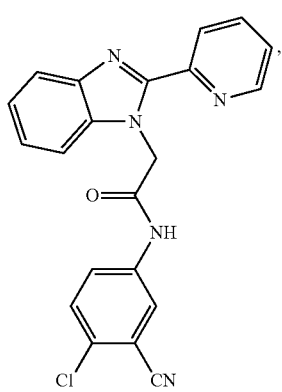
54
-continued
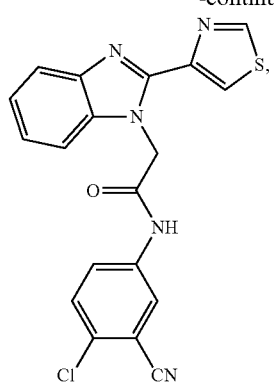
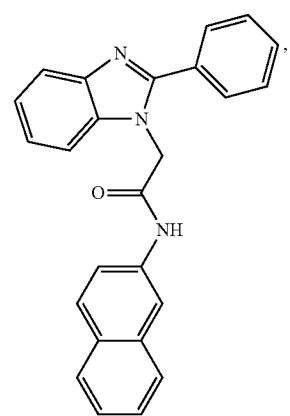
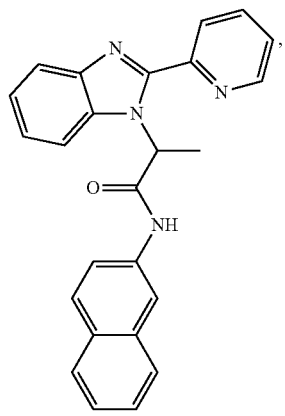
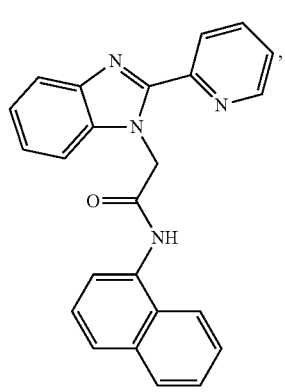

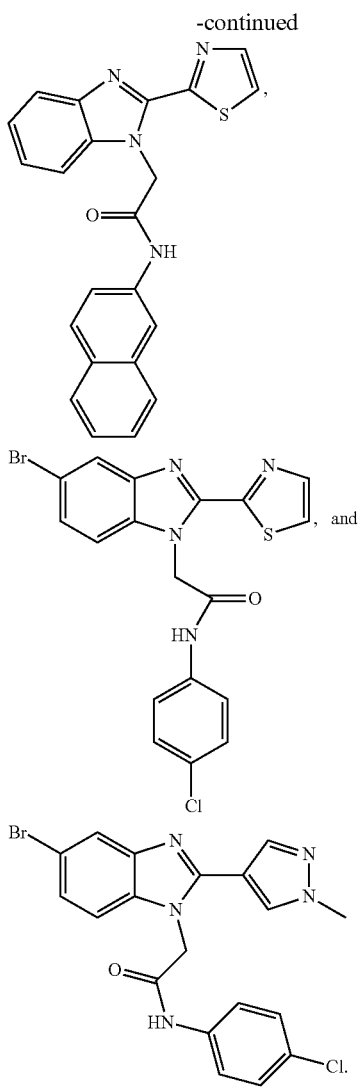

In certain embodiments, the invention relates to a compound, or a pharmaceutically acceptable salt thereof, represented by Formula VII:

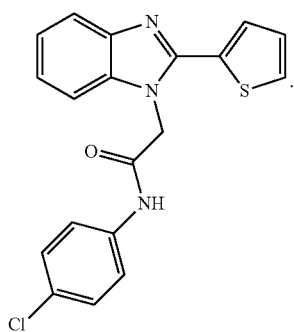

Formula VII

In certain embodiments, the invention relates to a compound, or a pharmaceutically acceptable salt thereof, represented by Formula VIII:

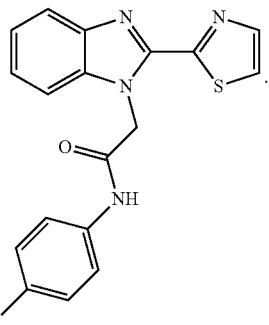

Formula VIII

Phthalazinone Series

In certain embodiments, the invention relates to a compound, or a pharmaceutically acceptable salt thereof, represented by Formula IX:

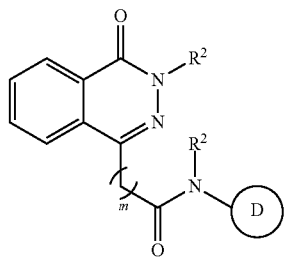

Formula IX wherein, independently for each occurrence,
$R^2$ is hydrogen or alkyl;
m is 0, 1, or 2;

is aryl, heteroaryl, amino, alkyl, cycloalkyl, heterocycloalkyl, or aralkyl;
wherein, any of the aforementioned alkyl, aryl, heteroaryl, or aralkyl may be substituted with one or more groups independently selected from the group consisting of halo, azido, alkyl, haloalkyl, aralkyl, alkenyl, alkynyl, cycloalkyl, heterocyclyl, aryl, heteroaryl, heteroaralkyl, hydroxy, alkoxy, aryloxy, heteroaryloxy, amino, nitro, sulfhydryl, imino, amido, phosphonate, phosphinate, acyl, carboxyl, alkoxycarbonyl, acyloxy, silyl, alkylthio, sulfonate, sulfonyl, sulfonamido, formyl, cyano, and isocyano.

In certain embodiments, the invention relates to any one of the aforementioned compounds, wherein $R^2$ is hydrogen.

In certain embodiments, the invention relates to any one of the aforementioned compounds, wherein $R^2$ is alkyl.

In certain embodiments, the invention relates to any one of the aforementioned compounds, wherein $R^2$ is methyl, ethyl, n-propyl, i-propyl, n-butyl, s-butyl, i-butyl, or t-butyl.

In certain embodiments, the invention relates to any one of the aforementioned compounds, wherein m is 0 or 1.

In certain embodiments, the invention relates to any one of the aforementioned compounds, wherein m is 0.

In certain embodiments, the invention relates to any one of the aforementioned compounds, wherein m is 1.

In certain embodiments, the invention relates to any one of the aforementioned compounds, wherein

D is alkyl, amino, benzyl,

[structures shown with substituents $(R^5)_q$, $(R^5)_p$, $(R^5)_m$, including phenyl, naphthyl, pyrimidinyl, pyridinyl, benzodioxinyl, benzodioxolyl, thiazolyl, furanyl, pyrrolyl, thienyl, pyrazolyl-N-R², indanyl, benzofuranyl, quinolinyl, thiadiazolyl, imidazolyl]

p is 0, 1, 2, or 3; q is 0, 1, 2, 3, or 4; and $R^5$ is halo, azido, alkyl, haloalkyl, aralkyl, alkenyl, alkynyl, cycloalkyl, heterocyclyl, aryl, heteroaryl, heteroaralkyl, hydroxy, alkoxy, haloalkyloxy, aryloxy, heteroaryloxy, amino, nitro, sulfhydryl, imino, amido, phosphonate, phosphinate, acyl, carboxyl, alkoxycarbonyl, acyloxy, alkylthio, sulfonate, sulfonyl, sulfonamido, formyl, cyano, or isocyano.

In certain embodiments, the invention relates to any one of the aforementioned compounds, wherein

D is alkyl.

In certain embodiments, the invention relates to any one of the aforementioned compounds, wherein

D is methyl, ethyl, n-propyl, i-propyl, n-butyl, s-butyl, i-butyl, or t-butyl.

In certain embodiments, the invention relates to any one of the aforementioned compounds, wherein

D is n-butyl.

In certain embodiments, the invention relates to any one of the aforementioned compounds, wherein

D is s-butyl.

In certain embodiments, the invention relates to any one of the aforementioned compounds, wherein

 is t-butyl.

In certain embodiments, the invention relates to any one of the aforementioned compounds, wherein

 is amino.

In certain embodiments, the invention relates to any one of the aforementioned compounds, wherein

 is 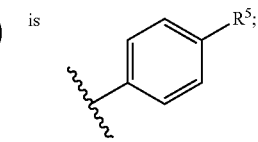;

and $R^5$ is amido, alkoxy, halo, haloalkyl, aryl, haloaryl, alkyl, hydroxy, alkylthio, sulfonyl, haloalkoxy, or cyano.

In certain embodiments, the invention relates to any one of the aforementioned compounds, wherein

 is 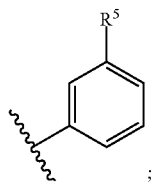;

and $R^5$ is alkoxy or halo.

In certain embodiments, the invention relates to any one of the aforementioned compounds, wherein

 is 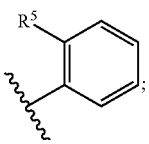;

and $R^5$ is halo.

In certain embodiments, the invention relates to any one of the aforementioned compounds, wherein

 is 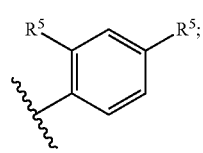;

and $R^5$ is halo or cyano.

In certain embodiments, the invention relates to any one of the aforementioned compounds, wherein

 is 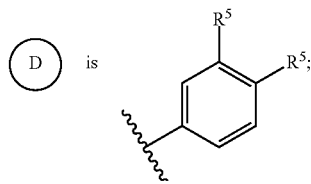;

and $R^5$ is amido, halo, or cyano.

In certain embodiments, the invention relates to any one of the aforementioned compounds, wherein

 is 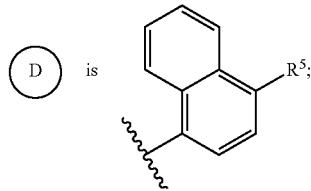;

and $R^5$ is halo.

In certain embodiments, the invention relates to any one of the aforementioned compounds, wherein

 is 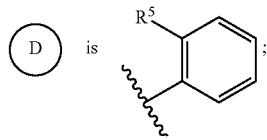;

and $R^5$ is amido.

In certain embodiments, the invention relates to a compound, or a pharmaceutically acceptable salt thereof, selected from the group consisting of

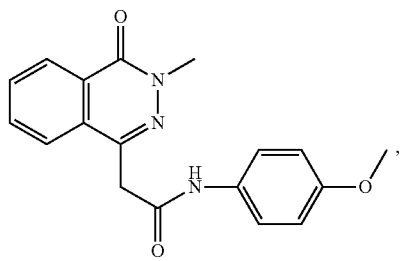

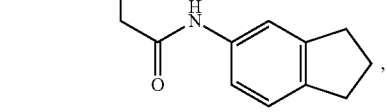

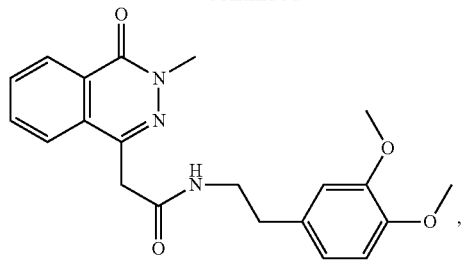
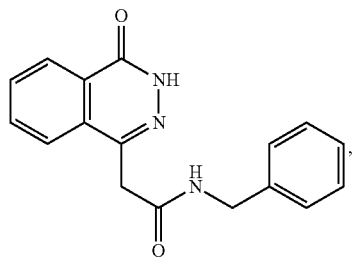
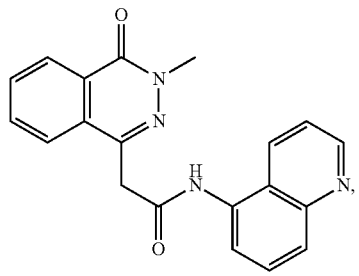
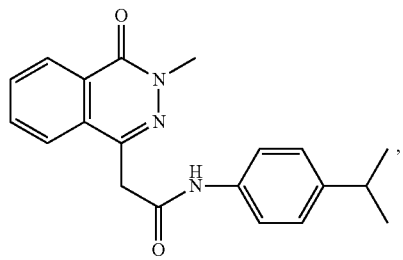
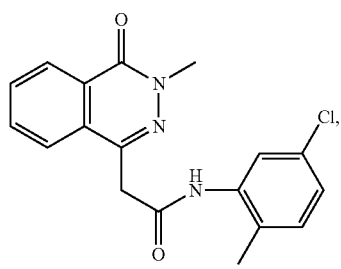
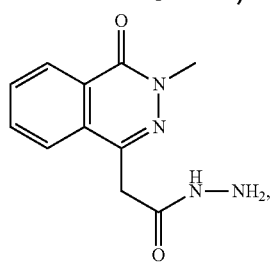
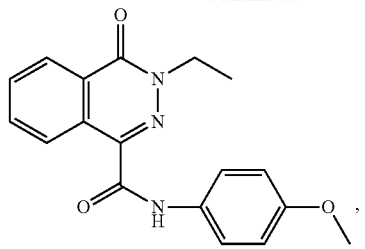
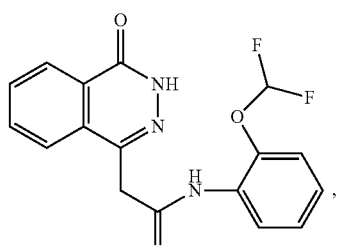
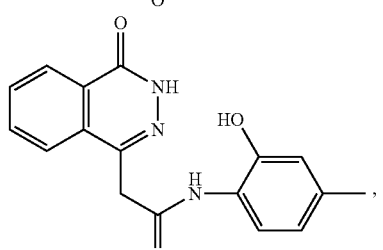
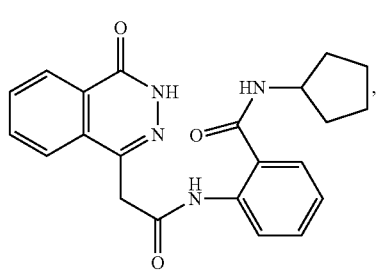
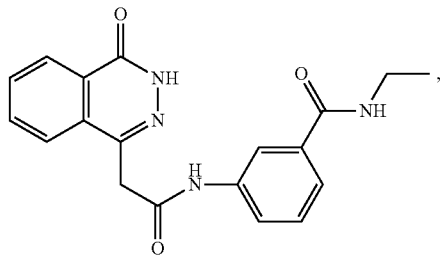
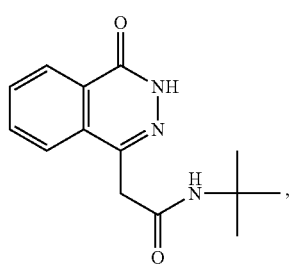

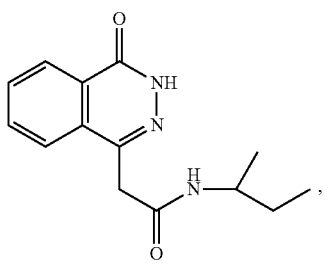
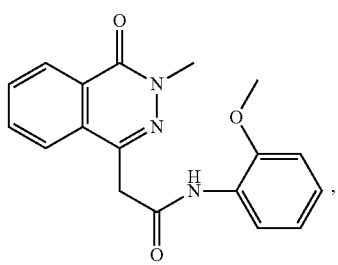
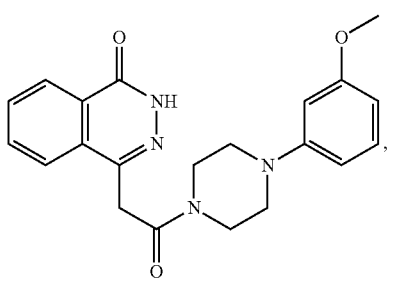
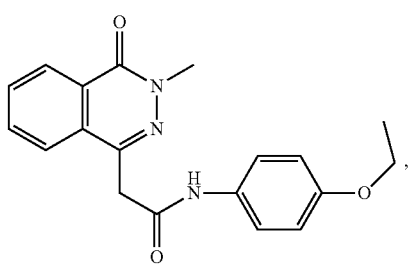
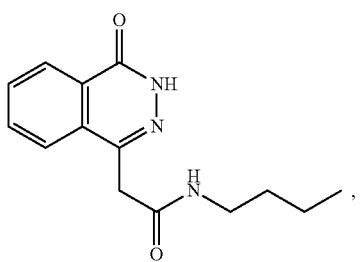
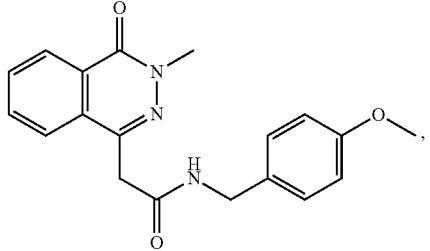
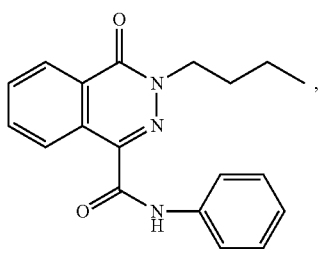
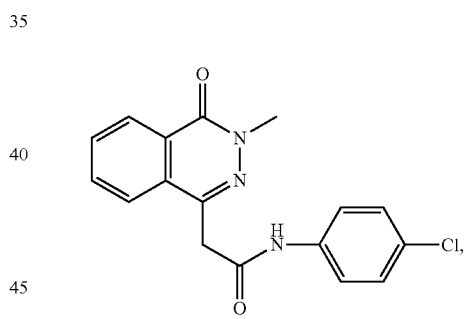
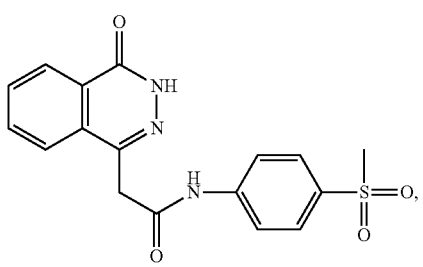
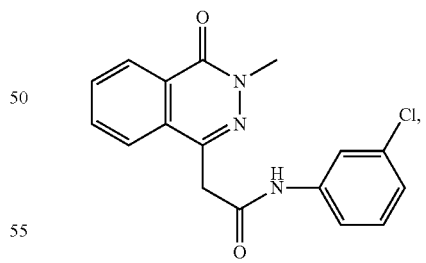
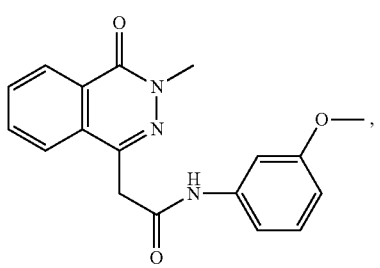
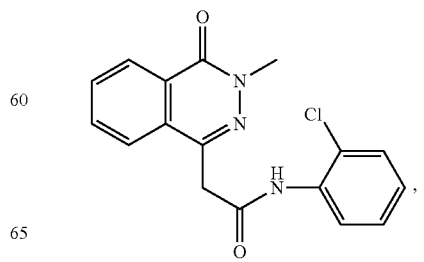

65
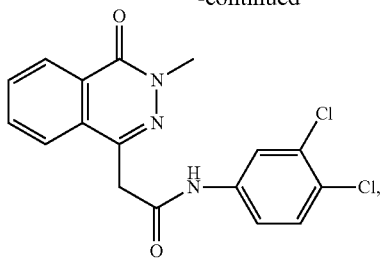
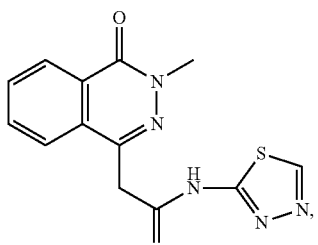
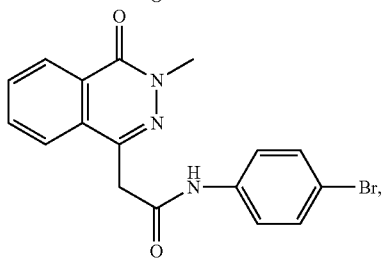
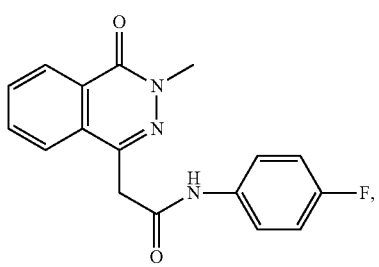
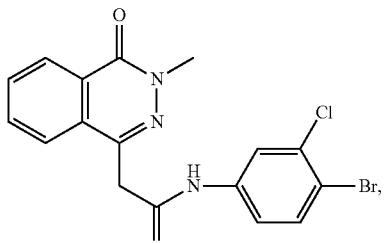
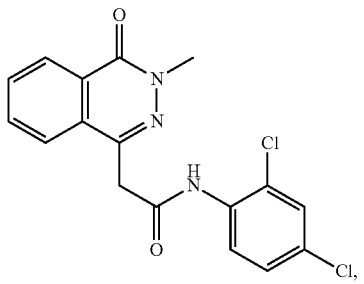
66
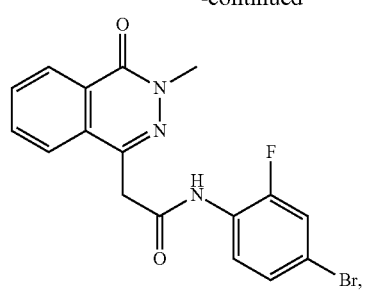
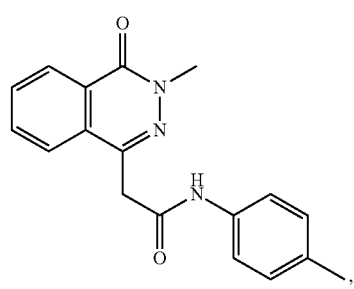
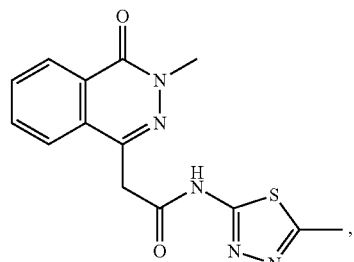
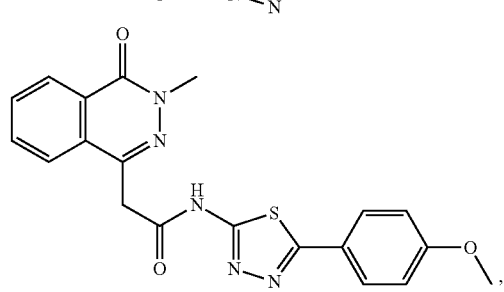
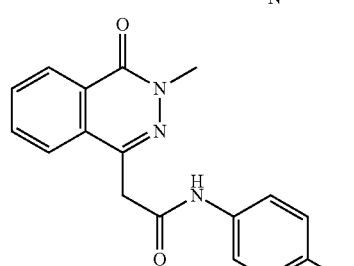
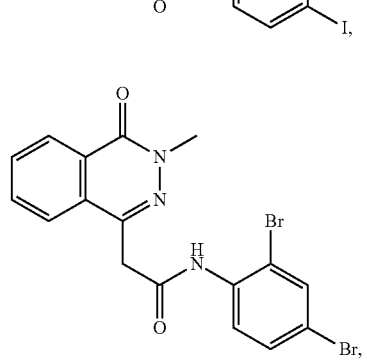

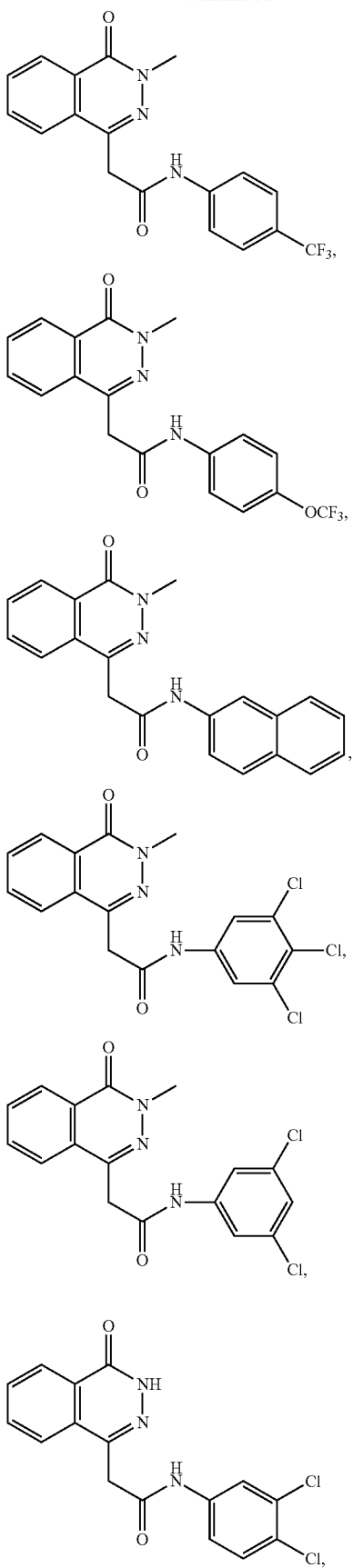
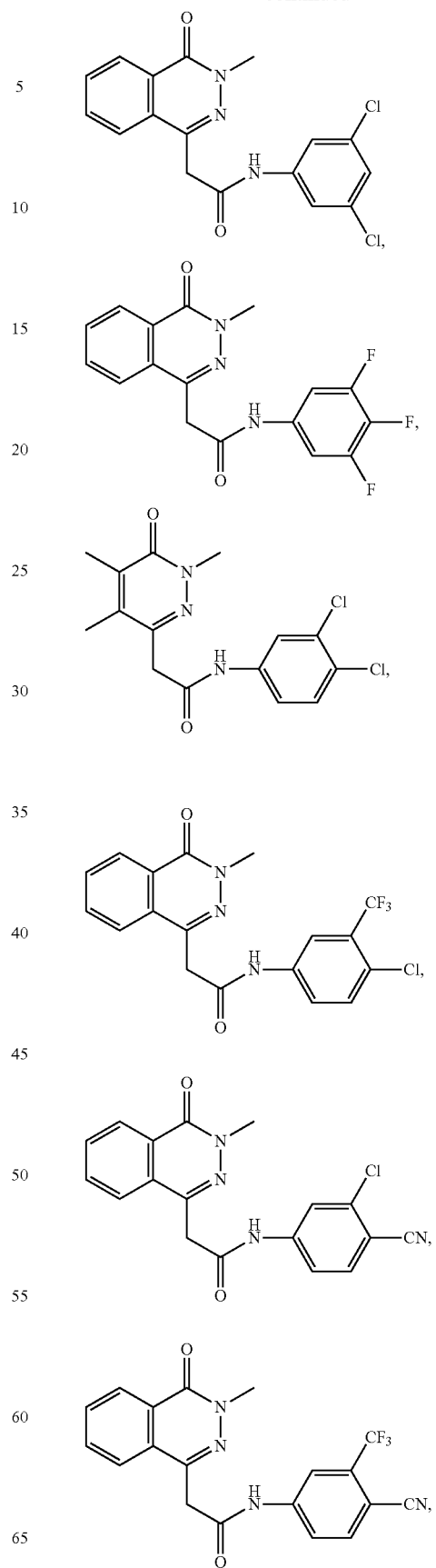

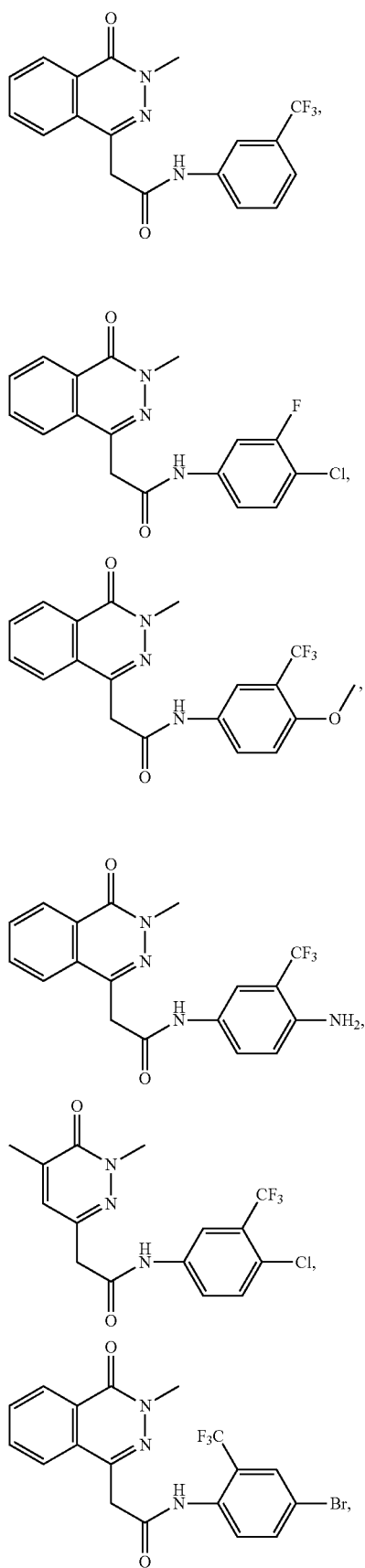
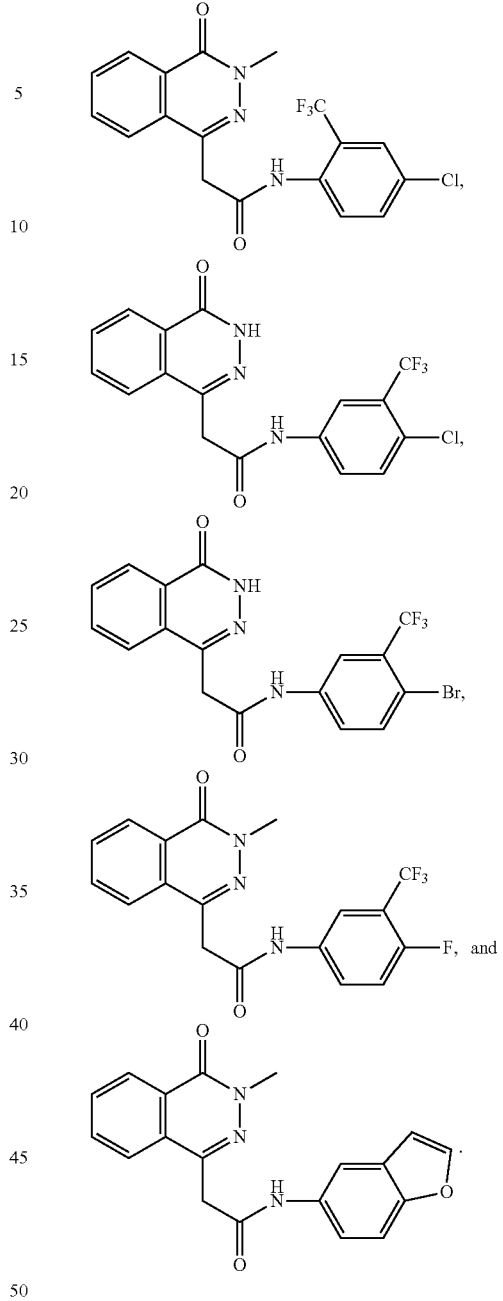
Naphthimidazole Series
In certain embodiments, the invention relates to a compound, or a pharmaceutically acceptable salt thereof, represented by Formula X:
Formula X
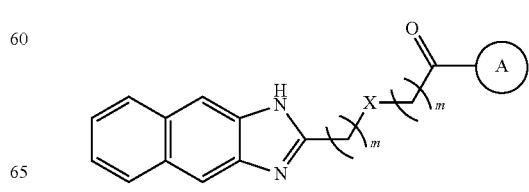

wherein, independently for each occurrence, m is 0, 1, 2, or 3;

X is absent, O, S, or NH; and (A)

is aryl or heteroaryl;

wherein, any of the aforementioned aryl or heteroaryl, may be substituted with one or more groups independently selected from the group consisting of halo, azido, alkyl, haloalkyl, aralkyl, alkenyl, alkynyl, cycloalkyl, heterocyclyl, aryl, heteroaryl, heteroaralkyl, hydroxy, alkoxy, aryloxy, heteroaryloxy, amino, nitro, sulfhydryl, imino, amido, phosphonate, phosphinate, acyl, carboxyl, alkoxycarbonyl, acyloxy, silyl, alkylthio, sulfonate, sulfonyl, sulfonamido, formyl, cyano, and isocyano.

In certain embodiments, the invention relates to any one of the aforementioned compounds, wherein one occurrence of m is 0; and one occurrence of m is 1.

In certain embodiments, the invention relates to any one of the aforementioned compounds, wherein one occurrence of m is 0; and one occurrence of m is 2.

In certain embodiments, the invention relates to any one of the aforementioned compounds, wherein one occurrence of m is 0; and one occurrence of m is 3.

In certain embodiments, the invention relates to any one of the aforementioned compounds, wherein X is O.

In certain embodiments, the invention relates to any one of the aforementioned compounds, wherein X is S.

In certain embodiments, the invention relates to any one of the aforementioned compounds, wherein X is NH.

In certain embodiments, the invention relates to any one of the aforementioned compounds, wherein (A) is [phenyl-(R$^5$)$_q$], [naphthyl], or [quinolinyl];

R$^5$ is halo, azido, alkyl, haloalkyl, aralkyl, alkenyl, alkynyl, cycloalkyl, heterocyclyl, aryl, heteroaryl, heteroaralkyl, hydroxy, alkoxy, haloalkyloxy, aryloxy, heteroaryloxy, amino, nitro, sulfhydryl, imino, amido, phosphonate, phosphinate, acyl, carboxyl, alkoxycarbonyl, acyloxy, alkylthio, sulfonate, sulfonyl, sulfonamido, formyl, cyano, or isocyano; and q is 0 to 5 inclusive.

In certain embodiments, the invention relates to any one of the aforementioned compounds, wherein (A) is [phenyl-R$^5$];

and R$^5$ is selected from the group consisting of halo, alkoxy, haloalkyloxy, alkylthio, amido, and cyano.

In certain embodiments, the invention relates to any one of the aforementioned compounds, wherein (A) is [phenyl-R$^5$];

and R$^5$ is halo.

In certain embodiments, the invention relates to any one of the aforementioned compounds, wherein (A) is [phenyl-R$^5$];

and R$^5$ is chloro.

In certain embodiments, the invention relates to any one of the aforementioned compounds, wherein (A) is [phenyl-R$^5$];

and R$^5$ is bromo.

In certain embodiments, the invention relates to any one of the aforementioned compounds, wherein (A) is [phenyl-R$^5$];

and R$^5$ is alkoxy.

In certain embodiments, the invention relates to any one of the aforementioned compounds, wherein

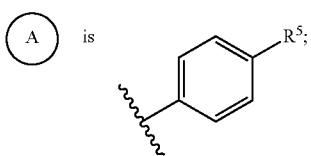 is and $R^5$ is methoxy.

In certain embodiments, the invention relates to any one of the aforementioned compounds, wherein

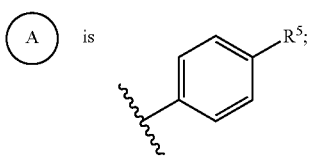

and $R^5$ is haloalkyloxy.

In certain embodiments, the invention relates to any one of the aforementioned compounds, wherein

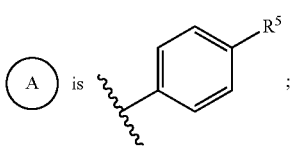

and $R^5$ is trifluoromethoxy.

In certain embodiments, the invention relates to any one of the aforementioned compounds, wherein

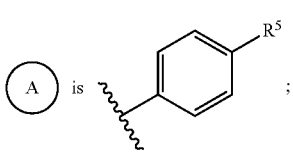

and $R^5$ is alkylthio.

In certain embodiments, the invention relates to any one of the aforementioned compounds, wherein

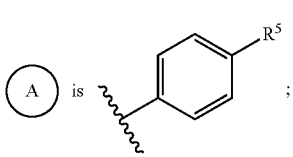

and $R^5$ is methylthio.

In certain embodiments, the invention relates to any one of the aforementioned compounds, wherein

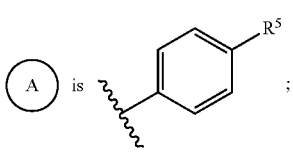

and $R^5$ is cyano.

In certain embodiments, the invention relates to any one of the aforementioned compounds, wherein

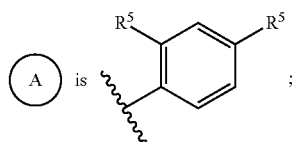

and $R^5$ is halo.

In certain embodiments, the invention relates to any one of the aforementioned compounds, wherein

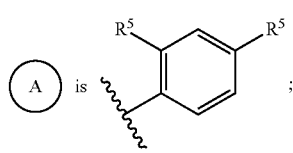

and $R^5$ is chloro.

In certain embodiments, the invention relates to any one of the aforementioned compounds, wherein

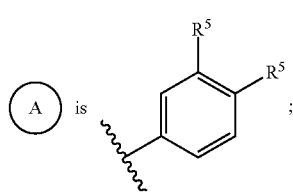

and $R^5$ is halo or cyano.

In certain embodiments, the invention relates to any one of the aforementioned compounds, wherein

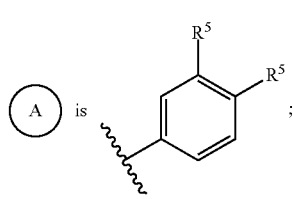

and $R^5$ is halo.

In certain embodiments, the invention relates to any one of the aforementioned compounds, wherein

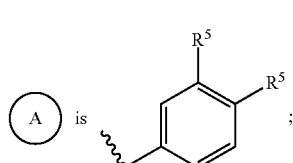

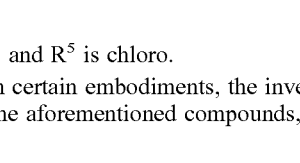

and $R^5$ is chloro.

In certain embodiments, the invention relates to any one of the aforementioned compounds, wherein

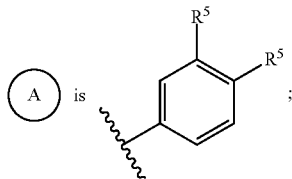

one instance of $R^5$ is halo; and one instance of $R^5$ is cyano.

In certain embodiments, the invention relates to any one of the aforementioned compounds, wherein

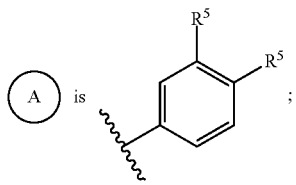

one instance of $R^5$ is halo; and one instance of $R^5$ is amido.

In certain embodiments, the invention relates to any one of the aforementioned compounds, wherein

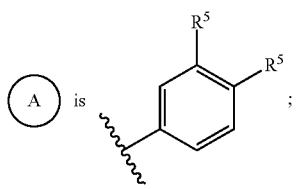

one instance of $R^5$ is chloro; and one instance of $R^5$ is cyano.

In certain embodiments, the invention relates to any one of the aforementioned compounds, wherein

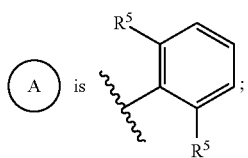

and $R^5$ is halo.

In certain embodiments, the invention relates to any one of the aforementioned compounds, wherein

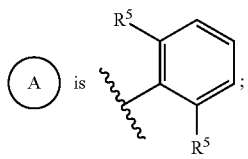

and $R^5$ is chloro.

In certain embodiments, the invention relates to any one of the aforementioned compounds, wherein

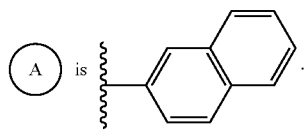

In certain embodiments, the invention relates to any one of the aforementioned compounds, wherein

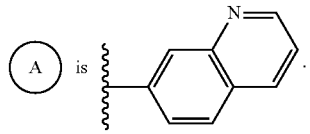

In certain embodiments, the invention relates to a compound, or a pharmaceutically acceptable salt thereof, selected from the group consisting of

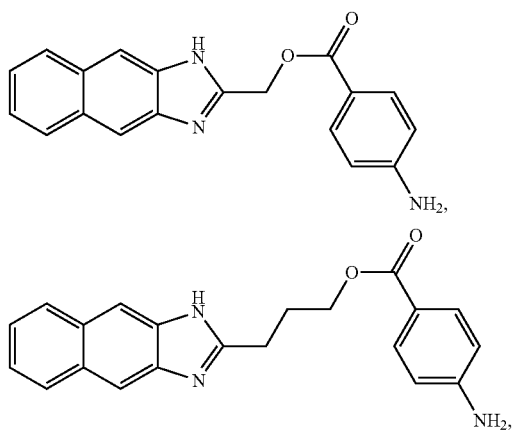

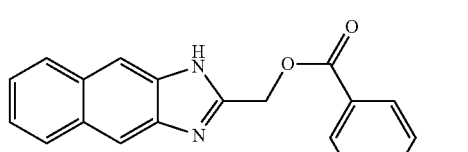

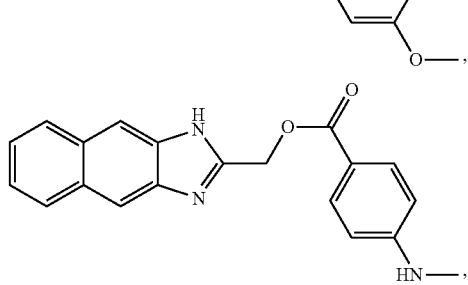

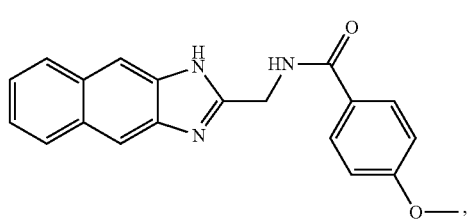

-continued

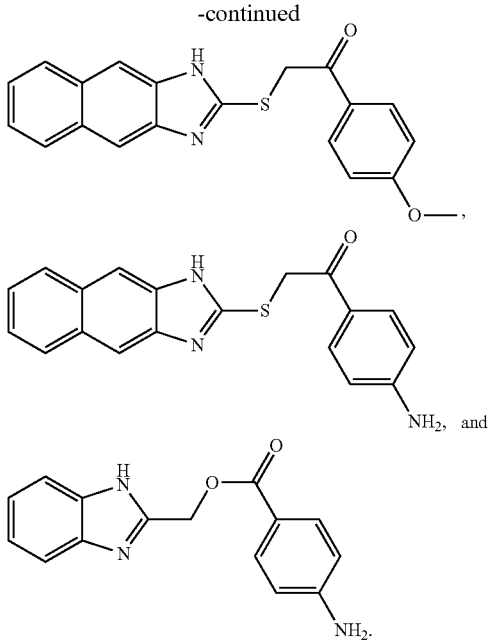

Pyrazole Series

In certain embodiments, the invention relates to a compound, or a pharmaceutically acceptable salt thereof, represented by Formula XI:

Firgure XI

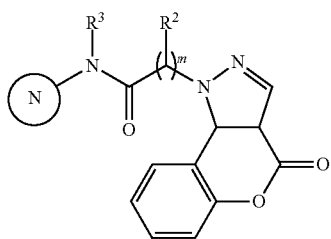

wherein, independently for each occurrence,
m is 0, 1, or 2;
$R^2$ is hydrogen or alkyl;
$R^3$ is hydrogen or alkyl; and

is aryl or heteroaryl;
wherein, any of the aforementioned alkyl, aryl, or heteroaryl may be substituted with one or more groups independently selected from the group consisting of halo, azido, alkyl, haloalkyl, aralkyl, alkenyl, alkynyl, cycloalkyl, heterocyclyl, aryl, heteroaryl, heteroaralkyl, hydroxy, alkoxy, aryloxy, heteroaryloxy, amino, nitro, sulfhydryl, imino, amido, phosphonate, phosphinate, acyl, carboxyl, alkoxycarbonyl, acyloxy, silyl, alkylthio, sulfonate, sulfonyl, sulfonamido, formyl, cyano, and isocyano.

In certain embodiments, the invention relates to any one of the aforementioned compounds, wherein m is 1.

In certain embodiments, the invention relates to any one of the aforementioned compounds, wherein m is 1 or 2; and $R^2$ is hydrogen.

In certain embodiments, the invention relates to any one of the aforementioned compounds, wherein m is 1 or 2; and $R^2$ is alkyl.

In certain embodiments, the invention relates to any one of the aforementioned compounds, wherein m is 1 or 2; and $R^2$ is methyl.

In certain embodiments, the invention relates to any one of the aforementioned compounds, wherein

is alkyl, amino, benzyl,

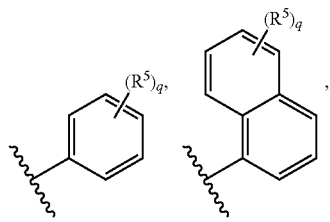

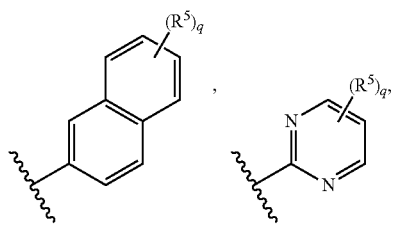

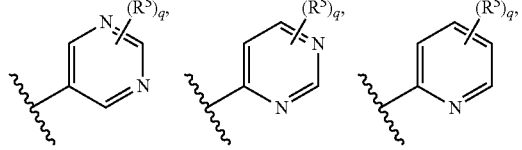

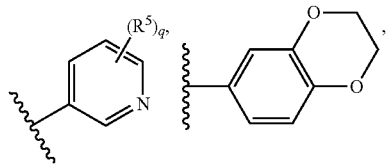

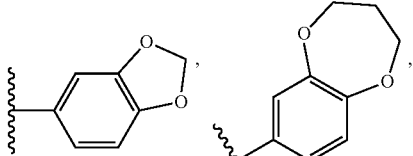

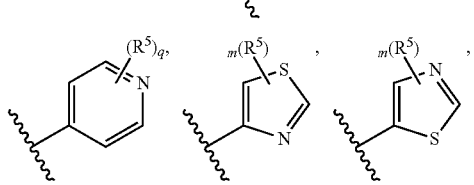

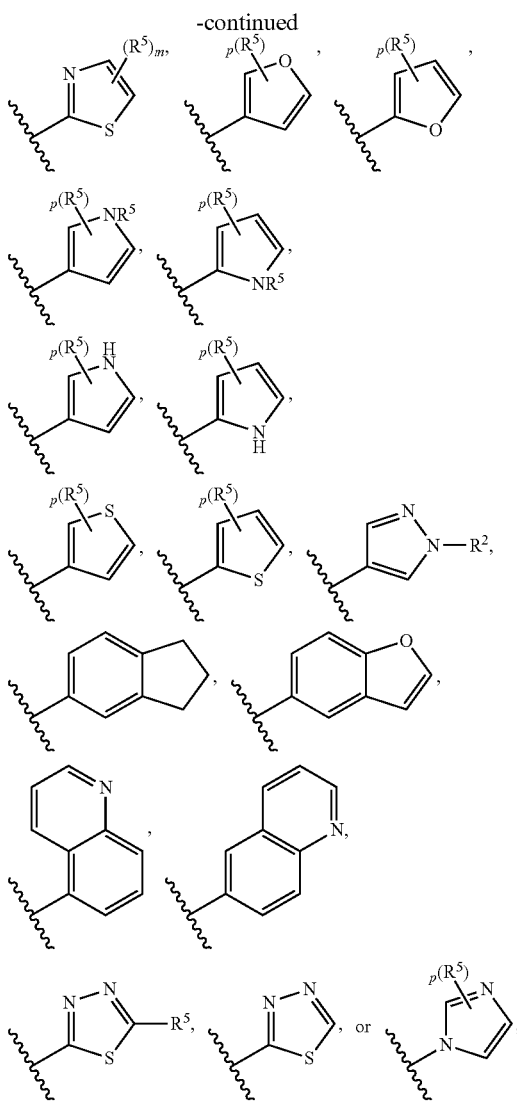

p is 0, 1, 2, or 3; q is 0, 1, 2, 3, or 4; and R⁵ is halo, azido, alkyl, haloalkyl, hydroxyalkyl, aminoalkyl, aralkyl, alkenyl, alkynyl, cycloalkyl, heterocyclyl, aryl, heteroaryl, heteroaralkyl, hydroxy, alkoxy, haloalkyloxy, aryloxy, heteroaryloxy, amino, nitro, sulfhydryl, imino, amido, phosphonate, phosphinate, acyl, carboxyl, alkoxycarbonyl, carboxylic acid, acyloxy, alkylthio, sulfonate, sulfonyl, sulfonamido, formyl, cyano, or isocyano.

In certain embodiments, the invention relates to any one of the aforementioned compounds, wherein

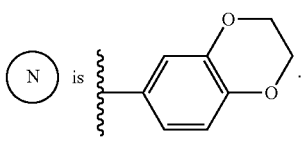

In certain embodiments, the invention relates to any one of the aforementioned compounds, wherein

In certain embodiments, the invention relates to any one of the aforementioned compounds, wherein

In certain embodiments, the invention relates to any one of the aforementioned compounds, wherein

In certain embodiments, the invention relates to any one of the aforementioned compounds, wherein In certain embodiments, the invention relates to a compound, or a pharmaceutically acceptable salt thereof, selected from the group consisting of

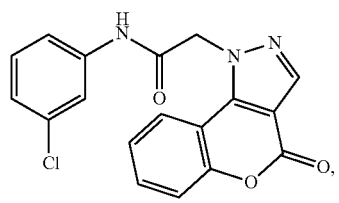
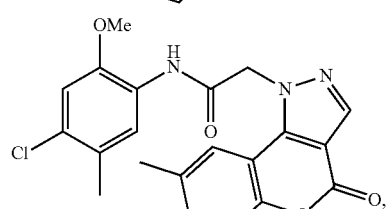
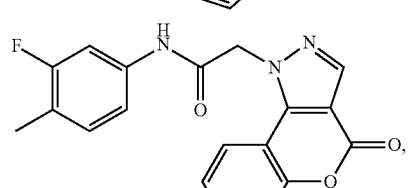
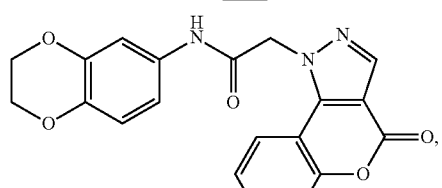
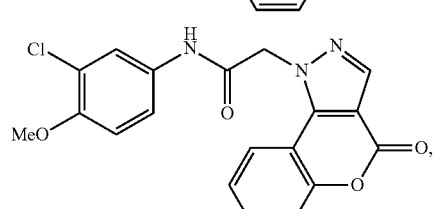
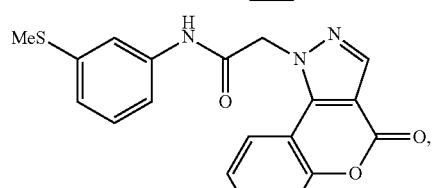
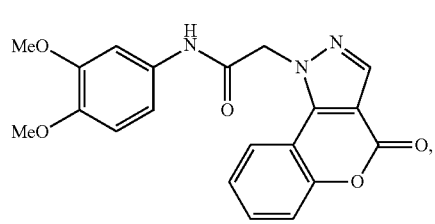
-continued
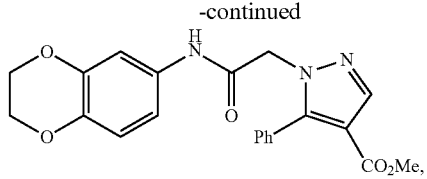
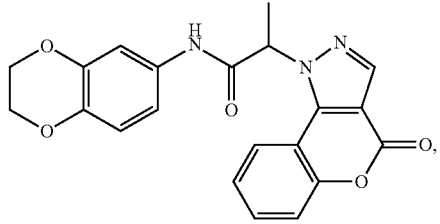
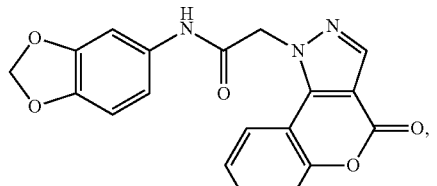
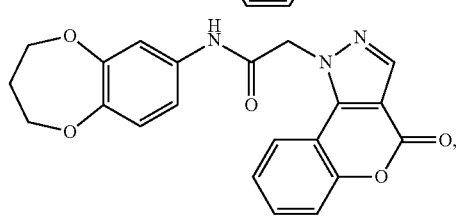
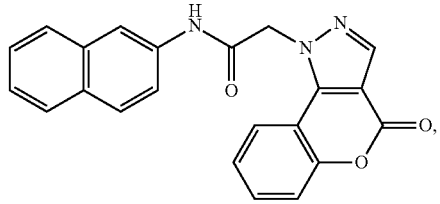
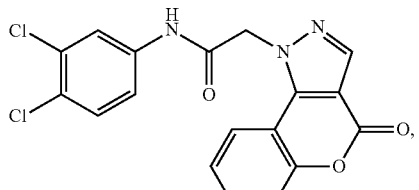
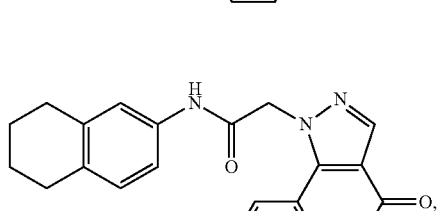
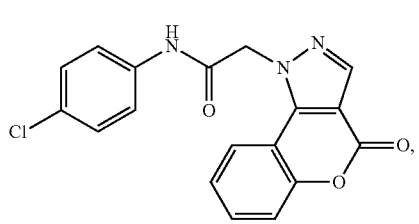

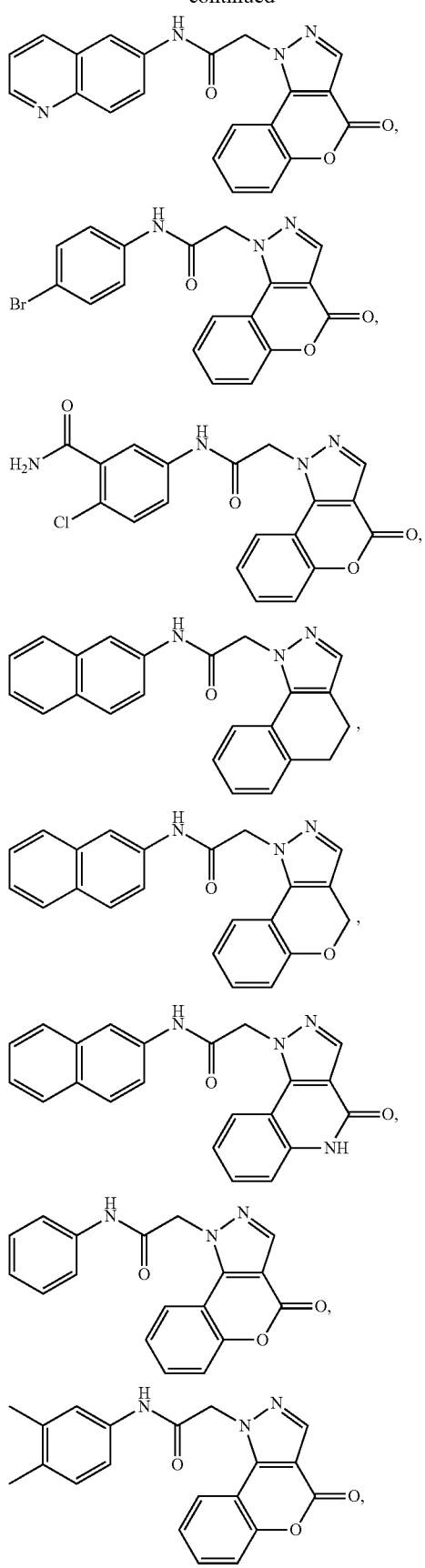

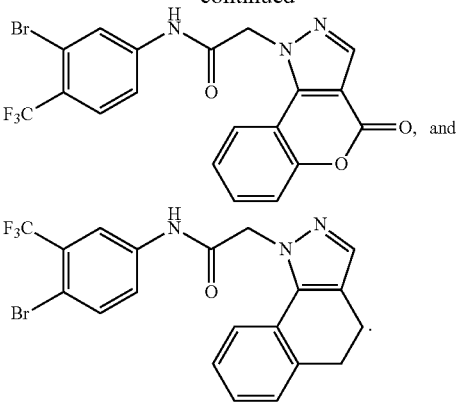

Urea Series

In certain embodiments, the invention relates to a compound, or a pharmaceutically acceptable salt thereof, represented by Formula XII:

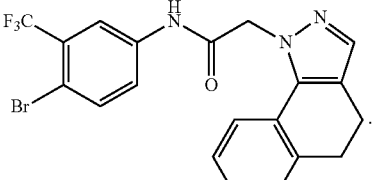

Firgure XII wherein, independently for each occurrence,
m is 0, 1, or 2;
R² is hydrogen or alkyl;

is aryl or heteroaryl; and

is aryl or heteroaryl;
wherein, any of the aforementioned alkyl, aryl, or heteroaryl may be substituted with one or more groups independently selected from the group consisting of halo, azido, alkyl, haloalkyl, aralkyl, alkenyl, alkynyl, cycloalkyl, heterocyclyl, aryl, heteroaryl, heteroaralkyl, hydroxy, alkoxy, aryloxy, heteroaryloxy, amino, nitro, sulfhydryl, imino, amido, phosphonate, phosphinate, acyl, carboxyl, alkoxycarbonyl, acyloxy, silyl, alkylthio, sulfonate, sulfonyl, sulfonamido, formyl, cyano, and isocyano.

In certain embodiments, the invention relates to any one of the aforementioned compounds, wherein m is 0.

In certain embodiments, the invention relates to any one of the aforementioned compounds, wherein m is 1.

In certain embodiments, the invention relates to any one of the aforementioned compounds, wherein m is 1 or 2; and R² is hydrogen.

In certain embodiments, the invention relates to any one of the aforementioned compounds, wherein m is 1 or 2; and R² is alkyl.

In certain embodiments, the invention relates to any one of the aforementioned compounds, wherein
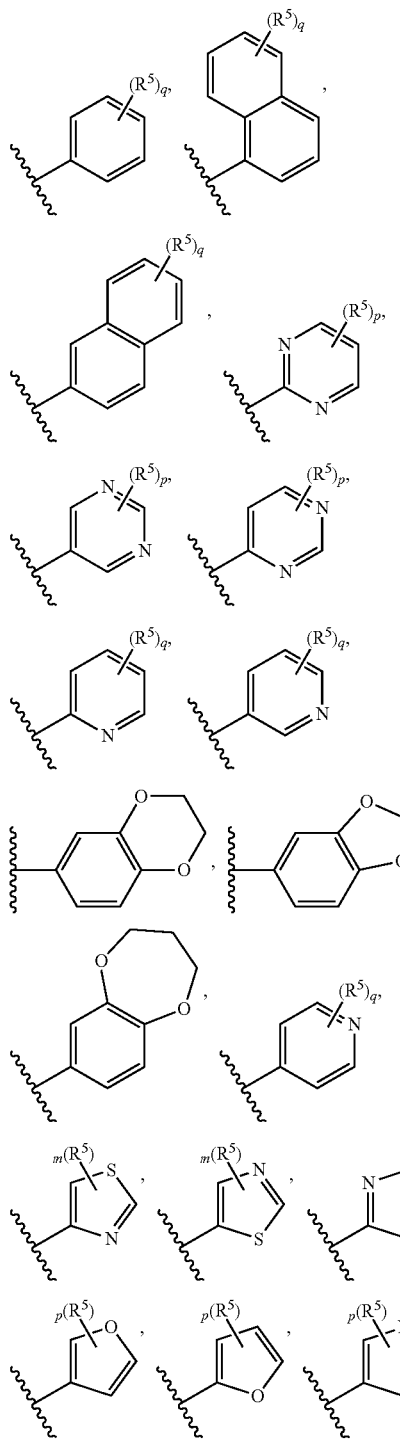
is alkyl, amino, benzyl,
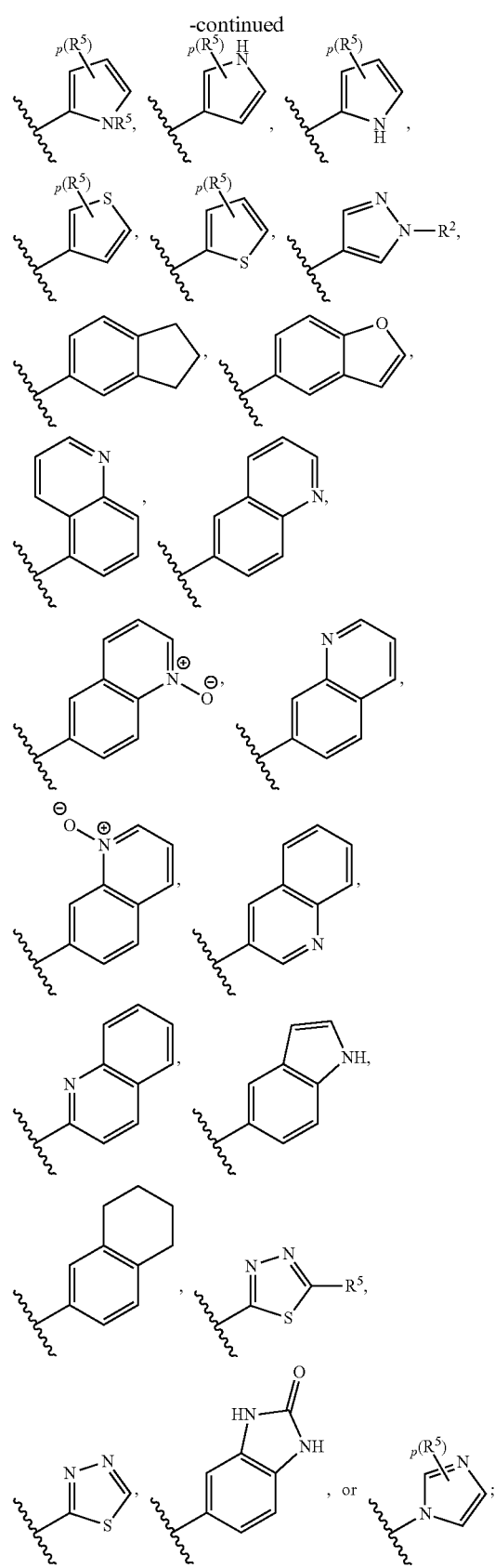
p is 0, 1, 2, or 3; q is 0, 1, 2, 3, or 4; and $R^5$ is halo, azido, alkyl, haloalkyl, hydroxyalkyl, aminoalkyl, aralkyl, alkenyl, alkynyl, cycloalkyl, heterocyclyl, aryl, heteroaryl, heteroaralkyl, hydroxy, alkoxy, haloalkyloxy, aryloxy, heteroaryloxy, amino, nitro, sulfhydryl, imino, amido, phosphonate, phosphinate, acyl, carboxyl, alkoxycarbonyl, carboxylic acid, acyloxy, alkylthio, sulfonate, sulfonyl, sulfonamido, formyl, cyano, or isocyano.

In certain embodiments, the invention relates to any one of the aforementioned compounds, wherein

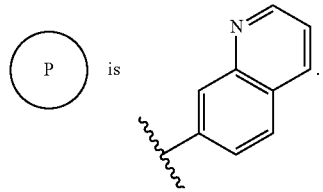

In certain embodiments, the invention relates to any one of the aforementioned compounds, wherein

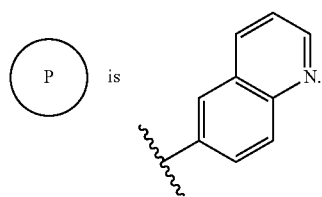

In certain embodiments, the invention relates to any one of the aforementioned compounds, wherein

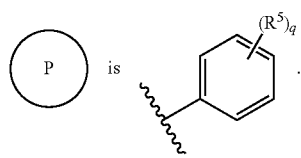

In certain embodiments, the invention relates to any one of the aforementioned compounds, wherein

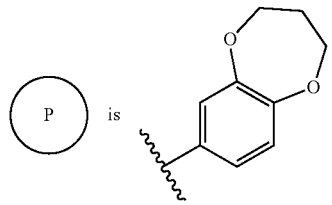

In certain embodiments, the invention relates to any one of the aforementioned compounds, wherein

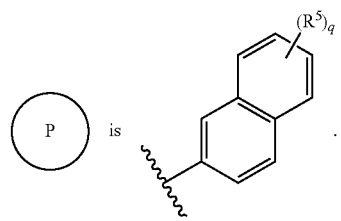

In certain embodiments, the invention relates to any one of the aforementioned compounds, wherein

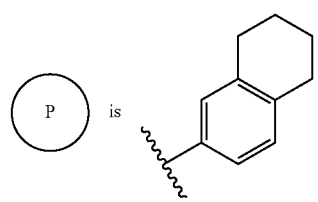

In certain embodiments, the invention relates to any one of the aforementioned compounds, wherein

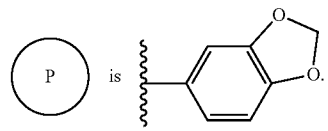

In certain embodiments, the invention relates to any one of the aforementioned compounds, wherein

is alkyl, amino, benzyl,

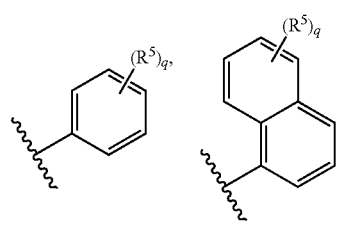

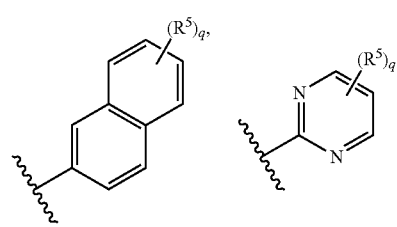

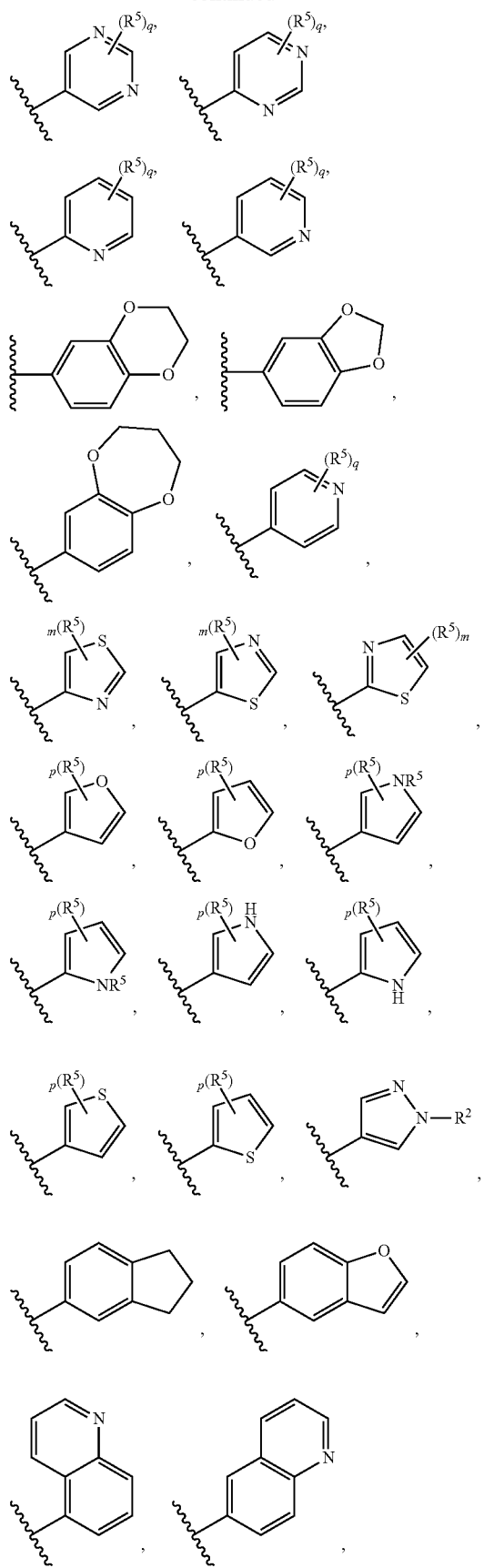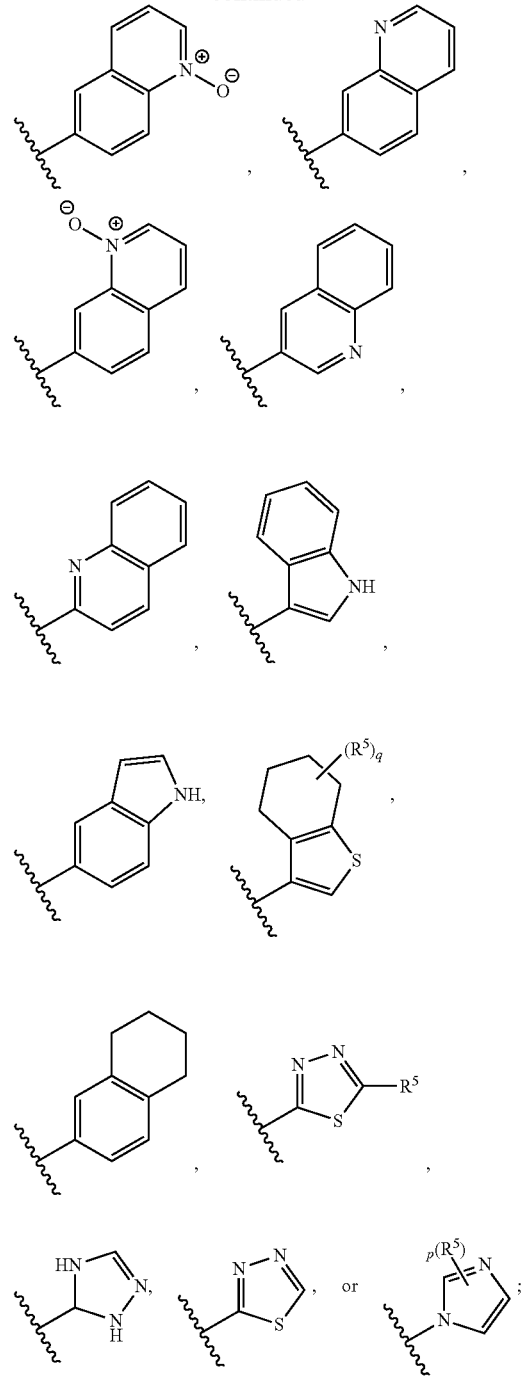

p is 0, 1, 2, or 3; q is 0, 1, 2, 3, or 4; and $R^5$ is halo, azido, alkyl, haloalkyl, hydroxyalkyl, aminoalkyl, heterocycloalkyl, aralkyl, alkenyl, alkynyl, cycloalkyl, heterocyclyl, aryl, heteroaryl, heteroaralkyl, hydroxy, alkoxy, haloalkyloxy, aryloxy, heteroaryloxy, amino, nitro, sulfhydryl, imino, amido, phosphonate, phosphinate, acyl, carboxyl, alkoxycarbonyl, carboxylic acid, acyloxy, alkylthio, sulfonate, sulfonyl, sulfonamido, formyl, cyano, oxime, or isocyano.

In certain embodiments, the invention relates to any one of the aforementioned compounds, wherein

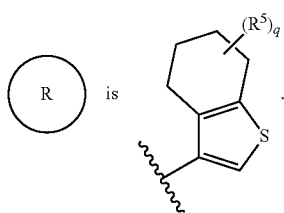
In certain embodiments, the invention relates to any one of the aforementioned compounds, wherein
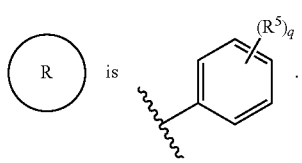
In certain embodiments, the invention relates to any one of the aforementioned compounds, wherein
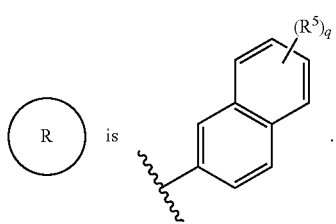
In certain embodiments, the invention relates to a compound, or a pharmaceutically acceptable salt thereof, selected from the group consisting of
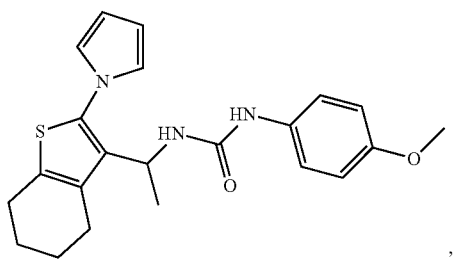
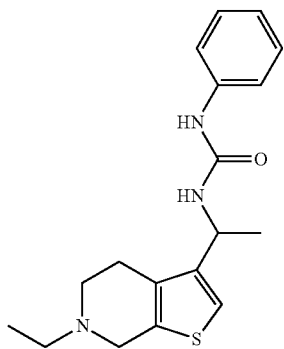
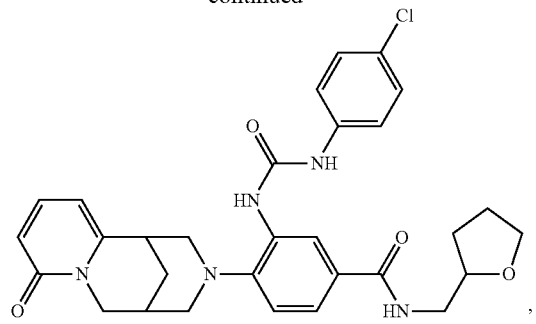
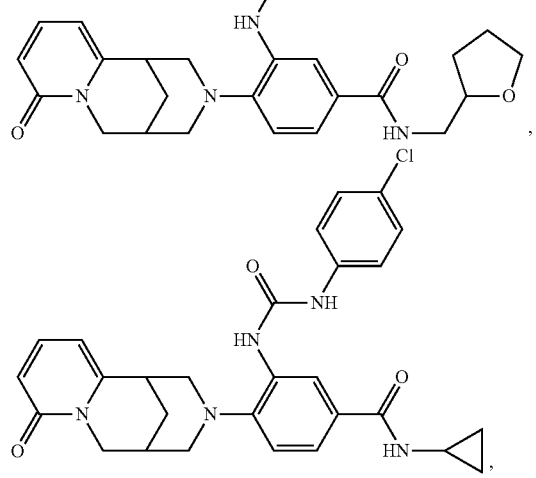
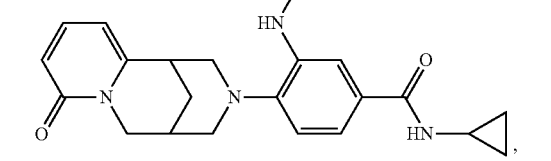
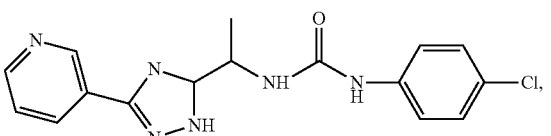
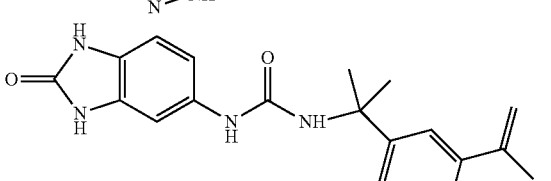
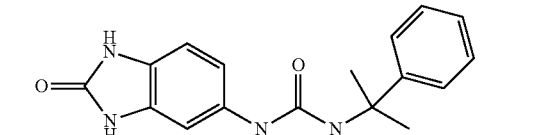
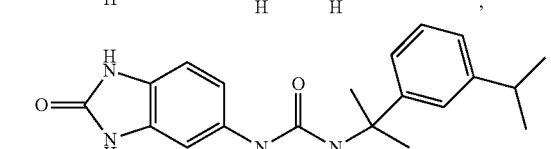
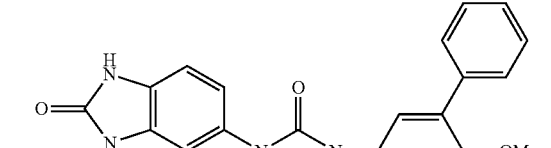
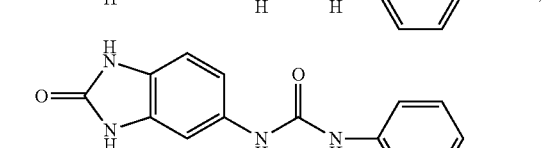

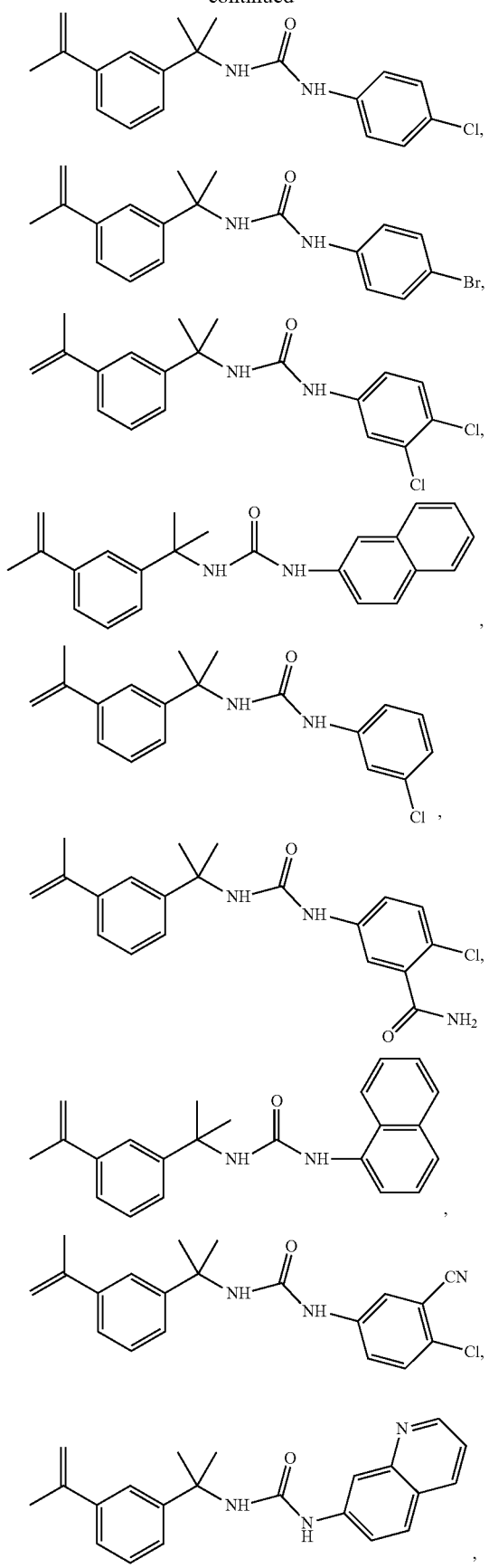
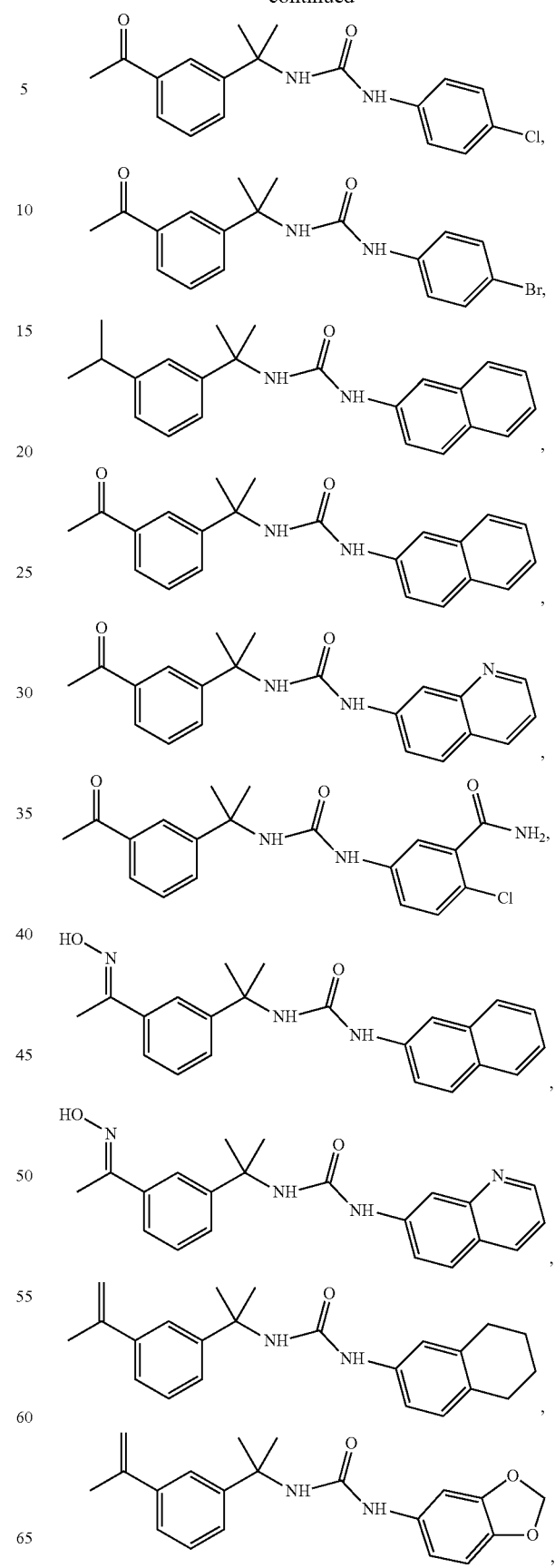

95
-continued
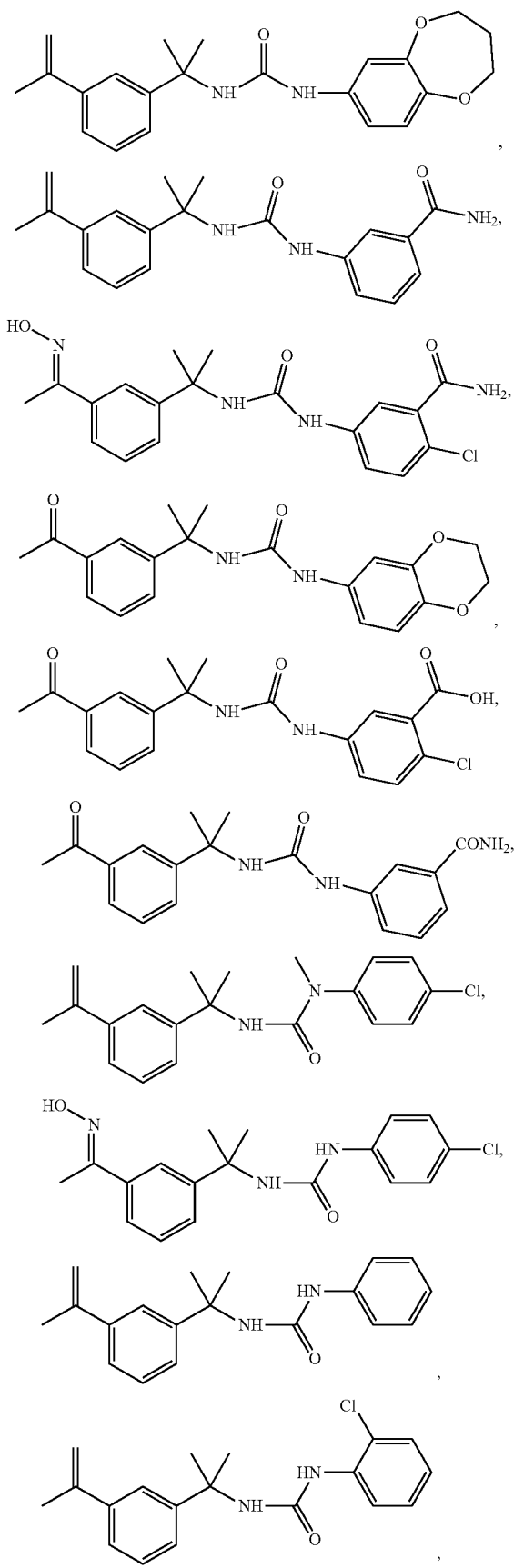
96
-continued
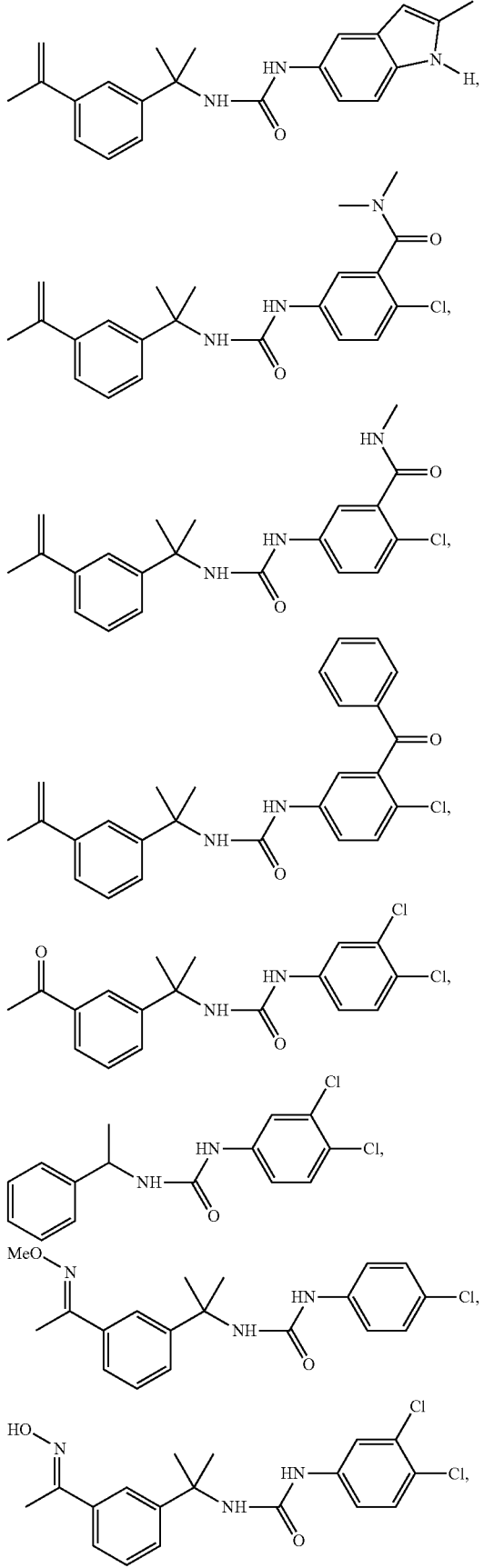

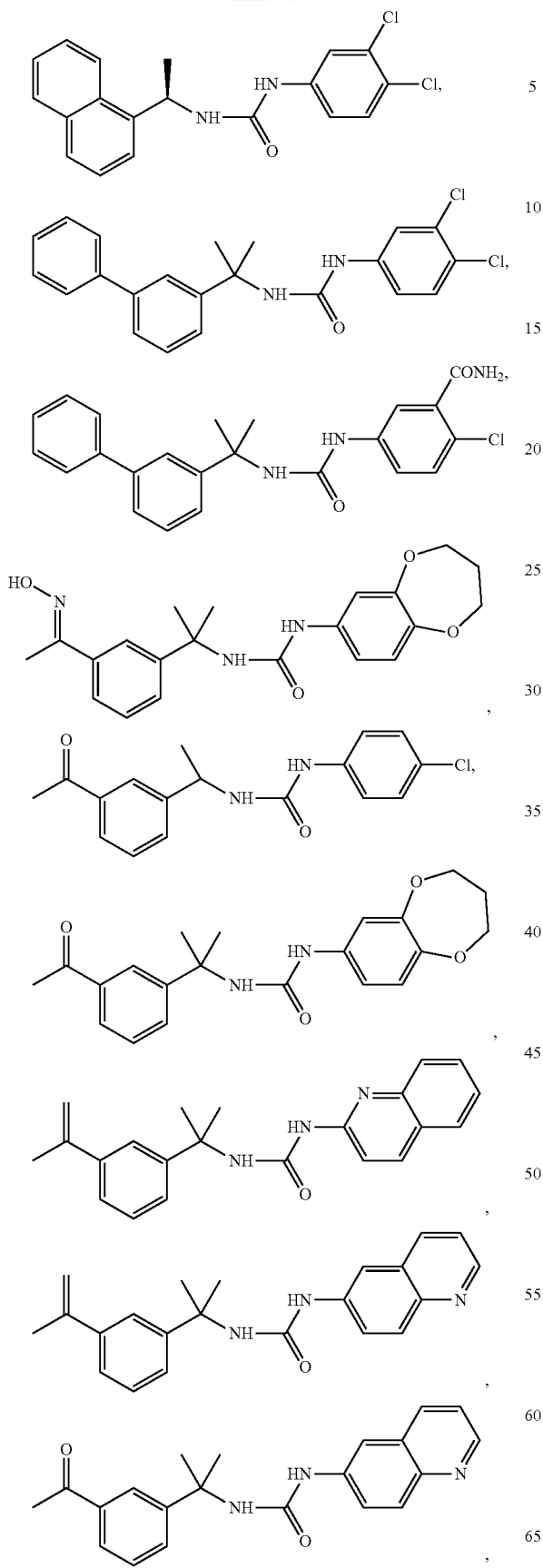
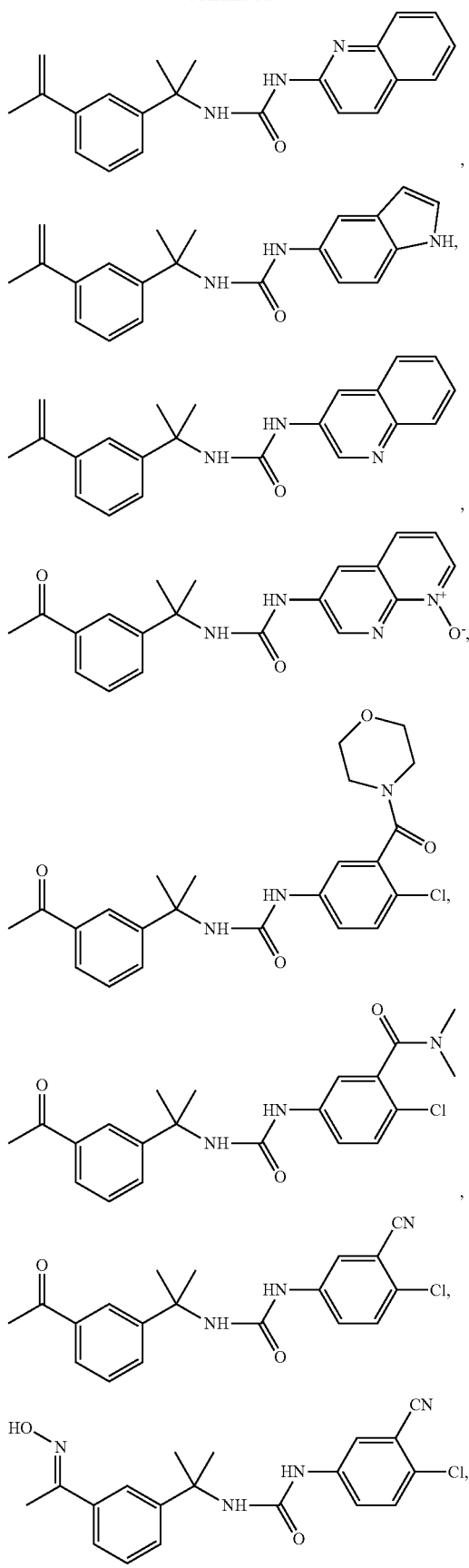

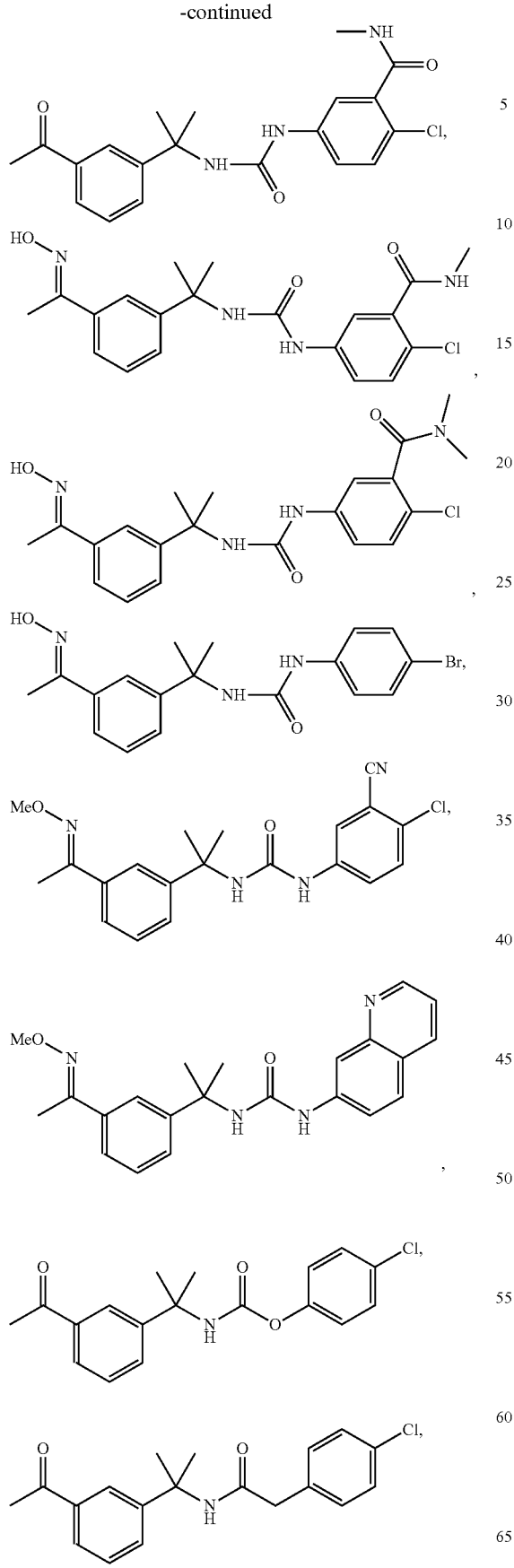
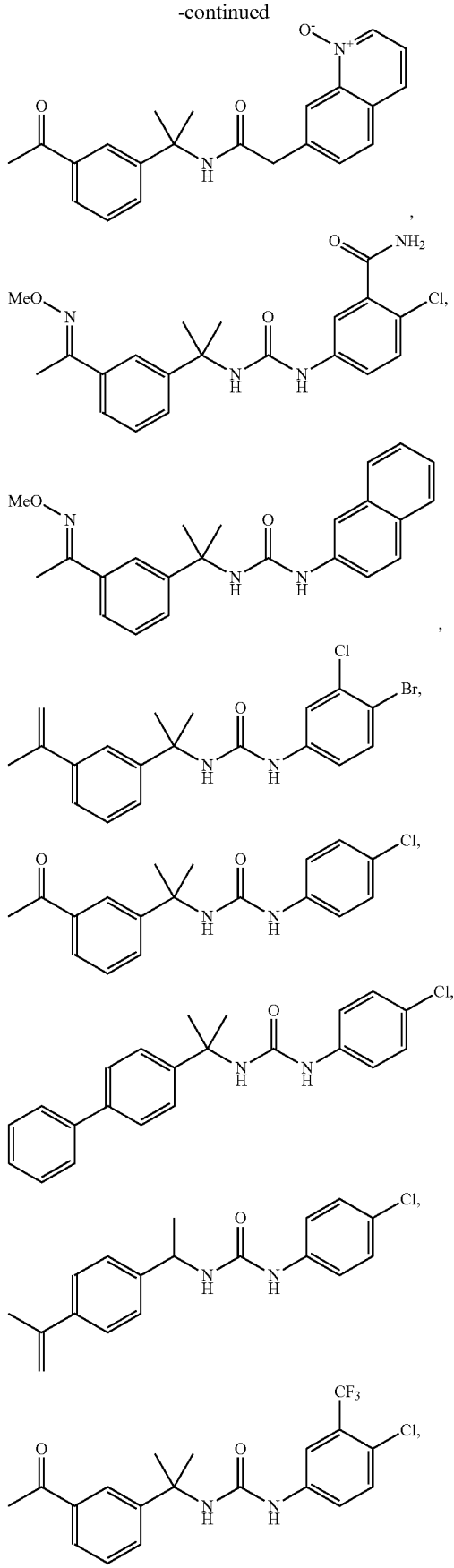

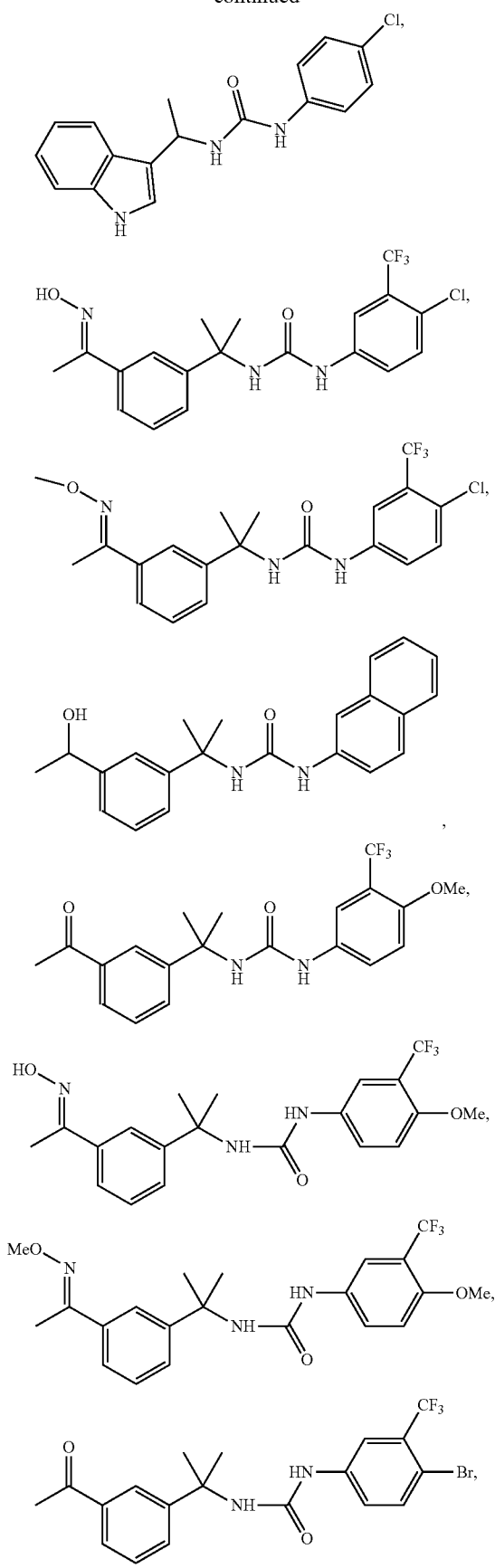
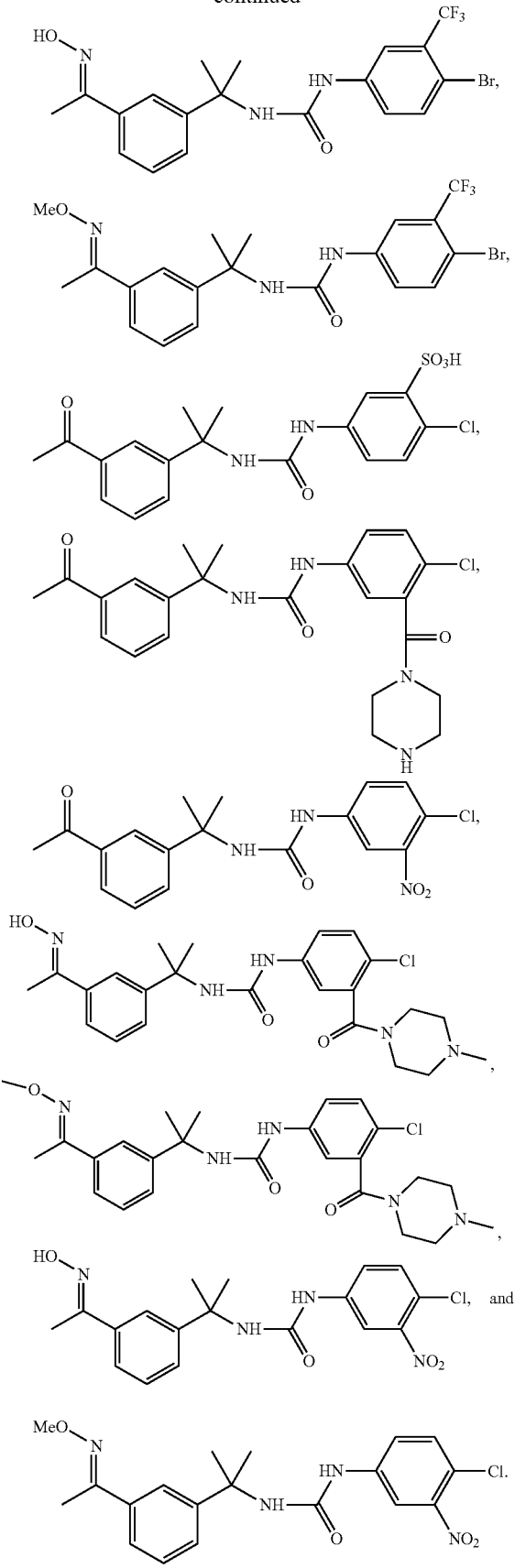

Benzoxazole Series

In certain embodiments, the invention relates to a compound, or a pharmaceutically acceptable salt thereof, represented by Formula XIII:

Formula XIII

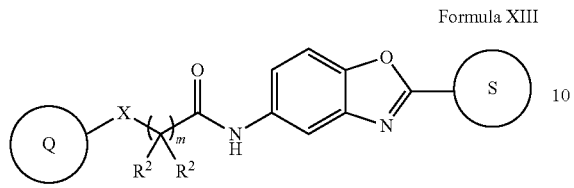

wherein, independently for each occurrence,
X is absent or O;
m is 0, 1, or 2;
$R^2$ is hydrogen or alkyl;

is hydrogen, aryl, or heteroaryl; and

is hydrogen, aryl, alkyl, or heteroaryl;
wherein, any of the aforementioned alkyl, aryl, or heteroaryl may be substituted with one or more groups independently selected from the group consisting of halo, azido, alkyl, haloalkyl, aralkyl, alkenyl, alkynyl, cycloalkyl, heterocyclyl, aryl, heteroaryl, heteroaralkyl, hydroxy, alkoxy, aryloxy, heteroaryloxy, amino, nitro, sulfhydryl, imino, amido, phosphonate, phosphinate, acyl, carboxyl, alkoxycarbonyl, acyloxy, silyl, alkylthio, sulfonate, sulfonyl, sulfonamido, formyl, cyano, and isocyano.

In certain embodiments, the invention relates to any one of the aforementioned compounds, wherein X is absent.

In certain embodiments, the invention relates to any one of the aforementioned compounds, wherein X is O.

In certain embodiments, the invention relates to any one of the aforementioned compounds, wherein m is 0.

In certain embodiments, the invention relates to any one of the aforementioned compounds, wherein m is 1.

In certain embodiments, the invention relates to any one of the aforementioned compounds, wherein m is 1; and $R^2$ is hydrogen.

In certain embodiments, the invention relates to any one of the aforementioned compounds, wherein m is 1; and $R^2$ is alkyl.

In certain embodiments, the invention relates to any one of the aforementioned compounds, wherein

is hydrogen, alkyl, amino, benzyl,

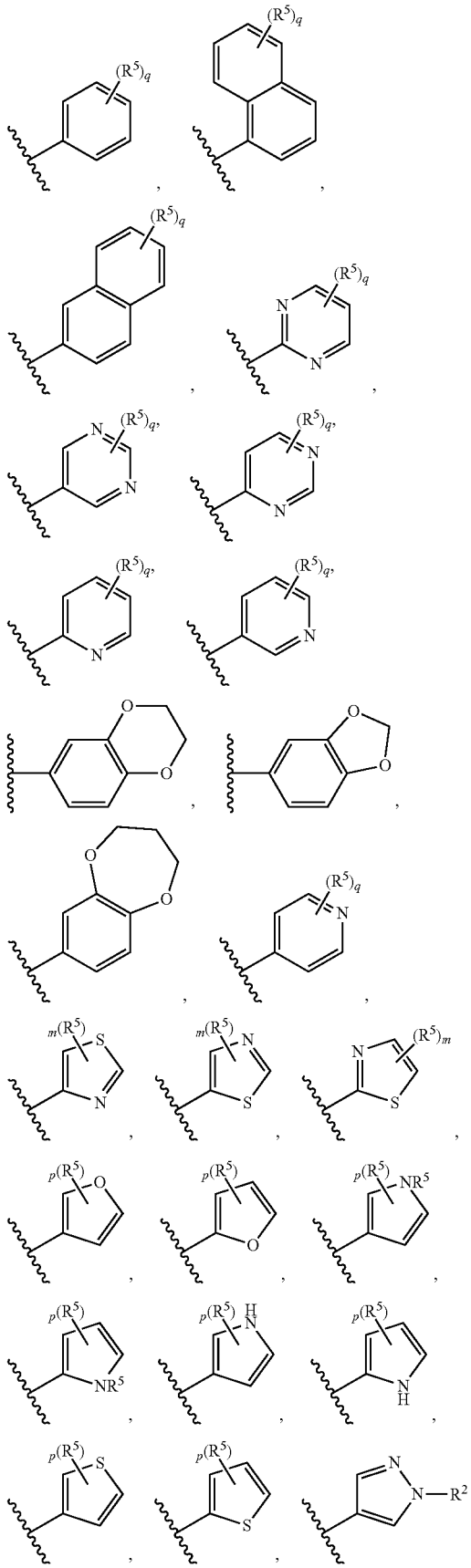

-continued

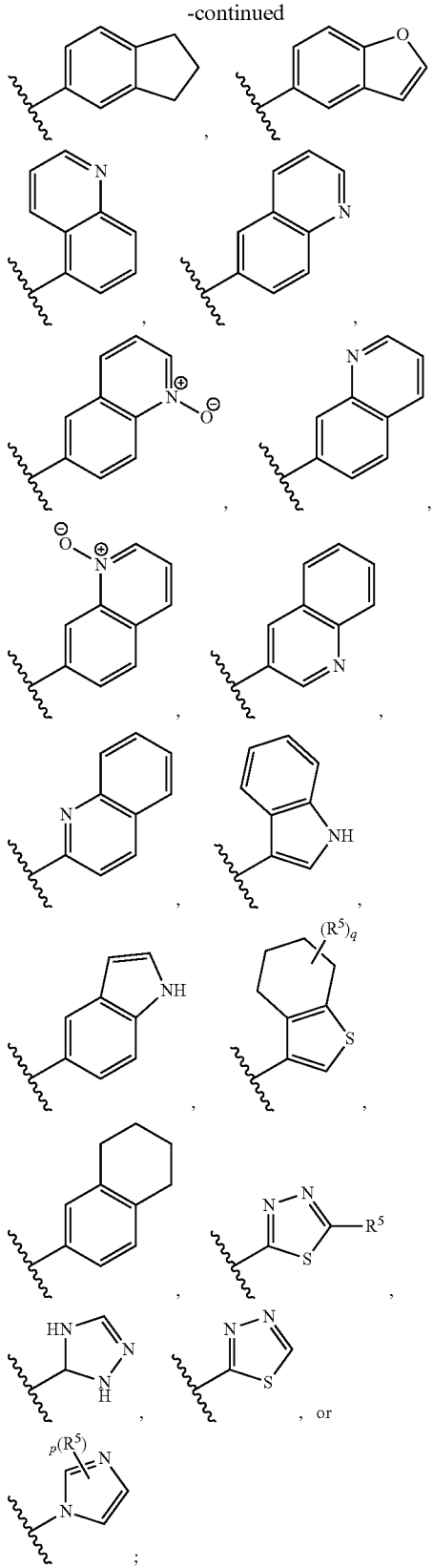

p is 0, 1, 2, or 3; q is 0, 1, 2, 3, or 4; and $R^5$ is halo, azido, alkyl, haloalkyl, hydroxyalkyl, aminoalkyl, heterocycloalkyl, aralkyl, alkenyl, alkynyl, cycloalkyl, heterocyclyl, aryl, heteroaryl, heteroaralkyl, hydroxy, alkoxy, haloalkyloxy, aryloxy, heteroaryloxy, amino, nitro, sulfhydryl, imino, amido, phosphonate, phosphinate, acyl, carboxyl, alkoxycarbonyl, carboxylic acid, acyloxy, alkylthio, sulfonate, sulfonyl, sulfonamido, formyl, cyano, oxime, or isocyano.

In certain embodiments, the invention relates to any one of the aforementioned compounds, wherein

⓪ S is hydrogen.

In certain embodiments, the invention relates to any one of the aforementioned compounds, wherein ⓪ S is [aryl with $(R^5)_q$].

In certain embodiments, the invention relates to any one of the aforementioned compounds, wherein ⓪ S is [pyridyl with $(R^5)_q$].

In certain embodiments, the invention relates to any one of the aforementioned compounds, wherein ⓪ S is [pyridyl with $(R^5)_q$].

In certain embodiments, the invention relates to any one of the aforementioned compounds, wherein ⓪ S is [thiazolyl with $m(R^5)$].

In certain embodiments, the invention relates to any one of the aforementioned compounds, wherein

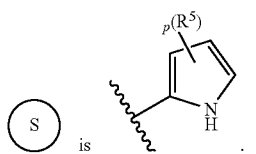 is
In certain embodiments, the invention relates to any one of the aforementioned compounds, wherein
Q is hydrogen, alkyl, amino, benzyl,
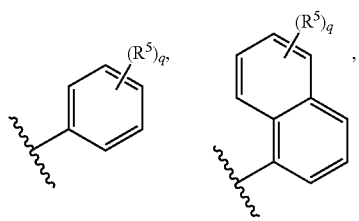
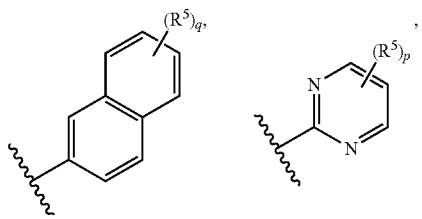
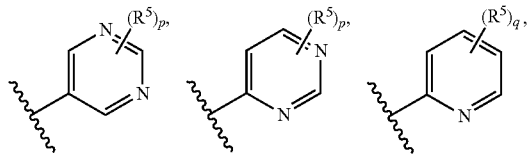
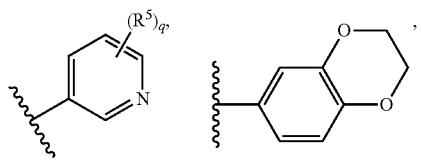
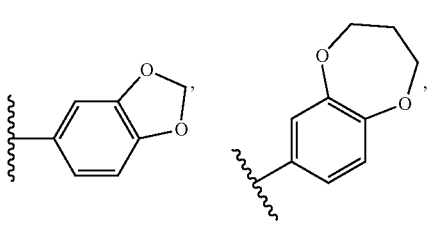
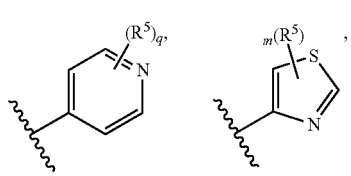
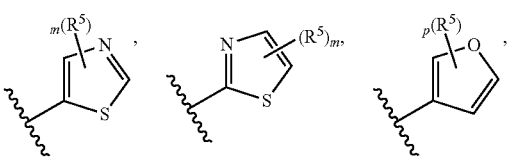
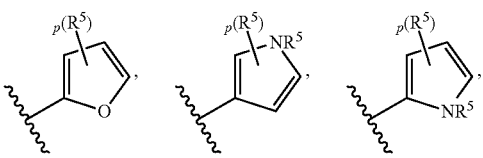
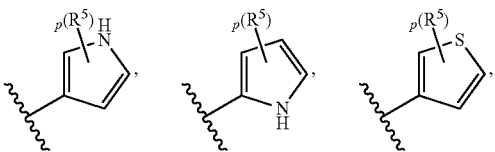
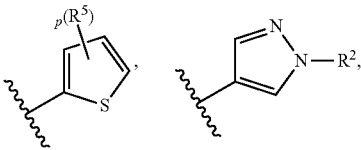
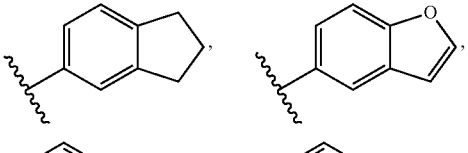
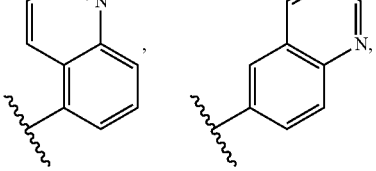
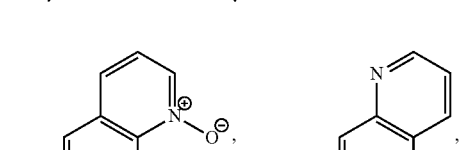
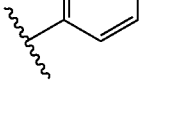
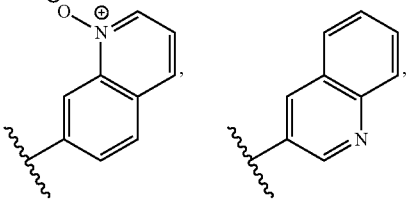
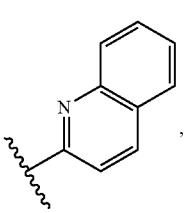

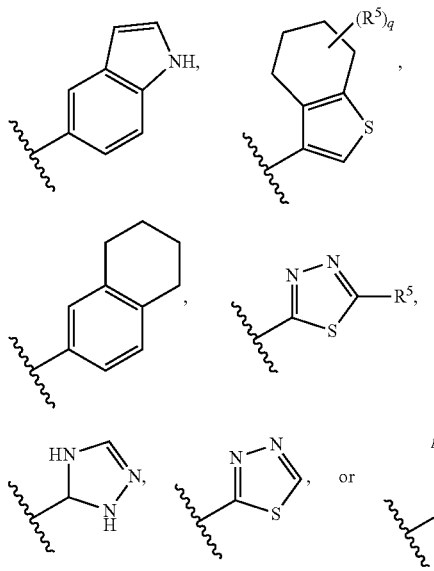

p is 0, 1, 2, or 3; q is 0, 1, 2, 3, or 4; and $R^5$ is halo, azido, alkyl, haloalkyl, hydroxyalkyl, aminoalkyl, heterocycloalkyl, aralkyl, alkenyl, alkynyl, cycloalkyl, heterocyclyl, aryl, heteroaryl, heteroaralkyl, hydroxy, alkoxy, haloalkyloxy, aryloxy, heteroaryloxy, amino, nitro, sulfhydryl, imino, amido, phosphonate, phosphinate, acyl, carboxyl, alkoxycarbonyl, carboxylic acid, acyloxy, alkylthio, sulfonate, sulfonyl, sulfonamido, formyl, cyano, oxime, or isocyano.

In certain embodiments, the invention relates to any one of the aforementioned compounds, wherein (Q)

is hydrogen.

In certain embodiments, the invention relates to any one of the aforementioned compounds, wherein (Q)

is alkyl.

In certain embodiments, the invention relates to any one of the aforementioned compounds, wherein (Q) is [phenyl with $(R^5)_q$]

.

In certain embodiments, the invention relates to any one of the aforementioned compounds, wherein (Q) is [naphthyl with $(R^5)_q$]

.

In certain embodiments, the invention relates to a compound, or a pharmaceutically acceptable salt thereof, selected from the group consisting of

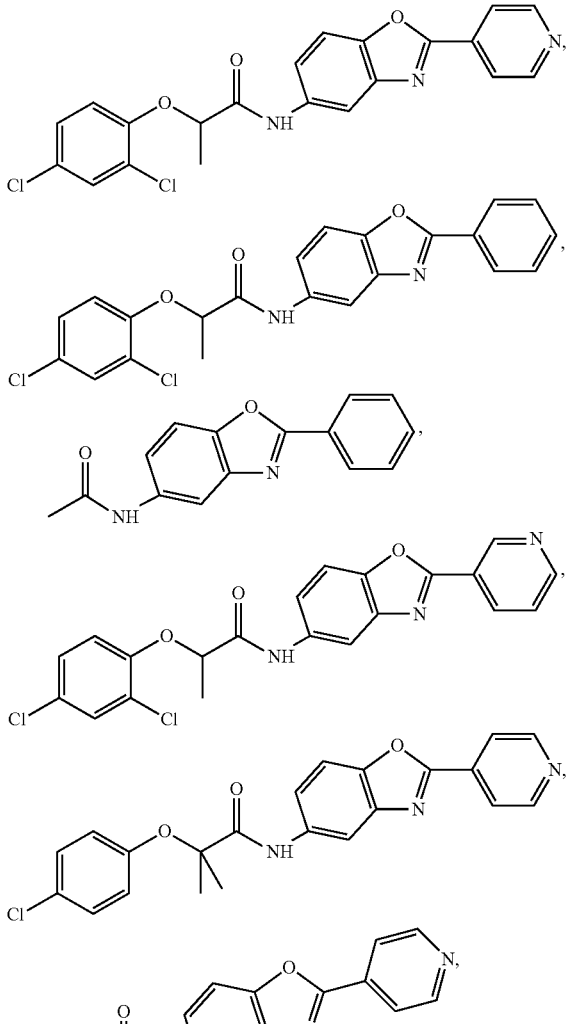

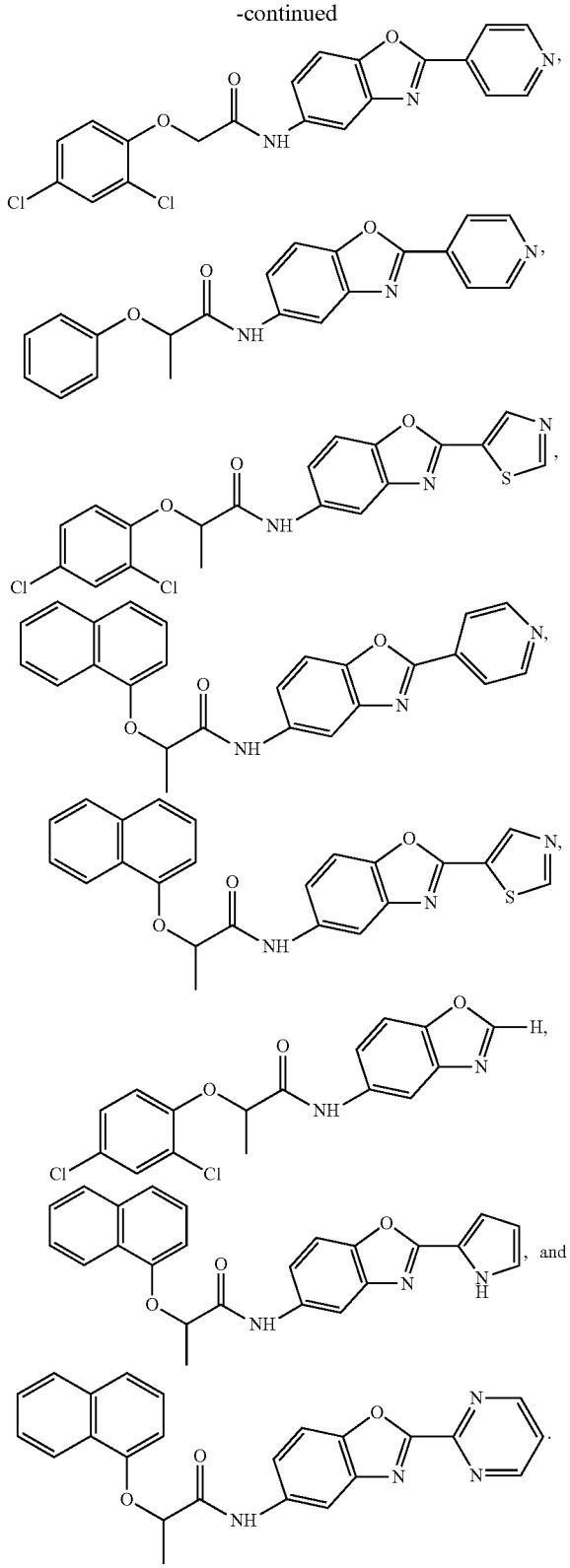

General Considerations for Exemplary Compounds of the Invention

When stereochemistry is not specifically indicated, the compounds of the invention may contain one or more asymmetric carbon atoms and thus may occur as racemates and racemic mixtures, single enantiomers, diastereomeric mixtures and individual diastereomers. All such isomeric forms of these compounds are included in the present invention, unless expressly excluded. Each stereogenic carbon may be of the R or S configuration.

In addition, the compounds of the invention described above may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

Pharmaceutical Compositions of the Invention

In certain embodiments, the invention relates to a pharmaceutical composition, comprising a pharmaceutically acceptable carrier, adjuvant, or vehicle; and any one of the aforementioned compounds.

In certain embodiments, the invention relates to any one of the aforementioned compositions, further comprising an antimicrobial agent.

In certain embodiments, the invention relates to any one of the aforementioned compositions, further comprising an antibiotic, antifungal, or antiprotozoal agent.

In certain embodiments, the invention relates to any one of the aforementioned compositions, further comprising an antibiotic agent selected from the group consisting of vancomycin, metronidazole, amoxicillin, ciprofloxacin, doxycycline, gentamicin and clindamycin.

In certain embodiments, the invention relates to any one of the aforementioned compositions, further comprising an antifungal selected from the group consisting of terbinafine, flucytosine, fluconazole, itraconazole, ketoconazole, voriconazole, nikkomycin Z, caspofungin, micafungin (FK463), anidulafungin (LY303366), amphotericin B (AmB), and nystatin.

In certain embodiments, the invention relates to any one of the aforementioned compositions, further comprising an antiprotozoal agent selected from the group consisting of eflornithine, furazolidone, melarsoprol, metronidazole, ornidazole, paromomycin sulfate, pentamidine, pyrimethamine, and tinidazole.

In certain embodiments, the invention relates to any one of the aforementioned compositions, further comprising an immunosuppression agent.

In certain embodiments, the invention relates to any one of the aforementioned compositions, further comprising an immunosuppression agent selected from the group consisting of cyclosporin A, FK506, rapamycin, leflunomide, deoxyspergualin, prednisone, azathioprine, mycophenolate mofetil, OKT3, ATAG, interferon and mizoribine.

In certain embodiments, the invention relates to any one of the aforementioned compositions, further comprising an anti-cancer agent.

In certain embodiments, the invention relates to any one of the aforementioned compositions, further comprising an anti-cancer agent selected from the group consisting of cis-platin, actinomycin D, doxorubicin, vincristine, vinblastine, etoposide, amsacrine, mitoxantrone, tenipaside, taxol, colchicine, cyclosporin A, phenothiazines, interferon and thioxantheres.

In certain embodiments, the invention relates to any one of the aforementioned compositions, further comprising an anti-viral agent.

In certain embodiments, the invention relates to any one of the aforementioned compositions, further comprising an anti-viral agent selected from the group consisting of cytovene, ganciclovir, trisodium phosphonoformate, Ribavirin, d4T, ddI, AZT, and acyclovir.

In certain embodiments, the invention relates to any one of the aforementioned compositions, further comprising an anti-vascular hyperproliferative agent.

In certain embodiments, the invention relates to any one of the aforementioned compositions, further comprising an anti-vascular hyperproliferative selected from the group consisting of HMG Co-A reductase inhibitors such as lovastatin, thromboxane A2 synthetase inhibitors, eicosapentanoic acid, ciprostene, trapidil, ACE inhibitors, low molecular weight heparin, mycophenolic acid, rapamycin and 5-(3'-pyridinylmethyl)benzofuran-2-carboxylate.

The compounds of the invention are defined to include pharmaceutically acceptable salts or prodrugs thereof. A "pharmaceutically acceptable salt or prodrug" means any pharmaceutically acceptable salt, ester, salt of an ester, or other derivative of a compound of the invention which, upon administration to a recipient, is capable of providing (directly or indirectly) a compound of this invention. Particularly favored prodrugs are those that increase the bioavailability of the compounds of the invention when such compounds are administered to a mammal (e.g., by allowing an orally administered compound to be more readily absorbed into the blood) or which enhance delivery of the parent compound to a biological compartment (e.g., the brain or lymphatic system) relative to the parent species. Exemplary prodrugs include derivatives where a group which enhances aqueous solubility or active transport through the gut membrane is appended to the structure of the compounds of the invention.

Pharmaceutically acceptable salts of the compounds of the invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium), alkaline earth metal (e.g., magnesium), and ammonium salts. This invention also envisions the quaternization of any basic nitrogen-containing groups of the compounds disclosed herein. Water or oil-soluble or dispersible products may be obtained by such quaternization.

In certain embodiments, the invention relates to a pharmaceutical composition, wherein the pharmaceutical composition comprises any one of the aforementioned compounds or a pharmaceutically acceptable salt thereof; an additional agent selected from the group consisting of an immunosuppressant, an anti-cancer agent, an anti-viral agent, antiinflammatory agent, antifungal agent, antibiotic, and an anti-vascular hyperproliferation compound; and any pharmaceutically acceptable carrier, adjuvant or vehicle. In certain embodiments, the invention relates to any one of the aforementioned pharmaceutical compositions, wherein the pharmaceutical composition comprises any one of the aforementioned compounds or a pharmaceutically acceptable salt thereof; and a pharmaceutically acceptable carrier, adjuvant or vehicle. In certain embodiments, the invention relates to any one of the aforementioned pharmaceutical compositions, wherein the pharmaceutical composition optionally comprises an additional agent selected from the group consisting of an immunosuppressant, an anti-cancer agent, an anti-viral agent, antiinflammatory agent, antifungal agent, antibiotic, and an anti-vascular hyperproliferation compound.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of the invention include, but are not limited to, ion exchangers, alumina, aluminum stearate, lecithin, self-emulsifying drug delivery systems (SEDDS) such as d.alpha.-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of any one of the aforementioned compounds.

The pharmaceutical compositions of the invention may be administered orally, parenternally, by inhalation spray, topically, rectally, nasally, buccally, vaginally or via an implanted reservoir. The pharmaceutical compositions of the invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenternal as used herein includes subcutaneous, intracutaneous, intravenous, intramuscular, intra-articular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as those described in Pharmacopeia Helvetica, Ph. Helv., or a similar alcohol, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of the invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of the invention may also be administered in the form of suppositories for rectal administration. These compositions can be prepared by mixing a compound of the invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of the invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of the invention include, but are not limited to, mineral oil, liquid petroleum, white petroleum, propylene glycol, polyoxy-ethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of the invention may also be topically applied to the lower intestinal tract by rectal suppository formulation or in a suitable enema formulation. Topically-transdermal patches are also included in this invention.

The pharmaceutical compositions of the invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Dosage levels of between about 0.01 and about 100 mg/kg body weight per day, or between about 0.5 and about 75 mg/kg body weight per day, of the IMPDH inhibitory compounds described herein are useful in a monotherapy and/or in combination therapy for the prevention and treatment of IMPDH-mediated disease or infection. Typically, the pharmaceutical compositions of the invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Such preparations contain from about 20% to about 80% active compound.

When the compositions of the invention comprise a combination of an IMPDH inhibitor of the invention and one or more additional therapeutic or prophylactic agents, both the IMPDH inhibitor and the additional agent should be present at dosage levels of between about 10 to 100%, or between about 10 to 80% of the dosage normally administered in a monotherapy regimen. The additional agents may be administered separately, as part of a multiple dose regimen, from the compounds of this invention. Alternatively, those agents may be part of a single dosage form, mixed together with the compounds of the invention in a single composition.

Upon improvement of a patient's condition, a maintenance dose of a compound, composition or combination of the invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician.

In certain embodiments, the invention relates to a pharmaceutical composition for treatment or prevention of a protozoan infection, comprising a pharmaceutically acceptable carrier, adjuvant or vehicle and at least one of the aforementioned compounds, or a pharmaceutically acceptable salt or prodrug thereof.

In certain embodiments, the invention relates to any one of the aforementioned pharmaceutical compositions, wherein said protozoan infection is caused by a protozoan selected from the group consisting of the genera *Toxoplasma, Eimeria, Cryptosporidium, Plasmodium, Babesia, Theileria, Neospora, Sarcocystis, Giardia, Entamoeba, Trichomonas, Tritrichomonas, Leishmania* and *Trypanosoma*.

In certain embodiments, the invention relates to any one of the aforementioned pharmaceutical compositions, wherein said protozoan infection is caused by a protozoan selected from the genus *Cryptosporidium*.

In certain embodiments, the invention relates to any one of the aforementioned pharmaceutical compositions, wherein said protozoan infection is caused by *Cryptosporidium parvum*.

In certain embodiments, the invention relates to any one of the aforementioned pharmaceutical compositions, wherein the pharmaceutical composition further comprises an antimicrobial agent, such as an antibiotic, antifungal, or antiprotozoal agent. Examples of antibiotic agents include, but are not limited to, vancomycin, metronidazole, amoxicillin, ciprofloxacin, doxycycline, gentamicin and clindamycin. Examples of antifungal include, but are not limited to, terbinafine, flucytosine, fluconazole, itraconazole, ketoconazole, voriconazole, nikkomycin Z, caspofungin, micafungin (FK463), anidulafungin (LY303366), amphotericin B (AmB), and nystatin. Examples of antiprotozoal agents include, but are not limited to, eflornithine, furazolidone, melarsoprol, metronidazole, ornidazole, paromomycin sulfate, pentamidine, pyrimethamine, and tinidazole.

In certain embodiments, the invention relates to any one of the aforementioned pharmaceutical compositions, wherein the pharmaceutical composition is used for treatment or prevention of an IMPDH-mediated disease, and comprises a pharmaceutically acceptable carrier, adjuvant or vehicle and at least one aforementioned compound.

In certain embodiments, the invention relates to any one of the aforementioned pharmaceutical compositions, further comprising an immunosuppression agent. Examples of additional immunosuppression agents include, but are not limited to, cyclosporin A, FK506, rapamycin, leflunomide, deoxyspergualin, prednisone, azathioprine, mycophenolate mofetil, OKT3, ATAG, interferon, and mizoribine.

In certain embodiments, the invention relates to any one of the aforementioned pharmaceutical compositions, further comprising an anti-cancer agent. Examples of anti-cancer agents include, but are not limited to, cis-platin, actinomycin D, doxorubicin, vincristine, vinblastine, etoposide, amsacrine, mitoxantrone, tenipaside, taxol, colchicine, cyclosporin A, phenothiazines, interferon, and thioxantheres.

In certain embodiments, the invention relates to any one of the aforementioned pharmaceutical compositions, further comprising an anti-viral agent. Examples of anti-viral agents include, but are not limited to, cytovene, ganciclovir, trisodium phosphonoformate, Ribavirin, d4T, ddI, AZT, and acyclovir.

In certain embodiments, the invention relates to any one of the aforementioned pharmaceutical compositions, further comprising an anti-vascular hyperproliferative agent. Examples of anti-vascular hyperproliferative agents include, but are not limited to, HMG Co-A reductase inhibitors such as lovastatin, thromboxane A2 synthetase inhibitors, eicosapentanoic acid, ciprostene, trapidil, ACE inhibitors, low molecular weight heparin, mycophenolic acid, rapamycin, and 5-(3'-pyridinylmethyl)benzofuran-2-carboxylate.

Selected Methods of the Invention

In certain embodiments, the invention relates to a method of killing or inhibiting the growth of a microbe, comprising the step of contacting said microbe with an effective amount of any one of the aforementioned compounds.

In certain embodiments, the invention relates to any one of the aforementioned methods, wherein said microbe is a protozoon, a bacterium, or a fungus.

In certain embodiments, the invention relates to any one of the aforementioned methods, wherein said microbe is a protozoon or a bacterium selected from the group consisting of the genera *Toxoplasma, Eimeria, Cryptosporidium, Plasmodium, Babesia, Theileria, Neospora, Sarcocystis, Giardia, Entamoeba, Trichomonas, Tritrichomonas, Leishmania, Trypanosoma, Helicobacter, Borrelia, Salmonella, Shigella, Yersinia, Streptococcus, Campylobacter, Arcobacter, Bacteroides, Fusobacterium, Burkholderia, Clostridia, Neisseria, Mycobacterium*, and *Acinetobacter*.

In certain embodiments, the invention relates to any one of the aforementioned methods, wherein said microbe is a protozoon; and said protozoon is selected from the group consisting of the genera *Toxoplasma, Eimeria, Cryptosporidium, Plasmodium, Babesia, Theileria, Neospora, Sarcocystis, Giardia, Entamoeba, Trichomonas, Tritrichomonas, Leishmania* and *Trypanosoma*.

In certain embodiments, the invention relates to any one of the aforementioned methods, wherein said protozoon is selected from the genus *Cryptosporidium*.

In certain embodiments, the invention relates to any one of the aforementioned methods, wherein said protozoon is *Cryptosporidium parvum*.

In certain embodiments, the invention relates to any one of the aforementioned methods, wherein said microbe is a bacterium; and said bacterium is selected from the group consisting of the genera *Helicobacter, Borrelia, Salmonella, Shigella, Yersinia, Streptococcus, Campylobacter, Arcobacter, Bacteroides, Fusobacterium, Burkholderia, Clostridia, Neisseria, Mycobacterium*, and *Acinetobacter*.

In certain embodiments, the invention relates to a method of treating or preventing a microbial infection in a mammal, comprising the step of administering to a mammal in need thereof a therapeutically effective amount of any one of the aforementioned compounds.

In certain embodiments, the invention relates to a method of treating or preventing a parasitic infection in a mammal comprising the step of administering to a mammal in need thereof a therapeutically effective amount of any one of the aforementioned compounds.

In certain embodiments, the invention relates to any one of the aforementioned methods, wherein said microbial infection is caused by a protozoon, a bacterium, or a fungus.

In certain embodiments, the invention relates to any one of the aforementioned methods, wherein said microbial infection is caused by a protozoon or a bacterium selected from the group consisting of the genera *Toxoplasma, Eimeria, Cryptosporidium, Plasmodium, Babesia, Theileria, Neospora, Sarcocystis, Giardia, Entamoeba, Trichomonas, Tritrichomonas, Leishmania, Trypanosoma, Helicobacter, Borrelia, Salmonella, Shigella, Yersinia, Streptococcus, Campylobacter, Arcobacter, Bacteroides, Fusobacterium, Burkholderia, Clostridia, Neisseria, Mycobacterium*, and *Acinetobacter*.

In certain embodiments, the invention relates to any one of the aforementioned methods, wherein said microbial infection is caused by a protozoon; and said protozoon is selected from the group consisting of the genera *Toxoplasma, Eimeria, Cryptosporidium, Plasmodium, Babesia, Theileria, Neospora, Sarcocystis, Giardia, Entamoeba, Trichomonas, Tritrichomonas, Leishmania* and *Trypanosoma*.

In certain embodiments, the invention relates to any one of the aforementioned methods, wherein said protozoon is selected from the genus *Cryptosporidium*.

In certain embodiments, the invention relates to any one of the aforementioned methods, wherein said microbial infection is caused by *Cryptosporidium parvum*.

In certain embodiments, the invention relates to any one of the aforementioned methods, wherein said microbe is a bacterium; and said bacterium is selected from the group consisting of the genera *Helicobacter, Borrelia, Salmonella, Shigella, Yersinia, Streptococcus, Campylobacter, Arcobacter, Bacteroides, Fusobacterium, Burkholderia, Clostridia, Neisseria, Mycobacterium*, and *Acinetobacter*.

In certain embodiments, the invention relates to any one of the aforementioned methods, further comprising the step of co-administering to a mammal in need thereof a therapeutically effective amount of an antimicrobial agent.

In certain embodiments, the invention relates to any one of the aforementioned methods, wherein said antimicrobial agent is an antibiotic. In certain embodiments, the invention relates to any one of the aforementioned methods, wherein said antimicrobial agent is an antibiotic. In certain embodiments, the invention relates to any one of the aforementioned methods, wherein said antibiotic agent is selected from the group consisting of vancomycin, metronidazole, amoxicillin, ciprofloxacin, doxycycline, gentamicin, and clindamycin.

In certain embodiments, the invention relates to any one of the aforementioned methods, wherein said antimicrobial agent is an antifungal. In certain embodiments, the invention relates to any one of the aforementioned methods, wherein said antifungal agent is selected from the group consisting of terbinafine, flucytosine, fluconazole, itraconazole, ketoconazole, voriconazole, nikkomycin Z, caspofungin, micafungin (FK463), anidulafungin (LY303366), amphotericin B (AmB), and nystatin.

In certain embodiments, the invention relates to any one of the aforementioned methods, wherein said antimicrobial agent is an antiparasitic. In certain embodiments, the invention relates to any one of the aforementioned methods, wherein said antiparasitic agent is selected from the group consisting of eflornithine, furazolidone, melarsoprol, metronidazole, ornidazole, paromomycin sulfate, pentamidine, pyrimethamine, and tinidazole.

In certain embodiments, the invention relates to a method of treating or preventing an IMPDH-mediated disease in a mammal, comprising the step of administering to a mammal in need thereof a therapeutically effective amount of any one of the aforementioned compounds. If the pharmaceutical composition only comprises the IMPDH inhibitor of the invention as the active component, such methods may additionally comprise the step of administering to a mammal in need thereof a therapeutically effective amount of an agent selected from an antiinflammatory agent, immunosuppressant, an anti-cancer agent, an anti-viral agent, or an anti-vascular hyperproliferation compound. Such additional agents may be administered to the mammal prior to, concurrently with, or following the administration of the IMPDH inhibitor composition.

In certain embodiments, the invention relates to any one of the aforementioned methods, wherein the IMPDH-mediated disease is transplant rejection, graft versus host disease, rheumatoid arthritis, multiple sclerosis, juvenile diabetes, asthma, inflammatory bowel disease, Crohn's disease, ulcerative colitis, lupus, diabetes, mellitus myasthenia gravis, psoriasis, dermatitis, eczema, seborrhea, pulmonary inflammation, eye uveitis, hepatitis, Grave's disease, Hashimoto's thyroiditis, Behcet's or Sjorgen's syndrome, pernicious or immunohaemolytic anaemia, idiopathic adrenal insufficiency, polyglandular autoimmune syndrome, glomerulonephritis, scleroderma, lichen planus, vitelligo, autoimmune thyroiditis, alveolitis, HTLV-1, HTLV-2, HIV-1, HIV-2, nasopharyngeal carcinoma virus, HBV, HCV, HGV, yellow fever virus, dengue fever virus, Japanese encephalitis virus, human papilloma virus, Epstein-Barr, cytomegaloviruses, Herpes Simplex Type 1, Herpes Simplex Type 2, Herpes Simplex Type 6, restenosis, stenosis, artherosclerosis, lymphoma, leukemia, osteoarthritis, acute pancreatitis, chronic pancreatitis, asthma, or adult respiratory distress syndrome.

In certain embodiments, the invention relates to any one of the aforementioned methods, further comprising the step of co-administering to a mammal in need thereof a therapeutically effective amount of an agent selected from the group consisting of an antiinflammatory agent, immunosuppressant, an anti-cancer agent, an anti-viral agent, and an anti-vascular hyperproliferation compound.

In certain embodiments, the invention relates to any one of the aforementioned methods, wherein the method is useful in suppressing an immune response in a mammal. Such methods are useful in treating or preventing diseases, including, transplant rejection (e.g., kidney, liver, heart, lung, pancreas (islet cells), bone marrow, cornea, small bowel and skin allografts and heart valve xenografts), graft versus host disease, and autoimmune diseases, such as rheumatoid arthritis, multiple sclerosis, juvenile diabetes, asthma, inflammatory bowel disease (Crohn's disease, ulcerative colitis), lupus, diabetes, mellitus myasthenia gravis, psoriasis, dermatitis, eczema, seborrhea, pulmonary inflammation, eye uveitis, hepatitis, Grave's disease, Hashimoto's thyroiditis, Behcet's or Sjorgen's syndrome (dry eyes/mouth), pernicious or immunohaemolytic anaemia, idiopathic adrenal insufficiency, polyglandular autoimmune syndrome, glomerulonephritis, scleroderma, lichen planus, vitelligo (depigmentation of the skin), autoimmune thyroiditis, and alveolitis.

In certain embodiments, the invention relates to any one of the aforementioned methods, wherein the method comprises the step of administering to the mammal a composition comprising any one of the aforementioned compounds and a pharmaceutically acceptable adjuvant. In certain embodiments, the invention relates to any one of the aforementioned methods, further comprising the step of administering to a mammal in need thereof a composition comprising an additional immunosuppressant and a pharmaceutically acceptable adjuvant.

In certain embodiments, the invention relates to any one of the aforementioned methods, comprising the step of administering to a mammal in need thereof a composition comprising a compound of the invention; an additional immunosuppressive agent and a pharmaceutically acceptable adjuvant.

In certain embodiments, the invention relates to any one of the aforementioned methods, wherein the method is useful for inhibiting viral replication in a mammal. Such methods are useful in treating or preventing, DNA and RNA viral diseases caused by, for example, HTLV-1 and HTLV-2, HIV-1 and HIV-2, nasopharyngeal carcinoma virus, HBV, HCV, HGV, yellow fever virus, dengue fever virus, Japanese encephalitis virus, human papilloma virus, rhinoviruses and Herpes viruses, such as Epstein-Barr, cytomegaloviruses and Herpes Simplex, Types 1 and 2, or Type 6. See U.S. Pat. No. 5,380,879 (incorporated by reference).

In certain embodiments, the invention relates to any one of the aforementioned methods, wherein the method comprises the step of administering to the mammal a composition comprising any one of the aforementioned compounds, and a pharmaceutically acceptable adjuvant. In certain embodiments, the invention relates to any one of the aforementioned methods, further comprising the step of administering to a mammal in need thereof a composition comprising an additional anti-viral agent and a pharmaceutically acceptable adjuvant.

In certain embodiments, the invention relates to any one of the aforementioned methods, comprising the step of administering to a mammal in need thereof a composition comprising any one of the aforementioned compounds; an additional anti-viral agent and a pharmaceutically acceptable adjuvant.

In certain embodiments, the invention relates to any one of the aforementioned methods, wherein the method is useful for inhibiting vascular cellular hyperproliferation in a mammal. Such methods are useful in treating or preventing diseases, including, restenosis, stenosis, artherosclerosis and other hyperproliferative vascular disease.

In certain embodiments, the invention relates to any one of the aforementioned methods, comprising the step of administering to the mammal a composition comprising any one of the aforementioned compounds, and a pharmaceutically acceptable adjuvant. In certain embodiments, the invention relates to any one of the aforementioned methods, further comprising the step of administering to a mammal in need thereof a therapeutically effective amount of a composition comprising an additional anti-vascular hyperproliferative agent and a pharmaceutically acceptable adjuvant.

In certain embodiments, the invention relates to any one of the aforementioned methods, comprising the step of administering to a mammal in need thereof a therapeutically effective amount of a composition comprising any one of the aforementioned compounds; an additional anti-vascular hyperproliferative agent and a pharmaceutically acceptable adjuvant.

In certain embodiments, the invention relates to any one of the aforementioned methods, wherein the method is useful for inhibiting tumors and cancer in a mammal. Such methods are useful in treating or preventing diseases, including, tumors and malignancies, such as lymphoma, leukemia and other forms of cancer.

In certain embodiments, the invention relates to any one of the aforementioned methods, comprising the step of administering to the mammal a therapeutically effective amount of a composition comprising any one of the aforementioned compounds, and a pharmaceutically acceptable adjuvant. In certain embodiments, the invention relates to any one of the aforementioned methods, further comprising the step of administering to a mammal in need thereof a therapeutically effective amount of a composition comprising an additional anti-tumor or anti-cancer agent and a pharmaceutically acceptable adjuvant.

In certain embodiments, the invention relates to any one of the aforementioned methods, comprising the step of administering to a mammal in need thereof a composition comprising any one of the aforementioned compounds; a therapeutically effective amount of an additional anti-tumor or anti-cancer agent and a pharmaceutically acceptable adjuvant.

In certain embodiments, the invention relates to any one of the aforementioned methods, wherein the method is useful for inhibiting inflammation and inflammatory diseases in a mammal. Such methods are useful in treating or preventing diseases, including, osteoarthritis, acute pancreatitis, chronic pancreatitis, asthma and adult respiratory distress syndrome.

In certain embodiments, the invention relates to any one of the aforementioned methods, comprising the step of administering to the mammal a composition comprising a therapeutically effective amount of any one of the aforementioned compounds, and a pharmaceutically acceptable adjuvant. In certain embodiments, the invention relates to any one of the aforementioned methods, further comprising the step of administering to a mammal in need thereof a composition comprising a therapeutically effective amount of an antiinflammatory agent and a pharmaceutically acceptable adjuvant.

In certain embodiments, the invention relates to any one of the aforementioned methods, wherein the mammal is a primate, a bovine, an ovine, an equine, a porcine, a rodent, a feline, a mustelid, or a canine.

In certain embodiments, the invention relates to any one of the aforementioned methods, wherein the mammal is a primate.

In certain embodiments, the invention relates to any one of the aforementioned methods, wherein the mammal is a human.

Definitions

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of" "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The term "heteroatom" is art-recognized and refers to an atom of any element other than carbon or hydrogen. Illustrative heteroatoms include boron, nitrogen, oxygen, phosphorus, sulfur and selenium.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 80 or fewer carbon atoms in its backbone (e.g., $C_1$-$C_{80}$ for straight chain, $C_3$-$C_{80}$ for branched chain), and alternatively, about 30 or fewer. Likewise, cycloalkyls have from about 3 to about 10 carbon atoms in their ring structure, and alternatively about 5, 6 or 7 carbons in the ring structure. As used herein, "fluoroalkyl" denotes an alkyl where one or more hydrogens have been replaced with fluorines.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

The term "aryl" is art-recognized and refers to 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described herein, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, alkylthio, sulfonyl, sulfonamido, ketone, aldehyde, ester, heterocyclyl, aromatic or heteroaromatic moieties, trifluoromethyl, cyano, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl", "heteroaryl", or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, alkylthio, sulfonyl, ketone, aldehyde, ester, a heterocyclyl, an aromatic or heteroaromatic moiety, trifluoromethyl, cyano, or the like.

The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, alkylthio, sulfonyl, ketone, aldehyde, ester, a heterocyclyl, an aromatic or heteroaromatic moiety, trifluoromethyl, cyano, or the like.

The term "carbocycle" is art-recognized and refers to an aromatic or non-aromatic ring in which each atom of the ring is carbon.

The terms "monocyclic," "bicyclic," or "tricyclic" ring systems refers to 5 or 6 member monocyclic rings, 8, 9 and 10 membered bicyclic ring structures, and 11, 12, 13 and 14 membered tricyclic ring structures, wherein each bond in each ring may be possess any degree of saturation that is chemically feasible. When such structures contain substituents, those substituents may be at any position of the ring system, unless otherwise specified. As specified, such ring systems may optionally comprise up to 4 heteroatoms selected from N, O or S. Those heteroatoms may replace any carbon atoms in these ring systems as long as the resulting compound is chemically stable.

The term "monocyclic" ring system, as used herein, includes saturated, partially unsaturated and fully unsaturated ring structures. The term "bicyclic" ring system, as used herein, includes systems wherein each ring is independently saturated, partially unsaturated and fully unsaturated. Examples of monocyclic and bicyclic ring systems useful in the compounds of the invention include, but are not limited to, cyclopentane, cyclopentene, indane, indene, cyclohexane, cyclohexene, cyclohexadiene, benzene, tetrahydronaphthalene, decahydronaphthalene, naphthalene, pyridine, piperidine, pyridazine, pyrimidine, pyrazine, 1,2,3-triazine, 1,2,4-triazine, 1,3,5-triazine, 1,2,3,4-tetrazine, 1,2,4,5-tetrazine, 1,2,3,4-tetrahydroquinoline, quinoline, 1,2,3,4-tetrahydroisoquinoline, isoquinoline, cinnoline, phthalazine, quinazoline, quinoxaline, 1,5-naphthyridine, 1,6-naphthyridine, 1,7-naphthyridine, 1,8-naphthyridine, 2,6-naphthyridine, 2,7-naphthyridine, pteridine, acridine, phenazine, 1,10-phenatroline, dibenzopyrans, 1-benzopyrans, phenothiazine, phenoxazine, thianthrene, dibenzo-p-dioxin, phenoxathiin, phenoxthionine, morpholine, thiomorpholine, tetrahydropyran, pyran, benzopyran, 1,4-dioxane, 1,3-dioxane, dihyropyridine, dihydropyran, 1-pyrindine, quinuclidine, triazolopyridine, β-carboline, indolizine, quinolizidine, tetrahydronaphtheridine, diazaphenanthrenes, thiopyran, tetrahydrothiopyran, benzodioxane, furan, benzofuran, tetrahydrofuran, pyrrole, indole, thiophene, benzothiopene, carbazole, pyrrolidine, pyrazole, isoxazole, isothiazole, imidazole, oxazole, thiazole, 1,2,3-triazole, 1,2,4-triazole, 1,2,3-oxadiazole, 1,2,4-oxadiazole, 1,3,4 oxadiazole, 1,2,5-oxadiazole, 1,2,3-thiadiazole, 1,2,4-thiadiazole, 1,3,4-thiadiazole, 1,2,5 thiadiazole, tetrazole, benzothiazole, benzoxazole, benzotriazole, benzimidazole, benzopyrazole, benzisothiazole, benzisoxazole and purine.

Additional monocyclic and bicyclic structures falling within the above description may be found in A. R. Katritzky, and C. W. Rees, eds. "Comprehensive Heterocyclic Chemistry: Structure, Reactions, Synthesis and Use of Heterocyclic Compounds, Vol. 1-8," Pergamon Press, NY (1984), the disclosure of which is herein incorporated by reference.

It should be understood that heterocycles may be attached to the rest of the compound by any atom of the heterocycle which results in the creation of a stable structure.

The term "ring atom", as used herein, refers to a backbone atom that makes up the ring. Such ring atoms are selected from C, N, O or S and are bound to 2 or 3 other such ring atoms (3 in the case of certain ring atoms in a bicyclic ring system). The term "ring atom" does not include hydrogen.

The term "nitro" is art-recognized and refers to —$NO_2$; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —$SO_2$. "Halide" designates the corresponding anion of the halogens, and "pseudohalide" has the definition set forth on page 560 of "Advanced Inorganic Chemistry" by Cotton and Wilkinson, that is, for example, monovalent anionic groups sufficiently electronegative to exhibit a positive Hammett sigma value at least equaling that of a halide (e.g., CN, OCN, SCN, SeCN, TeCN, $N_3$, and $C(CN)_3$).

The terms "amine" and "amino" are art-recognized and refer to both unsubstituted and substituted amines, e.g., a moiety that may be represented by the general formulas:

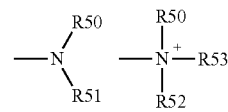

wherein R50, R51, R52 and R53 each independently represent a hydrogen, an alkyl, an alkenyl, —$(CH_2)_m$—R61, or R50 and R51 or R52, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In other embodiments, R50 and R51 (and optionally R52) each independently represent a hydrogen, an alkyl, an alkenyl, or —$(CH_2)_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and refers to a moiety that may be represented by the general formula:

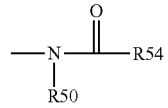

wherein R50 is as defined above, and R54 represents a hydrogen, an alkyl, an alkenyl or —$(CH_2)_m$—R61, where m and R61 are as defined above.

The term "amido" is art recognized as an amino-substituted carbonyl and includes a moiety that may be represented by the general formula:

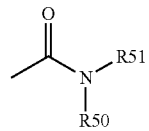

wherein R50 and R51 are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—$(CH_2)_m$—R61, wherein m and R61 are defined above. Representative alkylthio groups include methylthio, ethyl thio, and the like.

The term "carboxyl" is art recognized and includes such moieties as may be represented by the general formulas:

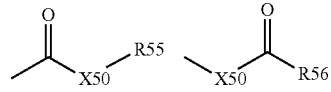

wherein X50 is a bond or represents an oxygen or a sulfur, and R55 and R56 represents a hydrogen, an alkyl, an alkenyl, —(CH$_2$)$_m$—R61 or a pharmaceutically acceptable salt, R56 represents a hydrogen, an alkyl, an alkenyl or —(CH$_2$)$_m$—R61, where m and R61 are defined above. Where X50 is an oxygen and R55 or R56 is not hydrogen, the formula represents an "ester." Where X50 is an oxygen, and R55 is as defined above, the moiety is referred to herein as a carboxyl group, and particularly when R55 is a hydrogen, the formula represents a "carboxylic acid." Where X50 is an oxygen, and R56 is hydrogen, the formula represents a "formate." In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The term "carbamoyl" refers to —O(C═O)NRR', where R and R' are independently H, aliphatic groups, aryl groups or heteroaryl groups.

The term "oxo" refers to a carbonyl oxygen (═O).

The terms "oxime" and "oxime ether" are art-recognized and refer to moieties that may be represented by the general formula:

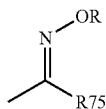

wherein R75 is hydrogen, alkyl, cycloalkyl, alkenyl, alkynyl, aryl, aralkyl, or —(CH$_2$)$_m$—R61. The moiety is an "oxime" when R is H; and it is an "oxime ether" when R is alkyl, cycloalkyl, alkenyl, alkynyl, aryl, aralkyl, or —(CH$_2$)$_m$—R61.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—R61, where m and R61 are described above.

The term "sulfonate" is art recognized and refers to a moiety that may be represented by the general formula:

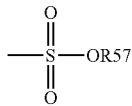

in which R57 is an electron pair, hydrogen, alkyl, cycloalkyl, or aryl.

The term "sulfate" is art recognized and includes a moiety that may be represented by the general formula:

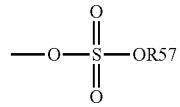

in which R57 is as defined above.

The term "sulfonamido" is art recognized and includes a moiety that may be represented by the general formula:

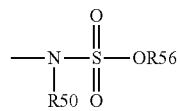

in which R50 and R56 are as defined above.

The term "sulfamoyl" is art-recognized and refers to a moiety that may be represented by the general formula:

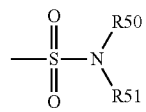

in which R50 and R51 are as defined above.

The term "sulfonyl" is art-recognized and refers to a moiety that may be represented by the general formula:

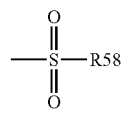

in which R58 is one of the following: hydrogen, alkyl, alkenyl, alkynyl, cycloalkyl, heterocyclyl, aryl or heteroaryl.

The term "sulfoxido" is art-recognized and refers to a moiety that may be represented by the general formula:

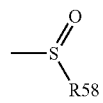

in which R58 is defined above.

The term "phosphoryl" is art-recognized and may in general be represented by the formula:

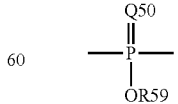

wherein Q50 represents S or O, and R59 represents hydrogen, a lower alkyl or an aryl. When used to substitute, e.g., an alkyl, the phosphoryl group of the phosphorylalkyl may be represented by the general formulas:

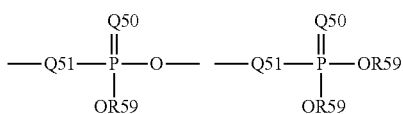

wherein Q50 and R59, each independently, are defined above, and Q51 represents O, S or N. When Q50 is S, the phosphoryl moiety is a "phosphorothioate."

The term "phosphoramidite" is art-recognized and may be represented in the general formulas:

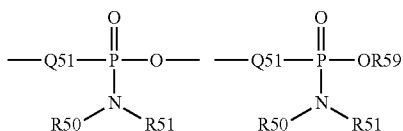

wherein Q51, R50, R51 and R59 are as defined above.

The term "phosphonamidite" is art-recognized and may be represented in the general formulas:

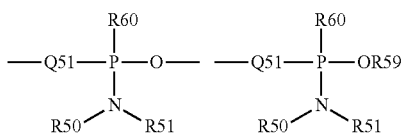

wherein Q51, R50, R51 and R59 are as defined above, and R60 represents a lower alkyl or an aryl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The term "selenoalkyl" is art-recognized and refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—R61, m and R61 being defined above.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The definition of each expression, e.g., alkyl, m, n, and the like, when it occurs more than once in any structure, is intended to be independent of its definition elsewhere in the same structure.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, "Handbook of Chemistry and Physics", 67th Ed., 1986-87, inside cover.

The term "treating" as used herein refers to the alleviation of symptoms of a particular disorder in a patient or the improvement of an ascertainable measurement associated with a particular disorder. As used herein, the term "patient" refers to a mammal, including a human.

While several embodiments of the present invention are described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

EXEMPLIFICATION

The invention now being generally described, it will be more readily understood by reference to the following examples which are included merely for purposes of illustration of certain aspects and embodiments of the present invention, and are not intended to limit the invention.

Example 1—General Synthetic Strategy for Triazole Inhibitors

Figure 8:
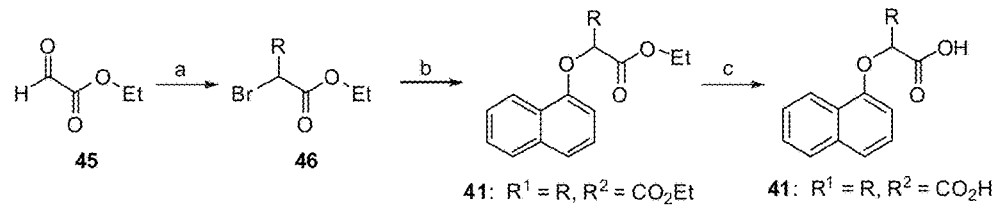
FIG. 8 depicts the synthesis of 41 [$R^1$=Et, $R^2$=$CO_2Et$]. Reagents and conditions: (a) (i) c-PrMgBr, THF, −20° C., 2 h, (ii) $Ph_3P$, $CBr_4$, DCM, 0° C., 2 h; (b) 1-naphthol, $K_2CO_3$, DMF, rt, 2 h; (c) 3 M NaOH, THF:$H_2O$ (2:1), 80° C., 6 h.

Various 1,2,3-triazole analogs were prepared according to FIG. 7. The common intermediate in the synthesis of these derivatives was propargyl ether 43. This intermediate was prepared using three different routes. In the first route ($R^1$=Me or H), 40 was alkylated utilizing either a Mitsunobu reaction with a propargyl alcohol or by treatment with propargyl bromide in the presence of potassium carbonate. The route using the Mitsunobu reaction also afforded enantiomerically enriched ethers stating with (S)- or (R)-but-3-yn-2-ol. When $R^1$=i-Pr and $R^2$=$CO_2H$, the acid 41 (prepared via FIG. 8) was reduced to the corresponding alcohol with $LiAlH_4$ and then oxidized to aldehyde 42. When $R^1$=Et, $R^2$=$CO_2Et$, the ester 41 (prepared via FIG. 8) was reduced directly to aldehyde 42 with DIBAL in THF at −78° C. Aldehyde 42 was converted to the corresponding alkyne. Ether 43 was converted to 1,2,3-triazole 44 in the presence of an aryl azide and CuI. In the case of N-oxide derivatives, 43 (X or Y=N) was first treated with m-CPBA. The N-oxide of 43 was then converted to 44 (X or Y=$N^+$—$O^-$).

Example 2—Synthesis of ethyl α-bromocyclopropaneacetate (46, R=c-Pr)

A flame dried two-neck round bottom flask fitted with a reflux condenser and $N_2$ outlet was charged with anhydrous THF, freshly activated Mg (120 mg, 4.95 mmol) and a catalytic amount of iodine. A small portion of cyclopropyl bromide dissolved in THF was added. After initiation of reflux, the reaction mixture was cooled to −20° C. and the remaining cyclopropyl bromide (500 mg, 4.13 mmol) was gradually added. After 30 min a freshly distilled solution of glyoxalate 45 (549 mg, 5.37 mmol) in THF was added over a 10 min period and the resulting solution was stirred at −20° C. for 2 h before being quenched with a small amount of water. After 10 min the reaction mixture was further diluted with water (50 mL) and extracted with ethyl acetate (3×50 mL). The organic extracts were combined, dried over anhydrous $MgSO_4$, filtered, concentrated in vacuo and purified by column chromatography eluting with ethyl acetate/n-hexane (a gradient of 10-20%) to furnish ethyl α-hydroxy-cyclopropaneacetate (422 mg, 71%) as a viscous oil. The oil (350 mg, 2.43 mmol) was dissolved in anhydrous DCM and cooled to 0° C. Then $Ph_3P$ (2.04 gm, 7.78 mmol) was added followed by $CBr_4$ (1.20 gm, 3.64 mmol). The reaction mixture was stirred at 0° C. for 2 h and then concentrated in vacuo. The $Ph_3PO$ was precipitated by addition of n-hexane and removed by filtration. The crude reaction mixture was purified by flash column chromatography to furnish ethyl α-bromocyclopropaneacetate (46, R=c-Pr): (311 mg, 62% yield).

Example 3—General Procedure for the Synthesis of 2-(1-naphthalenyloxy)acetic Acids (41)

Exemplified for 2-cyclopropyl-2-(1-naphthalenyloxy)acetic Acid (41, R=c-Pr)

To a solution of 1-naphthol (170 mg, 1.18 mmol) in anhydrous DMF (10 mL) was added $K_2CO_3$ (510 mg, 3.53 mmol) and ethyl α-bromocyclopropaneacetate (295 mg, 1.41 mmol). The mixture was stirred at room temperature for 2 h and then diluted with water (50 mL) and then extracted with ethyl acetate (3×50 mL). The organic extracts were combined, washed with brine, dried over anhydrous $MgSO_4$, filtered, concentrated in vacuo and purified by flash column chromatography using a mixture of ethyl acetate and n-hexane (1:9) to furnish ethyl 2-cyclopropyl-2-(1-naphthalenyloxy)acetate (8, R=c-Pr, 296 mg, 93%) as a white solid. The ester (250 mg, 0.92 mmol) was dissolved in 20 mL THF: $H_2O$ (2:1) and then 3M NaOH (111 mg, 2.77 mmol) was added. The reaction was heated at 80° C. for 6 h. After cooling, the reaction mixture was quenched with 1N HCL to a pH ~7 and then extracted with chloroform. The organic extract was dried over anhydrous $MgSO_4$, filtered, concentrated in vacuo and purified by flash column chromatography eluting with a mixture of ethyl acetate/n-hexane (a gradient of 2:1) to furnish 2-cyclopropyl-2-(1-naphthalenyloxy)acetic acid (41, R=c-Pr) (136 mg, 61%) as a white solid.

Example 4—General Procedure for the Preparation Propargyl Ether 43 Via the Mitsunobu Reaction Exemplified for 1-[(1-methyl-2-propyn-1-yl)oxy]naphthalene (43, $R^1$=Me, X=Y=CH)

To a solution of 1-naphthol (200 mg, 1.38 mmol) and but-3-yn-2-ol (146 mg, 2.07 mmol) in anhydrous DCM (10 mL) under a $N_2$ atmosphere and at 0° C. was added $Ph_3P$ (435 mg, 1.66 mmol) portion wise. The reaction mixture was stirred for 10 min and then DEAD (360 mg, 2.07 mmol) (70% solution in toluene) was slowly added. The resulting reaction solution was stirred at the room temperature for 24 h and then diluted with water (50 mL) and extracted with chloroform (3×50 mL). The combined organic extracts were washed with brine, dried over anhydrous $MgSO_4$, filtered concentrated in vacuo and the residue was purified by flash column chromatography using ethyl acetate/n-hexane (a gradient of 5-10%) to furnish 1-[(1-methyl-2-propyn-1-yl)oxy]naphthalene (176 mg, 65%) as a viscous oil.

Example 5—General Procedure for the Preparation Propargyl Ether 43 Via the Corey-Fuchs Reaction Exemplified for the synthesis of 1-(1-methylethyl)-2-propyn-1-yl]oxy]naphthalene (43, $R^1$=i-Pr, X=Y=CH): A the solution of 41 (R$^1$=i-Pr, R$^2$=CO$_2$OH, X=Y=CH, 880 mg, 3.27 mmol) in anhydrous THF was cooled to 0° C. and then LiAlH$_4$ (311 mg, 8.18 mmol) was added. The reaction mixture was stirred for 5 h at 0° C. and then quenched with water (50 mL). The mixture was stirred until the organic and aqueous layers separated. The mixture was extracted with chloroform (3×100 mL). The combined organic layers were washed with brine, dried over anhydrous MgSO$_4$, filtered, concentrated in vacuo and purified by flash column chromatography using ethyl acetate/n-hexane (a gradient of 2:1) to give alcohol 41 (R$^1$=i-Pr, R$^2$=CH$_2$OH, X=Y=CH, 466 mg, 62%) as a thick viscous oil.

A flame dried two neck round bottom flask containing oxalyl chloride (370 µL, 4.34 mmol) in anhydrous DCM was cooled at −78° C. under a nitrogen atmosphere. Next, anhydrous DMSO (679 mg, 8.7 mmol) was added drop wise via a syringe. The resulting solution was allowed to stir at −78° C. for 10 min and then alcohol 41 (R$^1$=i-Pr, R$^2$=CH$_2$OH, X=Y=CH, 400 mg, 1.74 mmol) dissolved in anhydrous DCM was added gradually via a syringe. The resulting reaction mixture was allowed to stir for 1 h at −78° C. and then quenched with triethylamine (1.95 mL, 13.9 mmol) before being allowed to warm to room temperature. The reaction mixture was extracted with DCM (3×50 mL), washed with brine, dried over anhydrous MgSO$_4$, filtered, and concentrated in vacuo to give aldehyde 42 (R$^1$=i-Pr, X=Y=CH), which was used without further purification.

A solution of 42 (R$^1$=i-Pr, X=Y=CH, 360 mg, 1.58 mmol) in DCM (10 mL) was cooled at 0° C. and then Ph$_3$P (1.24 gm, 4.74 mmol) and CBr$_4$ (785 mg, 2.37 mmol) were sequentially added. The resulting mixture was stirred at room temp for 2 h. The reaction mixture was concentrated in vacuo and the Ph$_3$PO was precipitated by addition of n-hexane and removed by filtration. The filtrate was concentrated and the residue purified using a filter column (ethyl acetate/n-hexane as eluent). The resulting material (360 mg, 1.58 mmol) was dissolved in anhydrous THF and cooled to −78° C. Next, n-BuLi (121 mg, 1.90 mmol) was gradually added and the resulting solution stirred for 2 h at −78° C. The mixture was quenched with water (50 mL), allowed to stir at room temperature for 30 min, and then extracted with ethyl acetate (3×100 mL). The combined organic extracts were dried over MgSO$_4$, filtered, concentrated in vacuo and purified by flash column chromatography eluting with ethyl acetate/n-hexane to furnish 1-(1-methylethyl)-2-propyn-1-yl]oxy]naphthalene (43, R$^1$=i-Pr, X=Y=CH, 282 mg, 72%) as a white solid.

Example 6—General Procedure for the Preparation of 1-H-1,2,3-triazoles 44 (Examples 6-24)

Exemplified for 1-(4-chlorophenyl)-4-(2-methyl-1-(1-naphthalenyloxy)propyl)-1H-1,2,3-triazole (3)

A single neck round bottom flask under an argon atmosphere was charged with 16 (R$^1$=i-Pr, X=Y=CH, 114 mg, 0.51 mmol), anhydrous acetonitrile (5 mL), 1-azido-4-chlorobenzene (78.3 mg, 0.51 mmol) and DIPEA (254 µL, 1.53 mmol). The reaction mixture was allowed to stir at room temperature for 10 min and then finely powdered CuI (194.2 mg, 1.02 mmol) was added portion wise. After 30 min of stirring at room temperature, the reaction mixture was quenched with saturated aqueous NH$_4$Cl, diluted with water (50 mL) and extracted with chloroform (3×50 mL). The combined organic extracts were washed with brine, dried over anhydrous MgSO$_4$, filtered, concentrated in vacuo and purified by flash column chromatography using ethyl acetate/n-hexane (a gradient of 10-20%) to furnish 3 (167 mg, 87%) as a gelatinous solid. $^1$H NMR (CDCl$_3$, 400 MHz) δ 1.16, 1.20 (dd, J=6.5, 22.0 Hz, 6H), 2.47-2.53 (m, 1H), 5.55 (d, J=5.0 Hz, 1H), 6.80 (d, J=8.0 Hz, 1H), 7.25 (m, 1H), 7.37-7.43 (m, 3H), 7.49 (m, 2H), 7.61 (d, J=9.0 Hz, 2H), 7.79 (m, 2H), 8.38 (m, 1H); ESI-HRMS for C$_{22}$H$_{21}$ClN$_3$O (M+H)$^+$ calcd. 378.1373. found 378.1383.

Example 7—1-(4-chlorophenyl)-4-(1-(naphthalene-1-yloxy)ethyl)-1H-1,2,3-triazole (1)

mp 98-100° C.; $^1$H NMR (CDCl$_3$, 400 MHz) δ 1.91 (d, J=6.0 Hz, 3H) 5.90 (q, J=6.8, 12.8 Hz, 1H), 6.92 (d, J=7.2 Hz, 1H), 7.26 (s, 1H), 7.31 (t, J=8.8 Hz, 1H), 7.41-7.51 (m, 5H), 7.63 (d, J=8.0 Hz, 2H), 7.80 (m, 1H), 7.88 (s, 1H), 8.34 (m, 1H); $^{13}$C NMR (CDCl$_3$, 100 MHz) δ 22.56, 69.90, 107.02, 119.08, 120.98, 121.87, 122.19, 125.53, 126.07, 126.14, 126.66, 127.80, 130.07, 134.73, 134.82, 135.64, 151.38, 153.21; ESI-HRMS for C$_{20}$H$_{17}$ClN$_3$O (M+H)$^+$ calcd. 350.1060. found 350.1074.

Example 8—1-(2,6-dichlorophenyl)-4-(1-(naphthalen-1-yloxy)ethyl)-1H-1,2,3-triazole (6)

yield 86%; Gummy solid; $^1$H NMR (CDCl$_3$, 500 MHz) δ 1.98 (d, J=6.0 Hz, 3H), 5.92 (q, J=6.5, 13.0 Hz, 1H), 6.91 (d, J=8.0 Hz, 1H), 7.26 (s, 1H), 7.31 (t, J=8.0 Hz, 1H), 7.37-7.49 (m, 6H), 7.79 (m, 1H) 8.32 (m, 1H); ESI-HRMS for C$_{20}$H$_{16}$Cl$_2$N$_3$O (M+H)$^+$ calcd. 384.0670. found 384.0672.

Example 9—4-(1-(4-chloronaphthalen-1-yloxy)ethyl)-1-(4-chlorophenyl)-1H-1,2,3-triazole (7)

yield 84%; Gummy solid; $^1$H NMR (CDCl$_3$, 500 MHz) δ 1.91 (d, J=6.5 Hz, 3H), 5.86 (q, J=6.5, 13.5 Hz, 1H), 6.85 (d, J=8.0 Hz, 1H), 7.26 (s, 1H), 7.39 (d, J=8.5 Hz, 1H), 7.46 (d, J=8.5 Hz, 1H), 7.56 (t, J=8.5 Hz, 1H), 7.62 (t, J=8.0 Hz, 3H), 7.87 (s, 1H), 8.20 (d, J=8.5 Hz, 1H), 8.36 (d, J=8.5 Hz, 1H); ESI-HRMS for C$_{20}$H$_{16}$Cl$_2$N$_3$O (M+H)$^+$ calcd. 384.0670. found 384.0684.

Example 10—4-(1-(1-(4-chlorophenyl)-1H-1,2,3-triazol-4-yl)ethoxy)quinoline (13)

yield 91%; mp. 128-130° C.; $^1$H NMR (CDCl$_3$, 400 MHz) δ 1.95 (d, J=6.4 Hz, 3H), 5.97 (q, J=6.4, 12.8 Hz, 1H), 6.89 (d, J=5.2 Hz, 1H), 7.47 (d, J=8.8 Hz, 2H), 7.53 (t, J=8.0 Hz, 1H), 7.64 (d, J=8.8 Hz, 2H), 7.71 (t, J=7.2 Hz, 1H), 7.91 (s, 1H), 8.03 (d, J=8.4 Hz, 1H), 8.28 (d, J=7.6 Hz, 1H), 8.70 (d, J=4.4 Hz, 1H); $^{13}$C NMR (CDCl$_3$, 100 MHz) δ 22.21, 70.05, 102.42, 119.17, 121.92, 121.99, 125.93, 129.23, 130.06, 130.14, 134.98, 135.48, 149.59, 150.01, 151.51, 160.17; ESI-HRMS for C$_{19}$H$_{16}$ClN$_4$O (M+H)$^+$ calcd. 351.1013. found 351.1002.

Example 11—4-(1-(1-(3,4-dichlorophenyl)-1H-1,2,3-triazol-4-yl)ethoxy)quinoline (14)

yield 89%; mp. 62-64° C.; $^1$H NMR (CDCl$_3$, 400 MHz) δ 1.95 (d, J=6.4 Hz, 3H), 5.97 (q, J=6.4, 12.8 Hz, 1H), 6.87 (d, J=5.6 Hz, 1H), 7.26 (s, 1H), 7.53 (t, J=7.6 Hz, 1H), 7.57 (s, 2H), 7.71 (t, J=7.2 Hz, 1H), 7.85 (s, 1H), 7.91 (s, 1H), 8.03 (d, J=8.4 Hz, 1H), 8.28 (d, J=8.4 Hz, 1H), 8.70 (d, J=4.4 Hz, 1H); $^{13}$C NMR (CDCl$_3$, 100 MHz) δ 22.21, 69.96, 102.37, 119.13, 119.69, 121.72, 121.97, 122.50, 125.98, 129.26, 130.10, 131.68, 133.35, 134.23, 135.98, 149.61, 150.28, 151.50, 160.10; Anal. ($C_{19}H_{14}Cl_2N_4O$)C, H, N.

Example 12—4-(4-(1-(quinolin-4-yloxy)ethyl)-1H-1,2,3-triazol-1-yl)benzonitrile (15)

yield 87%; mp. 176-178° C.; $^1$H NMR (CDCl$_3$, 400 MHz) δ 1.96 (d, J=6.8 Hz, 3H), 5.98 (q, J=6.0, 12.8 Hz, 1H), 6.87 (d, J=4.8 Hz, 1H), 7.26 (s, 1H), 7.54 (t, J=7.2 Hz, 1H), 7.72 (t, J=7.2 Hz, 1H), 7.80 (d, J=8.8 Hz, 2H), 7.88 (d, J=8.0 Hz, 2H), 8.03 (m, 1H), 8.28 (d, J=8.0 Hz, 1H), 8.70 (s, 1H); $^{13}$C NMR (CDCl$_3$, 100 MHz) δ 22.16, 69.90, 102.35, 112.86, 117.78, 118.98, 120.82, 121.94, 126.02, 129.25, 130.15, 134.11, 139.74, 149.59, 150.55, 151.45, 160.07; ESI-HRMS for $C_{20}H_{16}N_5O$ (M+H)$^+$ calcd. 342.1355. found 342.1355.

Example 13—2-chloro-4-(4-(1-(quinolin-4-yloxy)ethyl)-1H-1,2,3-triazol-1-yl)benzonitrile (16)

yield 85%; mp. 194-196° C.; $^1$H NMR (CDCl$_3$, 400 MHz) δ 1.96 (d, J=6.8 Hz, 3H), 5.98 (q, J=6.0, 12.8 Hz, 1H), 6.84 (d, J=4.8 Hz, 1H), 7.54 (t, J=7.2 Hz, 1H), 7.72 (t, J=8.0 Hz, 1H), 7.79 (q, J=8.4, 15.2 Hz, 2H), 7.97 (s, 1H), 8.00 (s, 1H), 8.04 (d, J=8.8 Hz, 1H), 8.23 (d, J=8.0 Hz, 1H), 8.69 (d, J=4.8 Hz, 1H); $^{13}$C NMR (CDCl$_3$, 100 MHz) δ 22.14, 69.81, 102.29, 113.53, 115.12, 118.60, 119.02, 121.51, 121.65, 121.91, 126.06, 129.27, 130.18, 135.53, 138.93, 140.24, 149.60, 150.82, 151.43, 159.98; ESI-HRMS for $C_{20}H_{15}ClN_5O$ (M+H)$^+$ calcd. 376.0965. found 376.0975.

Example 14—(R)-5-(1-(1-(4-chlorophenyl)-1H-1,2,3-triazol-4-yl)ethoxy)quinoline (21)

yield 82%; mp. 94-96° C.; $^1$H NMR (CDCl$_3$, 400 MHz) δ 1.92 (d, J=6.4 Hz, 3H), 5.89 (q, J=6.0, 12.8 Hz, 1H), 7.00 (d, J=8.0 Hz, 1H), 7.40 (dd, J=3.6, 8.0 Hz, 1H), 7.46 (d, J=8.4 Hz, 2H), 7.55 (t, J=8.4 Hz, 1H), 7.65 (d, J=8.0 Hz, 2H), 7.69 (d, J=8.8 Hz, 1H), 7.88 (s, 1H), 8.65 (d, J=8.0 Hz, 1H), 8.91 (s, 1H); $^{13}$C NMR (CDCl$_3$, 100 MHz) δ 22.36, 70.17, 107.39, 119.10, 120.52, 121.40, 121.87, 122.32, 129.56, 130.10, 131.00, 134.85, 135.56, 149.36, 150.76, 150.95, 152.95; ESI-HRMS for $C_{19}H_{16}N_4OCl$ (M+H)$^+$ calcd. 351.1013. found 351.1002.

Example 15—(R)-4-(1-(1-(3,4-dichlorophenyl)-1H-1,2,3-triazol-4-yl)ethoxy)quinoline (28)

yield 91%; mp. 62-64° C.; $^1$H NMR (CDCl$_3$, 400 MHz) δ 1.95 (d, J=6.8 Hz, 3H), 5.97 (q, J=6.4, 12.8 Hz, 1H), 6.87 (d, J=5.2 Hz, 1H), 7.54 (t, J=7.2 Hz, 1H), 7.58 (s, 2H), 7.72 (t, J=7.2 Hz, 1H), 7.85 (s, 1H), 7.91 (s, 1H), 8.05 (d, J=8.8 Hz, 1H), 8.28 (d, J=8.4 Hz, 1H), 8.70 (bs, 1H); ESI-HRMS for $C_{19}H_{15}N_4OCl_2$(M+H)$^+$ calcd. 385.0623. found 385.0605.

Example 16—(S)-4-(1-(1-(3,4-dichlorophenyl)-1H-1,2,3-triazol-4-yl)ethoxy)quinoline (30)

yield 89%; mp. 64-66° C.; $^1$H NMR (CDCl$_3$, 400 MHz) δ 1.95 (d, J=6.8 Hz, 3H), 5.98 (q, J=6.8, 12.8 Hz, 1H), 6.88 (d, J=4.8 Hz, 1H), 7.54 (t, J=6.4 Hz, 1H), 7.58 (d, J=1.2 Hz, 2H), 7.72 (m, 1H), 7.85 (s, 1H), 7.91 (s, 1H), 8.04 (d, J=8.0 Hz, 1H), 8.28 (d, J=8.4 Hz, 1H), 8.70 (d, J=5.6 Hz, 1H); ESI-HRMS for $C_{19}H_{15}N_4OCl_2$ (M+H)$^+$ Calcd. 385.0623. found 385.0628.

Example 17—(R)-2-chloro-4-(4-(1-(quinolin-4-yloxy)ethyl)-1H-1,2,3-triazol-1-yl)benzonitrile (29)

yield 92%; mp. 176-178° C.; $^1$H NMR (CDCl$_3$, 400 MHz) δ 1.96 (d, J=6.0 Hz, 3H), 5.98 (q, J=6.0, 12.8 Hz, 1H), 6.84 (d, J=5.6 Hz, 1H) 7.55 (t, J=7.2 Hz, 1H), 7.71-7.83 (m, 3H), 7.97 (m, 2H), 8.04 (d, J=8.4 Hz, 1H), 8.28 (d, J=8.8 Hz, 1H), 8.70 (d, J=5.2 Hz, 1H); ESI-HRMS for $C_{20}H_{15}N_5OCl$ (M+H)$^+$ calcd. 376.0965. found 376.0964.

Example 18—(S)-2-chloro-4-(4-(1-(quinolin-4-yloxy)ethyl)-1H-1,2,3-triazol-1-yl)benzonitrile (31)

yield 91%; mp. 176-178° C.; $^1$H NMR (CDCl$_3$, 400 MHz) δ 1.96 (d, J=6.8 Hz, 3H), 5.98 (q, J=6.0, 12.8 Hz, 1H), 6.84 (d, J=5.6 Hz, 1H), 7.54 (t, J=8.0 Hz, 1H), 7.71-7.82 (m, 3H), 7.98 (m, 2H), 8.04 (d, J=8.0 Hz, 1H), 8.28 (d, J=8.4 Hz, 1H), 8.70 (d, J=4.8 Hz, 1H); ESI-HRMS for $C_{20}H_{15}N_5OCl$ (M+H)$^+$ calcd. 376.0965. found 376.0974.

Example 19—4-((1-(4-chlorophenyl)-1H-1,2,3-triazol-4-yl)methoxy)quinoline (17)

yield 89%; mp. 230-232° C.; $^1$H NMR (CDCl$_3$, 400 MHz) δ 5.50 (s, 2H), 6.34 (d, J=8.0 Hz, 1H), 7.39 (t, J=7.2 Hz, 1H), 7.47 (d, J=8.4 Hz, 2H), 7.57-7.65 (m, 4H), 7.74 (d, J=8.0 Hz, 1H), 7.77 (s, 1H), 8.46 (d, J=8.0 Hz, 1H); $^{13}$C NMR (CDCl$_3$, 100 MHz) δ 48.81, 111.20, 115.77, 120.21, 121.92, 124.28, 127.49, 127.58, 130.24, 132.75, 135.29, 139.87, 143.11, 143.93, 178.46; ESI-HRMS for $C_{18}H_{14}ClN_4O$ (M+H)$^+$ calcd. 337.0856. found 337.0847.

Example 20—5-(1-(1-(4-chlorophenyl)-1H-1,2,3-triazol-4-yl)ethoxy)quinoline 1-oxide (25)

yield 81%; mp. 165-167° C.; $^1$H NMR (CDCl$_3$, 400 MHz) δ 1.93 (d, J=6.0 Hz, 3H), 5.90 (q, J=6.8 12.8 Hz, 1H), 7.13 (d, J=8.0 Hz, 1H) 7.26 (t, J=6.0 Hz, 1H), 7.47 (d, J=8.4 Hz, 2H), 7.60 (t, J=8.4 Hz, 1H), 7.65 (d, J=8.4 Hz, 2H), 7.91 (s, 1H), 8.20 (d, J=8.4 Hz, 1H) 8.29 (d, J=9.2 Hz, 1H), 8.53 (d, J=5.2 Hz, 1H); $^{13}$C NMR (CDCl$_3$, 100 MHz) δ 22.27, 70.58, 109.66, 112.34, 119.20, 120.13, 121.03, 121.91, 123.94, 130.26, 130.73, 135.01, 135.49, 136.33, 142.76, 150.15, 153.56; ESI-HRMS for $C_{19}H_{16}N_4O_2Cl$ (M+H)$^+$ calcd. 367.0962. found 367.0977.

Example 21—(R)-5-(1-(1-(4-chlorophenyl)-1H-1,2,3-triazol-4-yl)ethoxy)quinoline 1-oxide (32)

yield 88%; mp. 184-186° C.; $^1$H NMR (CDCl$_3$, 400 MHz) δ 1.93 (d, J=6.0 Hz, 3H), 5.90 (q, J=6.4, 12.8 Hz, 1H), 7.14 (d, J=8.0 Hz, 1H), 7.28 (m, 3H), 7.48 (d, J=9.2 Hz, 2H), 7.61 (t, J=8.4 Hz, 1H), 7.65 (d, J=9.2 Hz, 2H), 7.91 (s, 1H), 8.21 (d, J=8.4 Hz, 1H), 8.30 (d, J=9.2 Hz, 1H), 8.53 (d, J=5.2 Hz, 1H); ESI-HRMS for $C_{19}H_{16}N_4O_2Cl$ (M+H)$^+$ calcd. 367.0962. found 367.0947.

Example 22—4-(1-(1-(4-chlorophenyl)-1H-1,2,3-triazol-4-yl)ethoxy)quinoline 1-oxide (23)

yield 88%; mp. 158-160° C.; $^1$H NMR (d$_6$-DMSO, 400 MHz) δ 1.85 (d, J=6.8 Hz, 3H), 6.09 (q, J=6.0, 12.8 Hz, 1H), 7.20 (d, J=6.8 Hz, 1H), 7.67 (d, J=8.4 Hz, 2H), 7.74 (t, J=7.6 Hz, 1H), 7.86 (t, J=8.4 Hz, 1H), 7.95 (d, J=9.2 Hz, 2H), 8.25 (d, J=8.8 Hz, 1H), 8.50 (dd, J=6.4, 12.0 Hz, 2H), 9.06 (s, 1H); $^{13}$C NMR (d$_6$-DMSO, 100 MHz) δ 20.58, 69.53, 103.30, 119.27, 121.56, 121.82, 122.67, 122.80, 128.14,

Example 23—4-(1-(1-(3,4-dichlorophenyl)-1H-1,2,3-triazol-4-yl)ethoxy)quinoline 1-oxide (26)

yield 92%; mp. 216-218° C.; $^1$H NMR (d$_6$-DMSO, 400 MHz) δ 1.85 (d, J=6.0 Hz, 3H), 6.09 (q, J=6.0, 12.8 Hz, 1H), 7.19 (d, J=6.4 Hz, 1H), 7.74 (t, J=8.0 Hz, 1H), 7.86 (m, 2H), 7.98 (d, J=9.2 Hz, 1H), 8.26 (m, 2H), 8.50 (dd, J=7.2, 12.0 Hz, 2H), 9.12 (s, 1H); $^{13}$C NMR (d6-DMSO, 100 MHz) δ 20.58, 69.47, 103.33, 119.28, 120.16, 121.74, 121.85, 122.67, 122.78, 128.15, 130.76, 131.09, 131.81, 132.33, 135.39, 136.03, 140.71, 148.53, 150.21; ESI-HRMS for C$_{19}$H$_{15}$N$_4$O$_2$Cl$_2$(M+H)$^+$ calcd. 401.0571. found 401.0566.

Example 24—(R)-4-(1-(1-(4-chlorophenyl)-1H-1,2,3-triazol-4-yl)ethoxy)quinoline 1-oxide (33)

yield 91%; mp. 172-174° C.; $^1$H NMR (CDCl$_3$, 400 MHz) δ 1.96 (d, J=8.8 Hz, 3H), 5.92 (q, J=6.0, 12.8 Hz, 1H), 6.88 (d, J=6.8 Hz, 1H), 7.48 (d, J=8.8 Hz, 2H), 7.66 (d, J=8.8 Hz, 3H), 7.80 (t, J=7.2 Hz, 1H), 7.96 (s, 1H), 8.28 (d, J=8.0 Hz, 1H), 8.39 (d, J=6.8 Hz, 1H), 8.73 (d, J=8.4 Hz, 1H); ESI-HRMS for C$_{19}$H$_{16}$N$_4$O$_2$Cl (M+H)$^+$ calcd. 367.0962. found 367.0948.

Example 25—General Procedure for the Preparation Propargyl Ether Quinoline N-Oxides

Exemplified for (R)-5-(but-3-yn-2-yloxy)quinoline 1-oxide (43, R$^1$=(R)-Me, X=N$^+$—O$^-$, Y=CH)

To a 0° C. solution of 43 (R$^1$=(R)-Me, X=N, Y=CH, 120 mg, 0.61 mmol) in anhydrous dichloromethane under a nitrogen atmosphere was added m-chloroperbenzoic acid (163 mg, 0.73 mmol, 77%). The reaction mixture was stirred at room temperature for 2 h, concentrated in vacuo and purified by flash column chromatography eluting with methanol/chloroform (a gradient of 5-10%) to furnish (R)-5-(but-3-yn-2-yloxy)quinoline 1-oxide (43, R$^1$=(R)-Me, X=N$^+$—O$^-$, Y=CH, 120 mg, 93%) as a white solid. mp. 156-158° C.; $^1$H NMR (CDCl$_3$, 400 MHz) δ 1.82 (d, J=6.8 Hz, 3H), 2.54 (s, 1H), 5.05 (q, J=6.8, 13.6 Hz, 1H), 7.20 (d, 1H, J=8.0 Hz, 1H) 7.26 (t, J=8.0 Hz, 3H), 7.68 (t, J=9.2 Hz, 1H), 8.15 (d, J=9.2 Hz, 1H), 8.35 (d, J=8.8 Hz, 1H), 8.54 (d, J=5.2 Hz, 1H); $^{13}$C NMR (CDCl$_3$, 100 MHz) δ 22.32, 64.68, 75.09, 81.96, 109.52, 112.49, 120.09, 121.28, 123.85, 130.57, 136.32, 142.64, 153.36; ESI-HRMS for C$_{13}$H$_{12}$NO$_2$ (M+H)$^+$ calcd. 214.0868. found 214.0875.

Example 26

Figure 9:
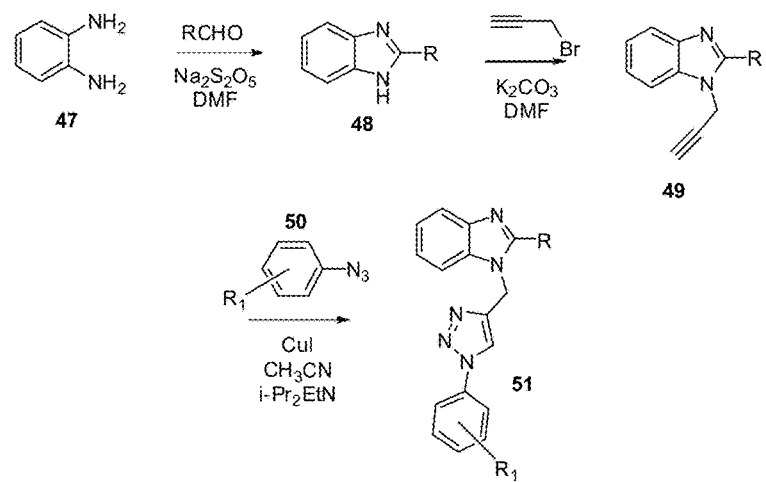
FIG. 9 depicts a representative synthetic scheme for the formation of triazoles 51.
Figure 10:
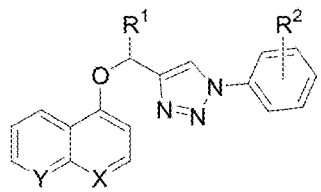
FIG. 10 depicts the $IC_{50}$ determinations for inhibition of *C. parvum* IMPDH by 1,2,3-triazole derivatives; $^a$=0.05% Fatty acid free bovine serum albumin; $^b$=Not Determined.

Other 1,2,3-triazoles were prepared according to FIG. 9.

Example 27—General Synthetic Strategy Towards Various Amides

Figure 35:
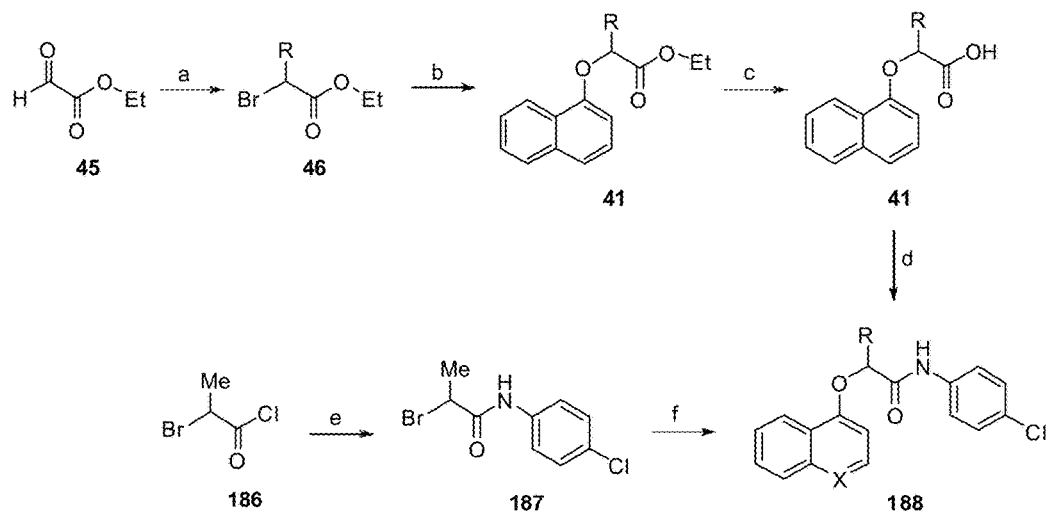
FIG. 35 depicts two syntheses of 188. Reagents and conditions: (a) (i) c-PrMgBr, THF, −20° C., 2 h, (ii) Ph$_3$P, CBr$_4$, DCM, 0° C., 2 h; (b) 1-naphthol, K$_2$CO$_3$, DMF, rt, 2 h; (c) 3 M NaOH, THF:H$_2$O (2:1), 80° C., 6 h; (d) 4-chloroaniline, 0° C., EDCI.HCl, rt, 12 h; (e) 4-chloroaniline, cat. DMAP, DCM, rt, 2 h; (f) 4-hydroxyquinoline, K$_2$CO$_3$, DMF, 0° C., rt, 12 h.
Figure 36:
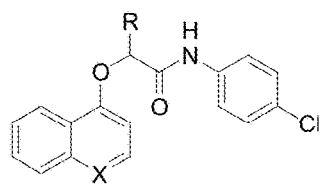
FIG. 36 depicts IC$_{50}$ values for inhibition of recombinant *C. parvum* IMPDH by amide derivatives; $^a$=0.05% Fatty acid free bovine serum albumin; $^b$=Not Determined.
Figure 43:
FIG. 43 depicts phthalazinone compounds D19-D36 and their respective IC$_{50}$ values against recombinant *C. parvum* IMPDH.
Figure 45:
FIG. 45 depicts phthalazinone compounds D55-D61 and their respective IC$_{50}$ values against recombinant *C. parvum* IMPDH.

Various amide analogs were prepared according to FIG. 35. Ethyl glyoxylate was allowed to react with c-PrMgBr to give a corresponding alcohol that was subsequently converted to bromide 46 (R=c-Pr) with carbon tetrabromide and triphenylphosphine. Various other bromide derivatives of 46 were commercially available. Treatment of 46 with 1-naphthol in the presence of base (K$_2$CO$_3$) gave ester 41. The ester was saponified with 3 N sodium hydroxide in THF to give acid 41, which was subsequently converted to amide 188 (X=CH) with the aid of EDCI.HCl. In the case of a quinoline analog of 188 (X=N), the acetyl chloride derivative 186 was first converted to amide 187, which was treated with 4-hydroxyquinoline to give 188 (X=N).

Example 28—General Procedure for the Synthesis of N-(4-chlorophenyl)-2-(1-naphthalenyloxy)acetamides (188, X=CH) (Examples 29-31)

Exemplified for N-(4-chlorophenyl)-2-cyclopropyl-2-(1-naphthalenyloxy)acetamide (119)

To a solution of 2-cyclopropyl-2-(1-naphthalenyloxy)acetic acid (120 mg, 0.49 mmol) and 4-chloroaniline (44.0 μL, 0.49 mmol) in anhydrous DCM (10 mL) under N$_2$ cooled at 0° C. was added EDCI.HCl (187.9 mg, 0.98 mmol) portion wise. The resulting solution was stirred at room temperature for 12 h. The reaction mixture was diluted with water (50 mL) and extracted with ethyl acetate (3×100 mL). The organic extracts were combined, washed with brine, dried over anhydrous MgSO$_4$, filtered, and concentrated in vacuo. The residue was purified by flash column chromatography using ethyl acetate/n-hexane (a gradient of 5-10%) to furnish 119 (148 mg, 86%) as a white solid. mp 204-206° C.; $^1$H NMR (CDCl$_3$, 400 MHz) δ 0.65-0.78 (m, 4H0, 1.52 (m, 1H), 4.41 (d, J=6.4 Hz, 1H), 6.70 (d, J=8.0 Hz, 1H), 7.25 (d, J=6.0 Hz, 3H), 7.43 (d, J=8.4 Hz, 2H), 7.61-7.70 (m, 3H), 7.97 (s, 1H), 8.22 (d, J=8.4 Hz, 1H), 8.34 (d, J=8.0 Hz, 1H); $^{13}$C NMR (CDCl$_3$, 100 MHz) δ 2.70, 3.16, 14.42, 82.72, 108.01, 115.68, 121.47, 122.03, 122.96, 127.64, 128.43, 129.28, 129.63, 130.07, 132.96, 135.61, 152.83, 169.27; ESI-HRMS for C$_{21}$H$_{17}$ClNO$_2$(M−H)$^+$ calcd. 350.0948. found 350.0956.

Example 29—N-(4-chlorophenyl)-2-(1-naphthalenyloxy)propanamide (93)

mp. 146-148° C.; $^1$H NMR (CDCl$_3$, 400 MHz): δ 1.79 (d, J=6.8 Hz, 3H), 4.98 (q, J=6.8, 13.2 Hz, 1H), 6.87 (d, J=7.6 Hz, 1H), 7.26 (d, J=8.4 Hz, 2H), 7.37 (t, J=8.4 Hz, 1H), 7.46 (d, J=8.8 Hz, 2H), 7.56 (dd, J=7.8, 12.5 Hz, 3H), 7.86 (m, 1H), 8.24-8.32 (m, 2H). $^{13}$C NMR (CDCl$_3$, 100 MHz): δ 19.08, 76.26, 107.41, 121.42, 121.54, 122.47, 125.91, 126.04, 126.16, 127.03, 128.14, 129.26, 129.95, 134.93, 135.75, 152.61, 170.58; Anal. (C$_{19}$H$_{16}$ClNO$_2$) C, H, N.

Example 30—N-(4-chlorophenyl)-α-(1-naphthalenyloxy)benzeneacetamide (102)

yield 92%; mp. 176-178° C.; $^1$H NMR (CDCl$_3$, 400 MHz) δ 5.86 (s, 1H), 6.88 (d, J=8.0 Hz, 1H), 7.26-7.61 (m, 11H), 7.68 (d, J=7.2 Hz, 2H), 7.87 (d, J=7.2 Hz, 1H), 7.37 (d, J=8.0 Hz, 1H), 8.44 (s, 1H). $^{13}$C NMR (CDCl$_3$, 100 MHz): δ 81.09, 107.87, 121.41, 121.47, 122.58, 125.66, 126.01, 126.27, 126.61, 127.02, 128.25, 129.12, 129.15, 129.27, 130.06, 134.94, 135.71, 135.98, 152.34, 168.11; Anal. (C$_{24}$H$_{18}$ClNO$_2$) C, H, N.

Example 31—N-(4-chlorophenyl)-3-methyl-2-(1-naphthalenyloxy)butanamide (116)

yield 91%; mp. 150-152° C., $^1$H NMR (CDCl$_3$, 400 MHz) δ 1.22 (dd, J=6.8, 22.8 Hz, 6H), 2.54 (m, 1H), 4.68 (d, J=4.4 Hz, 1H), 6.83 (d, J=8.0 Hz, 1H), 7.25 (m, 2H), 7.35 (t, J=8.0 Hz, 1H), 7.40 (d, J=8.8 Hz, 2H), 7.52 (d, J=8.0 Hz, 1H), 7.54-7.60 (m, 2H), 7.86 (m, 1H), 8.01 (s, 1H), 8.38 (m, 1H);

$^{13}$C NMR (CDCl$_3$, 100 MHz) δ 17.47, 19.54, 32.48, 84.51, 106.81, 121.53, 122.20, 125.71, 126.12, 127.04, 128.15, 129.21, 129.97, 134.92, 135.57, 153.52, 169.68; Anal. (C$_{21}$H$_{20}$ClNO$_2$) C, H, N.

Example 32—Synthesis of 2-bromo-N-(4-chlorophenyl)propanamide (187)

To a solution of 4-chloroaniline (400 mg, 3.13 mmol) in anhydrous dichloromethane at room temperature under N$_2$ was added slowly 2-bromopropanoyl chloride (474 μL, 4.7 mmol). The reaction mixture was stirred at room temperature for 2 h and then diluted with water (50 mL) and extracted with ethyl acetate (3×50 mL). The organic extracts were combined, washed with brine, dried over anhydrous MgSO$_4$ and concentrated in vacuo to give 2-bromo-N-(4-chlorophenyl)propanamide, which was used without further purifications.

Example 33—Synthesis N-(4-chlorophenyl)-2-[[4-quinolinyl]oxy]propanamide (114)

To a solution of 4-hydroxyquinoline (100 mg, 0.69 mmol) in anhydrous DMF under N$_2$ was added K$_2$CO$_3$ (286 mg, 2.10 mmol) and a solution of 2-bromo-N-(4-chlorophenyl)propanamide (218 mg, 0.83 mmol) in DMF. The reaction mixture was stirred for 12 h at room temperature before being diluted with water (50 mL) and extracted with chloroform (3×50 mL). The combined organic extracts were dried over anhydrous MgSO$_4$, filtered, concentrated in vacuo and purified by flash chromatography using ethyl acetate/n-hexane (a gradient of 10%) to furnish 114 (207 mg, 92% yield) as a white solid. mp. 170-172° C., $^1$H NMR (CDCl$_3$, 400 MHz) δ 1.83 (d, J=6.4 Hz, 3H), 5.06 (q, J=6.8, 13.6 Hz, 1H), 6.76 (d, J=5.6 Hz, 1H), 7.28 (d, J=8.4 Hz, 2H), 7.46 (d, J=8.4 Hz, 2H), 7.61 (t, J=8.0 Hz, 1H), 7.77 (t, J=7.6 Hz, 1H), 8.09 (d, J=7.2 Hz, 1H), 8.26 (d, J=8.4 Hz, 1H), 8.76 (d, J=5.6 Hz, 1H); $^{13}$C NMR (CDCl$_3$, 100 MHz) δ 18.72, 75.83, 102.05, 122.27, 121.32, 121.58, 126.61, 129.34, 129.60, 130.34, 130.51, 135.40, 149.74, 151.48, 159.47, 169.20; ESI-HRMS for C$_{18}$H$_{16}$N$_2$O$_2$Cl (M+H)$^+$ calcd. 327.0900. found 327.0901.

Example 34—C. parvum IMPDH Screen

Recombinant C. parvum IMPDH was expressed in bacteria and purified as described previously [N. N. Umejiego et al., J Biol Chem 279, 40320-40327 (2004)].

Determining the IC$_{50}$ Values.

Inhibitors at varying concentrations (25 pM-5 μM) were incubated with 10 nM C. parvum in assay buffer for 10 min at room temperature. The reaction was initiated by the addition of NAD and IMP for final concentrations of 300 μM and 150 μM, respectively. Selectivity was measured against human type II and T. foetus IMPDH at 25° C. in assay buffer. The former was assayed in the presence of 300 μM NAD 40 μM IMP and 160 nM human type II IMPDH, and the latter in the presence of 300 μM NAD 20 μM IMP and 28 nM T. foetus IMPDH. The production of NADH was monitored spectrophotometrically at 340 nm (=6.22 mM$^{-1}$ cm$^{-1}$) using a Hitachi U-2000 spectrophotometer.

IC$_{50}$ values were calculated for each inhibitor according to the following equation: $v_i = v_o/(1+[I]/IC_{50})$, using the SigmaPlot program (SPSS, Inc.).

Example 35—Heliobacter pylori, Borrelia burgdorferi, and Streptococcus pyogenes IMPDH Screen The IC$_{50}$ values of various compounds of the invention were determined for recombinant IMPDHs from H. pylori, B. burgdorferi, and S. pyogenes.

Example 36—Structural Basis of Cryptosporidium-Specific IMP Dehydrogenase Inhibitor Selectivity Cryptosporidium parvum is a potential bio-warfare agent, an important AIDS pathogen and a major cause of diarrhea and malnutrition. No vaccines or effective drug treatment exist to combat Cryptosporidium infection. This parasite relies on inosine 5'-monophosphate dehydrogenase (IMPDH) to obtain guanine nucleotides and inhibition of this enzyme blocks parasite proliferation. Here we report the first crystal structures of CpIMPDH. These structures reveal the structural basis of inhibitor selectivity and suggest a strategy for further optimization. Using this information, we have synthesized low nanomolar inhibitors that display 10$^3$ selectivity for the parasite enzyme over human IMPDH2.

Cryptosporidium spp. are a major cause of the "vicious cycle" of diarrhea and malnutrition in the developing world and a potential bioterrorism agent. This disease is prolonged and life-threatening in immuno-compromised patients. Currently no effective therapy exists for Cryptosporidium infections. The parasite obtains guanine nucleotides via a streamlined pathway that requires inosine 5'-monophosphate dehydrogenase (IMPDH). Curiously, the gene encoding CpIMPDH appears to have been obtained from a bacteria via lateral gene transfer; we have exploited this unexpected divergence of parasite and host enzymes to identify CpIMPDH-specific inhibitors in a high throughput screen. Here we report x-ray crystal structures of CpIMPDH that explain the selectivity of one inhibitor series and use this information to design more potent and selective analogs.

Recombinant CpIMPDH was purified as described previously and crystallized using the hanging drop vapor diffusion method. Protein solution (4 mg/mL IMPDH, 50 mM Tris-HCl, pH 7.5, 150 mM KCl, 5% glycerol and 2 mM DTT) was mixed with well solution (34% PEG 4000, mM sodium acetate and 100 mM Tris-HCl, pH 8.5) in a 1:1 ratio. Data were collected from a single crystal at 100K at beamline 8-BM at Advanced Photon Source (Argonne National Laboratory, Argonne, Ill.). The crystals had the symmetry of space group P2$_1$2$_1$2. The asymmetric unit contains one tetramer, which is the active form of IMPDH. The structure was solved to 3.2 Å resolution (R=27%, R$_{free}$=33%) by molecular replacement using the structure of IMPDH from Borrelia burgdorferi (PDB accession 1EEP) as a search model. Only 301 of 400 residues are visible in the most structured monomer; the disordered regions include catalytically important segments 214-222, 299-333 and 380-400 as well as residues 92-122, which are not required for enzymatic activity. Unfortunately, we were unable to improve this crystal form. This structure has been deposited in the PDB (3FFS).

To facilitate crystallization, residues 90-134 were replaced with SerGlyGly; this modification has no effect on enzymatic activity. A crystallization screen was performed in the presence of IMP and various inhibitors that emerged from initial evaluation of the SAR. Compound C64 (aka 174) was a particularly attractive candidate for crystallization because of its improved potency relative to the parent compound C (aka 123) and the presence of a bromine atom which would allow the two aromatic groups to be easily distinguished. Crystals were obtained in the presence of saturating concentrations of inhibitor C64 (20 μM), IMP (1 mM), 100 mM sodium acetate, pH 4.6, 20 mM $CaCl_2$ and 30% MPD under oil. These crystals had the symmetry of space group $P2_1$ with two tetramers in the asymmetric unit. Data were collected at a wavelength of 0.9194 Å, enabling the simultaneous collection of bromine k-edge anomalous dispersion data. The structure was solved by molecular replacement to 2.8 Å resolution using the native CpIMPDH structure as the starting model (R=22.4%, $R_{free}$=26.6%).

Figure 70:
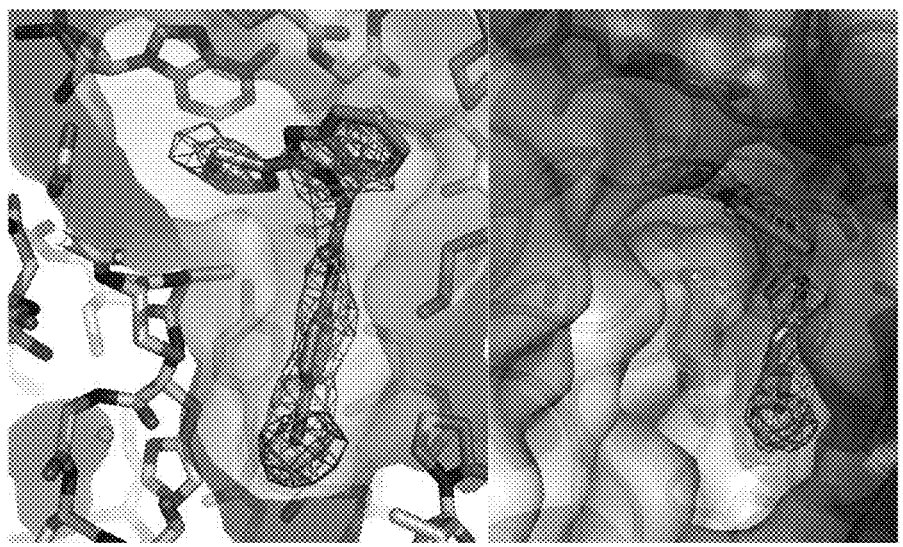
FIG. 70 depicts the x-ray crystal structure of CpIMPDH with IMP and C64 shown from two different perspectives. The electron density map prior to C64 modeling with coefficients 2Fo-Fc is contoured to 1σ and shown as a slate cage. The electron density map prior to C64 modeling with coefficients Fo-Fc is contoured to 3σ. Bromine K-edge peak anomalous dispersion map is contoured to 4σ.

While the overall structure of the E.IMP.C64 complex is similar to that of the unliganded enzyme, several additional residues are observed. Residues 214-226, which include the catalytic Cys219, are observed in most of the monomers, as are parts of the active site flap (residues 302-330) containing the characteristic ArgTyr motif. Lastly, the SerGlyGly linker is visible in all monomers. Electron density for IMP is observed in all eight monomers. Monomers B, D and H contained extra electron density near IMP (FIG. 70). Bromine k-edge anomalous dispersion maps allowed the unambiguous assignment of the bromine atom in C64 in all three monomers. The rest of C64 was modeled into the remaining electron density; similar conformations of C64 are obtained in all three monomers. This structure has been deposited in the PDB (3 KHJ).

Figure 71:
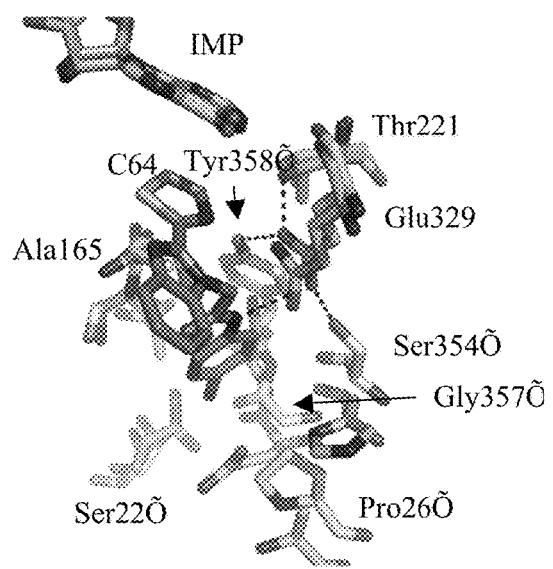
FIG. 71 depicts the C64 binding pocket of CpIMPDH superposed with human IMPDH2. CpIMPDH residues are labeled.

Surprisingly, C64 binds in an unprecedented fashion. Inhibitors of human IMPDH2 such as mycophenolic acid and merimepodib bind in the nicotinamide subsite, stacking against the purine ring of IMP in a parallel fashion, and extend either into the NAD site or into a pocket adjacent the active site but within the same monomer. In contrast, the thiazole ring of C64 stacks against the purine ring of IMP perpendicularly, and the remainder of C64 extends across the subunit interface into a pocket in the adjacent monomer, where the bromoaniline moiety interacts with Tyr358' (where ' denotes a residue from the adjacent subunit; FIG. 71). This residue forms a hydrogen bonding network involving Glu329, Ser354, Thr221 and possibly the amide nitrogen of C64 (FIG. 71). Ser22', Pro26', Ala165, Gly357' form the remainder of the inhibitor binding pocket. With the exception of Thr221, all of these residues are different in human IMPDHs (FIG. 71). Thus these interactions account for the selectivity of C64 for CpIMPDH over human IMPDHs.

The structure also revealed the presence of a cavity adjacent to the bromoaniline moiety (FIG. 70), which suggested that more potent inhibitors might be created by increasing the bulk of this substituent. Additional benzimidazole based inhibitors were prepared by condensing o-phenylenediamine (FIG. 55, 1) with thiazole carboxaldehydes (FIG. 55, 2) in the presence of the oxidizing reagent sodium metabisulfite (FIG. 55, 3). The resulting 2-substituted benzimidazoles (FIG. 55, 4) were then coupled with different bromoacetylamides (FIG. 55, 5) under mild basic conditions to give the new analogs (FIG. 55, 6).

The CpIMPDH inhibitory activity of the compounds was assessed by monitoring the production of NADH by fluorescence (FIG. 55). Replacing the p-MeO of the parent compound C with Cl or Br increased potency by 10-fold (C10, aka 126) and 20-fold (C14, aka 130), respectively, as has been similarly observed with another inhibitor series. To fill the cavity observed in the crystal structure, the para-substituted aniline group was replaced with 3,4-dichloroaniline (C86) or 2-naphthylamine (C90); the addition of a second Cl improved potency by a factor of 2, while fusing an additional aromatic ring increased potency by a factor of 8. Similar trends were observed when the thiazole ring was attached at the 2-position (C61 aka 171, C64 aka 174, C84 and C90). None of the compounds displayed significant inhibitory activity against human IMPDH2. The best CpIMPDH inhibitor, C90, has an $IC_{50}$=7.4 nM with selectivity >$10^3$ for the parasite enzyme.

In conclusion, the crystal structure of CpIMPDH reveals the structural basis of inhibitor selectivity and a strategy for further optimization. This information was used to design more potent and selective inhibitors of CpIMPDH that are potential lead compounds for the treatment of cryptosporidiosis.

Example 37—Structure-Activity Relationship Study of Selective Benzimidazole-Based Inhibitors of *C. parvum* IMPDH During a high throughput screening (HTS) process, the benzimidazole analog C1 (compound 123) was identified (FIG. 21) as a moderately potent but highly selective inhibitor for Cp-IMPDH ($IC_{50}$=1.2 μM) with no detectable activity against the human IMPDH-II enzyme ($IC_{50}$>50 μM). This molecule has demonstrated uncompetitive inhibition with respect to IMP and noncompetitive (mixed) inhibition with respect to $NAD^+$. It was also shown to bind the nicotinamide subsite and to directly or indirectly impose on the ADP site. Herein, we report a structure-activity relationship (SAR) study for this class of inhibitors.

The benzimidazole analogs were synthesized following the procedure outlined in FIG. 55. Various acetylamide derivatives (FIG. 55, 3) were prepared by treating substituted anilines (FIG. 55, 1) with bromo acetylchloride (FIG. 55, 2) in dichloromethane (DCM) and in the presence of catalytic amounts of N,N-dimethylaminopyridine (DMAP). Various 2-substituted benzimidazoles FIG. 55, 6) were prepared by condensing O-phenylene diamine (FIG. 55, 4) with aromatic aldehydes followed by oxidation in the presence of sodium metabisulfite. Finally, 2-substituted benzimidazoles were coupled with the acetylamides (FIG. 55, 3) in the presence of potassium carbonate to yield derivatives of C.

Evaluation of Cp-IMPDH inhibitory activity for the various prepared compounds was conducted utilizing an assay measuring the conversion of IMP to XMP by monitoring the production of NADH by fluorescence emission in the presence of varying inhibitor concentrations. Chlorine and bromine are found to be more effective substituents at the para-position of the aniline ring (FIGS. 21-23). On the contrary, ortho and meta substitutions were devoid of inhibition activity.

An electron donating group, such as thiomethyl (C39, compound 154) at the para position. Interestingly increasing the chain length, and making a benzyl derivative C18 results in the loss of activity towards Cp-IMPDH. In addition, any branched substitutions such as $SO_2Me$ (C40, compound 155) or isopropyl (C43, compound 157) at the para position resulted the loss of activity. Among all the derivatives we have synthesized, 2-naphyl (C90) and 3,4-dichloro derivatives (C86) are found to be the most potent inhibitors, which suggest that this part of the molecule contributes to the steric factor for the binding process than electronic factor.

However, surprisingly, the 1-naphthyl derivative C28 (compound 144) did not show any inhibition, whereas its positional isomer, 2-napthyl derivative found to be a potent inhibitor, which explains that indeed subtle changes in molecular orientation would have significant influence in determining the binding ability. Observed low $IC_{50}$ of C90 (7 nM) suggesting that C90 molecule could fit appropriately into the active site of the IMPDH. The SAR of this part of the inhibitor is similar to that has been previously reported with another series from our group. In addition, we have investigated the role of active methylene group by substituting various groups at the active methylene group, and found that any subtle changes at that position led to lose of inhibition ability (FIGS. 21-23).

Subsequently, the SAR of the thiazole ring, aniline ring is fixed as 4-chloro derivative, 2, 3 and 4 thiazoles are found to be twice as potent as the thiabendazole derivative C10 (compound 126) (FIGS. 21-23). When the ring system is changed to thiophene, C62 (compound 172) showed high potency towards Cp-IMPDH inhibition with 20 nM $IC_{50}$. Other heterocylic rings like pyrrole, oxazole, and pyrazole are also well tolerated. Replacing the thiazole ring (C61, compound 171) with thiophene (C62, compound 172) caused the drop in $IC_{50}$ values about 10 nM, however, replaced with pyrrole ring (C65, compound 175) increased the $IC_{50}$ values about 45 nM compared to C61 (compound 171). Thus, compared to thiazole, thiophene has effective while pyrrole proved to be much less effective inhibitor. Oxazole derivative (C69) is not as potent as the thiazole or thiophen derivatives but pyrazole derivative C100 was as potent as 2-thiazoles. When the thiazole ring is replaced by a methyl group (C38, compound 153) the compound lost its activity (FIGS. 21-23). Phenyl (C17, compound 133), pyridyl (C16, compound 132) rings are also tolerated in the 2-position. Substituted phenyls (C31 (compound 147), C59 (compound 169)) are not as active as the non-substituted.

Recently, the potent inhibitor C64 (compound 174) has been co-crystallized with Cp-IMPDH. The co-crystallized structure of Cp-IMPDH with C64 is solved and the SAR matches perfectly well with the structure. 2-aromatic substitution in the benzimidazole portion is important since it interacts with the IMP in the active site according to the crystal structure. The amide bond is also very important for the activity since it could potentially form hydrogen bonding with the active site residues.

Bulkier substituents are better at the para position of the aniline ring. Increasing the chain length either at the aniline as well in the benzimidazole results in the loss of activity. Replacing thiazole ring by phenyl, pyridyl and other heterocycles retain the activity but replacement with methyl results in the loss of activity. Replacing aniline by other non-aromatic cycles like morpholine, piperidine results in the loss of activity.

Selectivity plays a major role in determining the success of the drug molecules. After a detailed investigation of Cp-IMPDH inhibition ability of C-series molecules, we have evaluated their selectivity towards parasite Cp-IMPDH over human II-IMPDH. Intriguingly, all the molecules were showed excellent selectivity towards Cp-IMPDH over human II-IMPDH even though both the proteins share high identity in their binding site.

In conclusion we have studied SAR of new series of benzimidazole derivatives as potent inhibitors for Cp-IMPDH. Many of the derivatives have shown nanomolar inhibition towards IMPDH. The $IC_{50}$ was improved to 2 nM (C91) from 1200 nM for the identified lead compound C through a systematic SAR studies. Few of the compounds showed increased efficacy with the cell based assays. The crystal structure opens a new pathway to design structurally diversified potent inhibitors for the selective inhibition of Cp-IMPDH over Human II-IMPDH. The benzimidazole based CpIMPDH inhibitors described herein could serve as lead compounds for drug discovery to treat cryptosporidiosis.

Often in drug development, despite excellent inhibition ability, several molecules fail to show significant stability under metabolic conditions which is one of the key parameters for defining potent drug molecules. Thus, metabolic stability of selective inhibitors from several series has been investigated using human and mouse microsomes and human and mouse plasma. Results are summarized in FIG. 56. Several compounds showed excellent stability with mouse microsomes and most compounds showed excellent plasma stability over 2 hours, which is considered to be significant stability.

Figure 57:
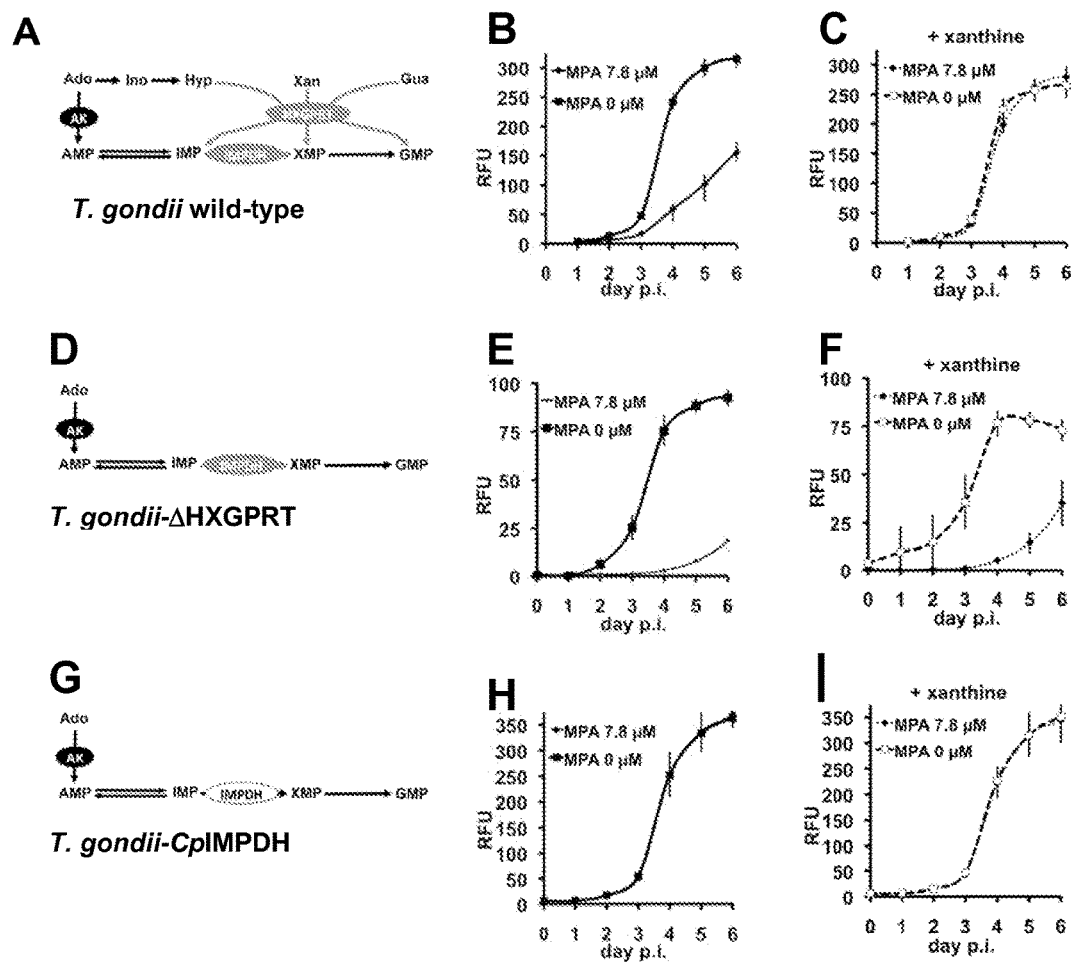
FIG. 57 depicts validation of the *T. gondii*-CpIMPDH reporter parasite. Schematics of the routes to GMP for the wild-type *T. gondii*, *T. gondii*-ΔHXGPRT, and *T. gondii*-CpIMPDH are shown in A, D & G respectively. Genetic studies have shown that the salvage of adenosine via adenosine kinase is the predominant route to GMP for *T. gondii* and IMPDH catalyzes the rate limiting step of this pathway. However, in the absence of adenosine kinase, TgHXGPRT allows for the salvage of adenosine, adenine and guanosine such that the activity of TgHXGPRT is sufficient for parasite proliferation. Several transporters for the uptake of nucleobases and nucleotides have been characterized in *T. gondii*. Unlike *T. gondii* and other Apicomplexa, *C. parvum* lacks HXGPRT and is dependent on the salvage of adenosine and thus the activity of CpIMPDH. A single adenosine transporter has been identified in the genome of *C. parvum*. The *T. gondii* pathways shown in grey highlight the genes disrupted in the parasite clones used in this study, TgHXGRT in a previous study (HXGPRT) and TgIMPDH in this study. Hyp, hypoxanthine; Xan, xanthine; Gua, guanine; Guo, guanosine; Ade, adenine; Ado, adenosine; Ino, inosine; AMP, adenosine monophosphate; IMP, inosine monophosphate; XMP, xanthosine monophosphate; GMP, guanosine monophosphate; HXGPRT, hypoxanthine xanthine gunanine phosphoribosyltransferase; IMPDH, IMP dehydrogenase, 1, adenine deaminase; 2, adenosine deaminase; 3, purine nucleoside phosphorylase; 4, adenosine kinase; 5, AMP deaminase; 6, adenoylsuccinate synthase and adenoylsuccinate lyase; 7, GMP synthase. Panels B, E & H show parasite growth in the presence of 0 µM and 7.8 µM MPA for wild-type T. gondii, T. gondii-ΔHXGPRT, and T. gondii-CpIMPDH respectively. Panels C, F, and I show parasite growth curves in the presence of 0 µM and 7.8 µM MPA, with the addition of 0.33 mM xanthine to the culture media, for wild-type T. gondii, T. gondii-ΔHXGPRT, and T. gondii-CpIMPDH respectively. Data are representative of two independent experiments.

Example 38—A Screening Pipeline for Antiparasitic Agents Targeting *Cryptosporidium* IMPDH Results Engineering a *Toxoplasma* Reporter Parasite Suitable for the Screening of CpIMPDH Inhibitors To facilitate screening of antiparasitic activity, we constructed a *T. gondii* reporter parasite that mirrors the *Cryptosporidium* purine metabolism. FIG. 57 summarizes the main differences between the two parasites in this pathway. We started with a *T. gondii* knockout mutant that, like *C. parvum*, lacks the ability to salvage xanthine and guanine via HXGPRT (*T. gondii*-ΔHXGPRT(10)) and introduced the CpIMPDH gene under the control of a *T. gondii* promoter. Next, the native *T. gondii* IMPDH gene was disrupted by replacing the entire coding sequence with a chloramphenicol acetyl transferase cassette using a new cosmid-based gene targeting approach. Successful disruption of the gene was confirmed by PCR and Southern blotting; note that numerous attempts by independent laboratories failed to target this locus using smaller plasmid-based constructs. This manipulation created strain *T. gondii*-CpIMPDH-ΔHXGPRT-ΔTgIMPDH. Lastly, we introduced a fluorescent protein cassette and isolated stable transgenic parasites by cell sorting. The resulting strain is referred to as *T. gondii*-CpIMPDH. The growth of this new parasite can be conveniently monitored in live cultures in 96 or 384 well format using a fluorescence plate reader. Similarly engineered fluorescent versions of wild-type *T. gondii* and *T. gondii*-ΔHXGPRT served as controls.

Pharmacological Validation of the *Toxoplasma* Reporter Parasite

Figure 63:
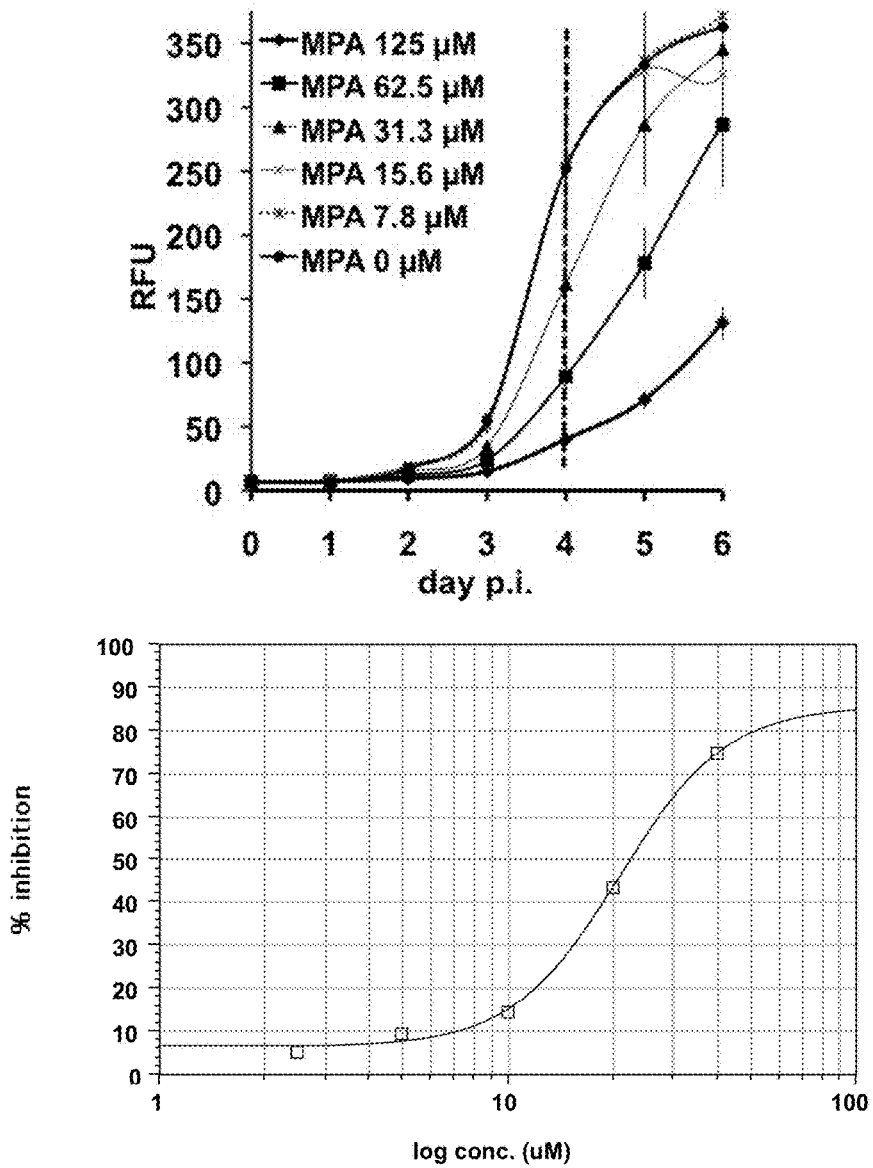
FIG. 63 depicts an overview of obtaining an $EC_{50}$ for T. gondii growth. Fluorescent T. gondii parasites are seeded into 96-well plates and spiked with test compound. Fluorescence is measured daily with a SpectraMax M22/M2e (Molecular Devices) plate reader for 6-7 days. The fluorescence readings on a day during the exponential phase of the growth curve, for example day 4 in panel A, are used to calculated percent growth inhibition. These values are fitted to using the 4 parameter model $y=D+(A-D)/(1+(x/C)^B)$ where D is the minimum value, A is the maximum value, C is the EC50 and B is the Hill coefficient, using the SoftMax Pro v5 software, as illustrated in panel B. The absolute $EC_{50}$ is recorded at the x intercept where y=50.

To determine if the proliferation of *T. gondii*-CpIMPDH depends on CpIMPDH as designed, we performed fluorescence growth assays in the presence of varying concentrations of mycophenolic acid (MPA) comparing wild-type *T. gondii*, *T. gondii*-ΔHXGPRT, and *T. gondii*-CpIMPDH parasites (FIG. 57). MPA is a potent inhibitor of eukaryotic IMPDHs including TgIMPDH but a very poor inhibitor of prokaryotic IMPDHs. CpIMDPH is of prokaryotic origin and not inhibited by MPA. As predicted, both wild-type *T. gondii* and *T. gondii*-ΔHXGPRT are sensitive to MPA (FIG. 57), but *T. gondii*-CpIMPDH is resistant (FIG. 57). *T. gondii*-ΔHXGPRT is the most sensitive strain due to its inability to salvage xanthine/guanine from the media ($EC_{50}$=0.29 µM versus 2.6 µM for the wild-type strain; FIG. 63 details how an $EC_{50}$ was derived from the parasite growth curves). Supplementation of the media with xanthine (0.33 mM) essentially renders wild-type *T. gondii* MPA resistant ($EC_{50}$≥78 µM), but has no effect on *T. gondii*-ΔHXGPRT (FIG. 57). In contrast, the MPA $EC_{50}$>65 µM for *T. gondii*-CpIMPDH is significantly higher, as expected given the resistance of the prokaryotic CpIMPDH, and is independent of xanthine supplementation (FIG. 57).

These results demonstrate that the *T. gondii* model system provides a powerful tool for the evaluation of in vivo efficacy, selectivity, and specificity of CpIMPDH inhibitors. Compounds that selectively inhibit CpIMPDH will block the proliferation of *T. gondii*-CpIMPDH but not the wild-type and *T. gondii*-ΔHXGPRT strains that depend on an enzyme much like the human host. In contrast, non-specific compounds that have off-target activities in the parasite or the host cell will inhibit the growth of all three strains. In the presence of xanthine, a general non-selective inhibitor of both prokaryotic and eukaryotic IMPDH inhibitors will block the proliferation of both *T. gondii*-CpIMPDH and *T. gondii*-ΔHXGPRT but will have no effect on the wild-type strain; note that such compounds should be detected in our enzyme assays and eliminated before they reach this screen. Lastly, compounds showing poor efficacy against the *T. gondii*-CpIMPDH parasite may signal problems pertaining to compound uptake, stability or metabolism. Examples of these varied outcomes are discussed below.

Figure 58:
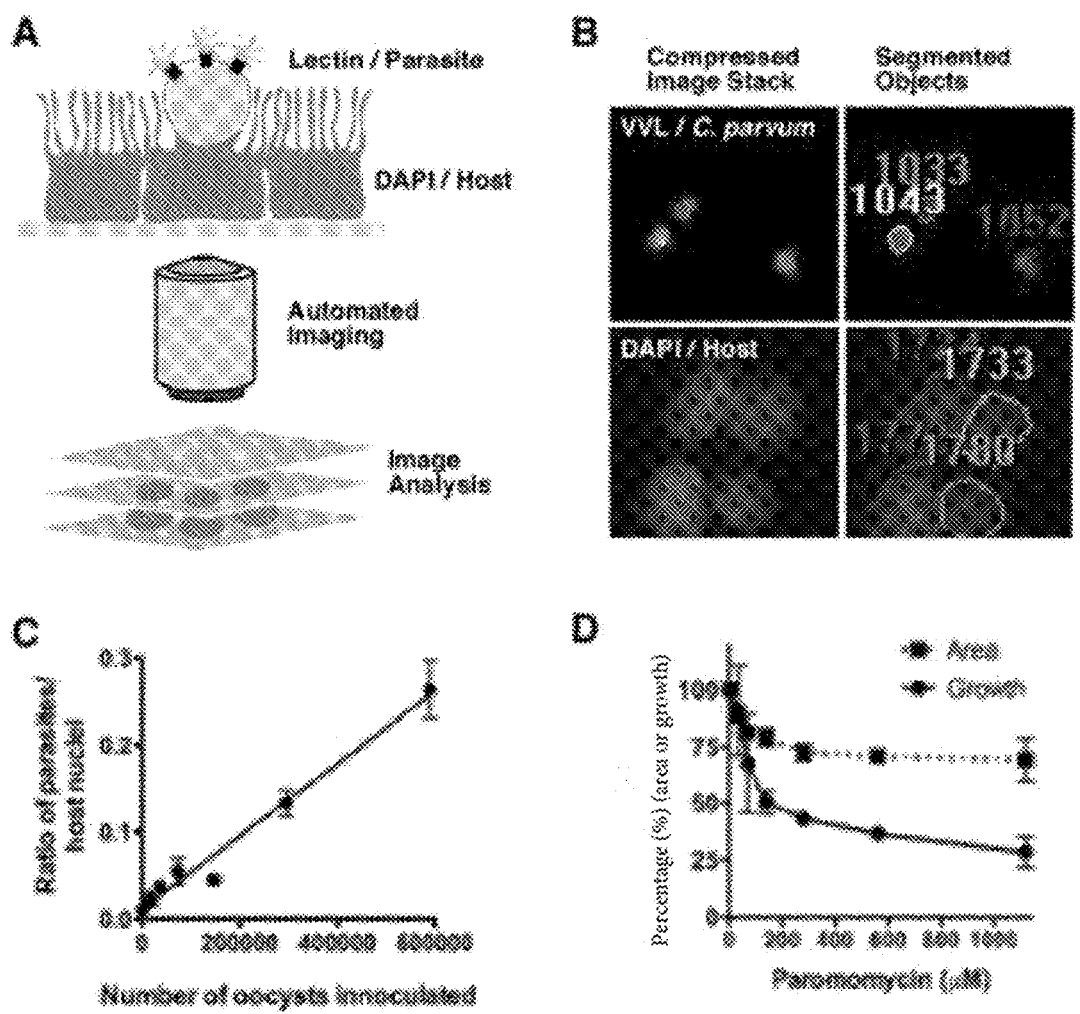
FIG. 58 depicts an overview and validation of the high content imaging C. parvum growth assay. A, schematic representation of differential labelling of parasite and host. B, detail of an exemplary micrograph obtained through the screening routine. Numbers indicate object identifies after segmentation analysis. Panel C shows a 2-fold titration of C. parvum oocysts where the top concentration was $1.2 \times 10^6$ oocysts per well. For panel D, the ratio of the number of FITC-VVL labelled C. parvum parasites to DAPI labelled HCT-8 host cell nuclei was used to standardize each well and percent C. parvum growth (solid line) was normalized to parasites receiving DMSO alone. The paromomycin $EC_{50}$ for C. parvum was growth was 97 µM. Paromomycin in addition to reducing parasite number also reduces the average size of the parasite (dashed line). The mean parasite area was measured per well for each treatment in triplicate. The percent area was then calculated by normalizing to the mean area of parasites receiving DMSO alone. Data shows the mean of two independent experiments set up with triplicate wells in a 96-well format.

A High-Content Imaging Assay to Evaluate Anti-Cryptosporidial Activity of Compounds While the *Toxoplasma* model provides outstanding throughput and an excellent first filter it does not model all aspects of *Cryptosporidium* biology. A direct and efficient assay of *Cryptosporidium* proliferation was also needed. Fluorescent *Vicia villosa* lectin (VVL) has been used previously to score *C. parvum* growth by fluorescence microscopy. VVL binds with high specificity to the *C. parvum* parasite, labelling sporozoites, intracellular stages, the inner oocyst wall, but not the outer oocyst wall. To accommodate the increasing number of compounds entering the SAR pipeline, we adapted the FITC-VVL immunofluorescence assay to a 96-well plate format and developed an automated imaging and analysis pipeline. FIG. 58 shows an overview of the methodology. Plates are fixed, permeabilized and stained with FITC-VVL and DAPI to numerate parasites and host cells, respectively. Using a spinning disc microscope, we imaged a X mm area of each well, providing a robust sample typically consisting of ~6000 host cells and ~2000 parasite stages. The instrument is programmed to automatically move from well to well, focus and acquire 20 µM deep image stacks for the entire plate. A series of automated image compression, manipulation, and object-finding algorithms was optimized for the recognition of host cells and parasites using the DAPI and FITC channels. To control for background staining and biological variability, control wells are included for background subtraction. The massive data output is stored, managed and accessed through an Accelrys pipeline database that performs further statistical analyses and transforms raw counts into percentage growth relative to a "no drug" control.

The $EC_{50}$ for paromomycin as measured with this assay was 97 µM (FIG. 58), which is in good agreement with several previous studies (reported $EC_{50}$ ranges from 65-130 µM. However, at very high concentrations of paromomycin we only detect ~70% reduction in parasite number, this may be due to the labelling of sporozoites that invade the host cell monolayer and subsequently die or become arrested in development. Interestingly paromomycin was also found to significantly reduce the mean parasite area in a dose responsive manner (FIG. 58) and might be consistent with the parasites present at high paromomycin concentrations being developmentally arrested. For several of the test compounds 90% growth inhibition was apparent at the higher range of concentrations tested, although unlike with paromomycin no apparent reduction in parasite area was detected (data not shown). FIG. 58 shows a 2-fold titration of oocysts where the highest inoculum as $1.2 \times 10^6$ oocysts per well, for *C. parvum* growth assays $5 \times 10^5$ oocysts were added per well.

Validation of the Fluorescent Host Cell Growth Assay

The differentiation of selective antiparasitic effects from those that are a secondary consequence of a host cell effect is a critical issue in drug discovery for intracellular parasites. Cytotoxicity assays commonly reflect plasma membrane integrity, and are a crude measure of host cell effects—it is conceivable that more subtle perturbations of host cell metabolism can have an adverse effect on parasite proliferation. Therefore we sought to develop a simple and inexpensive assay of host cell growth. The human ileocecal adenocarcinoma epithelial cell line, HCT-8, which is commonly used to maintain *C. parvum* infection in tissue culture, was engineered to constitutively express a green fluorescent protein (GFP). Growth of this cell line was monitored daily using a fluorescent plate reader. In agreement with previous reports, paromomycin had negligible effects on the growth of these cells. Sodium butyrate did inhibit HCT-8 growth in a dose-dependent manner in this assay, as anticipated due to previous reports of its apoptotic effects in colonic tumor cell lines. These experiments validate the use of the fluorescent HCT-8 cell growth assay.

Identification of Highly Selective CpIMPDH Inhibitors in the *T. gondii* Model

Figure 59:
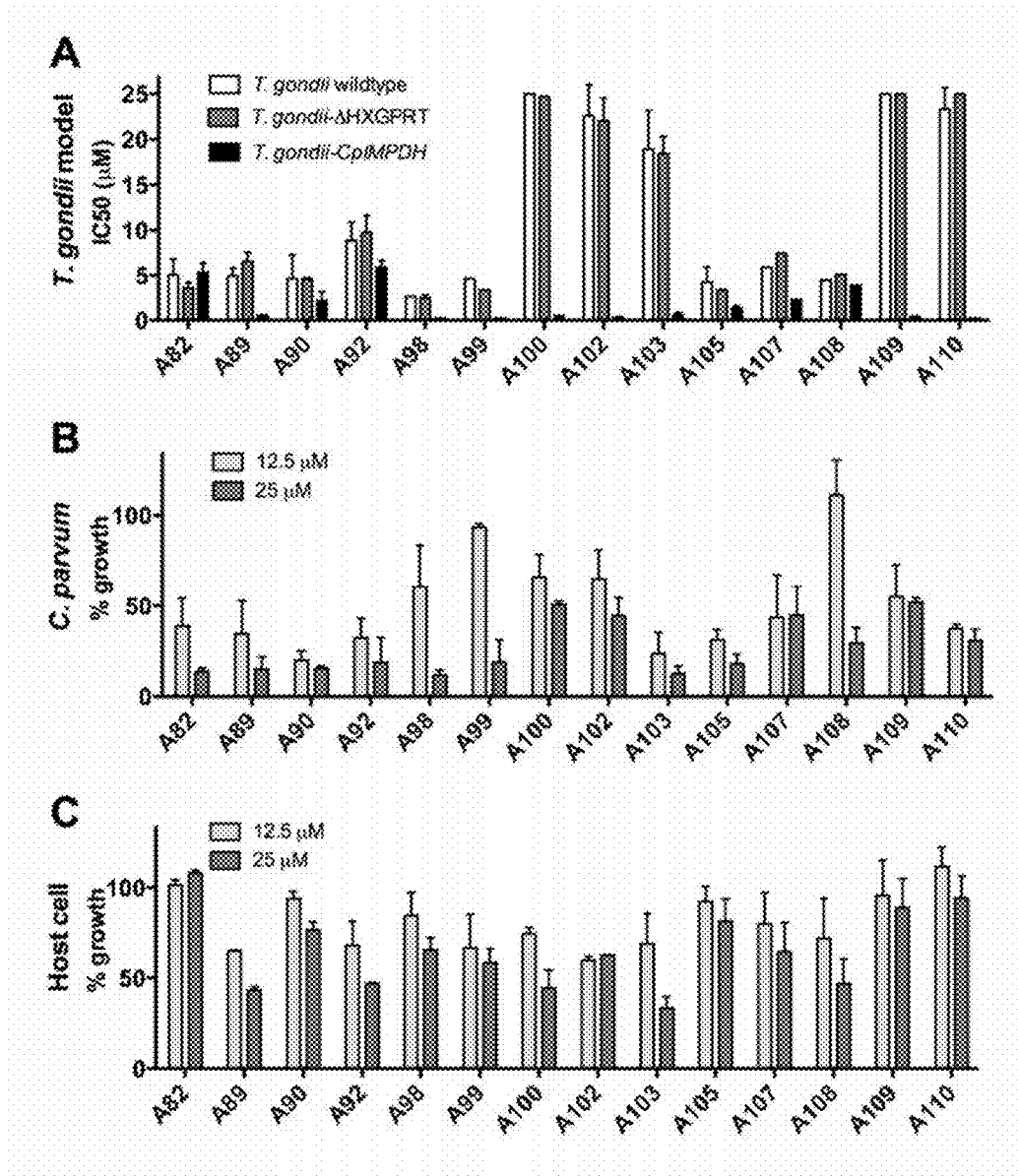
FIG. 59 depicts the identification of derivatives with high potency and selectivity in the T. gondii-CpIMPDH model. Panel A shows the $EC_{50}$ for a selection of compounds assayed in the T. gondii-CpIMPDH parasite model and demonstrates a range in compound selectivity and potency. Compounds were assayed in triplicate and growth inhibition was calculated on a day during the exponential phase of growth, by normalization to wells receiving DMSO alone. The $EC_{50}$ calculation was performed as described in FIG. 63. Compounds A82, A89, A90, A92, A102, A103, A105, and A110 were selected for rescreening and the mean for at least 2 replicate experiments are shown. These compounds were then tested for inhibition of C. parvum (panel B) and host cell growth (panel C). For panel B, percent C. parvum growth was determined using the high-content imaging assay, with compound at 12.5 µM and 25 µM. The ratio of FITC-VVL labeled C. parvum parasites to DAPI labeled HCT-8 host cell nuclei was used to standardize each well and percent growth was normalized to parasites receiving DMSO alone, the mean of triplicate wells is shown. A selection of compounds were selected for re-screening and the mean over at least 2 replicate experiments is shown for compounds A90, A92, A98, A103, A105, A109 and A110. Panel C shows percent host cell growth assayed using the pmaxGFP fluorescent HCT-8 cell line with compound at 12.5 µM and 25 µM. GFP expressing HCT-8 cells were seeded at 4000 cells per well into 96-well plates and triplicate wells were spiked with test compound. Fluorescence was measured daily with a SpectraMax M22/M2e (Molecular Devices) plate reader (Ex 485, Em 530) for 7 days. Percent growth inhibition was calculated on a day during the exponential phase of growth, by normalization to wells receiving DMSO alone. A selection of compounds A89, A90 and A92 were selected for re-screening and the mean over at least two replicate experiments is shown.

The antiparasitic activities of 26 compounds from our medicinal chemistry optimization program were evaluated in the *T. gondii* model system. The structures of the compounds are shown in FIG. 62A-D alongside a summary of findings. Three compounds, A17 (compound 60), A57 (compound 104) and A66 (102), do not inhibit CpIMPDH in vitro; as expected, none of these compounds selectively blocked the growth of *T. gondii*-CpIMPDH (FIG. 59, FIG. 62A-D). The remaining compounds inhibit CpIMPDH with values of $IC_{50}$ ranging from 9 nM to 2.6 µM. FIG. 59 shows representative data for fourteen 1,2,3-triazole derivatives in the *T. gondii* model. With the exception of A23 (79) and A31 (61), all compounds inhibit the growth of the *T. gondii*-CpIMPDH parasite with an $EC_{50}$<10 µM (FIG. 59, 62, 64). Five of the 1,2,3-triazole derivatives, A100 (23), A102 (25), A103 (26), A109 (32) and A110 (33), exhibit selectivity ≥36-fold for the *T. gondii*-CpIMPDH parasite over wild-type *T. gondii* (FIG. 59). Therefore, the antiparasitic effects of these compounds can be confidently attributed to the inhibition of CpIMPDH. A99 (22) is ≥17-fold selective and the remaining compounds range in selectivity from 0.9-14-fold (FIG. 59). All compounds have similar effects on both wild-type and *T. gondii*-ΔHXGPRT parasites (FIG. 59), indicating that the lack of selectivity derives from off-target effects unrelated to TgIMPDH.

Figure 60:
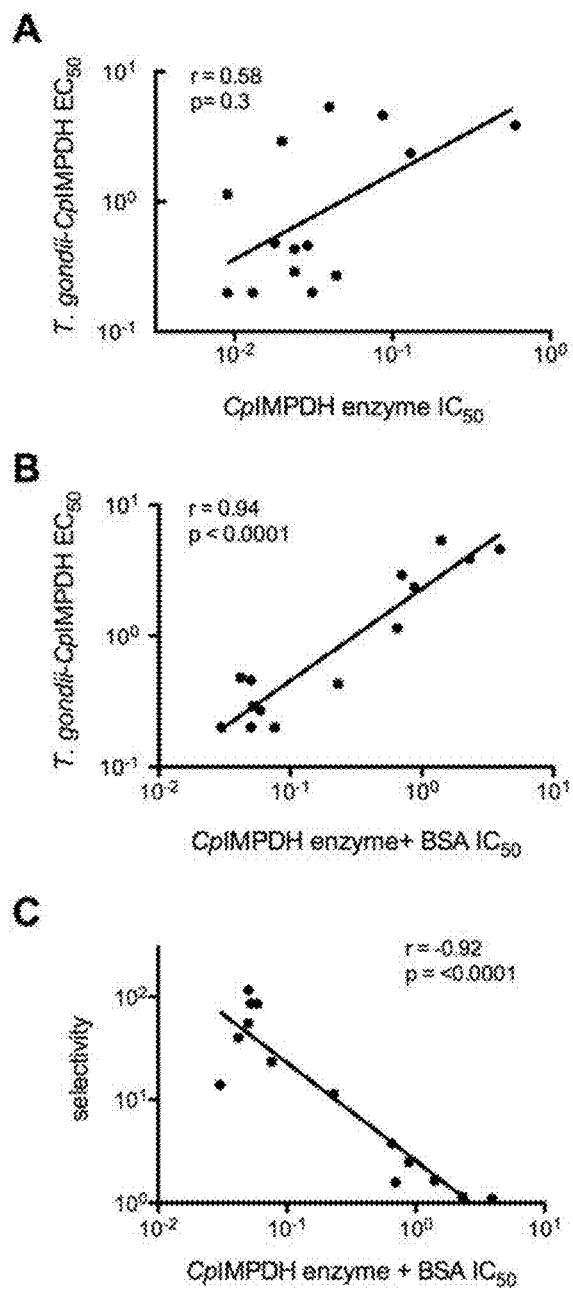
FIG. 60 depicts the correlation between CpIMPDH enzyme inhibition and potency and selectivity in the T. gondii-CpIMPDH model. Panel A shows a relatively weak (r=0.58) and statistically insignificant (p-value=0.3) correlation between the compound $IC_{50}$ values for the CpIMPDH enzyme and the $EC_{50}$ for proliferation of the T. gondii-CpIMPDH parasite. However a strong, positive correlation exists between the potency of CpIMPDH enzyme inhibition when assayed in the presence of BSA and inhibition of T. gondii-CpIMPDH proliferation (r=−0.94, p<0.0001; panel B). Panel C, shows that selectivity in the T. gondii model, determined by the relative inhibition of the T. gondii-CpIMPDH parasite over wild-type T. gondii clone, also correlates well with the potency of enzyme inhibition in the presence of BSA (r=−0.92, p<0.0001).

Surprisingly, initially we did not observe a significant correlation between the potency of a compound in the enzyme assay and inhibition of *T. gondii*-CpIMPDH proliferation (FIG. 60). We wondered if this may be an issue of bioavailability and linked to the presence of serum in the parasite growth medium. To test this hypothesis, enzyme inhibition was also evaluated in the presence of BSA. A strong positive correlation is observed between inhibition of *T. gondii*-CpIMPDH proliferation and potency of CpIMPDH enzyme inhibition in the presence of BSA (FIG. 60; r=−0.94, p<0.0001). Selectivity in the *T. gondii* model also correlates well with the potency of enzyme inhibition in the presence of BSA (FIG. 60; r=−0.92, p<0.0001). These observations indicate that the $IC_{50}$ value in the presence of BSA is a useful proxy for antiparasitic activity modelled by *T. gondii*-CpIMPDH proliferation.

The *T. gondii* Model and Predicting Off-Target Host Cell Effects

Figure 64:
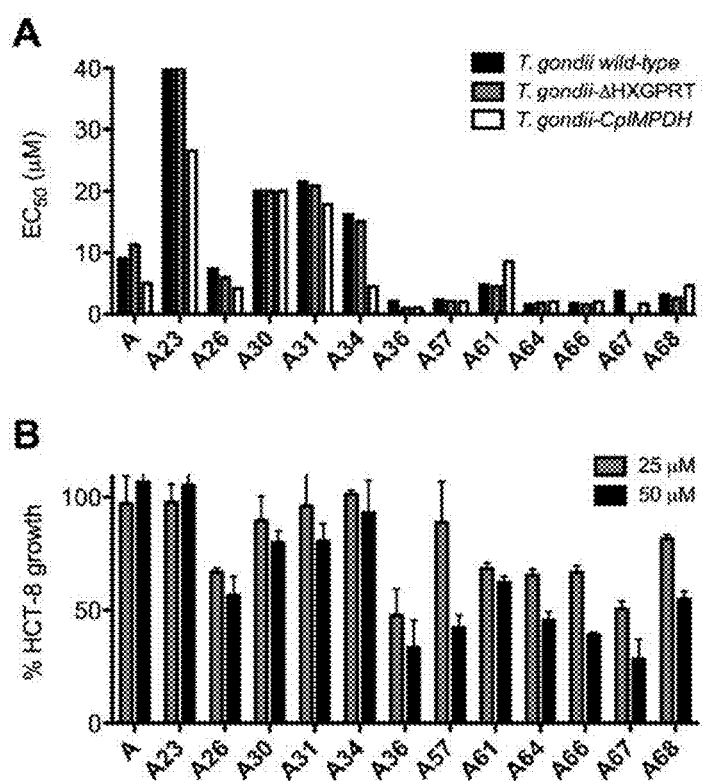
FIG. 64 shows results of various compounds in the surrogate T. gondii model. Panel A shows the $EC_{50}$ for a selection of compounds assayed in the T. gondii-CpIMPDH parasite model. Compounds were assayed in triplicate and growth inhibition was calculated on a day during the exponential phase of growth, by normalization to wells receiving DMSO alone. The $EC_{50}$ calculation was performed as described in figure S2. Note the highest concentration tested in panel A was for compound A30 was 20 µM. Panel B shows percent host cell growth assayed using the pmaxGFP fluorescent HCT-8 cell line with compound at 25 µM and 50 µM. GFP expressing HCT-8 cells were seeded at 4000 cells per well into 96-well plates and triplicate wells were spiked with test compound. Fluorescence was measured daily with a SpectraMax M22/M2e (Molecular Devices) plate reader (Ex 485, Em 530) for 7 days. Percent growth inhibition was calculated on a day during the exponential phase of growth, by normalization to wells receiving DMSO alone.
Figures 65, 66:
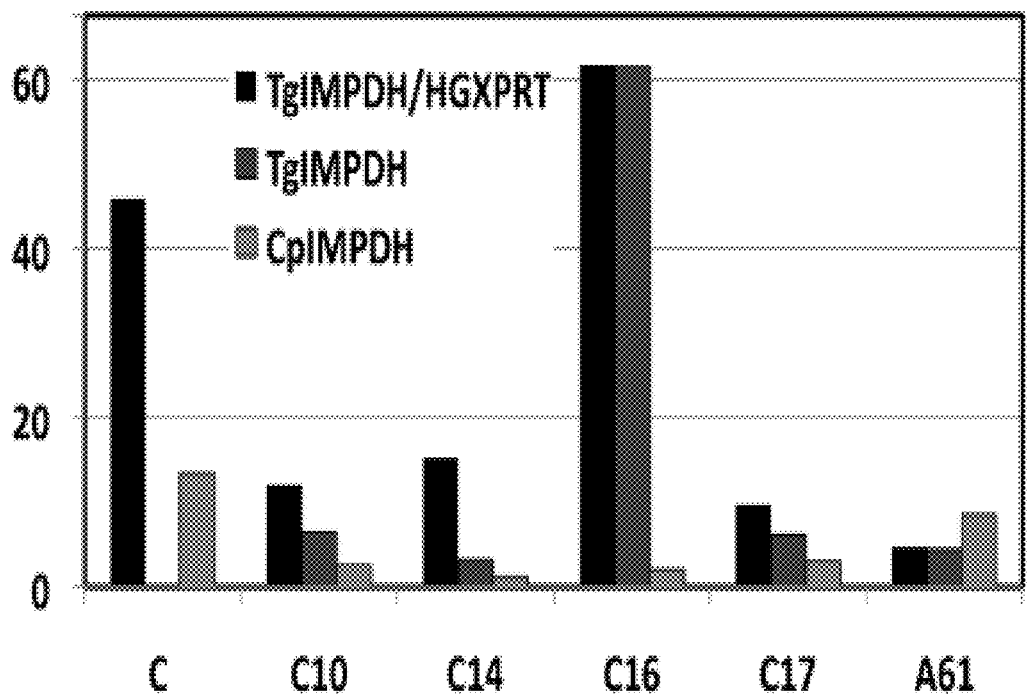
FIG. 65 depicts the selectivity of various compounds in the surrogate Toxo/CpIMPDH assay.
FIG. 66 tabulates activity levels of various compounds; the surrogate *Toxoplasma* model is predictive for anti-*Cryptosporidium* activity.

Host cell growth was also assayed to assess the contribution of host cell effects to antiparasitic activity (FIGS. 59, 62, and 64). In general, strong host cell effects are observed in compounds that display little selectivity in the *T. gondii* model (FIGS. 59, 62, and 64). With three exceptions (A98, A99, and A108), compounds that inhibited the proliferation of wild-type *T. gondii* with $EC_{50}$<10 μM also inhibited the proliferation of host cells. Three compounds (A82, A90, and A105) display little selectivity in the *T. gondii* model and do not inhibit host cell growth, suggesting that the antiparasitic activities of A82, A90, and A105 do not result from the inhibition of CpIMPDH or TgIMPDH. Instead, A82, A90, and A105 may act on other *T. gondii* targets not present in the host cell. Conversely, A100, A102, and A103 have $EC_{50}$>20 μM against wild-type *T. gondii* yet inhibit HCT-8 cell growth significantly at 12.5 μM and 25 μM (FIG. 62A-D).

CpIMPDH Inhibitors with Significantly Improved Anti-Cryptosporidial Activity

The high-content imaging assay was used to evaluate the anti-cryptosporidial activity of the 1,2,3-triazole CpIMPDH inhibitors at 12.5 μM and 25 μM (FIG. 59). All compounds inhibited *C. parvum* growth by at least 48% at a concentration of 25 μM (FIG. 59) and thus had equal or markedly improved anticryptosporidial efficacy when compared to parent compound A (53) ($EC_{50}$ 25 μM-50 μM). Unlike paromomycin, a significant reduction in parasite area was not detected (data not shown). The average area of the host cell nucleus was also recorded as a potential indicator of host cell cytotoxicity and likewise no significant change in host cell nuclei size was detected (data not shown). Encouragingly there was a negative trend between anticryptosporidial activity and host cell growth inhibition (data not shown), indicating that improvements in anticryptosporidial activity are not coincident with secondary effects on the host cell.

Figure 61:
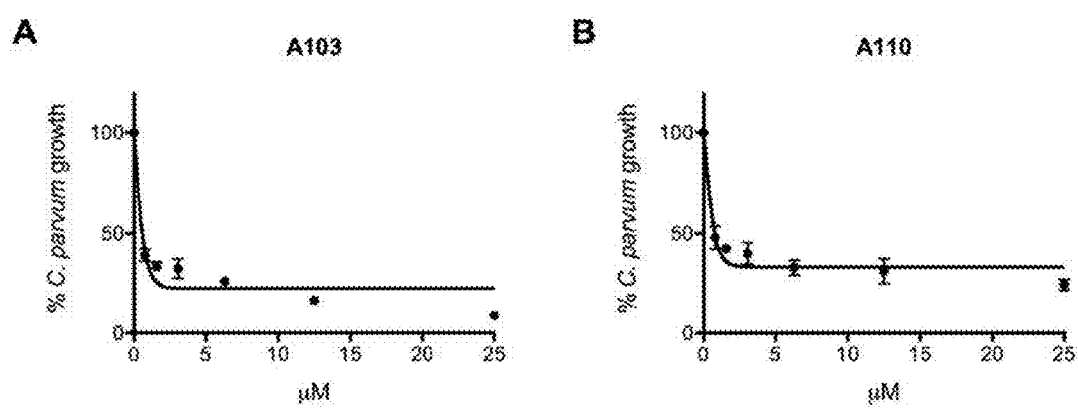
FIG. 61 depicts that compounds A103 and A110 are potent inhibitors of C. parvum growth. C. parvum growth was determined using the HCl assay. The ratio of the number of FITC-VVL labelled C. parvum parasites to DAPI labelled HCT-8 host cell nuclei was used to standardize each well and percent C. parvum growth was normalised to parasites receiving DMSO alone. Panels A and B show compounds A103 and A110 respectively ($EC_{50}$<0.8 µM). Data shows the mean of two independent experiments with triplicate wells.

To provide quantitative data to the SAR pipeline, the values of $EC_{50}$ were determined for seven compounds. A82 (7), A90 (14), A92 (16), A98 (21) and A105 (28) had $EC_{50}$ values between 3 μM and 13 μM (FIG. 62A-D). Compounds A103 (26) and A110 (33) were found to be potent inhibitors of *C. parvum* growth with $EC_{50}$ values of <0.8 μM (FIG. 61). As shown above, A103 and A110 also have negligible effects on host cell growth and exhibit good selectivity in the *T. gondii* model. Therefore, A103 and A110 have improved specificity, improved efficacy and a good therapeutic window.

While not every compound that showed activity against the *T. gondii*-CpIMPDH parasite had strong anticryptosporidial activity, none of the compounds showing poor activity in the *T. gondii*-CpIMPDH model display significant anticryptosporidial activity. The *T. gondii* assay also immediately flagged compounds with poor bioavailability and those that showed parasite killing due to off-target effects. We conclude that the *T. gondii*-CpIMPDH model provides valuable information regarding compound specificity and is a fast and highly informative filter for compound progression through medicinal chemistry optimization.

Discussion

Despite the tremendous public health impact of cryptosporidiosis efforts to develop new and more effective treatments for this diseases have been languishing. There are a number of reasons for this, but lack of suitable tissue culture and animal models to assess drug candidates is currently the most prominent roadblock. To overcome this challenge we have developed a facile screening pipeline to evaluate the antiparasitic activity of CpIMPDH inhibitors. The backbone of this pipeline is provided by a *T. gondii* model parasite that mirrors *Cryptosporidium* purine nucleotide pathways and depends on CpIMPDH. The *T. gondii* model reliably eliminates compounds from further consideration and provides a useful filter to identify off-target activities. However, efficacy in the *T. gondii* model does not always guarantee anti-cryptosporidial activity. This disparity likely arises from fundamental differences in the biology of the two parasites. *T. gondii* and *C. parvum* infect different tissues, and occupy different intracellular compartments. The parasitophorous membrane of *T. gondii* is in direct contact with the host cell cytoplasm. In contrast, *C. parvum* remains beneath the apical membrane of the host cell and is considered 'extracytoplasmic' due to the presence of a parasite induced host cell actin patch along with other peculiar and still largely uncharacterized structures including a dense band visible in electron micrographs. This band separates the parasite's parasitophorous vacuole from the host cell cytoplasm and has been hypothesized to be involved in drug and nutrient uptake. Furthermore, the two parasites, and their respective host cells, have different repertoires of drug efflux transporters, which can also account for the differences in inhibitor sensitivity. While the *T. gondii* assay does not fully negate the necessity of testing in *Cryptosporidium* directly, it has proven indispensible to winnow candidate compounds to a manageable number amenable to this more challenging model. We have used the pipeline to identify two promising candidates for anticryptosporidial chemotherapy: A103 and A110. These compounds are >100× more potent than paromomycin, the current standard for anticryptosporidial activity.

Supplemental Experimental Data

In Vitro Culture of *Cryptosporidium parvum*

The human ileocecal adenocarcinoma epithelial cell line, HCT-8, was used to support *C. parvum* infection in vitro. HCT-8 cells were maintained in RPMI-1640 (Hyclone) supplemented with 10% FBS, 1 mM sodium pyruvate, 50 U/m penicillin, 50 μg/mL streptomycin, and amphotericin B. *Cryptosporidium parvum* oocysts were a kind gift from either Dr. Mead (Emory University) of Dr Kissinger (University of Georgia). Purified oocysts were received in 2% potassium dichromate and stored at 4° C. for up to 4 months.

For the HCl assay the day prior to infection 200 000 HCT-8 cells were seeded into black, optical quality, thin bottom, 96-well plates (DB Falcom) to achieve a 70% confluent monolayer on the day of infection. To facilitate oocyst excystation a procedure described by Gut et al., was followed. Briefly, oocysts were washed twice with 1 mL of PBS (pH7.2), incubated for 10 minutes at 37° C. in 1 mL 10 mM of HCl and then incubated for a further 10 minutes in 0.2 mL of 200 μM sodium taurocholate at 15° C. This oocyst suspension was diluted directly with DMEM (Hyclone) supplemented with 2% FBS, 50 U/m penicillin, 50 μg/mL streptomycin, amphotericin B and 0.2 mM L-glutamine (infection medium) to inoculate host cell monolayers at 5×10$^5$ oocysts per well. Oocysts were cultured on host cell monolayers for 3 hours at 37° C. Unexcysted oocysts and oocyst walls were then removed by aspiration and each well washed with 0.2 mL PBS (pH7.2). Infection medium was then added to the monolayers and infection was allowed to progress for 48 hours.

*Vicia villosa* Lectin (VVL) Immunofluorescence Assay and High Content Imaging The VVL IFA was performed in a 96-well format as follows. Following 48 hours of culture *C. parvum* infected HCT-8 monolayers were washed with 0.2 mL/well PBS and the monolayer was fixed with 0.2 mL/well of 3% paraformaldehyde/PBS, permeabilized with 0.25% Triton-X-100/PBS and blocked with 4% BSA/PBS. When necessary plates were stored at 4° C. for up to 2 weeks. 0.1 mL of fluorescein (FITC)-conjugated VVL (Vector Labs) at 0.5 μg/mL in 1% BSA/PBS was applied to wells and incubated for 45 minutes. The plates were washed twice with 200 μL/well of PBS, in the first wash DAPI at 0.1 μg/mL was included. Finally 200 μL/well of PBS was added to the plates prior to storage at 4° C. protected from light.

Following the labelling of the *C. parvum* infected HCT-8 cell monolayer with FITC-VVL and DAPI, confocal images were acquired using a scanning microscope (BD Biosciences Bioimager P435).

Montage images of 9-16, 40× fields per well automatically focused, captured, compressed and saved. Images from each plate were analyzed using object-finding algorithms (Attovision Software, BD Biosciences) optimized for the recognition of FITC-VVL labelled *C. parvum* parasites or DAPI labelled host cell nuclei. The object finding analysis step recorded the number and area of objects per montage image, the output files and a plate map file were then passed onto an automated analysis pipeline (Pipeline Pilot Software, Accelrys) to calculate, the mean number of parasites, the ratio of parasite number to host cell nuclei number, the mean area of parasites and host cell nuclei by well and percentage growth by treatment as compared to the no drug control. These analyses were output in graphical format in one PDF file per plate and the numerical values tabulated in html format.

All test compounds were stored as 0.1 M stocks in DMSO at −20° C. and further diluted in DMSO to a 200× working stocks for each dilution, such that the final concentration of DMSO in the infection medium was 0.5%. For the no drug control DMSO alone was added to triplicate wells. As a control for *C. parvum* growth a high paromomycin concentration (0.8 mg/mL) was included on each plate in triplicate wells. Plates where this paromomycin control did not inhibit 70-80% of parasite growth were manually inspected to confirm appropriate imaging and analysis. Plates were omitted from final analysis where it was apparent that a lack of inhibition was due to poor parasite growth.

Fluorescent HCT-8 Host Cell Growth Assay

HCT-8 cells were transfected with the pmaxGFP plasmid (Amaxa) using Lipofectamine (Invitrogen) following the manufactures instruction. Fluorescent lines were then selected and cloned using FACS. Confluent monolayers of pmaxGFP expressing cells were harvested from T75 flasks and passed through a 40 μm cell strainer. Cells were then seeded at 4000 cells per well in a volume of 200 μL into black, optical quality, thin bottom, 96-well plates (DB Falcon). All test compounds were diluted in DMSO to prepare a 200× working stock for each dilution. Appropriate wells were spiked with 1 μl such that the final concentration of DMSO was 0.5%. The fluorescence was read daily with a SpectraMax M22/M2e (Molecular Devices) plate reader (Ex 485, Em 530) for 6-7 days. The percent inhibition was calculated on a day within the exponential phase of growth.

Example 39—Structural Determinants of Inhibitor Selectivity in Prokaryotic IMP Dehydrogenases The protozoan parasite *Cryptosporidium parvum* is a major cause of gastrointestinal disease; no effective drug treatment exists to treat this infection. Curiously, CpIMPDH is most closely related to prokaryotic IMPDHs, suggesting that the parasite obtained its IMPDH gene via horizontal transfer. We previously identified inhibitors of CpIMPDH that do not inhibit human IMPDHs. Here we show that these compounds also inhibit IMPDHs from *Helicobacter pylori*, *Borrelia burgdorferi*, and *Streptococcus pyogenes*, but not IMPDHs from *Escherichia coli*, *Tritrichomonas foetus* and *Leishmania donovani*. Importantly, a second generation inhibitor blocks *H. pylori* growth. The presence of Ala165 and Tyr358 comprise a structural motif that defines susceptible enzymes, as verified by site-directed mutagenesis of *E. coli* IMPDH. We propose that IMPDH-targeted inhibitors represent a new class of antibiotics for treatment of a wide variety of pathogenic bacteria, including extensively drug resistant strains.

In this study, we explore the possibility that the inhibitors of the CpIMPDH might be broad spectrum inhibitors of prokaryotic IMPDHs. We find that IMPDHs from *H. pylori* (the causative agent of gastric ulcer/stomach cancer), *Borrelia burgdorferi* (the causative agent of Lyme disease) and *Streptococcus pyogenes* (a major cause of nosocomial infections) are inhibited by these compounds while *Escherichia coli* IMPDH is resistant. Importantly, a second generation CpIMPDH inhibitor blocks *H. pylori* growth, demonstrating that these compounds have antibacterial activity. A structural motif is identified that defines susceptible enzymes; this motif is found in a wide variety of pathogenic bacteria. These observations suggest that IMPDH-targeted inhibitors can be developed into a new class of moderate-spectrum antibiotics.

Results and Discussion

Expression, Purification and Characterization of Recombinant IMPDHs

We expressed and purified prokaryotic IMPDHs from representative organisms: *H. pylori* (Gram negative ε proteobacteria), *E. coli* (Gram negative γ proteobacteria), *B. burgdorferi* (spirochete), *S. pyogenes* (Gram positive) and the protozoan parasite *T. foetus*, which also appears to have obtained its IMPDH gene from a prokaryote. We also expressed an additional eukaryotic IMPDH from the protozoan parasite *L. donovani*. CpIMPDH is most closely related to HpIMPDH (FIG. 68), but also has ~50% sequence identity to EcIMPDH, BbIMPDH and SpIMPDH. Sequence identity drops to 32% for TfIMPDH, which is comparable to that of the eukaryotic enzymes. EcIMPDH, BbIMPDH, TfIMPDH, SpIMPDH and LdIMPDH have been characterized previously. The kinetic parameters of HpIMPDH are very similar to those of CpIMPDH, and are generally characteristic of bacterial IMPDHs. Importantly, structures are available for TfIMPDH, SpIMPDH and BbIMPDH as well as for CpIMPDH and the human enzymes.

Spectrum of Inhibition of CpIMPDH Inhibitors.

Compounds A-H also inhibit HpIMPDH, the enzyme most similar to CpIMPDH. With the exception of G, all of the compounds have similar potency for both enzymes, with values of $IC_{50}$ ranging from 0.6 to 5 µM. A-H are noncompetitive (mixed) inhibitors of HpIMPDH with respect to $NAD^+$ (data not shown), as observed with CpIMPDH. Importantly, the values of $K_i$ and $IC_{50}$ are similar, as expected for noncompetitive inhibition. These observations suggest that the inhibitor binding sites are similar on both HpIMPDH and CpIMPDH.

The compounds also inhibit BbIMPDH with similar potency to CpIMPDH and HpIMPDH (FIG. 67). However, whereas G and H are submicromolar inhibitors of SpIMPDH, A-F are markedly less effective against this enzyme, with $IC_{50}$ values ranging from 13 to 90 µM. No inhibition of EcIMPDH and TfIMPDH is observed at 100 µM, indicating that the values of $IC_{50}$ for A-H must be >1000 µM. This result is especially surprising for EcIMPDH because this enzyme has the same overall similarity to CpIMPDH as the sensitive enzymes. As expected for a eukaryotic IMPDH, A-H do not inhibit LdIMPDH.

Inhibition of *H. pylori* Growth.

Figure 41:
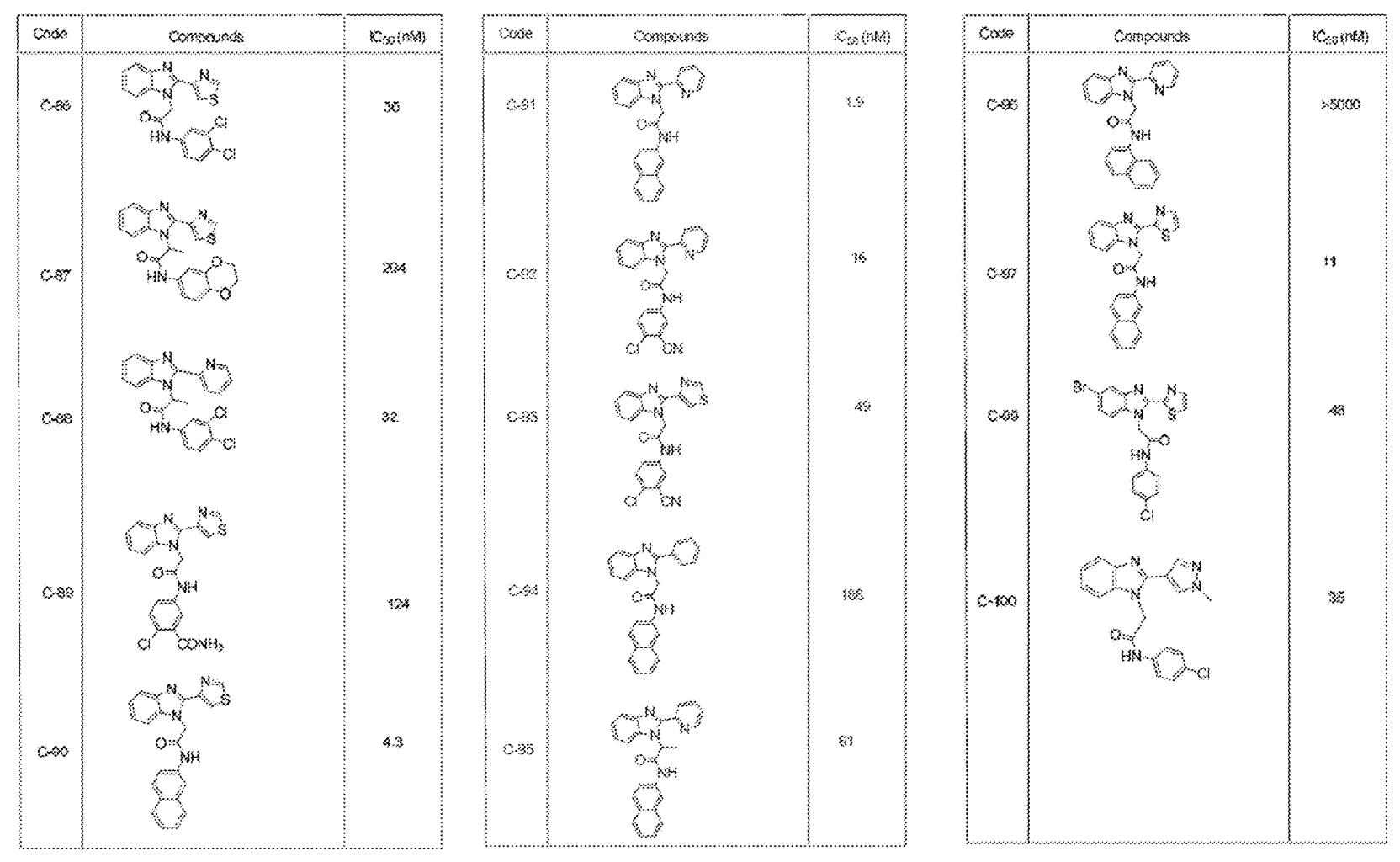

*H. pylori* is cultured in a nutrient rich medium (*Brucella* broth), which provides a stringent test for the antibiotic potential of IMPDH-targeted inhibitors. *H. pylori* contains a gene encoding xanthine/guanine phosphoribosyltransferase, suggesting that these bacteria can salvage xanthine and guanine from the media. If this salvage pathway is efficient, *H. pylori* will be resistant to IMPDH inhibitors. Therefore we investigated the sensitivity of *H. pylori* to a second generation CpIMPDH inhibitor, C91 (FIG. 41). C91 inhibits HpIMPDH with an $IC_{50}=25\pm3$ nM, which is comparable to that observed for inhibition of CpIMPDH ($IC_{50}=8\pm3$ nM; [13]).

Figure 69:
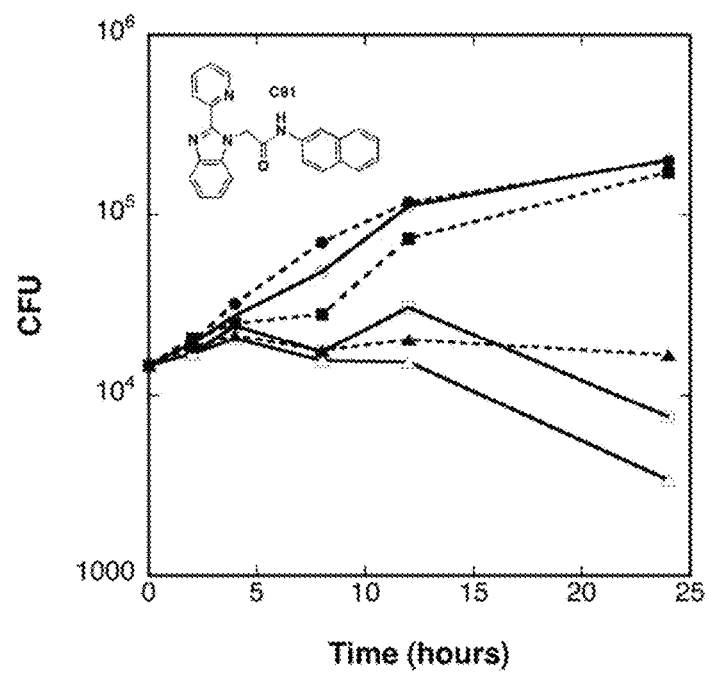
FIG. 69 depicts that C91 inhibits *H. pylori* growth. CFU, colony forming units. Filled circles, DMSO alone. C91 concentrations: open circles, 2 µM; closed squares, 7 µM; open squares, 20 µM; closed triangles, 60 µM; open triangles, 200 µM.

FIG. 69 shows that 20 µM C91 is sufficient to block the proliferation of a *H. pylori* culture exiting stationary phase. Higher concentrations of C91 display bacteriocidal effects, with only 23% of the colony forming units remaining after 24 hr treatment with 200 µM. Exponentially growing *H. pylori* cells are also sensitive to C91; a concentration of 60 µM is sufficient to block growth while higher concentrations are bacteriocidal.

Structural Determinants of Inhibitor Susceptibility.

The structure of CpIMPDH with the second generation inhibitor C64 identifies a possible binding site for the inhibitors A-H (FIGS. 70 and 71). IMPDH is a tetramer; surprisingly, C64 binds across a dimer interface, bending around Ala165 and stacking with Tyr358. Both Ala165 and Tyr358 are conserved in the sensitive enzymes, but diverged in the resistant enzymes, suggesting that these residues determine susceptibility to the C series inhibitors, and possibly the other compounds.

To determine the role of Ala165 and Tyr358 in defining the inhibitor susceptibility, we replaced the corresponding residues of the resistant EcIMPDH with their CpIMPDH counterparts to create three variants: S250A, L444Y and S250A/L444Y. The steady-state kinetic parameters of S250A and S250A/L444Y are comparable to those of wild-type EcIMPDH, though the value of $K_m$ for $NAD^+$ is increased by more than 5-fold in L444Y. Unlike EcIMPDH, significant inhibition is observed when the S250A and L444Y variants are incubated with 100 µM A-H, suggesting that the single mutations increase sensitivity by factors of at least 2-10 (unfortunately, the solubility of the compounds does not permit the values of $IC_{50}$ to be determined). In contrast, A-H are potent inhibitors of the S250A/L444Y enzyme, with values of $IC_{50}$ comparable to CpIMPDH (FIG. 67). These observations indicate that together Ala165 and Tyr358 define the structural motif required for susceptibility to A-H.

The Conformational Contribution to Inhibitor Selectivity.

Figure 68:
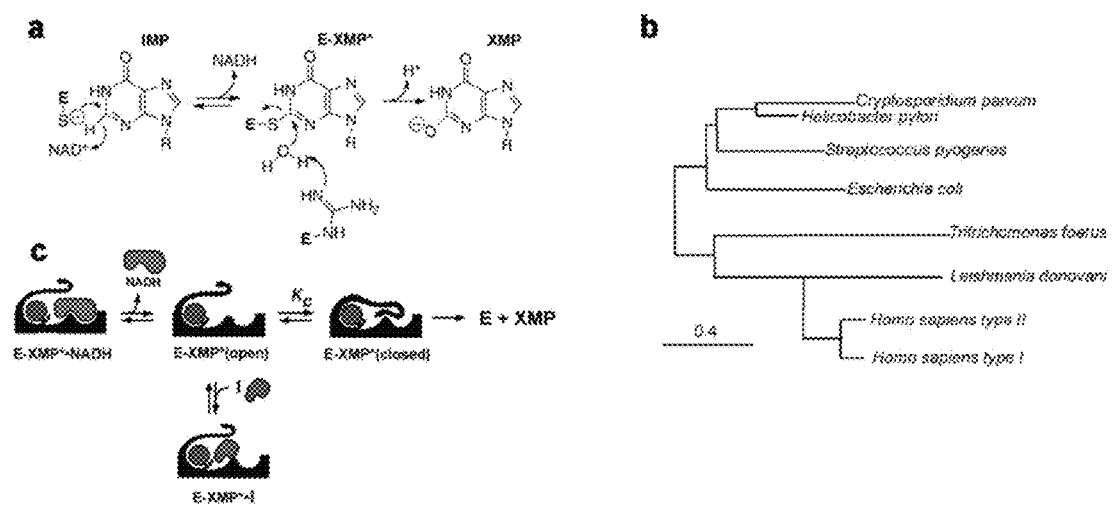
FIG. 68 depicts the IMPDH reaction: a. Chemical mechanism: a conserved Cys attacks C2 of IMP and hydride is transferred to $NAD^+$ producing the covalent intermediate E-XMP*. E-XMP* is hydrolyzed with a conserved Arg residue acting as a general base to produce XMP. b. The hydride transfer reaction proceeds in an open enzyme conformation. After NADH departs, a mobile flap folds into the NAD site, carrying the catalytic Arg into the active site. Inhibitors compete with the flap, so the equilibrium between open and closed states is a determinant of inhibitor affinity. c. Phylogenetic tree of IMPDHs.

As noted in the introduction, IMPDH undergoes a conformational change in the middle of its catalytic cycle that brings a mobile flap into the NAD site (FIG. 68). The competition of the flap for this site can be an important determinant of inhibitor susceptibility, and might explain the low susceptibility of SpIMPDH despite the presence of Ala165 and Tyr358 (FIG. 67). Therefore we determined the equilibrium between open and closed conformations ($K_c$) using a multiple inhibitor experiment.

Tiazofurin inhibition illustrates the magnitude of the conformational contribution to inhibitor selectivity. The tiazofurin binding site is conserved among prokaryotic IMPDHs, which predicts that CpIMPDH, HpIMPDH, BbIMPDH, SpIMPDH, EcIMPDH and TfIMPDH should all bind tiazofurin with similar affinity, yet the values of $K_i$ vary from 1-69 mM. When the observed values are adjusted for competition from the mobile flap, the resulting "intrinsic values" are indeed nearly identical, ranging from 0.3-0.7 mM. In contrast, the intrinsic values of $K_i$ for ADP range from 0.2-9 mM, reflecting the structural divergence of the ADP binding sites.

The Intrinsic Affinities of A-H.

We determined the intrinsic values of $IC_{50}$ for A-H in order to assess how competition with the mobile flap contributes to susceptibility (FIG. 67). Inspection of the intrinsic values of $IC_{50}$ reveals two distinct inhibitor binding modes. The intrinsic values of $IC_{50}$ of C range between 0.18-0.36 µM for CpIMPDH, HpIMPDH, BbIMPDH and S250A/L444Y (FIG. 67), reflecting the conservation of this binding site. Likewise, the intrinsic affinities of compounds A, B, D, E and F are within a factor of 2 for all four enzymes, indicating that the binding sites of these compounds are also conserved. These observations suggest that compounds A, B, D, E and F most likely occupy the same binding site as C.

In contrast, the intrinsic values of A-F for SpIMPDH are very different from CpIMDPH, indicating that this binding site is significantly different in SpIMPDH. Only one substitution is present within 3.5 Å of C64: Met326 is a Leu in SpIMPDH. However, the Leu substitution is also present in HpIMPDH and BbIMPDH, and therefore cannot account for the different susceptibility. The next nearest substitution is Thr for Ser164; the side chain of Ser164 is 5 Å away from C64, but might be closer to the A, B and D-F.

A very different trend is observed in the intrinsic affinities of G and H. SpIMPDH is most similar to CpIMPDH, while HpIMPDH and BbIMPDH display lower affinities for these compounds (FIG. 67). These observations suggest that G/H bind in a region that is conserved in SpIMPDH and CpIMPDH, but different in the other enzymes. Therefore, at least a portion of the G/H binding site must be distinct from the site that binds A-F.

Implications for the Design of Antibiotics Targeting IMPDH.

The above findings indicate that Ala165 and Tyr358 comprise a structural motif that defines enzymes susceptible to CpIMPDH inhibitors. A BLAST search reveals that these critical residues are present in IMPDHs from a wide variety of pathogenic bacteria in addition to *C. parvum, B. burgdorferi* and *H. pylori*: *Campylobacter lari* (food poisoning), *Campylobacter jejuni* (food poisoning), *Arcobacter butzleri* (food poisoning), *Bacteroides capillosis* (abscesses), *Fusobacterium nucleatum* (periodontitis, Lemierre's syndrome, skin ulcers), *Burkholderia cenocepacia* (infection in Cystic Fibrosis), *S. pneumoniae* (pneumonia), *Clostridia botulinum* (botulism), *Neisseria gonorrhoeae* (gonorrhea), *Mycobacterium tuberculosis* (tuberculosis), *M. leprae* (leprosy), *Neisseria meningitides* (bacterial meningitis), *Staphylococcus aureus* (major cause of nosocomial infection), *Acinetobacter baumannii* (wound infection), *Bacillus anthracis* (anthrax) and *Clostridium botulinum*. Importantly, several of these pathogens have developed multi-drug resistant strains, so new antibiotics are urgently needed. Our results suggest that IMPDH inhibition provides a promising strategy for the development of a new moderate spectrum antibiotic. Prokaryotic-specific inhibitors such as C91 will be invaluable in validating IMPDH as a target for antibiotic chemotherapy.

Significance

The rising tide of antibiotic resistance creates an urgent need for new drugs to treat bacterial infections, but years of neglect have depleted the antibiotic pipeline. The re-purposing of other drug development programs for antibiotic discovery is a promising strategy to address this problem. Inosine 5'-monophosphate dehydrogenase (IMPDH), a key enzyme in the biosynthesis of the precursors for RNA and DNA, presents an intriguing opportunity for such re-purposing. IMPDH is a promising target for drugs against the protozoan parasite *Cryptosporidium parvum*, a major cause of diarrhea and malnutrition and a potential bioterrorism agent. Curiously, CpIMPDH is most closely related to prokaryotic IMPDHs, suggesting that the parasite obtained its IMPDH gene via horizontal transfer. We previously identified inhibitors of CpIMPDH that do not inhibit human IMPDHs. Here we show that selective inhibitors of CpIMPDH also inhibit IMPDHs from the pathogenic bacteria *Helicobacter pylori*, *Borrelia burgdorferi*, and *Streptococcus pyogenes*. Importantly, a second generation CpIMPDH inhibitor blocks *H. pylori* growth in rich media, demonstrating that these compounds have antibacterial activity. Importantly, susceptible enzymes are defined by a structural motif that is found in IMPDHs from a wide variety of pathogenic bacteria, suggesting that IMPDH-targeted inhibitors can be developed into a new class of moderate spectrum antibiotics.

Experimental Procedures

Materials.

Compounds D, E, F, G, and H were purchased from ChemDiv Inc. (San Diego, Calif.), Compounds A, B and C were synthesized as described previously. Compound C91 was synthesized as described. All other chemicals were obtained from Fisher Scientific, unless mentioned otherwise. Plasmid containing the guaB gene of *S. pyogenes* was a generous gift of Dr. Cameron Ashbaugh. *H. pylori* total genomic DNA was obtained from American Type Culture Collection (ATCC). *L. donovani* IMPDH coding sequence was the gift of Dr. Buddy Ullman.

Enzyme Cloning and Purification.

Recombinant *T. foetus, B. burgdorferi, E. coli* and *C. parvum* IMPDH were expressed in guaB strains of *E. coli* (which lack endogenous IMPDH) and purified as described previously. The S250A, L444Y and S250A/L444Y mutants of *E. coli* IMPDH were constructed using Quikchange (Stratagene, La Jolla, Calif.). Enzymes were expressed and purified as previously described.

To express *L. donovani* IMPDH, a NcoI site was created at the beginning of the LdIMPDH coding sequence and the NcoI-PstI fragment was cloned into pKK233-2 to create the plasmid pLDI, which expresses LdIMPDH under control of the trc promoter. Cultures were induced with 0.5 mM IPTG and grown overnight. Cells were harvested by centrifugation, resuspended in Buffer A, lysed by sonication and clarified by centrifugation followed by filtration through a 45 μm cellulose acetate filter. Protein was applied to a Poros HS strong cation exchange resin (PerSeptive Biosystems) pre-equilibrated with 20 mM $NaP_i$, pH 7.5, 1 mM DTT (Buffer B). LdIMPDH was eluted with a gradient of 0-0.9 M NaCl. Fractions containing IMPDH activity were pooled and applied to IMP affinity resin. The column was washed with Buffer B and enzyme was eluted with Buffer B containing 0.5 M KCl, 1 mM IMP. The specific activity of the final preparation was 2.6 μmoles/min-mg.

The *H. pylori* and *S. pyogenes* guaB genes were cloned into pET28a with 6×His-tags. Bacteria were grown at 30° C. in LB medium containing 25 μg/mL kanamycin until the $OD_{600}$ reached approximately 0.6. Expression was initiated by the addition of 0.5 mM IPTG and the temperature was changed to 25° C. Bacteria were harvested after 16 hours. The cell pellet was rinsed (3×) with 50 mM phosphate buffer, 500 mM NaCl, 5 mM imidazole, pH 8.0, 1 mM IMP and 5 mM β-mercaptoethanol, and lysed by sonication. The lysate was clarified by centrifugation and loaded on a Ni-NTA column (Qiagen). The purified protein were eluted in 50 mM phosphate buffer, 500 mM NaCl, 250 mM imidazole, pH 8.0, 1 mM IMP and 5 mM β-mercaptoethanol, concentrated and dialyzed against 50 mM Tris-HCl, pH 8.0, and 10% glycerol. The protein concentration was determined by using Bradford dye procedure (BioRad).

Steady State Enzyme Kinetics:

IMPDH assays were performed in 50 mM Tris-HCl, pH 8.0, 100 mM KCl, 3 mM EDTA and 1 mM DTT. Activity was routinely assayed in the presence of 50 nM IMPDH at 25° C. NADH production was monitored either by following absorbance change at 340 nm using a Hitachi U-2000 spectrophotometer ($\delta$=6.2 $mM^{-1}$ $cm^{-1}$). IMPDHs are prone to $NAD^+$ substrate inhibition. Therefore the steady state kinetics for HpIMPDH were initially analyzed by varying $NAD^+$ at saturating IMP concentrations to determine the value of $K_m$ for $NAD^+$ then by varying IMP at the fixed $NAD^+$ concentration as close to saturating as practical. Using the SigmaPlot program (SPSS, Inc.), initial velocity data were fit to the Michaelis-Menten equation (Equation a) and/or the uncompetitive substrate inhibition equation (Equation b), as follows, $$v = V_m[S]/(K_m+[S]) \quad (a)$$

$$v = V_m/(1+K_m/[S]+[S]^2/K_{ii}) \quad (b)$$

where v represents the velocity, $V_m$ is the maximal velocity, S is the substrate concentration, $K_m$ is the Michaelis constant, $K_{ii}$ is the intercept inhibition constant (X-Y). The values of $k_{cat}$ determined under both conditions are in good agreement.

Inhibitor Kinetics.

Enzyme was incubated with inhibitor (50 pM-100 μM) for 10 min at room temperature prior to addition of substrates. $IC_{50}$ values were calculated for each inhibitor according to Equation c using the SigmaPlot program (SPSS, Inc.):

$$v_i = v_0/(1+[I]/IC_{50}) \quad (c)$$

where $v_i$ is initial velocity in the presence of inhibitor (I) and $v_0$ is the initial velocity in the absence of inhibitor.

Assays were carried out in assay buffer at 25° C. with 50 nM IMPDH and NADH production was monitored by following fluorescence. The values of $K_i$ with respect to $NAD^+$ were determined by using fixed concentrations of IMP and varied $NAD^+$ concentrations. Data were fitted according to Equation d (noncompetitive inhibition) using SigmaPlot program (SPSS, Inc.):

$$v=V_m[S]/\{K_m(1+[I]/K_{is})+[S](1+[I]/K_{ii})\} \quad (d)$$

where $K_{ii}$ and $K_{is}$ represent the intercept and slope inhibition constants, respectively. The best fits were determined by the relative fit error.

Multiple Inhibitor Kinetics.

Multiple inhibitor experiments with tiazofurin and ADP were performed at constant IMP and $NAD^+$ (see Table S3 for concentrations). Initial velocities were fit to equation e using SigmaPlot:

$$v=v_0/[1+[I]/K_i+[J]/K_j+[I][J]/\alpha K_i K_j] \quad (e)$$

where v is the initial velocity, $v_0$ is the initial velocity in the absence of inhibitor, $K_i$ and $K_j$ are the inhibition constants for the inhibitors I and J, respectively and $\alpha$ is the interaction constant. In wild-type IMPDH, the tiazofurin and ADP are strongly synergistic inhibitors with an interaction constant $\alpha=0.007$. This observation suggests that one inhibitor shifts the enzyme into the open conformation, thus promoting the association of the second inhibitor. Further, the value of $\alpha$ approximates the fraction of enzyme in the open conformation, so the value of $K_c$ can be obtained:

$$K_c=(1-\alpha)/\alpha \quad (f)$$

H. pylori Growth Assays.

A stationary culture of H. pylori strain G27 'Merrell' was diluted into Brucella broth with fresh 10% fetal bovine serum to an $OD_{600}=0.025$ (~$10^4$ colony forming units/µl). Cultures (200 µl) were incubated with C91 added in 2 µl aliquots of DMSO solution, or 2 µl of DMSO alone, for 24 hrs. Colony forming units were determined. Alternatively, exponentially growing cultures were diluted to ~$10^4$ colony forming units/µl and treated as described.

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A compound, or a pharmaceutically acceptable salt thereof, represented by Formula XIII:

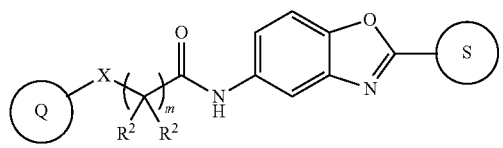

Formula XIII wherein, independently for each occurrence,

X is O;

m is 1;

one occurrence of $R^2$ is hydrogen, and the other occurrence of $R^2$ is alkyl;

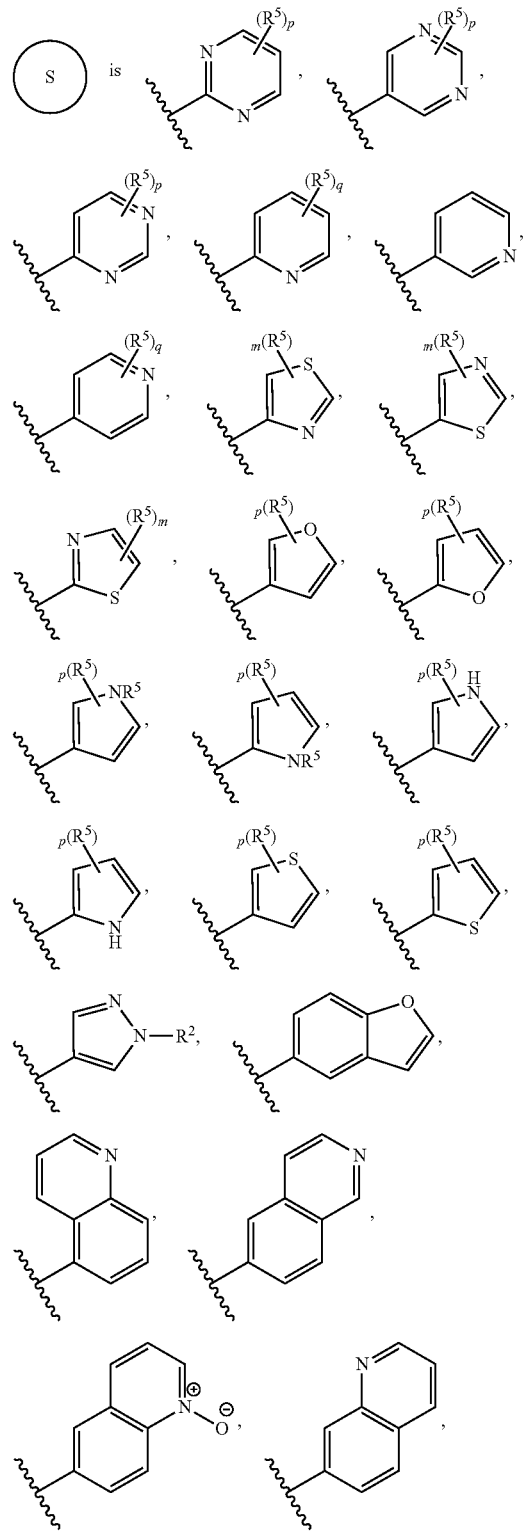

-continued

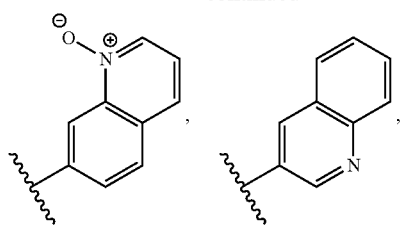

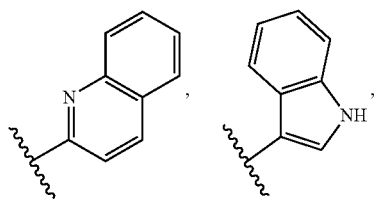

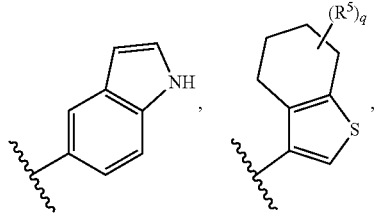

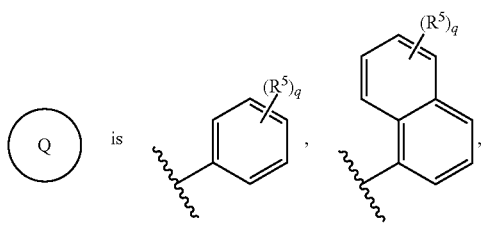

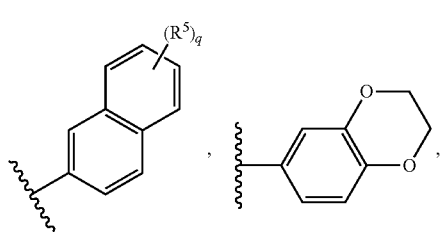

-continued

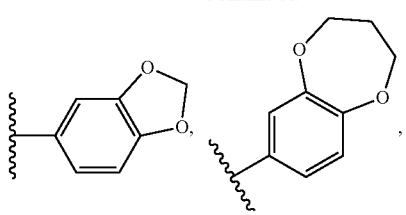

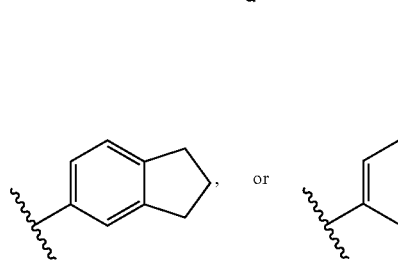

p is 0, 1, 2, or 3;

q is 0, 1, 2, 3, or 4; and $R^5$ is halo, azido, alkyl, haloalkyl, hydroxyalkyl, aminoalkyl, heterocycloalkyl, aralkyl, alkenyl, alkynyl, cycloalkyl, heterocyclyl, aryl, heteroaryl, heteroaralkyl, hydroxy, alkoxy, haloalkyloxy, aryloxy, heteroaryloxy, amino, nitro, sulfhydryl, imino, amido, phosphonate, phosphinate, acyl, carboxyl, alkoxycarbonyl, carboxylic acid, acyloxy, alkylthio, sulfonate, sulfonyl, sulfonamido, formyl, cyano, oxime, or isocyano;

wherein any of the aforementioned alkyl, aryl, or heteroaryl may be substituted with one or more groups independently selected from the group consisting of halo, azido, alkyl, haloalkyl, aralkyl, alkenyl, alkynyl, cycloalkyl, heterocyclyl, aryl, heteroaryl, heteroaralkyl, hydroxy, alkoxy, aryloxy, heteroaryloxy, amino, nitro, sulfhydryl, imino, amido, phosphonate, phosphinate, acyl, carboxyl, alkoxycarbonyl, acyloxy, silyl, alkylthio, sulfonate, sulfonyl, sulfonamido, formyl, cyano, and isocyano.

2. The compound of claim 1, wherein

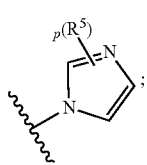 is 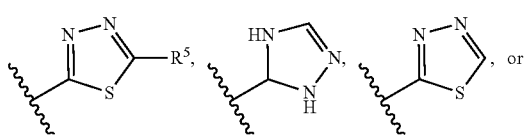

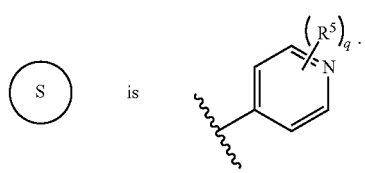

3. The compound of claim 1, wherein

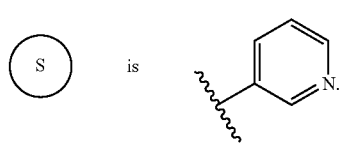

4. The compound of claim 1, wherein
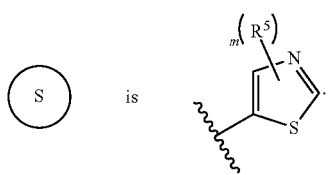
5. The compound of claim 1, wherein
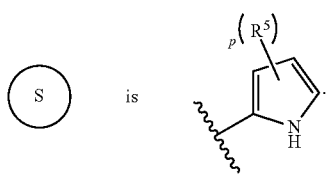
6. The compound of claim 1, wherein
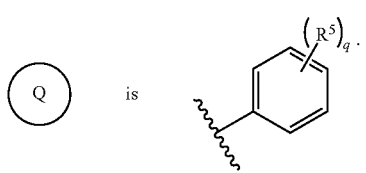
7. The compound of claim 1, wherein
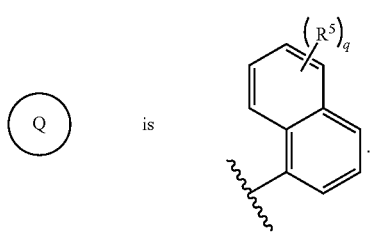
8. A compound, or a pharmaceutically acceptable salt thereof, selected from the group consisting of
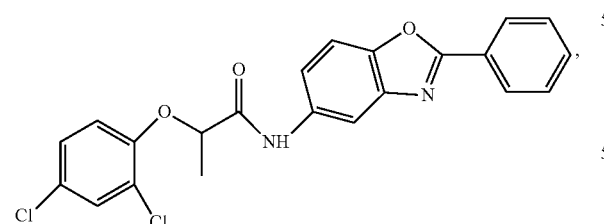
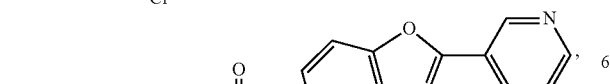
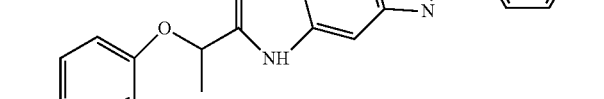
-continued
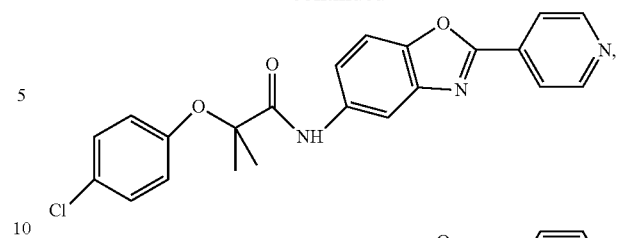
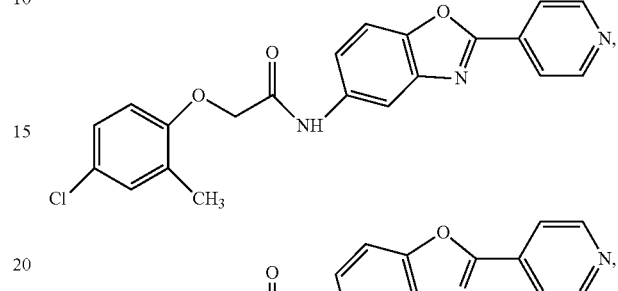
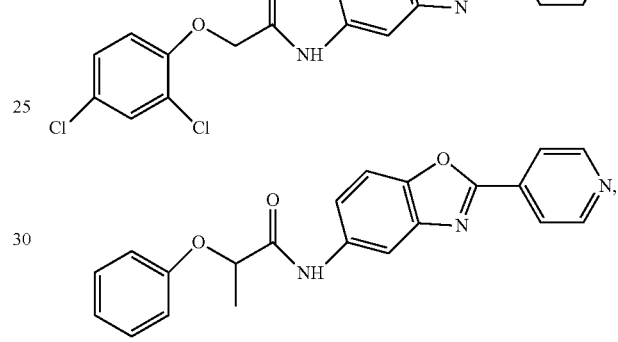
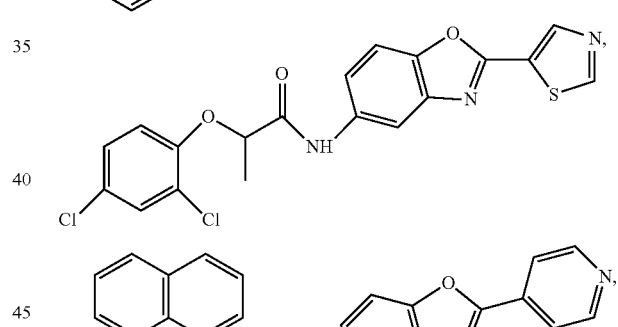
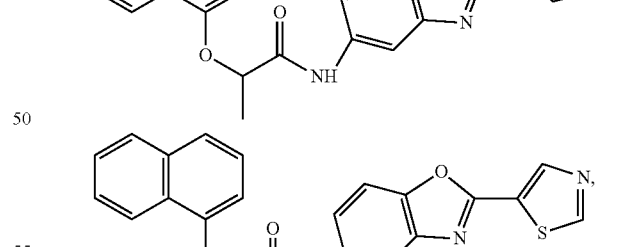
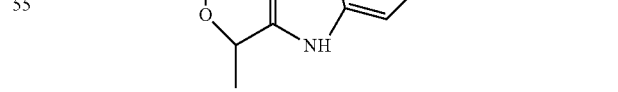
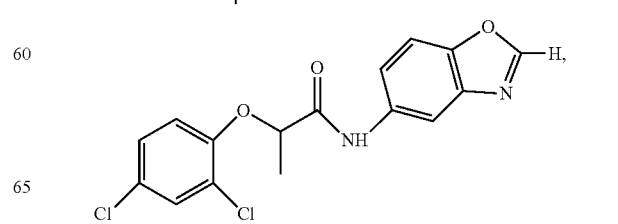

-continued

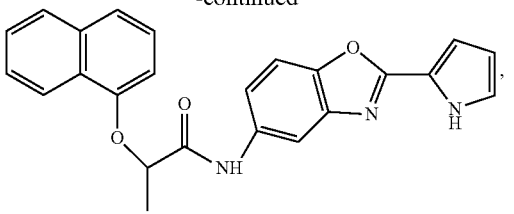

and

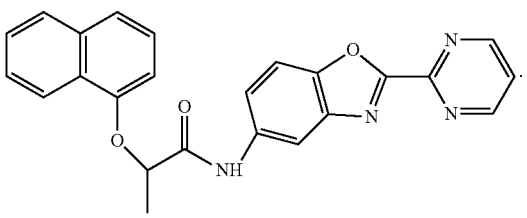

9. The compound of claim 1, wherein one occurrence of $R^2$ is hydrogen, and the other occurrence of $R^2$ is methyl.

10. A method of killing or inhibiting the growth of a microbe, comprising the step of contacting said microbe with an effective amount of a compound of claim 1.

11. The method of claim 10, wherein said microbe is a protozoon, a bacterium, or a fungus.

12. The method of claim 10, wherein said microbe is a protozoon or a bacterium selected from the group consisting of the genera *Eimeria, Cryptosporidium, Babesia, Theileria, Neospora, Sarcocystis, Giardia, Entamoeba, Trichomonas, Tritrichomonas, Leishmania, Trypanosoma, Helicobacter, Borrelia, Streptococcus, Campylobacter, Arcobacter, Bacteroides, Fusobacterium, Burkholderia, Clostridia, Neisseria, Mycobacterium,* and *Acinetobacter.*

13. The method of claim 11, wherein said microbe is a protozoon; and said protozoon is selected from the group consisting of the genera *Eimeria, Cryptosporidium, Babesia, Theileria, Neospora, Sarcocystis, Giardia, Entamoeba, Trichomonas, Tritrichomonas, Leishmania* and *Trypanosoma.*

14. The method of claim 11, wherein said microbe is a bacterium; and said bacterium is selected from the group consisting of the genera *Helicobacter, Borrelia, Streptococcus, Campylobacter, Arcobacter, Bacteroides, Fusobacterium, Burkholderia, Clostridia, Neisseria, Mycobacterium,* and *Acinetobacter.*

15. A method of treating or preventing a microbial infection in a mammal comprising the step of administering to a mammal in need thereof a therapeutically effective amount of a compound of claim 1.

16. The method of claim 15, wherein said microbial infection is caused by a protozoon, a bacterium, or a fungus.

17. The method of claim 15, wherein said microbial infection is caused by a protozoon or a bacterium selected from the group consisting of the genera *Eimeria, Cryptosporidium, Babesia, Theileria, Neospora, Sarcocystis, Giardia, Entamoeba, Trichomonas, Leishmania, Trypanosoma, Helicobacter, Borrelia, Streptococcus, Campylobacter, Arcobacter, Bacteroides, Fusobacterium, Burkholderia, Clostridia, Neisseria, Mycobacterium,* and *Acinetobacter.*

18. The method of claim 16, wherein said microbial infection is caused by a protozoon; and said protozoon is selected from the group consisting of the genera *Eimeria, Cryptosporidium, Babesia, Theileria, Neospora, Sarcocystis, Giardia, Entamoeba, Trichomonas, Tritrichomonas, Leishmania* and *Trypanosoma.*

19. The method of claim 15, wherein said microbial infection is caused by a bacterium; and said bacterium is selected from the group consisting of the genera *Helicobacter, Borrelia, Streptococcus, Campylobacter, Arcobacter, Bacteroides, Fusobacterium, Burkholderia, Clostridia, Neisseria, Mycobacterium,* and *Acinetobacter.*

20. The method of claim 13, wherein the protozoon is of the genera *Cryptosporidium.*

21. The method of claim 18, wherein the protozoon is of the genera *Cryptosporidium.*

* * * * *

UNITED STATES PATENT AND TRADEMARK OFFICE
CERTIFICATE OF CORRECTION

PATENT NO. : 10,125,116 B2
APPLICATION NO. : 14/571673
DATED : November 13, 2018
INVENTOR(S) : Lizbeth K. Hedstrom et al.

It is certified that error appears in the above-identified patent and that said Letters Patent is hereby corrected as shown below:

At Column 1, Lines 18-21, please replace:
"This invention was made with government support under Grant No. U01 AI-75466 awarded by the National Institutes of Health. The government has certain rights in the invention."

With:
-- This invention was made with government support under Grant No. U01AI075466 awarded by the National Institutes of Health. The government has certain rights in the invention. --

Signed and Sealed this
Twenty-fifth Day of December, 2018

Andrei Iancu
*Director of the United States Patent and Trademark Office*